US007238475B2

(12) United States Patent
Rubin et al.

(10) Patent No.: US 7,238,475 B2
(45) Date of Patent: Jul. 3, 2007

(54) APOLIPOPROTEIN GENE INVOLVED IN LIPID METABOLISM

(75) Inventors: Edward Rubin, Berkeley, CA (US); Len A. Pennacchio, Sebastopol, CA (US)

(73) Assignee: The Regents of The University of California, Oakland, CA (US)

( * ) Notice: Subject to any disclaimer, the term of this patent is extended or adjusted under 35 U.S.C. 154(b) by 354 days.

(21) Appl. No.: 10/229,834

(22) Filed: Aug. 27, 2002

(65) Prior Publication Data

US 2003/0150003 A1 Aug. 7, 2003

Related U.S. Application Data

(60) Provisional application No. 60/315,210, filed on Aug. 27, 2001.

(51) Int. Cl.
*C12Q 1/68* (2006.01)
*C12P 19/34* (2006.01)
*C07H 21/04* (2006.01)

(52) U.S. Cl. ........................ 435/6; 435/91.2; 536/24.3; 536/24.31

(58) Field of Classification Search .................... 435/6, 435/91.2; 536/24.3, 24.31
See application file for complete search history.

(56) References Cited

U.S. PATENT DOCUMENTS 5,939,260 A 8/1999 Spector et al.
6,030,778 A 2/2000 Acton et al.
6,228,582 B1 5/2001 Rodier et al.
6,355,427 B1 3/2002 Jupe et al.
6,383,751 B1 5/2002 Barendse
2003/0150003 A1* 8/2003 Rubin et al. .................. 800/18

FOREIGN PATENT DOCUMENTS

WO PCT/IB00/01011 6/2000

OTHER PUBLICATIONS

Brookes, Anthony J, "The essence of SNPs," Gene 234 (1999) 177-186.

Aalto-Setala K, et al., "DNA polymorphisms of apolipoprotein A-I/C-III and insulin genes in familial hypertriglyceridemia and coronary heart disease," Atherosclerosis , vol. 66 (No. 1-2), p. 145-152, (Jul. 1987).

Ahn Yi et al., "DNA polymorphisms of the apolipoprotein AI/CIII/ AIV gene cluster influence plasma cholesterol and triglyceride levels in the Mayans of the Yucatan Peninsula, Mexico," Hum Hered. , vol. 41 (No. 5), p. 281-289, (1991).

Aouizerat Be, et al., "A genome scan for familial combined hyperlipidemia reveals evidence of linkage with a locus on chromosome 11 ," Am J Hum Genet, No. 65, p. 397-412, (1999).

Dammerman M, et al., An apolipoprotein CIII haplotype protective against hypertriglyceridemia is specified by promoter and 3' untranslated region polymorphisms. Proc. Natl Acad Sci U S A 90:4562-4566 (1993).

Groenedijk M, et al., The apoAI-CIII-AIV gene cluster. Atherosclerosis 157 (1):1-11 (2001).

Groenendijk M, et al., Two newly identified SNPs in the APO AI-CIII intergenic region are strongly associated with familial combined hyperlipidaemia. Atherosclerosis 158:369-376 (2001).

Hoffer MJ, et al., Increased risk for endogenous hypertriglyceridaemia is associated with an apolipoprotein C3 haplotype specified by the SstI polymorphism. Eur J Clin Invest 28:807-812 (1998).

Landro JA, HTS in the new millennium: The role of pharmacology and flexibility. J. of Pharmalogical and Toxicological Methods 44 (2000) 273-289.

Monsalve MV, et al., Study of DNA polymorphisms of the apolipoprotein AI-CIII-AIV gene cluster in patients with peripheral arterial disease. Clin Sci (Lond) 76:221-228 (1989).

Nabika T, et al., The genetic effect of the apolipoprotein AV gene on the serum triglyceride level in Japanese (Dec. 2002) Atherosclerosis 165:201-204.

Paul Weber B, et al., (1988) Genetic variation in the apolipoprotein AI-CIII-AIV gene cluster and coronary heart disease. Atherosclerosis 73:125-133.

Pennacchio LA, et al., Two independent apolipoprotein A5 haplotypes influence human plasma triglyceride levels. Hum. Mol. Genet., Nov. 15, 2002; 11(24): 3031-3038.

Pennacchio LA, et al., An Apolipoprotein Influencing Triglycerides in Humans and Mice Revelaed by Comparative Sequencing. Science (Oct. 5, 2001) 294 :169-173.

Olivieri O, et al., ApoC-III gene polymorphisms and risk of coronary artery disease. J. Lipid Res., Sep. 1, 2002; 43(9): 1450-1457.

Rees A, et al., DNA polymorphism adjacent to human apoprotein A-1 gene: relation to hypertriglyceridaemia. Lancet 1: 444-446 (1983).

Shoulders CC, et al., Variation in the apo AI/CIII/AIV gene complex: its association with hyperlipidemia. Atherosclerosis 80:111-118 (1989).

(Continued)

*Primary Examiner*—Anne-Marie Falk
*Assistant Examiner*—Anoop K. Singh
(74) *Attorney, Agent, or Firm*—Townsend and Townsend and Crew LLP

(57) ABSTRACT

Methods and materials for studying the effects of a newly identified human gene, APOAV, and the corresponding mouse gene apoAV. The sequences of the genes are given, and transgenic animals which either contain the gene or have the endogenous gene knocked out are described. In addition, single nucleotide polymorphisms (SNPs) in the gene are described and characterized. It is demonstrated that certain SNPs are associated with diseases involving lipids and triglycerides and other metabolic diseases. These SNPs may be used alone or with SNPs from other genes to study individual risk factors. Methods for intervention in lipid diseases, including the screening of drugs to treat lipid-related or diabetic diseases are also disclosed.

28 Claims, 6 Drawing Sheets

OTHER PUBLICATIONS

Shoulders CC, et al., Variation at the apo AI/CIII/AIV gene complex is associated with elevated plasma levels of apo CIII. Atherosclerosis 87:239-247 (1991).
Stocks J, et al., Haplotypes identified by DNA restriction-fragment-length polymorphisms in the A-1 C-III A-IV gene region and hypertriglyceridemia. Am J Hum Genet 41 (2):106-118 (1987).
Surguchov AP, et al Polymorphic markers in apolipoprotein C-III gene flanking regions and hypertriglyceridemia. Arterioscler. Thromb.Vasc.Biol 16 (8):941-947 (1996).
Tahvanainen E, et al., Haplotypes of the ApoA-I/C-III/A-IV gene cluster and familial combined hyperlipidemia. Arterioscler Thromb Vasc Biol 18:1810-1817 (1998).
Talmud P, et al., Relative Contribution of Variation within the APOC3/A4/A5 gene cluster in determining plasma triglycerides. Human Mol. Genetics, vol. 11, No. 24, 3039-3046 (2002).
Tangirala RK et al., Regression of Atherosclerosis Induced by Liver-directed Gene Transfer of Apolipoprotein A-I in Mice. Circulation 1999; 100:1816-1822.
Tsukamoto K et al., Comparison of human apoA-I expression in mouse models of atherosclerosis after gene transfer using a second generation adenovirus. J. Lipid Res. 38, 1869-1876 (1997).
Tybjaerg-Hansen A, et al., (1993) Genetic markers in the apo AI-CIII-AIV gene cluster for combined hyperlipidemia, hypertriglyceridemia, and predisposition to atherosclerosis. Atherosclerosis 100 (2):157-169.
Van Der Vliet HN, et al., Apolipoprotein A-V. (Nov. 30, 2001) J. Biol. Chem. 276:44512-44520.
Groenendijk M, et al., Two polymorphims in the apoA-IV gene and familial combined hyperlipidemia. Atherosclerosis 158, 369-376 (2001).

* cited by examiner

| Haplotype | Freq. | -1131T>C (SNP3) | c.-3A>G (SNP6) | c.56C>G (SNP5) | IVS3+476G>A (SNP2) | c.1259T>C (SNP1) |
|---|---|---|---|---|---|---|
| *APOA5*1* | 81.6% | T | A | C | G | T |
| *APOA5*2* | 8.0 | **C** | **G** | C | **A** | **C** |
| *APOA5*3* | 8.0 | T | A | **G** | G | T |

**Associations of *apoA V* genotypes with plasma lipid parameters (mg/dL ± SEM)**

| Genotype | SNP1 1,1 | SNP1 1,2 | p | SNP2 1,1 | SNP2 1,2 | p | SNP3 1,1 | SNP3 1,2 | p | SNP4 1,1 | SNP4 1,2 | SNP4 2,2 | p |
|---|---|---|---|---|---|---|---|---|---|---|---|---|---|
| n | 364 | 72 | | 358 | 67 | | 354 | 72 | | 172 | 213 | 55 | |
| **Triglyceride** | | | | | | | | | | | | | |
| Random diet | 119.3±3.8 | 144.4 ± 11.3 | 0.02 | 119.8±3.8 | 150.7±12.0 | 0.003 | 116.5±3.6 | 151.7±11.2 | 0.0002 | 126.8±5.8 | 124.6±5.6 | 117.4±9.8 | 0.7 |
| High fat diet | 98.6±3.2 | 129.8±12.1 | 0.0006 | 98.4±3.2 | 134.9±13.0 | <0.0001 | 96.5±2.9 | 132.9±12.1 | <0.0001 | 107.9±5.4 | 110.2±7.7 | 91.7±5.6 | 0.39 |
| Low fat diet | 127.0±4.4 | 171.7±21.9 | 0.0015 | 128.5±4.6 | 175.9±23.4 | 0.0012 | 126.1±4.5 | 174.7±21.8 | 0.0006 | 138.7±7.4 | 137.6±9.1 | 131.5±13.3 | 0.92 |
| **VLDL mass** | | | | | | | | | | | | | |
| High fat diet | 73.9±3.3 | 108.0±11.8 | 0.0002 | 73.7±3.3 | 112.8±12.7 | <0.0001 | 70.6±3.2 | 113.7±11.8 | <0.0001 | 82.1±5.7 | 82.6±6.5 | 71.7±6.8 | 0.67 |
| Low fat diet | 116.5±4.9 | 152.9±16.8 | 0.0065 | 112.9±5.0 | 155.6±18.1 | 0.0071 | 116.0±5.0 | 155.2±16.9 | 0.0037 | 122.8±7.7 | 127.5±7.8 | 123.3±15.5 | 0.91 |
| **LDL-cholesterol** | | | | | | | | | | | | | |
| High fat diet | 122.0±1.8 | 122.5±3.9 | 0.90 | 122.7±1.8 | 122.2±4.1 | 0.91 | 123.5±1.9 | 122.7±4.2 | 0.86 | 121.8±2.5 | 121.4±2.4 | 126.2±4.6 | 0.65 |
| Low fat diet | 111.7±1.6 | 110.5±4.0 | 0.76 | 112.5±1.6 | 109.8±4.2 | 0.51 | 112.8±4.2 | 109.9±4.6 | 0.50 | 110.8±2.3 | 111.3±2.2 | 115.7±4.4 | 0.59 |
| **HDL-cholesterol** | | | | | | | | | | | | | |
| High fat diet | 48.6±0.7 | 46.8±1.5 | 0.26 | 48.4±0.7 | 47.7±1.5 | 0.66 | 48.7±0.7 | 47.7±1.6 | 0.86 | 48.1±0.9 | 48.3±0.9 | 49.2±1.9 | 0.83 |
| Low fat diet | 41.6±0.5 | 40.5±1.3 | 0.40 | 41.6±0.5 | 40.8±1.3 | 0.52 | 41.8±0.5 | 40.6±1.4 | 0.37 | 41.5±0.8 | 41.2±0.7 | 42.6±1.4 | 0.66 |

| | SNP1 | SNP2 | SNP3 | SNP4 |
|---|---|---|---|---|
| SNP1 | | 0.870 | 1.000 | 0.219 |
| SNP2 | 0.870 | | 1.000 | 0.328 |
| SNP3 | 1.000 | 1.000 | | 0.308 |
| SNP4 | 0.219 | 0.328 | 0.308 | |

C

| Group | n | BMI | Age | TG | SNP3 1,1 | SNP3 1,2 | SNP3 2,2 | p value |
|---|---|---|---|---|---|---|---|---|
| Total TG>90% | 161 | 29.0±4.6 | 49.2±16.3 | 340.6±249.4 | 125 (77.6 ) | 35 (21.7 ) | 1 (0.6) | >0.0001 |
| Total TG<10% | 298 | 25.7±4.1 | 49.9±15.7 | 54.6±13.4 | 278 (93.3 ) | 20 ( 6.7) | 0 | |
| Male TG>90% | 97 | 28.9±3.7 | 50.1±16.6 | 336.4±155.3 | 67 (69.1 ) | 29 ( 29.9) | 1 (1.0) | >0.0001 |
| Male TG<10% | 192 | 26.5±3.8 | 54.4±15.6 | 57.4±12.3 | 184 (95.8) | 8 (4.2) | 0 | |
| Female TG>90% | 64 | 29.3±6.0 | 47.8±15.8 | 347.1±349.6 | 58 (90.6) | 6 (9.4) | 0 | 0.69 |
| Female TG<10% | 106 | 24.1±4.2 | 42.4±12.8 | 50.0±13.8 | 94 (88.7) | 12 (11.3) | 0 | |

APOLIPOPROTEIN GENE INVOLVED IN LIPID METABOLISM

CROSS-REFERENCE TO PRIOR APPLICATION

This application claims priority to Application No. 60/315,210, which was filed on Aug. 27, 2001.

STATEMENT OF GOVERNMENT SUPPORT

This invention was made during work supported in part by the U.S. Department of Energy, Office of Biological and Environmental Research, under Contract No. DE-AC03-76SF00098. The government has certain rights in this invention.

REFERENCE TO SEQUENCE LISTING

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

This invention generally relates to human lipid metabolism, particularly to apolipoproteins, genes encoding these apolipoproteins, related proteins, and their mutations and polymorphisms as they relate to cardiovascular, coronary and other diseases.

2. Description of the Related Art

Cardiovascular diseases are the number one cause of death in Western societies. Studies repeatedly show that individuals with high levels of very low-density lipoprotein, (VLDL) and/or low levels of high density lipoprotein (HDL) have significantly increased chances of developing cardiovascular disease. It has been established that strategies to reverse the levels of these lipoprotein particles will lower disease risk in susceptible individuals.

Lipoproteins function as transport vehicles for triacylglycerols (triglycerides), cholesterol and other lipids. These complexes solubilize highly hydrophobic lipids, and regulate entry and exit of particular lipids at specific targets. Lipoproteins form micelle-like particles that consist of a nonpolar core of triacylglycerols, more commonly known as triglycerides, and cholesteryl esters surrounded by a coating of protein, phospholipids, and cholesterol. The lipoproteins are classified according to density. Lipoprotein particles are composed of lipids and proteins and are such particles as chylomicrons, very low-density lipoproteins (VLDL), intermediate-density lipoproteins (IDL), low-density lipoproteins (LDL), and high-density lipoproteins (HDL). (Voet and Voet, *Biochemistry,* 1990; Stryer, *Biochemistry,* 1995). The protein components of lipoproteins are known as apolipoproteins.

Van der Vliet, H N et al., report on a gene that shares homology to APOAV and note its increase in expression following rat liver hepatectomy in *J Biol Chem*. Nov. 30, 2001;276(48):44512-20. The rat (GenBank Accession Nos. AF202888 and AF202887), mouse (GenBank Accessions No. AF327059) and human (GenBank Accessions Nos. AF202890 and AF202889) versions of these sequences were deposited in GenBank and entitled, *Regeneration-associated protein* 3 (*Rap* 3) *mRNA, complete cds*. Rap3 is noted in GenBank as an "apolipoprotein-like serum protein; concentration elevated after a 70% partial hepatectomy" in rats.

The human genomic region containing the DNA sequence for APOAV was sequenced by the Human Genome Project and deposited in GenBanK under Accesssion Numbers AC007707 and/or AC074203. These deposits cover approximately 200 kb of human genomic DNA. The deposits are associated with clustered 11q23 and 22q11 breakpoints, but no coding regions are described. Computational analyses indicate the previously described APOA-I, APOC-III, and APOA-IV are contained within this interval.

The GenBank Accession Number AC007707 sequence shows the opposite strand (reverse complement) of the sequences of the present invention. The reverse complement of AC007707 was used as the starting point of the present invention for finding the APOAV gene and coding sequence.

Yen et al., in PCT Publication WO 01/007803, entitled "Apolipoprotein A-IV-related protein: Polypeptide, polynucleotide sequences and bi-allelic markers thereof" describe a gene corresponding to the present APOAV. The gene is described as encoding an apolipoprotein A-IV-related protein (AA4RP) as well as regulatory sequences at the 5' and 3' end. Also disclosed are biallelic markers of the AA4RP gene useful in genetic analysis. However, Yen et al. describe their biallelic markers differently than the SNP's of the present invention. They disclose no description of any known linkages between these markers and any known disease phenotype.

Several human cDNA sequences derived from the APOAV gene have been previously disclosed in GenBank. A sequence file generated by the NCBI annotation project in July 2001 (transcript version 1) is disclosed as human mRNA/cDNA sequence, XM_052110. A second sequence file generated by the NCBI annotation project identifies in July 2001 (transcript version 2) can be found as XM_052109. AF202890 (called RAP3) is a third cDNA sequence that is related to the van der Vliet et al. Human ortholog of rat liver regeneration associated protein (transcript version 1). AF202889 (called RAP3) is the fourth cDNA sequence related to the van der Vliet et al. No. AF401201and was made public on 7 Oct. 2001.

Other related sequences include mouse mRNA/cDNA sequence (AF327059), called RAP3, which is the sequence identified as the mouse ortholog of rat liver regeneration associated protein. Three publicly generated mouse full-length cDNAs for apoAV are found under the following Accession Nos.: AK004903 (transcript version 2), BC011198 (transcript version 2), and AK004936 human ortholog of rat liver regeneration associated protein (transcript version 2).

Human protein sequences were predicted from mRNA sequences AF202890 and AF202889 and called AAF25662 and AAF25661, which correspond to the APOAV protein, which can be found under NP_443200 in NCBI.

The mouse genomic region (which includes additional genes sequenced and used used to create the knock-out mice described herein) is SEQ ID NO: 7 in this application. This sequence was deposited in GenBank under GenBank Accession (transcript version 1). The mouse RAP3 protein (GenBank Accession No. AAG49600) is the protein sequence predicted from mRNA sequence AF327059.

BRIEF SUMMARY OF THE INVENTION

The present invention involves a human apolipoprotein gene and its expressed product, Apolipoprotein A-V (herein referred to as "APOAV" or "APOA5"), located near a previously described apolipoprotein AI/CIII/AIV gene cluster (a region repeatedly implicated in various cardiovascular diseases) and its association with elevated levels of triglycerides.

The various aspects of the invention, as described below, are useful in the genetic analysis of cardiovascular disease. Patients with genetic predispositions to certain conditions may be screened with the analyses provided herein. High levels of APOAV protein expression are associated with lowered triglyceride levels, and low levels of APOAV expression (as demonstrated in "knock-out mice") are associated with increased levels of triglycerides. Furthermore, various polymorphisms have been identified which are correlated with different plasma triglyceride levels. Specifically, individuals with minor alleles for several SNPs near APOAV consistently display increased plasma triglyceride levels.

In addition, the present invention involves identification of a strong association between uncommon alleles of SNPs in the APOAV gene and increased plasma triglyceride levels in the general human population. Thus the present invention enables genetic testing for APOAV variants and their correlation to increased triglyceride levels in people having APOAV polymorphisms deviating from the normal or "wild type" phenotype. Further, a combination test with APOCIII is suggested. Genetic testing may be carried out on a patient's DNA or RNA or protein, provided that antibodies capable of distinguishing mutant from wild type APOAV protein are available. Furthermore, genetic testing using the markers disclosed herein may be used to identify individuals at risk for diabetes and/or insulin resistance. Genetic testing may also be used to determine an individuals' susceptibility to Familial hypercholesterolemia or other forms of hypercholesterolemia.

The invention also provides means for identifying haplotypes that are linked to the diseases of hyperlipidemia (CHL) and familial combined hyerlipidemia (FCHL).

Association studies indicate the existence of three haplotypes (APOA5*1, APOA5*2, APOA5*3) in APOA present in the general human population, that are associated with triglycerides. These three haplotypes are composed of five biallelic markers (SNPs 1-3, 5, and 6).

Thus, the invention includes using various methods for screening for genetic APOAV haplotypes or SNPs in humans. Fragments of various lengths of APOAV SEQ ID NOS: 1-7 may be placed onto solid supports for use in gene chips or other parallel formats for assay purposes. The sequences used will span a SNP and have sufficient flanking bases for specificty and binding, e.g. 10 bases on either side (5' and 3') of the nucleotide bearing the SNP. As few as 2 and as many as 1,000 bases may be used, depending on test design considerations.

Other methods for diagnostic purposes in this invention include but are not limited to, making antibodies to APOAV and its variants, attachment of the APOAV sequences disclosed herein onto solid supports for array and gene chips, and other hybridization assays.

The invention provides non-human animals that over-express the human version of APOAV. The over-expression of this gene results in these animals having dramatically reduced plasma triglyceride levels (~3-fold). In addition to decreased triglyceride levels these mice also have corresponding decreases in VLDL levels.

The invention also provides homozygous knockout non-human animals that are lacking apoA5 and therefore do not produce apoA5 protein. These animals have increased VLDL and triglyceride levels. This invention also includes recombinant vectors and DNA targeting constructs, such as the one used by the inventors to delete mouse apoA5 and was built using PCR products and primers made from SEQ ID NO: 7.

This invention also provides non-human animals for further animal studies by pharmaceutical companies to study human or mouse apoA5. Animal studies that explore the regulation and expression of human or mouse apoA5, its interaction with other apolipoproteins, production of antibodies for mutant and wild-type apoA5, and further in vivo study of apoA5. For example, mice lacking wild-type apoA5 may be exposed to various test substances to determine the triglyceride lowering effect of the test substance on individuals having a non-wild-type apoAV gene. The invention provides non-human animals useful for studying apoCIII since its levels are altered in these mouse models.

The invention can be further characterized as including an isolated polypeptide wild type APOAV protein as set forth in SEQ ID NO: 4, which corresponds to the ideal normal APOA5*1 haplotype. One mutant protein is encoded by DNA carrying the uncommon SNP5, described below as variation SNP5 at position 12974 is set forth in SEQ ID NO: 3 and corresponds to haplotype APOA5*3.

Another aspect of the invention is that stratification of populations based on APOA5 markers may identify a subset of individuals that respond differently to current and future drug therapies. These studies would contribute in understanding which of these drug therapies or combinations of drug therapies are the most beneficial to lower triglyceride levels in individuals having haplotypes APOA5*1, APOA5*2 or APOA5*3.

The SNPs disclosed herein can also be studied for association with other diseases including, but not limited to, diabetes, obesity, metabolic syndrome, or other generic disorders. The inter-relatedness of these conditions is well established in the literature. APOA5-increased expression or other means for protein delivery may prove to be successful to treat numerous symptoms of these diseases.

This invention also provides the means of combination therapy which uses high levels of APOAV expression or protein regardless of genotype or haplotype to treat any condition of high triglycerides. This strategy could also be combined with stratification-based studies. A further aspect of the invention is gene therapy to deliver active drugs to liver cells to over-express APOAV and thereby decrease triglycerides. Delivery of APOAV therapies can be by such methods as but not limited to, injection of active APOAV, delivery by pill form, and inhalation by spray to deliver APOAV to lungs and the blood to reduce triglycerides.

The inventions also encompasses drug screening and design of therapeutic agents to be used in methods for increasing APOAV expression, and thereby lowering triglycerides, based on the APOAV polynucleotides and polypeptides described herein is also an important aspect of the invention, especially in the identification of genes, regulatory elements, ligands, drugs and other therapeutic agents to be used to modulate and regulate APOAV expression. Such therapeutic agents include current drug therapies for high triglyceride levels such as fibrates or other drug agents which are known to reduce triglycerides.

BRIEF DESCRIPTION OF THE DRAWINGS

FIG. 5. Table of genotyping data from 501 individuals (A); pair-wise measures of linkage disequilibrium (B); and SNP3 genotyping data from a different set of individuals stratified by triglyceride levels (C).

DETAILED DESCRIPTION OF THE PREFERRED EMBODIMENT

Definitions

Figure 1:
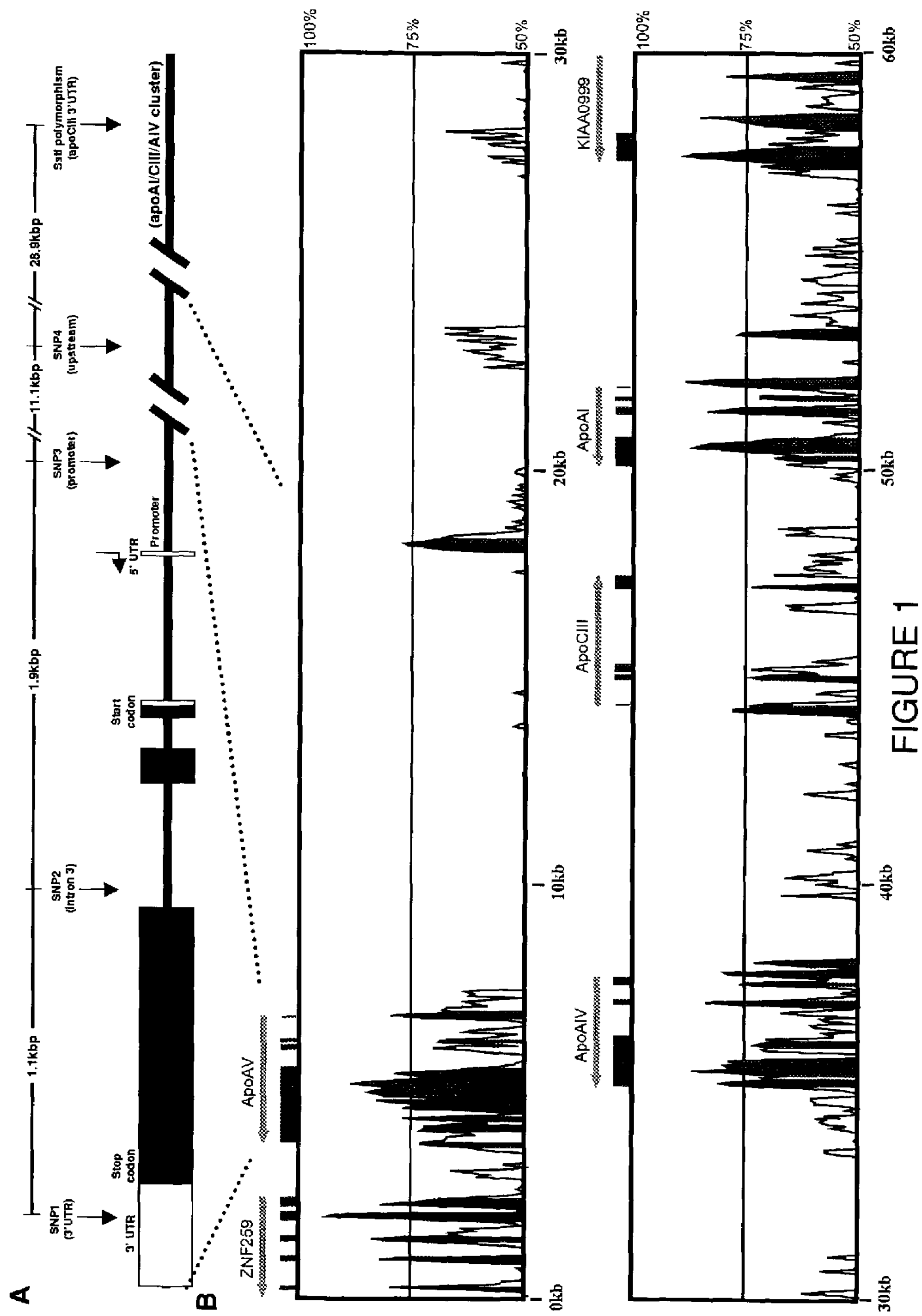
FIG. 1. A diagram showing the genomic organization of the human APOAI/CIII/AIV cluster (1a) and VISTA plot showing similarities between the mouse and human sequences in this region.

The term "triglycerides" is used in its ordinary medical sense. However, the tests of the present invention for disposition towards elevated triglyceride levels may also include elevated triacyglycerol, cholesterol, and other related lipid levels, very low density lipoprotein (VLDL) levels, or levels of other closely related apolipoproteins or lipoprotein particles such as chylomicrons, intermediate density lipoprotein (IDL), or low density lipoprotein (LDL) or high density lipoprotein (HDL) levels.

"Single nucleotide polymorphisms" (SNPs), which are defined in relation to a population, are variations in DNA at a single base that are found in at least 1% of the population. The terms "biallelic marker," "marker," "polymorphism" and "allele" are also used to denote variations at a single base and are used interchangeably.

The term, "genotype," is used herein to mean a specifi allele or alleles an individual carries at a given locus. It can also be used to describe a set of alleles for multiple loci.

A "haplotype" is a set of alleles for closely spaced polymorphisms along a chromosome that tend to be inherited together. Alternatively a haplotype can be thought of as a combination of alleles of closely linked loci that are found in a single chromosomal interval and tend to be inherited together. An individual SNP allele can be used to define a given haplotype.

The term, "phenotype," is used herein to mean the form taken by some character (or group of characters) in a specific individual. It can also mean the detectable outward manifestations of a specific genotype.

The term, "proband" is used to mean an affected individual in a family.

The term, "allele" is used herein to mean one of the different forms of a gene that can exist at a single locus. An allele is also used to describe a given version of a polymorphism.

The term, "allele frequency" is used to mean a measure of the commonness of an allele in a population; the proportion of all alleles of that gene or polymorphism in the population that are of this specific type.

The term, "Hardy-Weinberg" is used to refer to calculating the Hardy-Weinberg equilibrium for genotypes, whereby the stable frequency distribution of genotypes AA, Aa, and aa, in the proportions $p^2$, $2pq$ and $q^2$, respectively (where p and q are the frequencies of the alleles A and a), that is a consequence of random mating in the absence of mutation, migration, natural selection or random drift.

The term, "P-value" is used herein to mean the probability that the results were not significant. For example, a p-value of 0.05 means that there are 5 chances in 100 that the results are not significant.

The term, "SEM" is used to mean the standard of the mean.

The term "linkage disequilibrium" is used herein to refer to the relationship that is said to exist between a allele found at a single polymorphic site and alleles found at nearby polymorphisms if the presence of one allele is strongly predictive of the alleles present at the nearby polymorphic sites. Thus, the existence of linkage disequilibrium (LD) enables an allele of one polymorphic marker to be used as a surrogate for a specific allele of another.

"Substantial homology or similarity" means that a nucleic acid or fragment thereof is "substantially homologous" (or "substantially similar") to another if, when optimally aligned (with appropriate nucleotide insertions or deletions) with the other nucleic acid (or its complementary strand), using BLASTN there is nucleotide sequence identity in at least about 60% of the nucleotide bases, usually at least about 70%, more usually at least about 80%, preferably at least about 90%, and more preferably at least about 95-98% of the nucleotide bases. To determine homology between two different nucleic acids, the percent homology is to be determined using the BLASTN program "BLAST 2 sequences". This program is available for public use from the National Center for Biotechnology Information (NCBI) over the Internet (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

The terms "substantial homology" or "substantial identity", when referring to polypeptides, indicate that the polypeptide or protein in question exhibits at least about 30% identity using BLASTP with an entire naturally-occurring protein or a portion thereof, usually at least about 70% identity over the common lengths, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The term "polynucleotide" refers to a chain of nucleotides without regard to length of the chain.

The term "polypeptide" refers to a polymer of amino acids without regard to the length of the polymer; thus, peptides, oligopeptides, and proteins are included in this term.

A. Sequences of Apolipoprotein A-V

Despite the previous availability of sequence in the human apoAI/CIII/AIV genomic interval, the gene APOAV was characterized by human/mouse sequence comparison, using the power of comparative sequence analysis to prioritize potential functional regions of the genome. APOAV represents a fourth member of the clinically important apolipoprotein gene cluster on human 11q23. The human and mouse data, both when taken independently and combined, indicate an important role for APOAV in plasma triglyceride homeostasis. While previous data have associated the apoCIII locus with extremely high plasma triglyceride levels in humans, the results of the present studies suggest the possible use of APOAV polymorphisms as prognostic indicators for hyper-triglyceridemia susceptibility and the focus on APOAV modulation as a potential strategy to reduce this known cardiovascular disease risk factor.

FIG. 1 shows human and mouse comparative sequence analysis of the apoAI/CIII/AIV gene cluster. (A) A schematic of the genomic organization of human APOAV and the relative SNP positions (arrows). APOAV exons are shown with solid boxes and the distance between each SNP is indicated above the line. The predicted transcription start site is depicted by a bent arrow and the relative position of the promoter, and start and stop codons are shown. (B) In each panel 30 kbp of contiguous human sequence is illustrated horizontally. Above each panel arrows correspond to known genes and their orientation with each exon depicted by a box (gene names are indicated above each arrow). The VISTA (VISualization Tools for Alignment—www-gsd.lbl.gov/vista) plot displays the level of homology between human and the orthologous mouse sequence. Human sequence is represented on the x-axis and the percent similarity with the mouse sequence is plotted on the y-axis (ranging from 50-100% identity).

A preferred embodiment involves a human apolipoprotein gene, APOAV, located near a previously described apolipoprotein AI/CIII/AIV gene cluster (a region repeatedly implicated in various cardiovascular diseases). Electronic homology searches with human apoAI, apoCIII, and apoAIV mRNA sequences using the BLAST algorithm (S. F. Altschul, W. Gish, W. Miller, E. W. Myers, D. J. Lipman, *J Mol Biol* 215, 403-10 (1990)) identified a genomic bacterial artificial chromosome (BAC) clone containing the complete apoAI/CIII/AIV gene cluster (GenBank Accession No. AC007707).

The predicted 368-amino acid sequence shows significant homology to various known apolipoproteins, with the strongest similarity to mouse apoAIV (24% identity and 49% similarity). Examination of the orthologous human genomic sequence indicates a similar genomic structure to the mouse region and predicts an open reading frame encoding a 366-amino acid protein with high sequence homology to mouse apoAV (71% identity and 78% similarity), as well as human apoAIV (27% identity, 48% similarity). Protein structure analyses predicts several amphipathic helical domains and an N-terminal signal peptide in both human and mouse APOAV, which are characteristic features of lipid-binding apolipoproteins.

Transcripts approximately 1.3- and 1.9-kilobases (kb) in length were identified predominantly in liver tissue from both species by Northern blots analysis, where mRNA from several different human and mouse tissues was hybridized with APOAV cDNA probes from human and mouse, respectively. The full-length sequences of mouse cDNAs indicate the two transcripts in mice are likely the result of alternative poly-adenylation. The mouse apoA5 cDNA sequences are available under GenBank Accession Nos. AK004936 and AK004903.

(1) Brief Description of the Sequences (SEQ ID NOS: 1-48)

SEQ ID NO: 1 and 2 are cDNA sequences corresponding to the coding sequence of a "wild type" APOAV gene and are deposited in GenBank under Accession No. AF202889.1 and AF202890.1. Both cDNAs contain the normal wild type alleles. SEQ ID NO: 1 is a 1.3 kb transcript of the APOAV gene. SEQ ID NO: 2 is an alternatively spliced 1.8 kb transcript of the APOAV gene. The protein is encoded on the reverse complement. SNP5 is the only SNP in the group that changes an amino acid (Serine (S19)→Tryptophan (W19)) at position 19 of the putative protein. The substitution of G for A in SNP6 is in a critical nucleotide of the Kozak consensus sequence (−3 bp).

SEQ ID NO: 3 is the human genomic sequence comprising the present wild type APOAV gene, certain of its regulatory elements, and the SNPs associated with the genomic sequence. The indicated SNPs are numbered as follows: SNP 4, 3, 6, 5, 2, 1 in the order in which they appear in the sequence. The following table indicates the base pair positions in SEQ ID NO: 3 where these polymorphisms are found. Profiles for each of these SNPs can be found in GenBank under the following Accession Numbers: 2266788 (SNP1), 2072560 (SNP2), 662799 (SNP3), 3199916 (SNP4), 3135506 (SNP5), 651821 (SNP6) and 3135507 (V153M).

TABLE 1

SNPs shown in SEQ ID NO: 3

| SNP number | Position Number in SEQ ID NO: 3 | Original allele>Rare allele | Location in APOA5 |
|---|---|---|---|
| 4 | 567 | T>C | Between APOA5 and APOA4 |
| 3 | 11674 | T>C | Upstream |
| 6 | 12802 | A>G | 5'untranslated region |
| 5 | 12974 | C>G | causing an amino acid change in the APOA5 gene product (S19→W19) |
| 2 | 13555 | G>A | Intervening sequence 3 + 476 |
| 1 | 14695 | T>C | Coding sequence 1259 |

SEQ ID NO: 3 and 4 are annotated to show certain regulatory regions (CAAT box and TATAA box); the exons; and start and stop codons and the untranslated regions.

SEQ ID NO: 4 is the ideal wild type genomic sequence of human APOAV gene and contains the alleles in their major form, as do the corresponding GenBank sequences.

SEQ ID NO: 5 is the human DNA sequence used to create the transgenic mice expressing human APOAV. This sequence has not been deposited in GenBank.

SEQ ID NO: 6 is the working draft sequence of the mouse apoA5 that was deposited by the inventors in GenBank and recently released for publication to the public. It is the mouse genomic apoA5 region used to generate the homozygous knock-out mice. It consists of 75 unordered and unoriented contigs, wherein the gaps of unknown length are denoted as an 'n' in the sequence.

SEQ ID NO: 7 is the amino acid sequence of the protein product generated from SEQ ID NO: 4. A suitable wild-type APOAV protein is set forth in SEQ ID NO: 7. One mutant protein is encoded by DNA carrying the uncommon SNP5, is set forth in SEQ ID NO: 3.

SEQ ID NOs: 8-9 are the forward and reverse primers used to isolate mouse genomic DNA in Example 1 from the pooled mouse BAC library.

SEQ ID NOs: 10-11 are the forward and reverse primers used to genotype transgenic mouse for the human APOAV gene.

SEQ ID NOs: 12-15 are the PCR primers that were used to build the homology arms in the targeting construct to delete mouse apoA5 in knockout mice.

SEQ ID NOs: 16-17 were used to amplify the external 3' probe when creating the apoA5 knockout animals.

SEQ ID NOs: 18-19 and SEQ ID NOS: 37-38 are the primers used to genotype the apoA5 knockout animals. SEQ ID NOS:18-19 are the forward and reverse primers to genotype for the presence of the apoA5 gene;

SEQ ID NOs: 20-21 are the forward and reverse primers used to amplify and gentoype SNP3.

SEQ ID NOs: 22-23 are the degenerate primers used to genotype the transgenic animals for the presence of APOAV and to probe PCR amplified liver cDNA for human or mouse APOAV cDNAs.

SEQ ID NOs: 24-25 are the forward and reverse primers used to genotype SNP5. SEQ ID NOS: 26-27 are the reverse and forward primers used to genotype the V153M polymorphism.

SEQ ID NOs: 28-36 are the probes and INVADER sequences used to perform the INVADER assays to genotype SNPs 5, 6 and V153M.

SEQ ID NOs: 37-38 are the forward and reverse primers used to genotype the presence of the neomycin gene in preparing the apoA5 knockout mice.

SEQ ID NOs: 39-48 are primers used to genotype the six SNPs as shown in Table 3. SEQ ID NOs: 39-40 are the forward and reverse primers used to amplify or genotype SNP1. SEQ ID NOs: 41-42 are the forward and reverse primers used to amplify or genotype SNP2. SEQ ID NOs: 43-44 are the forward and reverse primers used to amplify or genotype SNP5. SEQ ID NOs: 45-46 are the forward and reverse primers used to amplify or genotype SNP3 and SNP6. SEQ ID NOs: 47-48 are the forward and reverse primers used to amplify or genotype SNP4.

(2) Applications for APOAV Sequences

In another embodiment, a polynucleotide fragment is also contemplated wherein the fragment comprises a contiguous span of at least 12 nucleotides of SEQ ID NO: 3, where said contiguous span encompasses one or more SNPs 1-3, 5 or 6 as described in SEQ ID NO: 3.

A further preferred embodiment consists of a purified, isolated, synthesized or recombinant nucleic acid that hybridizes with an SNP nucleotide-containing the nucleotide sequence of SEQ ID NOs: 3 or 5, or a complementary sequence or a variant that is substantially homologous.

B. APOAV DNA Constructs and Recombinant Vectors

The present embodiment encompasses a recombinant vector comprising a polynucleotide that is substantially homologous to any of the polynucleotides described herein, including regulatory sequences, coding sequences and polynucleotide constructs, as well as any APOAV primer or probe. In a first preferred embodiment, a recombinant vector comprises expression vectors comprising either a regulatory polynucleotide of APOAV or a coding nucleic acid of the present embodiment, or both. Within some embodiments, the expression vectors are employed in the in vivo expression of APOAV in non-human animals. In other embodiments, the expression vectors are used for constructing transgenic animals and gene therapy.

Depending on the host organism or cell wherein the APOAV gene will be expressed, one skilled in the art can adapt the recombinant vector to further comprise genetic elements, including but not limited to, an origin of replication in the desired host, suitable promoters and enhancers, any necessary ribosome binding sites, polyadenylation signal, splice donor and acceptor sites, transcriptional termination sequences, selectable markers and non-transcribed flanking sequences. Various types of gene delivery vectors can be used including, but definitely not limited to, plasmids, YACs (Yeast Artificial Chromosomes), BACs (Bacterial Artificial Chromosomes), bacterial vectors, bacteriophage vectors, viral vectors (for example, retroviruses, adenoviruses and viruses commonly used for gene therepy), non-viral synthetic vectors, and recombinant vectors, etc.

A second embodiment comprises a host cell that has been transformed or transfected with one of the APOAV polynucleotides described herein, in particular a polynucleotide comprising SEQ ID NO: 1, 2 or 5 or a fragment or variant thereof. Appropriate host cells can be prokaryotic host cells, such as *E. coli, Bacillus subtilis, Salmonella typhimurium*, and strains from species including but not limited to, *Pseudomonas, Streptomyces* and *Staphylococcus*. Alternatively eukaryotic host cells can be used, including but not limited to, HeLa cells, HepG2 and other mammalian host cells. A preferred embodiment is a mammalian host cell comprising the APOAV genomic region, wherein the APOAV gene is disrupted by homologous recombination with a knockout vector.

In order to study the physiological and phenotypic consequences of a lack of synthesis of the APOAV protein, both at the cellular level and at the organism level, the preferred embodiment also encompasses DNA constructs and recombinant vectors enabling conditional expression of a specific allele or haplotype of the APOAV genomic sequence as described in SEQ ID NO: 3, 5 or 6 or an APOAV cDNA (SEQ ID NO: 1, 2) in a transgenic non-human animal. The embodiment also encompasses DNA constructs to generate animals having multiple copies of the APOAV protein expressed and animals having no APOAV protein that is expressed ("knock-out animals").

The targeting construct can be built by various methods known in the art including but not limited to, PCR primers for integration by homologous recombination, using a repressor/marker promotor construct, Cre-LoxP system, and antisense constructs. The method preferred is using PCR products and primers to build the targeting construct. To build such a construct to make knockout non-human animals and cells, one would need the homology "arms" that flank each side of the sequence to be deleted or disrupted, and a selectable marker inserted between the arms to select for the marker function. The sequence to be deleted can be the whole APOAV gene as the inventors did in Example 3, single or multiple exons, intervening genomic sequences, short peptide sequences and even single base pair deletions. After delivery of the construct into embryonic stem cells, selection for the marker permits gene deletion. Or for instance, APOAV gene function can be disrupted by insertion of the selectable marker, by inserting insertion of the marker in the promoter, splice sites, or the open reading frame.

To make transgenic non-human animals, designing the construct should include as much flanking sequence of APOAV as to include all the regulatory elements that may be found in the flanking genomic DNA. One needs to consider the neighboring genes and whether or not they should be over-expressed as well. See Thomas, K. R. and Capecchi, M. R., Site-directed mutagenesis by gene targeting in mouse embryo-derived stem cells. *Cell* 51:503, 1987.

Figure 2:
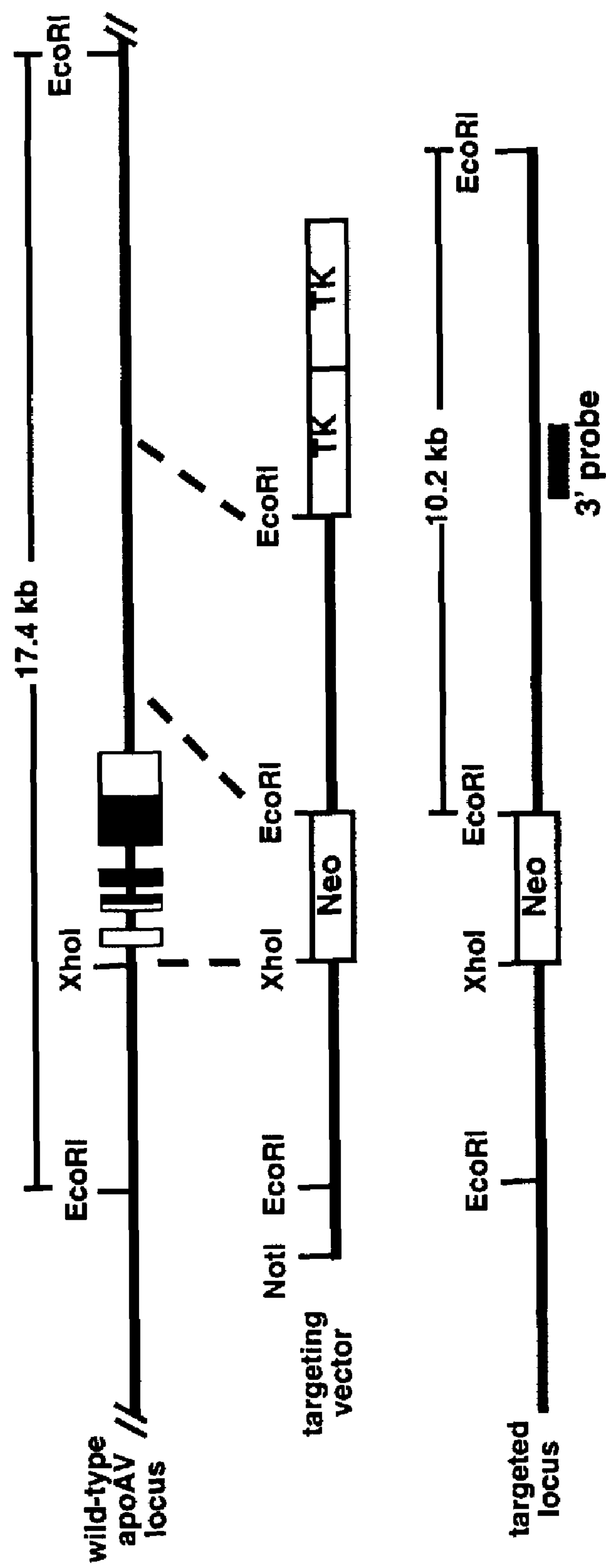
FIG. 2. A diagram of the targeting construct used to generate apoA5-deficient mice. Homology arms were designed to delete the coding exons of the gene (depicted by black boxes.

Thus in a specific embodiment, SEQ ID NO: 5, which is the 26 Kb XhoI isolated polynucleotide of the human APOAV region, can be used to create constructs that includes APOAV and APOAV flanking sequence but does not include neighboring APO genes. In a preferred embodiment, the targeting construct to delete mouse apoAV can be built using PCR products and primers made from SEQ ID NO: 7. For example, apoA5 knockout mice were generated by deleting the three exons predicted to encode apoA5 (FIG. 1A, FIG. 2).

In order to effect expression of the polynucleotides and polynucleotide constructs of the preferred embodiment, these constructs must be delivered to the host cell, where once it has been delivered to the cell, it may be stably integrated into the genome of the host cell and effectuate cellular expression. This delivery can be accomplished in vitro, for laboratory procedures for transforming cell lines, or in vivo or ex vivo, for the creation of therapies or treatments of diseases. Mechanisms of delivery include, but are not limited to, viral infection (where the expression construct is encapsulated in an infection viral particle), other non-viral methods known in the art such as, calcium phosphate precipitation, DEAE-dextran, electroporation, direct micro-injection, DNA-loaded liposomes, and receptor-mediated transfection of the expression construct. In a preferred embodiment, the delivery of the construct is by micro-injection into the appropriate host cell or by intravenous injection in the organism.

C. Correlation of APOAV Sequence Variants with Human Plasma Triglyceride Levels

Single nucleotide polymorphisms (SNPs) were first identified across and surrounding the human APOAV locus to serve as genetic markers for association. Six markers with relatively high minor allele frequencies (>8%) were obtained. Five of the SNPs were separated by three kbp within APOAV (SNP1-3, 5 and 6), while the fourth SNP (SNP4) was located ~11 kbp upstream of the gene (FIG. 1A). These markers were scored in approximately 500 random unrelated normo-lipidemic Caucasian individuals who had been phenotyped for numerous lipid parameters before and after consumption of high- and low-fat diets.

Figure 4:
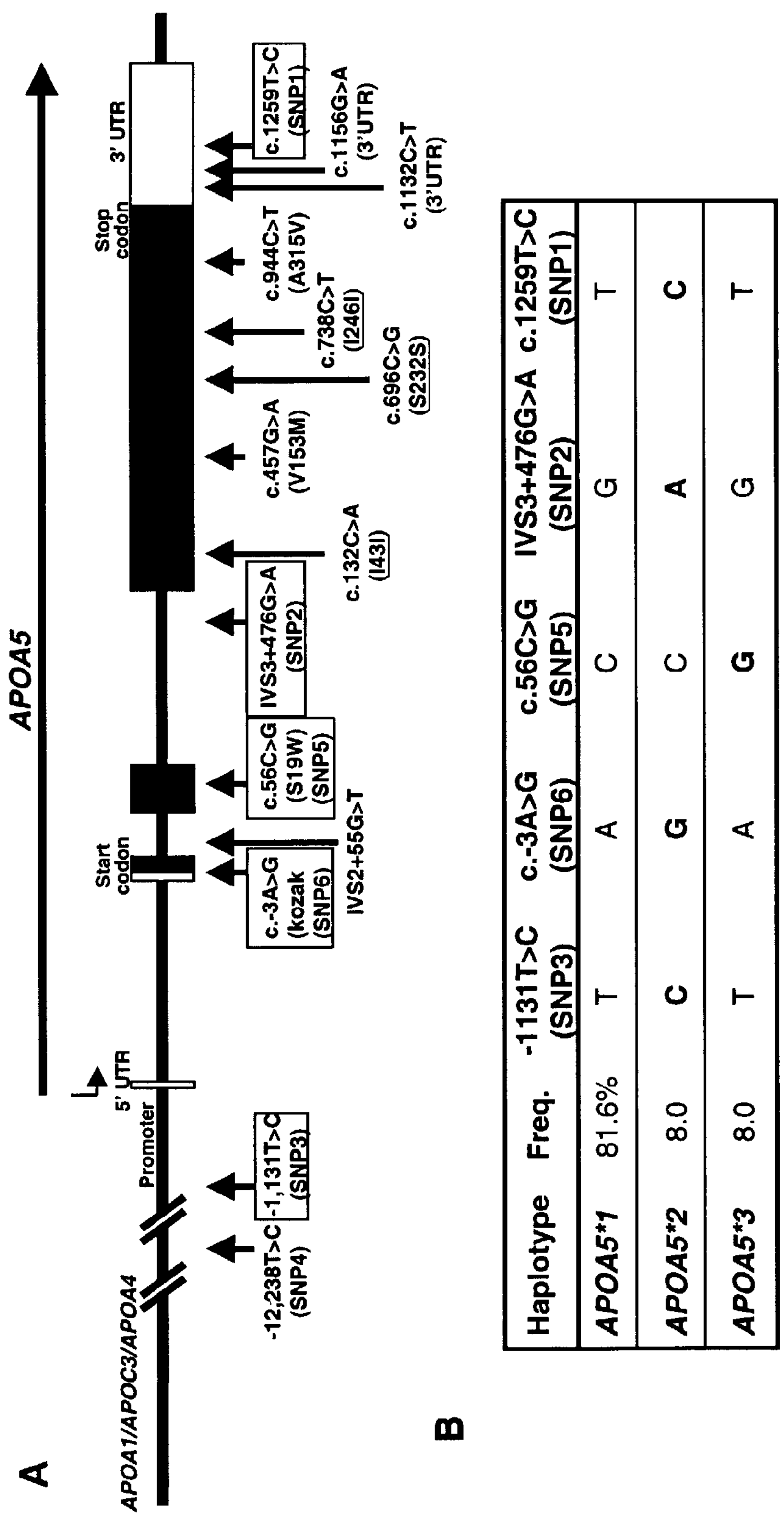
FIG. 4. (A) New SNP map of the APOAV genomic locus. Exons are depicted by rectangles with coding sequence filled in with black and untranslated regions with white. The gene is transcribed in the right to left direction. (B) Minor allele frequencies are approximately 10% in Caucasians for SNPs 1, 2, 3, 5, 6, and ~40% for SNP4. Minor alleles for SNPs 1, 2, 3, and 6 form a common haplotype (~10%). SNP5 is part of a second independent haplotype (~10%).

Significant associations were found between both plasma triglyceride levels and VLDL mass and the five neighboring SNPs 1-3, 5 and 6 within APOAV but not with the distant upstream SNP4 (FIGS. 1A, 5A). Specifically, the minor allele of each of these SNPs (SNPs1-3, 5 and 6) was associated with higher triglyceride levels independent of diet. Independent analysis of each of SNPs 1-3, 5 and 6 revealed plasma triglyceride levels were 20-30% higher in individuals having one minor allele compared to individuals homozygous for the major allele (FIG. 4A). Two independent groups of individuals displayed increased triglycerides. First is a group of individuals with minor alleles at SNPs1-3, 6, while the second group of individuals contained the minor allele at SNP5.

Since the Caucasian population has two different apparent causative chromosomes for increased triglycerides and the allele frequency is ~8% for both haplotypes, this observation effects a large number of individuals in the general population. (A minor allele frequency of 8% means there is an 8% probability for the rare haplotypes to occur on each chromosome.) Based on Hardy-Weinberg, the expected genotype distributions for such SNPs in the population can be calculated yielding 84.6% homozygous for the major allele, 14.7% heterozygous, D. Transgenic Non-human Animals to Assess Function of APOAV The preferred embodiment also provides non-human animals to assess APOAV function. These non-human animals are preferably mammalian, even more preferably from the group consisting of mouse, rat, dog, chimpanzee, orangutan, baboon and macaque. These non-human animals are most preferably of the species *Mus musculus*, over-expressing human APOAV, as well as mice lacking apoA5 through standard mouse transgenic and gene knockout technologies (FIG. 2) (See K. A. Frazer, G. Narla, J. L. Zhang, E. M. Rubin, Nat Genet 9, 424-31 (1995) and C. Paszty, et al., *Nat Genet* 11, 33-39 (1995)). apoA5 knock-out animals and transgenic animals exhibit dramatic, but opposite effects on plasma triglyceride levels. apoA5 knockout animals exhibit a hyper-triglyceride phenotype, while the APOAV transgenic animals which over-express APOAV protein, exhibit a hypo-triglyceride phenotype.

APOAV transgenic animals, depending on the genetic background and the amount of overexpression, should exhibit at least two fold lower levels of plasma triglyceride. Multiple copies of the human APOAV gene result in an observed over-expression of the APOAV gene which can be determined by Northern blot analysis and result in reduced plasma triglyceride levels.

In addition to decreased triglyceride levels APOAV transgenic non-human animals should also have corresponding decreases in VLDL levels. This finding is consistent with the general knowledge that the majority of plasma triglyceride is carried on VLDL particles. VLDL levels can be characterized by fast protein liquid chromatography of lipoprotein particles from the animals or by other standard methods of lipoprotein determination such as ultra-centrifugation.

An alternate embodiment also provides homozygous knockouts that are lacking apoA5 protein or lacking functional apoA5 protein. Transformed or transgenic cells, cell lines or non-human animals are obtained by homologous recombination of at least one apoA5 exon in embryonic stem cells, transfer of these stem cells to embryos, selection of the chimeras affected at the level of the reproductive lines, and growth of the said chimeras. Following successful germ-line transmission, heterozygous animals are then intercrossed.

The levels of very low-density lipoprotein (VLDL) particles increase in homozygous knockout animals and decrease in transgenic animals as compared with controls. Heterozygous knockout animals should exhibit VLDL levels intermediate between the homozygous knockout and control mouse. The peak VLDL elution volumes should remain similar in all animals, supporting comparable VLDL particle size, and that levels of other lipoproteins are not significantly altered.

To generate non-human animals which over-express APOAV, SEQ ID NO: 5, which is a 26.6 kbp XhoI human genomic DNA fragment predicted to contain only human APOAV, can be integrated into the genome of non-human embryos, thereby resulting in the expression of several copies of the human APOAV gene by the non-human animals. In addition, transgenic animals such as rats and rabbits, or transgenic continuous cell lines can be made. Furthermore, transgenic animals can be made using cDNA encoding human APOAV, both in its wild type and variants as described herein.

Transgenic non-human animals over-expressing the APOAV gene could be obtained by transfection of multiple copies of said APOAV gene under the control of a strong promoter of an ubiquitous nature, or promoters selective for a type of tissue, preferably liver tissue.

This embodiment also provides non-human animals for further animal studies by pharmaceutical companies to study APOAV. Animal studies that explore the regulation and expression of APOAV, its interaction with other apolipoproteins or other plasma, membrane or cellular proteins, production of antibodies for mutant and wild-type apoA5, and further in vivo study of apoA5. For example, mice lacking wild-type apoA5 may be exposed to various test substances to determine the triglyceride lowering effect of the test substance on individuals having a non-wild-type apoA5 gene. If a certain drug is no longer able to work, it would indicate that apoa5 is needed for the given drug to exert its affect.

Preferably, said transformed cells or mammals of the preferred embodiment will be used as a model allowing, in particular, the selection of products which make it possible to combat the pathologies induced by high levels of triglycerides.

In another embodiment, the non-human animals can be used to reveal the mechanism behind how apoA5 exerts its affect. Studies using the non-human animals can enable the elucidation of different mechanisms of triglyceride regulation, including but not limited to, clearance from the liver, secretion, production, catabolism and lipolysis of triglycerides. For example, to study clearance, one can identify a liver receptor or an alteration in the rate of VLDL clearance from the liver that apoA5 works through, which would prove to be a significant future target for drugs. The non-human animals may be used to show how apoA5 works in the liver to move triglycerides from the liver to the plasma, or if it is involved in increased lipolysis in the peripheries, or whether apoA5 has an effect on inflammation that leads to altered triglyceride levels.

E. Effects on Other Apolipoproteins in Transgenic Non-Human Animals

The observed changes in plasma triglyceride levels in apoA5 knockout and transgenic animals are directly opposite those previously reported in apoC3 knockout and transgenic mice (Y. Ito et al., *Science* 249, 790-3 (1990); N. Maeda, et al., *J Biol Chem* 269, 23610-6 (1994)). The apoA5 knockouts displayed an approximately 400% increase in plasma triglycerides compared to the 30% decrease noted in ApoC3 knockouts, while apoA5 transgenics showed decreased triglyceride levels compared to the increase reported in apoC3 transgenics.

The transgenic mice over-expressing human APOAV showed a decrease in apoCIII levels thereby suggesting a mechanism behind APOAV's effect on plasma triglyceride levels. Furthermore, mice lacking APOAV have increased apoCIII levels. Whether this direct association is coincidence or causal of the triglyceride phenotype remains to be determined.

Altered apoA5 expression affects apoC3 protein but not transcript levels in both apoA5 transgenic and knockout animals; apoC3 levels were increased 90% in apoA5 knockouts and decreased ~40% in apoA5 transgenics. These data suggest that apoC3 may exert its effect on triglyceride levels by altering apoA5 levels.

Because alterations in apoA5 expression lead to changes in apoC3 protein levels, the effect on triglycerides may be mediated through apoC3. The fact that apoA5 transgenic mice have two-fold lower triglycerides than the previously described apoC3 knockout mice indicate that changes in apoC3 alone can not explain the entire effect of apoA5. In addition to APOC3, the over-expression of several human apolipoprotein transgenes has been shown to increase triglyceride levels in mice, while only the APOAV transgene leads to decreased triglycerides suggesting a novel mechanism behind this effect.

While not being bound to one theory, the inventors theorize that the APOAV gene product (protein) interacts with other proteins in the apo family (e.g. APOC3) in such a way as to affect their levels, and thereby triglyceride levels. The inventors describe a direct correlation between APOAV and APOC3. Thus, this embodiment also provides non-human animals to explore the regulation and expression of apoA5 and apoC3, the interaction between these two apolipoproteins and other apolipoproteins, and further in vivo study of APOC3. APOC3 is known to inhibit triglyceride lipolysis on VLDL, thus contributing to higher levels of plasma triglyceride and VLDL. The transgenic mice over-expressing human APOAV showed a decrease in APOC3 levels thereby suggesting a mechanism behind APOAV's effect on plasma triglyceride levels. Furthermore, mice lacking APOAV have increased APOC3 levels.

Therefore, the preferred embodiment includes a method for determining predisposition towards elevated triglyceride levels of an individual, comprising determining the level of APOAV gene expression, wherein elevated APOAV gene expression is associated with decreased elevated triglycerides and lowered APOAV gene expression is associated with increased elevated triglycerides. The method further comprising determining the level of APOC3 gene expression, wherein lowered APOC3 gene expression is associated with decreased elevated triglycerides and elevated APOC3 gene expression is associated with increased elevated triglycerides.

F. APOAV Haplotypes and Frequencies

The population frequency for each haplotype is the percentage of individuals who have a given haplotype. Statistically, approximately 50-75% of the population is homozygous for the common haplotype (*1/*1) that is correlated with lower triglyceride levels, while approximately 25-50% of the population contains at least one copy of the minor haplotypes (APOA5*2 and/or APOA5*3) which is correlated with increased triglyceride levels. In addition, approximately 0.6-1.5% of the population is homozygous with both chromosomes containing the rare haplotypes (*2/*2, *3/*3 or *2/*3), which is correlated with the highest triglyceride levels.

Association studies that were conducted indicate the existence of three haplotypes in APOAV present in the human population, which are associated with plasma triglyceride levels. Preliminary studies in this population found no significant association of triglyceride levels with the Sst1 polymorphism in APOC3 (located ~40 kbp upstream of APOAV) (FIG. 1A) which has been previously associated with severe hyper-triglyceridemia (M. R. Hayden, et al., *Am J Hum Genet* 40, 421-30 (1987); M. Dammerman, L. A. Sandkuijl, J. L. Halaas, W. Chung, J. L. Breslow, *Proc Natl Acad Sci USA* 90, 4562-6 (1993). This finding suggests the APOC3 Sst1 polymorphism is not a marker for the metabolic effect defined by the APOAV haplotypes.

The three haplotypes (APOA5*1, APOA5*2, APOA5*3) are composed of biallelic markers at the following positions on APOAV: −1131T>C (SNP3), c.−3A>G (SNP6), c.56C>G (SNP5), IVS3+476G>A (SNP2) and c.1259>C (SNP1). Table 2 shows the three haplotypes and the relative frequencies that each appears in the Caucasian general population.

TABLE 2

| Haplotype | Frequency | −1131T>C (SNP3) | c.−3A>G (SNP6) | c.56C>G (SNP5) | IVS3 + 476G>A (SNP2) | c.1259T>C (SNP1) |
|---|---|---|---|---|---|---|
| APOA5*1 | 81.6% | T | A | C | G | T |
| APOA5*2 | 8.0% | C | G | C | A | C |
| APOA5*3 | 8.0% | T | A | G | G | T |

The frequency listed for each haplotype is the relative frequency per chromosome, meaning that statistically, approximately 75% of the Caucasian population is homozygous for the common haplotype (*1/*1) that is correlated to low triglyceride levels, approximately 25% of the Caucasian population is heterozygous with one chromosome having the common haplotype and the other containing a rare haplotype (APOA5*2 or APOA5*3) which is correlated to raised triglyceride levels and approximately 0.6% or less than 1 percent of the population is homozygous with both chromosomes containing the rare haplotypes (*2/*2, *3/*3 or *2/*3), which correlates to the highest triglyceride levels. In addition to APOAV's strong association with triglyceride levels in Caucasians, a strong effect is also seen African-Americans and Hispanics where the minor allele frequencies are higher. Thus, a larger percent of African-Americans and Hispanics display increased triglycerides due to the genetic effect of APOAV. Specifically, APOA5*2 and/or APOA5*3 is present in 36% of African Americans and 51% of Hispanics and results in an ~25% increase in triglycerides compared to APOA5*1 homozygotes.

Thus, the preferred embodiment includes a method of determining an individual's total risk of lipid-related diseases or disorders by identifying an individual's APOAV haplotype on each chromosome. One needs only genotype individuals at two different polymorphic loci, wherein one of those loci is SNP5, to determine which haplotypes the individual possesses, and whether the individual is heterozygous or homozygous for the rare or normal alleles (defining APOA5*3). The haplotypes can be easily determined by detecting the genotype of individuals at SNPs 1-3 or 6 (APOA5*2) and at SNP5 (APOA5*3) for both copies of chromosome 11. Based on the knowledge of what haplotypes the individual possesses, the amount of risk for lipid-related diseases or disorders can then be determined or predicted. For example, if the individual is genotyped and found to have a T at SNP3 on one chromosome and a C at SNP3 on the other chromosome, then it can be determined that the individual is heterozygous, having APOA5*2 haplotype on one of the chromosomes. Then genotyping the individual at SNP5 will distinguish whether the other chromosome is a rare haplotype (APOA5*3) or the normal haplotype (APOA5*1). Methods of detecting SNPs and genotyping are discussed in the Diagnostic Applications section.

G. Diagnostic Applications

The present embodiment enables genetic testing for APOAV and its correlation to increased triglyceride levels in people having polymorphisms deviating from the normal or "wild type" phenotype. Further, a combination test with APOC3 is suggested. Genetic testing may be carried out on a patient's DNA or RNA or protein, provided that antibodies capable of distinguishing mutant from wild type APOAV protein are available.

1. Antibodies to APOAV and its Variants

Antibodies including both polyclonal and monoclonal antibodies, and drugs that modulate the production of activity of APOAV possess certain diagnostic applications and may, for example, be utilized for the purpose of detecting the identity of the haplotype of individuals. For example, wild type APOAV and its variants may be used to produce both polyclonal and monoclonal antibodies in a variety of cellular media, by known techniques such as the hybridoma technique utilizing, for example, fused mouse spleen lymphocytes and myeloma cells. Likewise small molecules that mimic or agonize the activity(ies) of APOAV may be discovered or synthesized, and may be used in diagnostic and/or therapeutic protocols.

The general methodology for making monoclonal antibodies by hybridomas is well known. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against APOAV peptides can be screened for various properties; i.e., isotype, epitope, affinity, etc. Of particular interest are monoclonal antibodies that specifically bind and identify the alleles of APOAV, and can distinguish between the rare and the normal alleles of APOAV. In one preferred embodiment, a monoclonal antibody can be generated that specifically binds to the W19 position of the APOAV protein, which results from the rare SNP5 allele. Such monoclonals can be readily identified in, for example, gel-shift assays. High affinity antibodies are also useful when immunoaffinity purification of native or recombinant APOAV is possible.

A preferred method of generating these APOAV allele-specific antibodies is by first synthesizing peptide fragments. These peptide fragments should cover at least SNP5 and the adjacent amino acid sequence. Subsequent antibodies should be screened for their ability to distinguish the two protein variants. Since synthesized peptides are not always immunogenic on their own, the APOAV peptides should be conjugated to a carrier protein before use. Appropriate carrier proteins include but are not limited to Keyhole limpet hemacyanin (KLH). The conjugated peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal APOAV allele-specific antibodies can be purified by passing the harvested antibodies through an affinity column. Monoclonal antibodies are preferred over polyclonal antibodies and can be generated according to standard methods known in the art of creating an immortal cell line which expresses the antibody.

Additionally, spleen cells can be harvested from the immunized animal (typically rat or mouse) and fused to myeloma cells to produce a bank of monoclonal antibody-secreting hybridoma cells. The bank of hybridomas can be screened for clones that secrete immunoglobulins that bind the protein of interest specifically, i.e., with an affinity of at least $1\times10^7$ $M^{-1}$. Animals other than mice and rats may be used to raise antibodies; for example, goats, rabbits, sheep, and chickens may also be employed to raise antibodies reactive with an APOAV protein. Transgenic mice having the capacity to produce substantially human antibodies also may be immunized and used for a source of antiserum and/or for making monoclonal antibody secreting hybridomas.

Bacteriophage antibody display libraries may also be screened for phage able to bind peptides and proteins specifically. Combinatorial libraries of antibodies have been generated in bacteriophage lambda expression systems and may be screened as bacteriophage plaques or as colonies of lysogens. For general methods to prepare antibodies, see Antibodies: A Laboratory Manual (1988), E. Harlow and D. Lane, Cold Spring Harbor Laboratory, Cold Spring Harbor, N.Y., incorporated herein by reference.

These antibodies can in turn be used to isolate APOAV proteins from normal or recombinant cells and so can be used to purify the proteins as well as other proteins associated therewith. Such antibodies are useful in the detection of specific alleles of APOAV proteins in samples and in the detection of cells comprising APOAV proteins in complex mixtures of cells. Such detection methods have application in screening, diagnosing, and monitoring lipid metabolism related diseases and other conditions, such as high levels of triglycerides.

2. Genotyping and Haplotyping

Any method known in the art can be used to identify the nucleotide present at one of the disclosed APOA5 polymorphic sites. Since the SNPs and haplotypes to be detected have been identified and specified in the present invention, detection will prove simple for one of ordinary skill in the art. Any number of techniques to detect the haplotype of an individual by genotyping the individual at certain polymorphic sites can be used, including, but not limited to, the following.

The nucleotide can be determined by sequencing analysis after DNA samples are subjected to PCR amplification. Preferably, the amplified DNA is subjected to automated dideoxy terminator sequencing reactions using a dye-primer cycle sequencing protocol. The sequencing reactions are then sequenced using any number of commercially available sequencing machines such as the ABI 377 or 3700 Sequence Analyzer (Applied Biosystems, Foster City, Calif.).

Techniques and methods of synthesizing and amplifying polynucleotides by ligation of multiple oligomers (LMO) onto a template-bound primer are also described by Akhavan-Tafti in U.S. Pat. Nos. 5,998,175; 6,001,614; 6,013,456; and 6,020,138, which are hereby incorporated by reference in their entirety. Short polynucleotides, 5 to 10 bases long, can be supplied as a library of oligonucleotides and are simultaneously ligated, using a suitable ligase enzyme, to a template-bound primer in a contiguous manner to produce a complementary strand of template polynucleotide. If the sequence to be synthesized is known, a set containing the minimum number of oligomers can be used and are then ligated by DNA Ligase in the correct order starting from the primer, uni- or bi-directionally, to produce the complementary strand of a single-stranded template sequence.

A preferred method is to use sequence detection/amplification assays such as the INVADER assays which are commercially available from Third Wave Technologies (Madison, Wis.) to genotype samples. Such systems rely on an enzyme-substrate reaction to amplify signal generated when a perfect match with an (rare) allele of APOAV is detected. See Dahlberg, J. et al., U.S. Pat. Nos. 5,846,717 and 5,888,780, which are hereby incorporated by reference in their entirety.

A third preferred method is using methods that have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis) See U.S. Pat. Nos. 5,547,835; 6,221,601; 6,194,144 which are hereby incorporated by reference in their entirety. Other methods of SNP analysis are performed by companies such as Sequenom (San Diego, Calif.), which can genotype many samples very quickly and with great accuracy, non-sequencing methods such as MALDI-TOF, miniaturized chip-based array formats and mass spectrometry.

Other genotyping methods suited for detection of SNPs include, but are in no way limited to, LCR (ligase chain reaction), Gap LCR (GLCR), using allele-specific primers, mismatch detection assays, microsequencing assays, and hybridization assay methods.

3. Oligonucleotide Primers and Probes

Various methods for screening for genetic APOAV abnormalities in individuals can be employed. Polynucleotides according to SEQ ID NOs: 1-3 and 5-7 can also be used in gene marker assays, probes, primers for uses including, but not limited to, PCR, sequencing, hybridization assays and probes. Variations that are at least 95% or more homologous to the sequences of APOAV polynucleotides (e.g. SEQ ID NOs: 1-3, 5and 6) may also be used for comparison studies and in any of the above listed types of assays. In another embodiment, polypeptides that are at least 95% of more homologous to APOAV protein (e.g. SEQ ID NO: 4) or to the protein generated from polynucleotide sequences selected from the group consisting of SEQ ID NO: 1-3, 5-6 may be used for lipid studies.

The preferred embodiment also encompasses APOAV oligonucleotide primers made from SEQ ID NO: 3 and 4 and capable of amplifying the DNA sequence of and surrounding each of SNPs 1-6. Basic primer design considerations such as annealing/melting temperature, length, repetitive DNA, proximity to the SNP, and specificity will be appreciated and addressed by one skilled in the art. Many programs that enable one to pick and design custom primers address these considerations, such as PRIMER3 (S. Rozen and H. J. Skaletsky).

Suitable primers such as those disclosed in Table 3, SEQ ID NOs: 8-36 and primers made from sequence up to about 500 base pairs away from the SNP can be used for amplification, may be used to assay SNP5 (position 12974). and/or sequencing these SNPs. For example, SEQ ID NO: 24 (AV1-F 5' TGCTCACCTGGGCTCTGGCTCTTC) and SEQ ID NO: 25 (AV1-R 5' CCAGAAGCCTTTCCGTGC-CTGGGCGGC) which lie in SEQ ID NO: 3 and 4 at positions 12824-12847 and 12976-13002 respectively Furthermore, depending upon the genotyping strategy used, other probes and primers can be designed from SEQ ID NOs: 1-6 for use in such assays as PCR-RFLP and PCR INVADER assays (Third Wave Technologies, Madison, Wis.).

The following table shows primers that can be used to amplify genomic DNA surrounding SNPs 1-6 by such methods as PCR. The examples of forward and reverse primers that can also be used to amplify sequence containing each of the described SNPs 1-6. The resulting amplified product can be genotyped by methods including, but not limited to, sequencing, mass spectrometry, RFLP, and INVADER assays. Primers such as those disclosed in Table 3, SEQ ID NOS: 8-36 and primers made from sequence up to about 500 base pairs away from the SNP can be used for amplification and/or sequencing these SNPs. For example, SEQ ID NO: 24 (AV1-F 5' TGCTCACCTGGGCTCTGGCTCTTC) and SEQ ID NO: 25 (AV1-R 5' CCAGAAGCCTTTCCGTGCCTGGGCGGC

TABLE 3

| ApoA5 SNP | SEQ ID NO | Primer Sequence | | Position on ApoA5 gene | Length of amplified sequence |
|---|---|---|---|---|---|
| ApoA5-SNP1 | 39 | ATGACCTGTGGGAAGACATCACT | Forward | 14470-14492 | 455 bp |
| | 40 | AGCCAGAAGTGACTAGAGCCAAA | Reverse | 14902-14924 | |
| ApoA5-SNP2 | 41 | AGTCCCCAGAATCAAAGGATGAT | Forward | 13341-13363 | 497 bp |
| | 42 | ATCGTGTAGGGCTTCAGTTGCT | Reverse | 13816-13837 | |
| ApoA5-SNP5 | 43 | CCTGTCTTCTCAGAGCAGGTAATG | Forward | 12784-12807 | 285 bp |
| | 44 | AGCCATCTTCTGCTGATGGATCT | Reverse | 13046-13068 | |
| ApoA5-SNP3 + SNP6 | 45 | AAGACACCCTAGCCTCCTTGACT | Forward | 12602-12624 | 566 bp |
| | 46 | ACAGAGGTTGAGGCAGCAGAG | Reverse | 13147-13167 | |
| ApoA5-SNP4 | 47 | GTAGTGAAAATCAGGGGCCTTCT | Forward | 484-506 | 158 bp |
| | 48 | ATGCATAAACCCAAAGGGAAAAT | Reverse | 619-641 | |

In one embodiment of the invention, fragments of various lengths of APOAV DNA may be placed onto solid supports for use in gene chips or other parallel formats for assay purposes. In general, these methods employ arrays of oligonucleotide probes that are complementary to targeted nucleic acid sequences, and allow for detection when the sample hybridizes to a probe on the array. In preferred embodiments, the nucleic acid sequences are APOAV fragments of about 15-30 nucleotides in length, specifically sequences containing APOAV SNPs 1-6. In further embodiments, the chip may comprise an array including at least one of the sequences selected from the group consisting of amplification primers listed in Tables 3 and 4. See D. J. Lockhart, et al., "Expression monitoring by hybridization to high-density oligonucleotide arrays," *Nature Biotechnology,* 14:1675-1680, December 1996, for useful methods and heuristics in designing oligonucleotide probes from APOAV fragments.

Chips of various formats from companies such as Agilent Technologies (Palo Alto, Calif.) and Affymetrix (Santa Clara, Calif.) can be produced on a customized basis by various methods. Alternatively, DNA microarray chips are fairly inexpensive to make and assemble. Individual samples to be tested are then contacted with the oligonucleotide probes and the genotype and/or haplotype of the sample can be determined based on detection of the hybridization between the probes and the sample. A suitable DNA microarray is disclosed in Brown et al. U.S. Pat. No. 5,807,522

H. Modulating and Regulating APOAV Expression

The preferred embodiment also encompasses methods of modulating and regulating APOAV expression. Current therapies known to effect lipid metabolism can also be studied for their effect in modulating and regulating APOAV expression. Current methods include but are not limited to, administration of fibrates and other molecules important in inflammatory response, cholesterol regulating drugs, and glucose and insulin regulatory molecules.

For example, fibrates are hypolipidemic drugs with pleiotropic effects on lipid metabolism including the reduction of plasma triglycerides. Suitable fibrate drugs are disclosed in U.S. Pat. No. 4,318,923 issued to Hamayaki et al. And hereby incorporated by reference. Classically, the triglyceride lowering action of fibrates is explained by decreased hepatic secretion of VLDL and an enhancement in plasma triglyceride clearance. Several studies established that this effect is mediated through the induction of lipoprotein lipase expression and down-regulation of APOC3 expression by fibrates. A major means by which fibrates regulate the expression of lipid metabolism-related genes by fibrates has been shown to be via activation of the peroxisome proliferator-activated receptor alpha (PPARα). Three distinct PPARs (α, β, and γ) have been described in different species. Whereas PPARβ appears ubiquitously expressed, PPARα and PPARγ are mainly expressed in liver and in adipose tissue, respectively. PPARs are ligand-activated nuclear receptors that dimerize with the retinoid X receptor (RXR) and bind to specific DNA sequence defined as peroxisome proliferator response elements (PPRE). Upon binding, PPARs activate gene transcription.

Given the determinant link between APOAV and plasma triglycerides and the widespread use of fibrates in the treatment of dyslipidemia, one could investigate how fibrates affect APOAV gene expression and consequently influence plasma triglyceride levels. It is very likely that studies in mice and in vitro studies with human hepatocytes reveal that fibrates dramatically increase APOAV expression.

To determine if fibrates effect on apoa5 is mediated via the PPARα pathway, sequence conservation comparison, in vitro promoter analyses and functional studies of putative PPREs to the APOAV gene can be performed. These and other studies may identify fibrates acting via PPARα as a crucial regulator of the new apolipoprotein APOAV and suggest a novel and likely clinically relevant mechanism of how PPARα activators can act on lipid homeostasis. Modulation of APOAV via a PPARα pathway would prove to offer a new target for therapeutic interventions designed at correcting hypertriglyceridemia and at limiting triglyceride-associated cardiovascular risk.

I. Drug Design and Therapies Based on Sequence Variations

1. Drug Screening and Design

In addition to modulating the expression of the APOAV gene, the present embodiment further contemplates an alternative method for identifying specific agonists and activators using various screening assays known in the art.

The preferred embodiment contemplates screens for small molecule ligands or ligand analogs and mimics, as well as screens for natural ligands that bind to and agonize APOAV activity in vivo or result in lowered levels of triglycerides. For example, natural products libraries can be screened using assays of the invention for molecules that agonize APOAV activity. Knowledge of the primary sequence of the various APOAV allele variants and other structural motifs of APOAV (i.e., amphipathic α-helices), and the similarity of those sequences with domains contained in other proteins, can provide an initial clue to agonists of the protein. Identification and screening of agonists is further facilitated by determining structural features of the protein, e.g., using X-ray crystallography, neutron diffraction, nuclear magnetic resonance spectrometry, and other techniques for structure determination. These techniques provide for the rational design or identification of agonists of APOAV that will reduce triglyceride levels.

Another approach uses recombinant bacteriophage to produce large libraries. Using the "phage method" Scott and Smith, 1990, *Science* 249: 386-390 (1990); Cwirla, et al., *Proc. Natl. Acad. Sci.,* 87: 6378-6382 (1990); Devlin et al., *Science,* 249: 404-406 (1990), very large libraries can be constructed. A second approach uses primarily chemical methods, of which the Geysen method, Geysen et al., *Molecular Immunology* 23: 709-715 (1986); Geysen et al. *J. Immunologic Method* 102: 259-274 (1987), and the method of Fodor et al. *Science* 251: 767-773 (1991) are examples. Houghton in U.S. Pat. No. 4,631,211, and Rutter et al., U.S. Pat. No. 5,010,175, describe methods to produce a mixture of peptides that can be tested as agonists or antagonists.

In another aspect, synthetic libraries and the like can be used to screen for ligands that recognize and specifically bind to APOAV and its variants. In one such example, a phage library can be employed. Phage libraries have been constructed which when infected into host *E. coli* produce random peptide sequences of approximately 10 to 15 amino acids, Parmley and Smith, *Gene,* 73: 305-318 (1988), Scott and Smith, *Science,* 249: 386-249 (1990). Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of APOAV. After a specified incubation period, the filters can be thoroughly washed and developed for autoradiography.

Plaques containing the phage that bind to the radioactive binding domain can then be identified. These phages can be further cloned and then retested for the ability to bind to APOAV and/or its variants. Once the phages have been purified, the binding sequence contained within the phage can be determined by standard DNA sequencing techniques. Once the DNA sequence is known, synthetic peptides can be generated which represent these sequences.

The effective peptide(s) can be synthesized in large quantities for use in in vivo models and eventually in humans to reduce triglyceride levels. Synthetic peptide production is relatively non-labor intensive, easily manufactured, quality controlled and thus, large quantities of the desired product can be produced quite cheaply. Similar combinations of mass produced synthetic peptides have recently been used with great success. Patarroyo, *Vaccine,* 10: 175-178 (1990). The peptides may be prepared according to known pharmaceutical technology. They may be administered singly or in combination, and may further be administered in combination with other cardiovascular drugs. They may be conventionally prepared with excipients and stabilizers in sterilized, lyophilized powdered form for injection, or prepared with stabilizers and peptidase inhibitors of oral and gastrointestinal metabolism for oral administration.

Another embodiment is to create a cell system which has the 5' regulatory region of the human APOAV gene coupled to a reporter gene, such as luciferase, as is known in the art. The luciferase gene is positioned at the start of the APOAV gene. Candidate drugs are screened against the cell system and scored for their ability to upregulate the luciferase expression. These drugs will have use in lowering plasma triglycerides, according to the findings of the inventors that increased levels of the APOAV protein cause lowered plasma triglycerides as shown by Example 3.

Other high-thoughput methods of drug design and discovery are discussed in Landro, J. A. et al., "HTS in the new millennium, the role of pharmacology and flexibility," *J Pharmacol Toxicol Methods*. 2000 July-August; 44(1):273-89, describing target identification, reagent preparation, compound management, assay development, high-throughput library screening and other methods for drug discovery and screening, and is hereby incorporated by reference in its entirety.

While lowering triglyceride levels is an aim of the preferred embodiment, other embodiments target other metabolite levels such as insulin or glucose levels, by modulating APOAV gene expression. As show in Example 9, APOAV levels can lead to changes in plasma glucose or insulin levels or other metabolite levels. Therefore, alternate embodiments contemplate the aforementioned methods of drug screening and drug design for the purpose of modulating APOAV to affect other metabolite levels.

2. Gene Therapy with APOAV

The preferred embodiment also encompasses uses of the APOAV gene for gene therapeutics such as those described by Gabor M. Rubanyi, "The future of gene therapy," *Molecular Aspects of Medicine* 22(2001): 113-142, and is hereby incorporated by reference in its entirety. Rubanyi describes existing and future methods of gene therapy and the technical hurdles gene therapy faces in the future are made possible through the sequences disclosed in SEQ ID NO: 1-7. Other examples are drug therapies aimed at raising the levels of APOAV in any human patient with high triglyceride levels. These will provide a suitable way to reduce triglyceride levels and thereby reduce the risk of cardiovascular disease. Further aims include determining how APOAV exerts its effect upon triglyceride and other metabolite levels and to stimulate that pathway by non-APOAV means as a way to lower triglycerides or modulate other metabolite levels.

As described in an earlier section, various types of gene delivery vectors can be used including, but definitely not limited to, plasmids, YACs (Yeast Artificial Chromosomes), BACs (Bacterial Artificial Chromosomes), bacterial vectors, bacteriophage vectors, viral vectors (for example, retroviruses, adenoviruses and viruses commonly used for gene therepy), non-viral synthetic vectors, and recombinant vectors. Delivery of the vector and/or construct for gene therapy in a preferred embodiment is by viral infection or injection intravenously although delivery can be by any other means as described previously.

A preferred embodiment is modelled after the method described by Tangirala R K et al., *Circulation.* 26 Oct. 1999;100(17):1816-22, wherein the regression of atherosclerosis was induced by liver-directed gene transfer of apolipoprotein A-I in mice. The preferred embodiment contemplates a similar protocol of gene transfer as Tangirala et al. based on the same target tissue and the desire to express APOAV endogenously in the liver. A second-generation recombinant adenovirus encoding SEQ ID NO: 1 or 2, human APOAV cDNA can be constructed as described by Tsukamoto K. et al., *Journal of Lipid Research*, 1997:38, 1869-1876. Briefly, pAdCMV APOAV can be linearized with an enzyme and co-transfected into cells along with adenoviral DNA isolated and digested. The cells are then overlaid with agar and incubated at 32° C. for about 15 days. Plaques positive for APOAV cDNA are subjected to a second round of plaque purification, and the recombinant adenovirus is then expanded in cells at 32° C. A null adenovirus can be constructed and expanded in an identical manner. All viruses are then purified and stored appropriately.

While much of gene therapy uses vectors as a means of delivery, other methods of delivery to the somatic cells of a patient may be utilized. The preferred embodiment also contemplates the delivery of APOAV polynucleotides by encapsulation by compositions such as, hydrogels and microgels, liposomes, and other lipid or polymer carriers. Furthermore, the APOAV polynucleotides can be delivered naked, without any means of receptor-mediated entry or other carrier into the patient's cells.

3. Therapeutics Using APOAV

The presently disclosed APOAV polynucleotides and polypeptides, and fragments thereof, may be prepared according to known pharmaceutical technology. They may be administered singly or in combination, and may further be administered in combination with other cardiovascular or triglyceride-lowering drugs. They may be conventionally prepared with excipients and stabilizers in sterilized, lyophilized powdered form for injection, or prepared with stabilizers and peptidase inhibitors of oral and gastrointestinal metabolism for oral administration. They may also be administered by methods including, but not limited to, intravenous, infusion, rectal, inhalation, transmuscosal or intramuscular administration.

The APOAV polynucleotides and polypeptides can be isolated, recombinant or synthesized, so long as the polynucleotides and polypeptides maintain APOAV functionality. In a preferred embodiment, the APOAV polynucleotide of SEQ ID NO: 1-3 or 5 is delivered in the therapy whereby the APOAV gene is over expressed in the organism. In other preferred embodiments, the polypeptide or active APOAV protein of SEQ ID NO: 4 is delivered to lower triglyceride levels.

Combining data from stratification and genetic studies with diagnostic tests to determine the best method of treatment for person based upon such criteria as specific haplotype, age, gender and ethnicity. For example, after finding in a genetic study that individuals having haplotypes APOA5*1/*2 and a specified triglyceride level, respond to a certain dosage of fibrates (e.g. their triglyceride levels dramatically are reduced by an average 50 dl/mL), physicians and medical providers can tailor triglyceride therapy to prescribe the most effect dosage of triglyceride lowering medication. After ordering the diagnostic tests described earlier for individuals to determine what haplotype they possess, doctors and other medical providers can then prescribe the most effective dosage to achieve the goal of dramatically reducing triglycerides to persons having the haplotypes of APOA5*1/*2. In other embodiments, the sample of individuals can be broken down according to other criteria, including, but not limited to, age, gender, ethnicity, diet or the presence or absence of certain disease symptoms.

J. Methods of Genetic Analysis and Association Studies

In general, the SNPs of this invention find use in any method known in the art to demonstrate a statistically significant correlation between a genotype and phenotype, and between a haplotype and phenotype. Preferably, the SNPs are used in studies to determine their correlation to lipid metabolism disorders. More preferably, the SNPs are used in studies to determine whether they are causative mutations of lipid metabolism disorders.

The described polymorphisms can be used to separate individuals based on any phenotypic trait. For instance, patients can be treated with fibrates and their triglyceride levels can be determined. Individuals can then be separated based on their APOAV genotype/haplotype (APOA5*1, APOA5*2, or APOA5*3) and their average triglyceride level determined. This will enable a physician to address if APOAV polymorphisms influence how responsive an individual will be to a triglyceride therapy.

A similar strategy could be used for any drug therapy. As another example, a certain diseased group of individuals could be separated based on their APOAV genotype/haplotype, and all the average phenotypes from these groups can be examined for differences. If any phenotype display shows a difference, this would be a phenotype that APOAV may influence. For instance, a group of diabetics could be separated based on their APOAV genotype. Numerous phenotypes in these subgroups can be averaged and compared, such as glucose levels. If there is a difference in glucose levels, this would support the proposal that APOAV influences glucose levels in diabetes. Another example would be to look at every type of cardiovascular disease and see if there is an increased frequency of the minor haplotypes in the diseased group compared to controls. If there is a difference then APOAV likely contributes to this disease.

Criteria or methods for selecting individuals for treatments, drug trials and any of the studies described herein include, but are not limited to, such criteria for eligibility as: willingness to participate in program, no medication use likely to interfere with lipid metabolism, percentage of ideal body weights according to such tables and indices available such as Metropolitan Life Insurance Company Tables (1985), certain body mass index, free of chronic disease, nonsmoker, daily alcohol consumption, related or unrelated to other subjects in the study, family and other relatives living and willing to donate blood samples or submit to studies, belonging to certain age and/or ethnicity groups, possessing defined levels of plasma total cholesterol, triacylglycerols and blood pressure, adherence to diet and/or exercise protocol and requirements, and any other measurable genotypic or phenotypic trait. In addition to meeting this criteria, analysis of the plasma lipids, lipoproteins, lipoprotein subfractions, triglycerides and apolipoproteins of the subjects should be done to develop complete profiles of each subject.

For more examples of preferred subject criteria and methods of measuring triglycerides, lipoproteins, cholesterol, and other related lipid metabolism proteins and methods for conducting clinical trials as herein described, see D. Dreon et al., *Arteriosclerosis, Thrombosis, and Vascular Biology*. 1997;17:707-714; D. Dreon et al., *Am J Clin Nutr*. 1998; 67:828-36; and Williams et al., *Arteriosclerosis, Thrombosis, and Vascular Biology*. 1997; 17:702-706, which are hereby incorporated by reference in their entirety.

The preferred embodiment permits genetic analysis studies between the disclosed SNPs 1-6, the APOAV haplotypes (APOA5*1/*2/*3) and any phenotype. In general, the SNPs and haplotypes of the present invention find use in any method known in the art to demonstrate a statistically significant correlation between a genotype and phenotype. The genetic analysis using the SNPs and haplotypes that may be conducted include but are not limited to linkage analysis, population association studies, allele frequencies, haplotype frequencies, and linkage disequilibrium.

Linkage analysis is based upon establishing a correlation between the transmission of genetic markers and that of a specific trait throughout generation within a family. Thus, the aim of linkage analysis is to detect marker loci that show co-segregation with a trait of interest. Linkage analysis correlating APOAV SNPs and haplotypes and the trait of high triglyceride levels within families or people/ethnic groups are an aim of this invention. The examples demonstrate linkage analysis studies that correlated the presence of either APOA5*2 or APOA5*3 with raised triglyceride levels in the Caucasian, African-American and Hispanic populations. Further linkage analysis is also contemplated for studies of other people and ethnic groups, and further regional studies including groups in other countries. Linkage analysis can be performed according to parametric or non-parametric methods.

Frequency of alleles and haplotypes in a population is also another genetic analysis study contemplated by the invention. Using the genotyping and haplotyping methods described in the earlier "Genotyping and Haplotyping" section, one skilled in the art can determine the frequency of SNPs 1-6 and haplotypes APOA5*1/*2/*3 in a given population. While several methods of estimating allele frequency are possible, genotyping individual samples is preferred over genotyping pooled samples due to higher sensitivity, reproducibility and accuracy. Furthermore, many genomic and large-scale sequencing centers enable rapid genotyping and haplotyping by sequencing methods and thereby provide rapid data production.

Association studies between APOAV SNPs and haplotypes and any phenotype can also be performed on a random sample of people, anywhere from a few hundred to tens of thousands. After collecting various parameters for each individual participating the study, such as height, weight, triglyceride levels, medical history, etc., the sample group can be separated according to various genotypes at APOAV. Any repeated differences in the parameters in individuals that are observed are likely traits that are associated with one of the APOAV genotypes or haplotypes. Examples show that there are differences in triglyceride levels that are associated with APOAV haplotypes *1, *2 and *3, however, there are likely other associations that can be subject to study. Other parameters to observe include, but are not limited, presence of cardiovascular disease risks, other lipid, lipoprotein or protein levels, instances of diabetes, obesity, inflammatory diseases, inflammatory response, apolipoprotein expression levels, alcoholism and drug abuse.

Alternate embodiments also encompass a method of determining if SNPs 1-6 are in linkage disequilibrium with any lipid-related or other disorders.

Studies correlating the genotype/haplotype with methods and treatments of high triglycerides or other lipid-related disorder are also contemplated. Segregation of individuals in the study according to their response (e.g. lowering of triglyceride levels) to various drug therapies and combinations and then according to the APOAV allele frequency. The result of stratification of population studies would enable doctors and medical care providers to prescribe therapy with greater accuracy, and with greater success rates. Thus, therapy prescribed would be "tailor-made" for individuals based upon their haplotypes.

Statistical methods and computer programs useful for linkage analysis, genetic analysis and association studies are well-known to those skilled in the art. Any statistical tool useful to test for statistically significant associations between genotypes, haplotypes and phenotypes, comparisons and correlations between a biological marker and any physical trait, and frequency comparisons may be used.

Statistical analyses can be carried out using the SAS computer program (SAS, Cary, N.C.) and similar programs. Plasma triglyceride concentrations can be compared among different genotype groups using Wilcoxon's test and the like. Allele frequencies should be compared using such tests as Fisher's exact test. To determine pairwise linkage disequilibrium (LD) between SNPs, haplotype frequencies, estimations can be done using the Expectation-Maximization (EM) algorithm implemented in the computer program ARLEQUIN v. 2.0 ((Excoffier and Slatkin, *Mol. Biol Evol.* 1995, 12 (5):921-927), and downloadable from http://lgb.unige.ch/arlequin/), an exploratory population genetics software environment.

Pair-wise measure of linkage disequilibrium (|D'|) can be calculated for all combinations of frequencies as described by R. C. Lewontin, *Genetics* 120, 849-52 (1988). A |D'| value of 1 indicates complete linkage disequilibrium between two markers.

Examples of useful statistical methods and techniques include Analysis of Variance (ANOVA), Fischer's test for pair-wise comparison and Wilcox's test, generally carried out using programs such as SPSS (Chicago, Ill.), STATVIEW and SAS (both available from SAS, Cary, N.C.).

EXAMPLE 1

Identifying and Isolating APOAV

Orthologous mouse genomic DNA was isolated from a pooled BAC library using the polymerase chain reaction (PCR) with mouse primers: apoAI-F1-5'-GAGGATGTGGAGCTCTACCGC-3' (SEQ ID NO:8) and apoAI-R1-5'-CTGTGTGCGCAGAGAGTCTACG-3'(SEQ ID NO:9) (RPCI-23, BACPAC Resources, Children's Hospital Oakland Research Institute; (See K. Osoegawa, et al., *Genome Res* 10, 116-28 (2000)). Positive clone RPCI-23-175F2 was identified, randomly sheared, sub-cloned and sequenced to approximately six-fold coverage according to methods described by I. Dubchak, et al., *Genome Res* 10, 1304-6 (2000) and G. G. Loots, et al., *Science* 288, 136-40 (2000). The sequence was deposited in GenBank (GenBank accession number AF401201). Human and mouse sequence comparisons were performed as previously described. Protein analyses were performed using the web-based Predict-Protein package, COILS (A. Lupas, et al., *Science* 252, 1162-4 (1991).), and SignalP (H. Nielsen, et al., *Protein Eng* 10, 1-6 (1997)). These analyses packages can be obtained at the following websites:

http://www.ch.embnet.org/software/COILS form.html;
http://www.embl-heidelberg.de/predictprotein/predictprotein.html;
http://www.cbs.dtu.dk/services/SignalP).

The VISTA (www-gsd.lbl.gov/vista) graphical plot in FIG. 1B displays the level of homology between human and the orthologous mouse sequence spanning the apoAI/CIII/AIV cluster. Human sequence is represented on the x-axis and the percent similarity with the mouse sequence is plotted on the y-axis (ranging from 50-100% identity). Once the mouse sequence had been generated and the comparison obtained, a relatively high level of homology was observed in the region of the present APOAV, as can be seen from the plot.

To identify expression patterns of APOAV, mice were sacrificed and tissues harvested for either total RNA isolation using the RNAeasy-midi protocol (Qiagen, Valencia, Calif.) or for polyA mRNA isolation using the FastTrack 2.0 system (Invitrogen, Carlsbad, Calif.). Approximately 10 μg of total RNA or 2 μg of polyA mRNA were separated in 1.0% agarose by gel electrophoresis and the RNA was transferred to a charged nylon membrane (Ambion, Austin, Tex.). The RNA blots were hybridized with [$\alpha$-$^{32}$P]dCTP random-primed mouse apoA5 and human APOAV probes in ULTRAhyb buffer (Ambion, Austin, Tex.). Probe templates were generated by PCR amplification of liver cDNA using degenerate primers degApoAV-F2-5'-GCGCGTG-GTGGGRGAAGACA-3' (SEQ ID NO:22) and degApoAV-R2-TCGCGCAGCTGGTCCAGGTT-3' (SEQ ID NO:23). Filters were washed in 2× saline sodium citrate at room temperature for 20 minutes and in 0.1×SSC at 42° C. for 20 minutes, followed by autoradiography visualization.

The results of the RNA blots are described herein. (A) A mouse apoA5 cDNA probe was hybridized to a multi-tissue RNA blot from wild-type mice. Each lane contained one of eight mouse tissues (Clontech, Palo Alto, Calif.), respectively: 1, heart; 2, brain; 3, spleen; 4, lung; 5, liver; 6, skeletal muscle; 7, kidney; and 8, testis. The probes hybridized only to two transcripts approximately 1.3 and 1.9 kb in size in liver tissue (lane 5). (B) A human APOA5 cDNA probe was hybridized to a RNA blot containing eight human tissues (Clontech, Palo Alto, Calif.), respectively: 1, heart; 2, brain; 3, placenta; 4, lung; 5, liver; 6, skeletal muscle; 7, kidney; and 8, pancreas. The probes hybridized only to two transcripts approximately 1.3 and 1.9 kb in size in liver tissue (lane 5). (C) A human-specific APOA5 cDNA probe was hybridized to total RNA blots from human apoA5 transgenic mice and controls. Lane assignments are as follow: 1,5 transgenic liver; 2,6 transgenic intestine; 3,7 wild-type liver; 4,8 wild-type intestine. The probes hybridized only to two transcripts approximately 1.3 and 1.9 kb in size in transgenic liver tissue (lanes 1 and 5). (E) Northern blot analysis of various genotype mice using mouse APOA5 probe following the apoA5 targeting event. Each lane contains liver mRNA from a wild-type (lane 1), heterozygous (lane 2) and homozygous knockout mouse (lane 3). To confirm similar amounts of RNA were loaded per lane, duplicate gels were examined by ethidium bromide staining. There was a large amount of transcript around 1.9-2 kb in lane 1 and a smaller band in lane 2 of same weight, while lane 3 showed no transcript.

EXAMPLE 2

Transgenic Non-human Animals to Assess the Function of APOAV and apoAV

Restriction enzyme predictions for human genomic sequence (Genbank Accession Number AC007707) indicated that the entire human APOAV gene, but not neighboring genes, was contained within a 26 kbp XhoI DNA fragment (corresponding to approximately 1-27 kbp in FIG. 1B). BAC DNA corresponding to the clone sequenced from this region was prepared by standard alkaline lysis with a chromatography column (Qiagen, Valencia, Calif.), digested with the restriction enzyme XhoI and separated in 1% agarose by pulse-field gel electrophoresis. The 26 kbp XhoI DNA fragment containing human APOAV was purified using QIAEX II gel purification (Qiagen, Valencia, Calif.), adjusted to a final concentration of ~1 ng/ml and microinjected into fertilized FVB inbred mouse eggs using standard procedures. See K. A. Frazer, G. Narla, J. L. Zhang, E. M. Rubin, *Nat Genet* 9, 424-31 (1995).

Two founder transgenic mice were identified as determined by PCR amplification using primers hAPOA5-intrn-F1-5'-CCCGCTGCAGTCCCCAGAAT-3' (SEQ ID NO:10) and hAPOA5-intrn-R1-5'-CAGGGTCGAGGGCTCT-TGTCCT-3' (SEQ ID NO:10). Each founder line was expanded by breeding to isogenic FVB strain mice (The Jackson Laboratory, Bar Harbor, Minn.).

The targeting construct to delete mouse apoA5 was built using PCR products amplified from BAC-RPCI-23-175F2 DNA (BACPAC Resources, Children's Hospital Oakland Research Institute). The first homology arm was PCR-amplified using primers containing introduced 5' restriction sites for XbaI and EcoRI, respectively: mAV-XbaI-F1-5'-TGACTCTAGATACCCTTGGTCCCATGTTCCAGAT-3' (SEQ ID NO:12) and mAV-EcoRI-R1-5'-CATTGAATTC-GACAAGAGAAAGACGGGGCTCAAG-3' (SEQ ID NO:13). The resulting 4.2 kbp PCR product was cloned into pXL-Topo (Invitrogen, Carlsbad, Calif.), DNA prepared by standard alkaline lysis (Qiagen, Valencia, Calif.) and digested with EcoRI according to the manufacturer's recommendations (New England Biolabs, Beverly, Mass.). A 4.2 kbp EcoRI fragment was gel-purified and cloned into the EcoRI site of the pPN2T vector to yield pPN2T-Arm1 (C. Paszty, et al., *Nat Genet* 11, 33-39 (1995)). Clones were PCR screened for inserts using the above described primers and positive clones were sequenced for proper orientation.

The second homology arm was PCR-amplified using primers mAV-NotI-F4-5'-TATGACTGCGGCCGCCAC-CAATCCCACATCTAAGCATCT-3' (SEQ ID NO:14), containing an introduced 5' NotI restriction site, and mAV-XhoI-R3-5'-GCTCGGTTCTGGGCACAGAGA-3'(SEQ ID NO:15). The resulting 5.3 kbp PCR product containing an endogenous internal XhoI restriction site was digested with NotI and XhoI to yield a 5.1 kbp fragment which was directionally cloned into the XhoI and NotI sites of the pPN2T-Arm1 vector to yield final vector pPN2T-apoAV-KO. 129/SvJ ES cells (Incyte Genomics, Palo Alto, Calif.) were electroporated with 20 μg of the NotI linearized targeting construct and subsequently selected in 200 μg/ml G418 and 0.5 μg/ml FIAU for 8 days. Individual clones were isolated, expanded and screened by Southern blot analysis.

The external 3' probe was amplified by PCR using primers mApoAV-3' probe-F2-5'-CTTGAGGATGGGCATCAGCTGTAT-3' (SEQ ID NO:16) and mApoAV-3'probe-R2-5'-GCTCACTAACAGCGCTCTTGCCT-3' (SEQ ID NO:17). Targeted clones were injected into C57BL/6 blastocysts and chimeric males were bred to C57BL/6 females (The Jackson Laboratory, Bar Harbor, Minn.). Agouti offspring were tested for germline transmission of the targeted allele by PCR using primers specific to the neomycin gene (NeoF1-5'-CTTTTTGTCAAGACCGACCTG-3' (SEQ ID NO:37) and NeoR1-5'-AATATCACGGGTAGCCAACGC-3'(SEQ ID NO:38)) and heterozygous animals were intercrossed to obtain homozygous deletion animals for the mouse apoA5 locus. Offspring were genotyped with PCR primers designed to the neomycin gene and with primers contained within the apoA5 deleted interval (mApoA5-F2-5'-ACAGTTGGAGCAAAGGCGTGAT-3' (SEQ ID NO:18) and mApoA5-R2-5'-CTTGCTCGAAGCTGCCTTTCAG-3'(SEQ ID NO:19)). Properly targeted embryonic stems cells were identified using an external 3' probe which detects a 17 kb EcoRI fragment wild-type allele and a 10 kb EcoRI fragment upon targeting.

EXAMPLE 3

Figure 3:
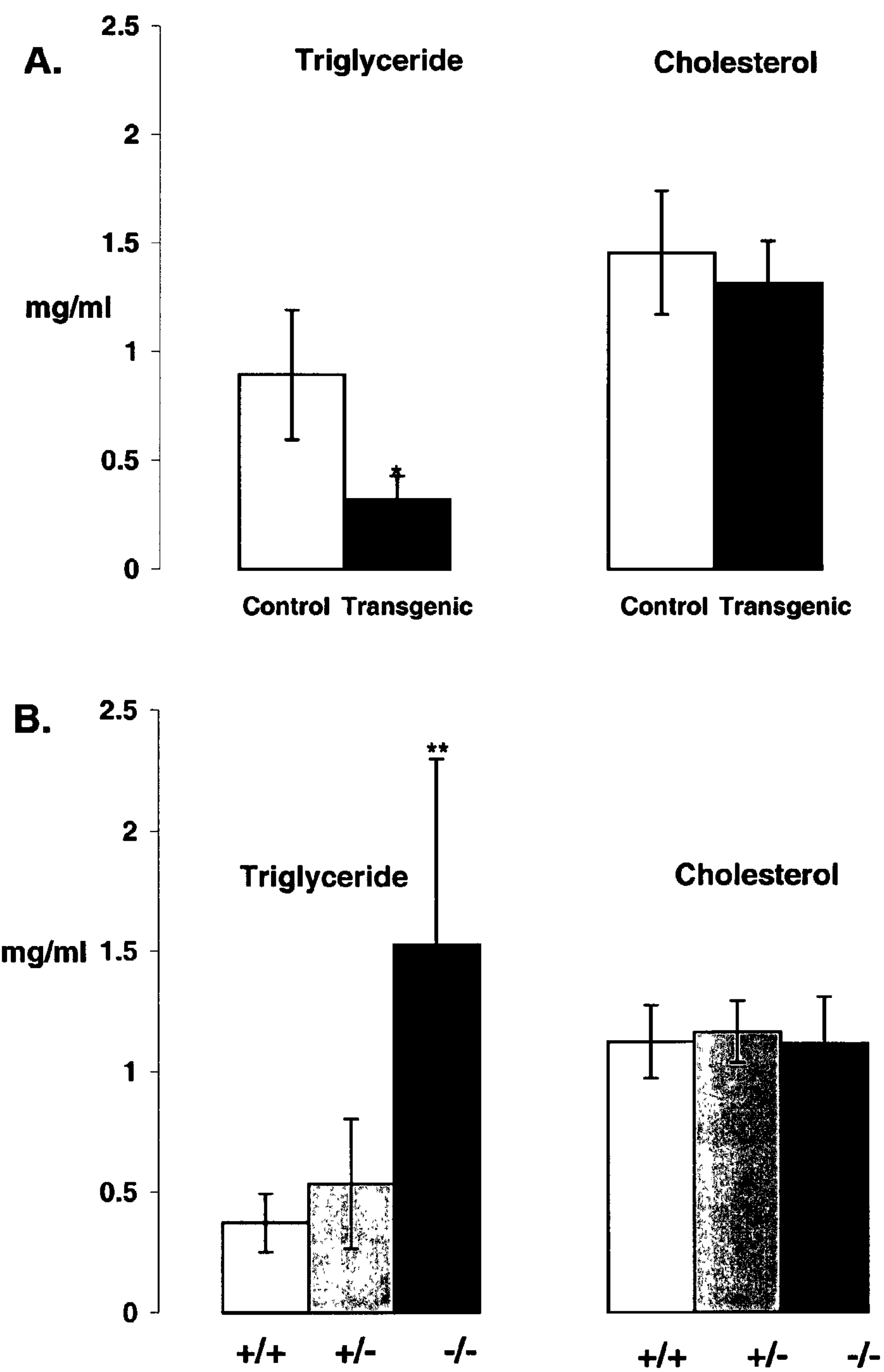
FIG. 3. Bar charts showing plasma triglyceride and cholesterol for human transgenic (FIG. 3A) mice and apoAV knockout mice (FIG. 3B).

Plasma Triglyceride and Cholesterol Levels for APOAV Transgenic and Knockout Mice Referring now to FIG. 3, results from the present human APOAV transgenic mice and the apoAV knockout mice are shown. Plasma triglyceride and cholesterol levels for apoAV transgenic and knockout mice on standard chow diet are illustrated. (A) Human APOAV transgenic mice compared to isogenic FVB strain control littermates (n=48 for transgenics; n=44 for controls; student t-test *p<0.0001 for transgenic versus control) have a ~70% decrease in triglyceride levels. (B) Mice lacking APOAV compared to mixed 129Sv/C57B16 strain controls littermates (n=13 for wild-type, +/+; n=22 for heterozygotes, +/−; n=10 for homozygous knockouts, −/−; student t-test **p<0.001 for wild-type versus knockout) have a 400% increase in triglyceride levels. Error bars correspond to the standard deviation for both graphs.

The transgenic mice had approximately three-fold lower levels of plasma triglyceride when compared with control littermates ((0.32±0.11 (S.D.) mg/ml versus 0.90±0.29; T-test p<0.0001). Similar data were obtained from a second independent founder line (data not shown).

Mice lacking apoA5 were compared to mixed 129Sv/C57B16 strain control littermates (n=13 for wild-type, +/+; n=22 for heterozygotes, +/−; n=10 for homozygous knockouts, −/−; student t-test p<0.001 for wild-type versus knockout) (FIG. 3B). Despite the lack of apoA5 transcript, mice homozygous for the deletion were born at the expected Mendelian rate and appeared normal. In contrast to the decreased triglyceride levels noted in APOAV transgenics, apoA5 knockout mice had approximately four-fold higher levels of plasma triglyceride when compared with wild-type littermates (1.53±10.77 (S.D.) mg/ml versus 0.37±10.12; T-test p<0.001) (FIG. 3**B). Error bars correspond to the standard deviation for both graphs.

Characterization of lipoprotein particles by fast protein liquid chromotography revealed that levels of very low density lipoprotein (VLDL) particles were increased in the homozygous knockout mice and decreased in the transgenic mice compared with controls. VLDL levels in a heterozygous knockout mouse were intermediate between the homozygous knockout and control mouse. The peak VLDL elution volumes were similar in all animals, indicating comparable VLDL particle size, and levels of other lipoproteins were not significantly altered.

EXAMPLE 4

Genotyping Human Individuals

Blood samples were collected after a 5-hour fast by retro-orbital bleeding using heparinized micro-hematocrit tubes. Total cholesterol and triglyceride concentrations were measured using enzymatic methods on a Gilford System 3500 analyzer (Gilford Instruments, Oberlin, Ohio).

For the entire genomic sequence of APOAV, overlapping sequence-tagged sites (STSs) of 400-498 bp in size were designed and tested using PCR-amplification on human genomic DNA as previously described in E. M. Beasley, R. M. Myers, D. R. Cox, L. C. Lazzeroni, *PCR Applications* (Academic Press, San Diego, Calif., 1999). Only primer pairs that resulted in a single PCR product of expected size were used for subsequent amplifications. For SNP discovery, STSs were PCR-amplified from eight samples of the Polymorphism Discovery Resource panel (PDR08, Coriell Cell Repository, Camden, N.J.), and products were purified through Millipore plates according to the manufacturer's recommendations (Millipore, Bedford, Mass.). Subsequent sequencing reactions with purified PCR products were performed using Big Dye Terminator chemistry and forward or reverse primers in separate sequencing reactions (Applied Biosystems, Foster City, Calif.).

Reactions were analyzed using a 3700 Sequence Analyzer (Applied Biosystems, Foster City, Calif.). Sequence traces were automatically analyzed using PhredPhrap and Polyphred (D. A. Nickerson, V. O. Tobe, S. L. Taylor, *Nucleic Acids Res* 25, 2745-51 (1997); B. Ewing, P. Green, *Genome Res* 8, 186-94 (1998)). For SNPs identified through this analysis, PCR INVADER assays (Third WaveTechnologies, Madison, Wis.) were designed and tested on 90 samples from the Polymorphism Discovery Resource panel (PDR90) (C. A. Mein, et al., *Genome Res* 10, 330-43 (2000)). Successful assays were subsequently used to analyze samples from our study. Genotypes were assigned automatically by cluster analysis. Differences among genotypes were analyzed by one way ANOVA using STATVIEW 4.1 software (Abacus Concepts, Inc., Berkeley, Calif.).

To genotype the C/T SNP3 polymorphisms upstream of APOAV (discussed in Example 5), oligonucleotides AV6-F-5'-GATTGATTCAAGATGCATTTAGGAC-3' (SEQ ID NO:20) and AV6-R-5'-CCCCAGGAACTGGAGCGAAATT (SEQ ID NO:21) were used to amplify a 187 bp fragment from genomic DNA. The penultimate base in AV6-R was changed to T to create a MseI site (TTAA) in the common allele. The PCR reactions were performed in 20 μl volumes containing 50 mmol/l KCl, 10 mmol/l Tris (pH 8.3), 1.5 mmol/l $MgCl_2$, 0.2 mmol/l of each dNTP, 1 U of Taq DNA polymerase and 200 pmol/l of each primer. DNA was amplified using the following conditions: initial denaturation of 96° C. for 2 min, followed by 32 cycles of 94° C. for 15 sec, 55° C. for 30 sec and 72° C. for 30 sec, and a final step at 72° C. for 3 min. 20 μls of PCR product were digested with 10 U of MseI (New England Biolab) at 37° C. for 3 h. The PCR products were size-fractionated on 3% agarose gels, stained with ethidium bromide and visualized on a UV transilluminator.

EXAMPLE 5

Human APOAV Polymorphisms and Lipid Association Studies

Referring now to FIG. 5, plasma lipid concentrations for a given genotype for four neighboring SNPs (SNPs1-4) are shown in Table 5A. For that study, 501 individuals were genotyped and the number of successfully scored individuals is approximately 430. The number of individuals of each SNP genotype is shown in row "n". In the row labelled "Genotype," 1,1=homozygous for the major allele; 1,2=heterozygous for the major and minor alleles. All individuals homozygous for the minor alleles of individual APOAV SNPs 1-3 were removed from the analysis (n=2) to prevent their over-representation. All sites were found to be in Hardy-Weinberg equilibrium (data not shown). The minor allele frequency for each SNP (SNPs 1-4) was 9.1, 8.4, 9.2 and 36.3%, respectively. Not shown is the lack of association between each of the four SNPs and IDL-, LDL-, HDL-mass, APOAI, and APOB levels (p>0.05, data not shown) FIG. 5B shows Pair-wise measure of linkage disequilibrium (|D'|) was calculated for all combinations of SNPs 1-4. A|D'| value of 1 indicates complete linkage disequilibrium between two markers. FIG. 5C shows a summary of SNP3 genotyping data from an independent set of individuals stratified based on triglyceride levels. P values were determined by Chi-square analysis. BMI=body mass index, TG=plasma triglyceride level (mg/dl±SEM).

Plasma lipid concentrations for a given genotype for four neighboring SNPs (SNPs 1-4) are shown in FIG. 5A for triglycerides, VLDL, LDL and HDL. 501 unrelated normolipidemic Caucasian individuals who had been phenotyped for numerous lipid parameters before and after consumption of high- and low-fat diets were used in this study. Subjects were a combined subset of 501 healthy, nonsmoking Caucasian individuals aged >20 years (429 men, 72 women) who had participated in previous dietary intervention protocols (R. M. Krauss, D. M. Dreon, *Am J Clin Nutr* 62, 478S-487S (1995); D. M. Dreonet al., *Arterioscler Thromb Vasc Biol* 17, 707-14 (1997)). All subjects had been free of chronic disease during the previous five years and were not taking medication likely to interfere with lipid metabolism. In addition, they were required to have plasma total cholesterol concentrations <6.74 mmol/L (260 mg/dL), triacylglycerol <5.65 mmol/L (500 mg/dL), resting blood pressure <160/105 mm Hg, and body weight <130% of ideal. Each participant signed a consent form approved by the Committee for the Protection of Human Subjects at EO Lawrence Berkeley National Laboratory, University of California, Berkeley, and participated in a medical interview. Fasting blood samples were obtained on their usual diets, and after 4-6 weeks of consuming diets containing high fat (35-46% energy) and low fat (20-24% energy). Plasma lipid and lipoprotein measurements were performed as previously described (R. M. Krauss, D. M. Dreon, *Am J Clin Nutr* 62, 478S-487S (1995); D. M. Dreonet al., *Arterioscler Thromb Vasc Biol* 17, 707-14 (1997)). In addition, on the high and low fat diets, total mass was measured by analytic ultracentrifugation.

Significant associations were found between both plasma triglyceride levels and VLDL mass and the three neighboring SNPs (SNPs1-3) within APOAV but not with the distant upstream SNP4 (FIGS. 1A, 4A). Specifically, the minor allele of each of these SNPs (SNPs1-3) was associated with higher triglyceride levels independent of diet. Independent analysis of each of these SNPs (SNP1-3) revealed plasma triglyceride levels were 20-30% higher in individuals having one minor allele compared to individuals homozygous for the major allele. Analysis of SNP allele frequencies in more than 1,000 chromosomes revealed that the three neighboring SNPs (SNPs 1-3) in APOAV were in significant linkage disequilibrium that does not extend to SNP4 (located ~11 kb upstream of APOAV). This finding supports the existence of a common haplotype in the APOAV region influencing plasma triglyceride levels (FIG. 4B). Furthermore, preliminary studies in this population found no significant association of triglyceride levels with a Sst1 polymorphism in APOC3 (located ~40 kbp upstream of APOAV) which has been previously associated with severe hyper-triglyceridemia (See M. R. Hayden, et al., *Am J Hum Genet* 40, 421-30 (1987), M. Dammerman, et al., *Proc Natl Acad Sci USA* 90, 4562-6 (1993)). All individuals homozygous for the minor alleles of individual APOAV SNPs 1-3 were removed from the analysis (n=2) to prevent their over-representation. All sites were found to be in Hardy-Weinberg equilibrium (data not shown). The minor allele frequency for each SNP (SNPs1-4) was 9.1, 8.4, 9.2 and 36.3%, respectively. No association between each of the four SNPs and IDL-, LDL-, HDL-mass, ApoAI, and ApoB levels (p>0.05) was observed.

Pair-wise measure of linkage disequilibrium (|D'|) was calculated for all combinations of APOAV SNPs as previously described by R. C. Lewontin, *Genetics* 120, 849-52 (1988). A |D'| value of 1 indicates complete linkage disequilibrium between two markers.

A summary of SNP3 genotyping data from an independent set of individuals stratified based on triglyceride levels. P values were determined by Chi-square analysis. BMI=body mass index, TG=plasma triglyceride level (mg/dl±SEM).

In a second human association study with SNP3 in an independently ascertained cohort using a different experimental design (FIG. 5C). SNP3 was chosen for genotyping in this study based on its strong association in our first study and its apparent complete linkage disequilibrium with the other two associated SNPs (SNPs 1-2). In the second study, we examined the allele frequencies for SNP3 in an unrelated group of Caucasians stratified according to plasma triglyceride levels. The two groups represented 115 individuals with triglyceride levels in the top tenth-percentile and 183 individuals from the bottom tenth-percentile. A significant over-representation of the heterozygous genotype (SNP3, APOA5*2) was found in individuals with high- compared to low-plasma triglyceride levels (18.3% versus 8.7%, respectively), thereby validating the effect in a second cohort. When the cohort was stratified based on gender, an even more pronounced over-representation of the heterozygous genotype was found in males with high- compared to low-plasma triglyceride levels (29.4% versus 5.2%, respectively).

Individuals that carry either of two independent SNPs described above have ~30% higher triglyceride levels. Population-wide this effect is large. 25% of Caucasians, 36% of African-Americans, and 51% of Hispanics carry at least one copy of these two alleles associated with elevated triglycerides.

EXAMPLE 6

APOAV Haplotypes: Linkage Disequilibrium and Association Studies

The present Example describes methods for establishing genetic profiles of individuals carrying various alleles of the present APOAV gene. These methods rely on Linkage Analysis studies and result in the identification of haplotyes including the SNP's described in connection with FIG. 5. The haplotypes are illustrated in FIG. 4B and are APOA5*1, APOA5*2 and APOA5*3.

The present study protocols were approved by the appropriate institutional review boards. Fasting blood samples were obtained from i) 116 hyperlipidemic patients including 34 with Type III hyperlipidaemia, 10 with familial combined hyperlipidemia, 24 with LDL cholesterol levels exceeding the 90$^{th}$ percentile, and 48 patients with plasma triglyceride levels exceeding 500 mg/dl; ii) 82 Caucasian men and 50 Caucasian women who were homozygous for the common allele of SNP3 (−1131 T) and who had plasma triglyceride concentrations above the 90$^{th}$ percentile for age and sex, and an equal number who were homozygous for the common allele of SNP3 (−1131T) and had plasma triglyceride concentrations below the 10$^{th}$ percentile for age and sex; and iii) 2660 residents of Dallas County selected at random from census tracts who participated in the Dallas Heart Disease Prevention Project (DHDPP), a population-based study of atherosclerotic heart disease.

DNA samples were also obtained from healthy, nonsmoking, Caucasian men (n=354) and women (n=65) who had participated in previous dietary intervention protocols and had plasma cholesterol levels below 260 mg/dl and plasma triglyceride levels below 500 mg/dl.

DNA sequencing: The exons and flanking intron sequences of the APOAV gene were screened for sequence polymorphisms by DNA sequencing. DNA fragments of ~400 basepairs spanning each exon were PCR amplified and sequenced using BigDyeTerminator Cycle Sequencing reagents on an ABI3100 automated sequencer.

such that the C to G substitution that changes codon 19 from serine to tryptophan creates an Eag I site. PCR was performed in 20 µl volumes containing 50 mM KCl, 10 mM Tris (pH 8.3), 1.5 mM $MgCl_2$, 0.2 mM of each dNTP, 1 U of Taq DNA polymerase and 200 pM of each primer. Reactions were performed in a PTC-200 Thermal cycler (MJ Research, South San Francisco, Calif.) using an initial denaturation step of 96° C. for 2 min, followed with 30 cycles of 94° C. for 15 sec, 70° C. for 20 sec and 72° C. for 30 sec. The PCR products were digested for 3 hr at 37° with 7 U of Eag I (New England Biolabs, Beverly, Mass.) in buffer provided by the manufacturer and analysed by electrophoresis in 3% agarose gels. For the V153M polymorphism, genomic DNA was amplified using the oligonucleotides AV150-R 5' TGGTGCACCACGAGGCTCTGCAGCAGTCCC (SEQ ID NO:26) and AV150-F5' AGGTGGCCCTGCGAGTG-CAGGAGCTGC (SEQ ID NO:27) as described above, except that the annealing temperature was 67° C. PCR products were digested with Nla III and assayed by electrophoresis in 3% polyacrylamide gels.

The SNP3 polymorphism was analyzed by mass spectrometry using the MASSARRAY system (Sequenom Corporation, San Diego, Calif.) (Buetow et al. 2001, *Proc. Natl. Acad. Sci. U.S.A* 98 (2):581-584). The oligonucleotides used in biplex INVADER genotyping assays (Sequenom Corporation, San Diego, Calif.) are shown in Table 4 below and are SEQ ID NOS: 28-36. The polymorphisms SNP5, SNP6, and V153M (location shown in FIG. 4A) are available in dbSNP under accession numbers ss4383597, ss4383596, and ss4383598, respectively and in GenBank under rs3135506 (SNP5), rs651821 (SNP6), and rs3135507 (V153M).

TABLE 4

| | SNP | | Sequence |
|---|---|---|---|
| SEQ ID NO: 28 | SNP 6 | Probe 1 | ATG ACG TGG CAG AC**G** TAA TGG CAA GCA TGG C |
| SEQ ID NO: 29 | | Probe 2 | CGC GCC GAG G**AT** AAT GGC AAG CAT GGC |
| SEQ ID NO: 30 | | Invader | GCC TCC CTC CAC CTG TCT TCT CAG AGC AGT |
| SEQ ID NO: 31 | SNP 5 | Probe 1 | ATG ACG TGG CAG AC**G** AAA ACG CTG TGG AGA G |
| SEQ ID NO: 32 | | Probe 2 | CGC GCC GAG G**CA** AAA CGC TGT GGA GAG |
| SEQ ID NO: 33 | | Invader | GCC **TTT** CCG TGC CTG GGT GGC CT |
| SEQ ID NO: 34 | V153M | Probe 1 | ATG ACG TGG CAG AC**G** TGG TGG GGG AAG AC |
| SEQ ID NO: 35 | | Probe 2 | CGC GCC GAG G**AT** GGT GGG GGA AGA C |
| SEQ ID NO: 36 | | Invader | AGG AGC TGC AGG AGC AGT TGC GCT |

SNP genotyping: The SNP5 (S19W) and V153M polymorphisms were assayed using PCR-RFLP and PCR INVADER assays (Third Wave Technologies, Madison, Wis.) as described previously. All PCR primers and probes used in biplex INVADER assays for this study are listed in Table 4. To assay the SNP5 polymorphism, oppositely-oriented oligonucleotides (AV1-F5' TGCTCAC-CTGGGCTCTGGCTCTTC (SEQ ID NO:24) and AV1-R5' CCAGAAGCCTTTCCGTGCCTGGGCGGC (SEQ ID NO:25)) were designed with a single nucleotide mismatch Statistical Analysis: Statistical analyses were carried out using the SAS computer program (Cary, N.C.). Plasma triglyceride concentrations were compared among different genotype groups using Wilcoxon's test. Allele frequencies were compared using Fisher's exact test. To determine pairwise linkage disequilibrium (LD) between SNPs, haplotype frequencies were estimated for 353 unrelated individuals using the Expectation-Maximization (EM) algorithm implemented in the computer program ARLEQUIN v. 2.0 (Excoffier and Slatkin, *Mol. Biol Evol.* 1995, 12 (5):921-

927). The resulting frequencies were used to calculate the pairwise LD parameter D' as discussed by Lewontin (*Genetics* 1988, 120 (3):849-852).

DNA sequencing: Screening of the coding regions and intron-exon boundaries of APOAV in 116 hyperlipidemic individuals revealed 10 new DNA sequence variations (FIG. 1A). An A to G substitution 3 nucleotides upstream of the initiation codon (SNP6) was found to be in strong linkage disequilibrium with three previously described polymorphisms (SNP 1, SNP2, SNP3, FIG. 1A) that define the APOA5*2 haplotype which is associated with increased plasma triglyceride concentrations (Pennacchio et al., 2001 *Science* 294 (5540):169-173). The A to G substitution results in a conservative change in the predicted Kozak consensus sequence (SNP6) (Kozak 1991, *J Cell Biol* 115 (4):887-903; Kozak, *Cell* 1986, 44 (2):283-292). two common nonsynonymous substitutions were also identified: A C→G substitution (SNP5) changed codon 19 from serine to tryptophan in 23 individuals, and a G→A substitution (c. 457G>A) changed codon 153 from valine to methionine in 14 individuals. A third nonsynonymous substitution (c.944C>T) that changed codon 315 from alanine to valine was identified in two hyperlipidemic individuals. This conservative substitution did not co-segregate with hyperlipidemia in the family members of one of these individuals (data not shown) and was not found in 108 normolipidemic individuals, therefore no further studies of this polymorphism were undertaken. The other six polymorphisms, including three silent substitutions (c.132C>A, c.695C>G, c.738C>T), and three polymorphisms each found only in single individuals (IVS2+55G>C, and c. 1132C>T and c.1156 G>A in the 3' UTR) were not evaluated further. Allele frequency and Linkage Disequilibrium: Five polymorphisms were found to define three common haplotypes (denoted APOA5*1, APOA5*2, and APOA5*3) in 419 unrelated Caucasian individuals (FIG. 4B). These three haplotypes represented 82%, 8%, and 8% of the APOAV chromosomes examined, and thus comprise more than 98% of APOAV haplotypes in this population. APOA5*2 is distinguished from the common haplotype (APOA5*1) by four nucleotide substitutions (−1131T>C, c.−3A>G, IVS3+476G>T, and c.1259T>C) and shown to be associated with increased plasma triglyceride levels and named SNP3, SNP6, SNP5, SNP2 and SNP1 respectively. APOA5*3 is distinguished from the common haplotype by the substitution of G for C at nucleotide c.56 (codon 19 in the amino acid sequence). To determine the relative frequencies of the APOA5*2 haplotype in African-Americans and Hispanics, the −1131 T>C SNP5 polymorphism was assayed in 1031 randomly selected individuals, including 545 African-Americans, 152 Hispanics, and 334 Caucasians. The allele frequency was significantly higher in African-Americans (0.12) and Hispanics (0.12), than in Caucasians (0.06, P<0.001). The frequency of the W19 allele (which defines haplotype APOA5*3) was similar in African-Americans (0.07) and Caucasians (0.06), but was substantially higher in Hispanics (0.15, P<0.001 compared to African-Americans).

Using this mathematical calculation specifically for SNP6 (APOA5*2) where the minor allele frequency is 6% in Caucasians, we find the distribution is 88% homozygous major, 11.6% heterozygous, 0.4% homozygous minor. Similarly, for SNP5(APOA5*3) the minor allele frequency is 6% for Caucasians, thus the distribution is 88% homozygous major, 11.6% heterozygous, 0.4% homozygous minor. Therefore, because SNP5 and SNP6 are independent of each other, 23.2% of the population is heterozygous (because 11.6%+11.6%=23.2%) and an additional 0.8% are homozygous for the minor allele. Thus, a large number (24%) of individuals in the general Caucasian population have elevated triglyceride levels solely due to the effect of APOAV polymorphisms.

In addition to APOAV's strong association with triglyceride levels in Caucasians, a strong effect is also seen African-Americans and Hispanics where the minor allele frequencies are higher. Thus, a larger percent of African-Americans and Hispanics display increased triglycerides due to the genetic effect of APOAV. Specifically, APOA5*2 and/or APOA5*3 are present in 36% of African Americans and 51% of Hispanics and results in an ~25% increase in triglycerides compared to APOA5*1 homozygotes.

For SNP6 (APOA5*2) in Hispanics and African-Americans, the minor allele frequency is 12% thus the distribution is 77.4% homozygous major, 21.1% heterozygous, 1.4% homozygous minor. For SNP5 (APOA5*3) in Hispanics, minor allele frequency is 15%. Thus the distribution is 72% homozygous major, 25.5% heterozygous, 2.3% homozygous minor. For African-Americans, SNP5 (APOA5*3) minor allele frequency is 7% thus the distribution is 86.7% homozygous major, 13.0% heterozygous, 0.5% homozygous minor. Thus, for Hispanics 23.5% of individuals carry APOA5*2 and 27.8% carry APOA5*3 for a total of 51.3% of Hispanics carry minor versions of APOAV associated with increased triglycerides. Using a similar logic, 36% of African-Americans carry minor versions of APOAV associated with increased triglycerides.

Abnormalities in APOAV may be solely responsible for human genetic forms of cardiovascular disease (similar to APOE or APOAI) in certain families and individuals. By screening this gene in families with individuals segregating cardiovascular or other types of disease, causative mutations may be found. This would have important diagnostic implications as well as provide therapeutic entry points. Furthermore, the data indicate that alleles in this gene are associated with increased plasma triglyceride levels thereby likely predisposing large numbers of individuals to increased susceptibility to coronary artery disease. A second implication of our findings is that this gene has sequence variations or single nucleotide polymorphisms that correlate to increased susceptibility to cardiovascular disease. The minor alleles of the polymorphisms disclosed herein associated with triglycerides occur in approximately 25% of the Caucasian population, 36% of African-Americans and 51% of Hispanics, thus representing a significant cross-section of the population. There is an approximate 25% chance that a Caucasian person is heterozygous for one or both of the two rare haplotypes and individuals having this rare allele have 20-30% higher triglyceride levels. Furthermore, the present studies suggest that the rare allele at the SNP5 locus (or any polymorphism in linkage disequilibrium with it) may have a major impact on plasma triglyceride levels in those persons predisposed to hypertriglyceridemia. Therefore, finding and exploring the significance of DNA sequence polymorphisms in APOAV and its subsequent effect on plasma triglyceride levels in humans is another important diagnostic implication of this embodiment.

Association Studies: To test for association between the two common, nonsynonymous polymorphisms identified in this study (SNP5 and V153M) and plasma triglyceride concentrations, the allele frequencies at these loci were compared in Caucasian men and women who had plasma triglyceride concentrations above the $90^{th}$ percentile or below the $10^{th}$ percentile for age and sex. To eliminate confounding by the APOA5*2 haplotype that was previously associated with high plasma triglyceride levels, individuals who carried this haplotype were excluded. In both sexes, the rare allele at codon 19 (W19) was significantly more common in individuals with plasma triglyceride levels above the $90^{th}$ percentile than in those with plasma triglyceride levels below the $10^{th}$ percentile (Table 5). Since individuals with the SNP3 allele were excluded, the association between the S19W (SNP5) polymorphism and plasma triglyceride concentrations is independent of the APOA5*2 haplotype that was previously shown to be associated with increased plasma triglyceride levels (Pennacchio et al. 2001).

The study showing the relationship between gender, genotype and triglyceride levels looked at men and women with high (>$90^{th}$ percentile) and low (<$10^{th}$ percentile) plasma triglyceride concentrations and is shown below.

TABLE 5

| | APOAV genotype | | | |
|---|---|---|---|---|
| | S19/S19 | S19/W19 | W19/W19 | P value |
| Men TG <10th percentile (n = 82) | 74 (90.5) | 7 (8.5) | 1 (1) | <0.005 |
| Men TG >90th percentile (n = 82) | 63 (77) | 19 (23) | 0 (0) | |
| Women TG <10th percentile (n = 50) | 50 (100) | 0 (0) | 0 (0) | <0.001 |
| Women TG >90th percentile (n = 50) | 39 (78) | 11 (22) | 0 (0) | |

Values are numbers of individuals in each group. S19 is the common allele of SNP5. The percentage of individuals with the genotype is given in parentheses. All individuals were homozygous for the common alleles at SNPs 3, 6, 2 and 1, which means that all individuals with APOA5*2 haplotype were excluded. P values were calculated using Fisher's exact test.

To further assess this association, the SNP5 polymorphism was assayed in 419 healthy independently-ascertained Caucasians (354 men and 65 women). Baseline blood samples were obtained from these individuals on their self-selected diets, and additional samples were drawn following the consumption of a defined high-carbohydrate or high-fat diet. On all three diets, individuals who were heterozygous for the SNP5 (W 19) allele and who lacked haplotype APOA5*2 had significantly higher plasma triglyceride concentrations than did individuals homozygous for the S19 (wild type) allele (Table 5).

The increase in mean plasma triglyceride levels associated with a single copy of the W19 allele was ~36%, which is similar to the increase in triglyceride levels associated with APOA5*2 haplotype (~32%) in these individuals. To determine if the W19 allele was associated with increased plasma triglyceride concentrations in other ethnic groups, the S19W polymorphism was assayed in a random sample of 1392 African-American, 420 Hispanic, and 848 Caucasians. In both sexes of all three ethnic groups, both the mean and the median plasma triglyceride concentrations were higher in W19 heterozygotes than in S19 homozygotes (Table 6 below). The difference was significant at the 0.05 confidence level for African-Americans and Caucasians in both sexes, but did not achieve the nominal significance threshold in Hispanics, presumably due to the smaller sample size in this group.

TABLE 6

| | | Plasma triglyceride levels (mg/dl) | | | |
|---|---|---|---|---|---|
| | | S19/S19 | S19/W19 | W19/W19 | P Value |
| African-American Women | Mean ± S.D. | 101 ± 169 | 131 ± 120 | 141 ± 50 | 0.0023 |
| | Median ± I.Q. | 80 ± 59 | 97 ± 85 | 192 | |
| | range n | (707) | (108) | (6) | |
| African-American Men | Mean ± S.D. | 132 ± 152 | 176 ± 319 | 264, 84 | 0.024 |
| | Median ± I.Q. | 94 ± 84 | 111 ± 92 | (2) | |
| | range n | (494) | (75) | | |
| Hispanic Women | Mean ± S.D. | 143 ± 95 | 174 ± 209 | 394 ± 534 | 0.057 |
| | Median ± I.Q. | 119 ± 92 | 135 ± 99 | 214 | |
| | range n | (185) | (57) | (7) | |
| Hispanic Men | Mean ± S.D. | 173 ± 139 | 204 ± 182 | 206, 124 | 0.087 |
| | Median ± I.Q. | 139 ± 108 | 157 ± 101 | (2) | |
| | range n | (119) | (50) | | |
| Caucasian Women | Mean ± S.D. | 124 ± 96 | 147 ± 90 | 237, 125 | 0.012 |
| | Median ± I.Q. | 100 ± 87 | 122 ± 110 | (2) | |
| | range n | (386) | (54) | | |
| Caucasian Men | Mean ± S.D. | 161 ± 121 | 255 ± 225 | (0) | 0.0012 |
| | Median ± I.Q. | 126 ± 116 | 183 ± 237 | | |
| | range n | (362) | (44) | | |

The nucleotide substitution (c. 457G>A) that changed codon 153 from valine to methionine was less common in men with high plasma triglyceride levels (3/82) than in men with low plasma triglyceride levels (7/82), but this difference was not statistically significant (P=0.12, Fisher's exact test). In 388 healthy Caucasian individuals, the mean plasma triglyceride level of 457G homozygotes was similar to that observed in 457GA heterozygotes (126.214.2 mg/dL (n=363) and 113.3±12.7 mg/dL (n=25), respectively, p=0.43).

EXAMPLE 7

Haplotype Linkage of APOAV Rare Alleles to Hyperlipidemia (CHL) and Familial Combined Hyperlipidemia (FCHL) Diseases Familial combined hyperlipidemia (FCHL) is a common disorder of lipid metabolism affecting 1-2% of individuals in Western society. The term FCHL was coined by Goldstein et al (1973) to describe a pattern of lipid abnormalities in 47 Seattle pedigrees, ascertained through survivors of myocardial infarction who had raised blood cholesterol and triglyceride levels. Herein, APOAV allele SNP6 (c.56G) is shown to have an increased transmission in affected FCHL members from large pedigrees.

This example involves linkage and linkage disequilibrium (LD) tests on the APOA1/C3/A4/A5 genomic interval in a substantial cohort of white British families with FCHL. The results show that the transmission of FCHL in a subset of these families is linked to the transmission of two independent haplotypes in the APOA1/C3/A4/A5 genomic interval. The first haplotype contains the rare allele at the SNP5 locus and a second the rare allele at the $APOC3^{c.386C>G}$ locus within the APOC3 (or "APOCIII") gene.

To establish the contribution of allelic variation at the APOA1/C3/A4/A5 genomic interval to FCHL susceptibility, linkage and LD tests were performed on a cohort of white British families. For the linkage test, 86 extended families were genotyped with two markers: D11SAPOC3 which resides within the third intron of the APOC3 gene, and D11S1998, which is located approximately 1.7 Mbp downstream of the APOAV gene (FIG. 1). The families contained 177 and 270 affected relative pairs for the CHL phenotype and the triglyceride trait of FCHL, respectively. The D11SAPOC3 marker produced nominal evidence for linkage (NPL+1.72, P=0.042) of the chromosome 11q23 genomic region to the triglyceride trait of FCHL, and this was attributable to an excess of allele sharing in the affected pedigree members of a subset (i.e.35) of the 86 families.

To substantiate evidence for linkage of the APOA1/C3/A4/A5 genomic interval to FCHL, we performed a PDT on 115 white British families using seven SNPs that span an interval of 108 Kbp, followed by a case-control study involving 181 white British probands and 268 pedigree founders. The "PDT," pedigree disequilibrium test, is described at "A Test for Linkage and Association in General Pedigrees: The Pedigree Disequilibrium Test" by Martin E R, Monks S A, Warren L L, and Kaplan N L. Am J Hum Genet 67:146-154, 2000. For a discussion of the SNP naming conventions used in this Example, see Antonarakis et al. "Recommendations for a nomenclature System for Human Gene Mutations," *Human* Mutation 11:1-3 (1998).

The SNPs are named using the annotation described previously, "IVS" means that the SNP is positioned in the intervening sequence, "c" means the SNP is positioned in the coding sequence, "−" indicates the location is upstream by a specified number of base pairs, and "+" indicates that the location is downstream by a specified number of base pairs.

The SNPs included two SNPs within the APOAV gene (SNP5 (APOA5$^{c.56C>G}$) and SNP6 (APOA5$^{c-3A>G}$)), a non-coding SNP within the APOC3 gene (APOC3$^{c\ 386C>G}$), three SNPs upstream of the APOAV locus (SNP3 (APOA5$^{-1,131T>C}$), SNP4 (APOA5$^{-12,238T>C}$), and APOA1$^{-3031C>T}$) and one SNP (APOA5$^{58,892C>T}$) downstream of APOAV.

The results of the PDT produced evidence for increased transmission of the rare alleles at the SNP5 and APOC3$^{c.386C>G}$ loci to affected subjects. For example, the rare alleles at the SNP5 and APOC3$^{c.386C>G}$ loci were respectively transmitted 1.95- and 1.45-fold more frequently to affected family members with the triglyceride trait of FCHL than an unaffected child individuals. The corresponding values for the CHL trait were 1.95 and 1.33, respectively. The rare alleles at the SNP6 and SNP3 loci were also transmitted 1.28 and 1.40 fold-more frequently to affected individuals with the CHL phenotypes of FCHL than to unaffected individuals (P=0.039 and 0.033).

The rare alleles at the SNP5, APOC3$^{c386C>G}$, SNP3 and SNP6 loci were also present at increased frequencies in FCHL probands versus pedigree founders (i.e. "married ins"). For example, the rare allele at the SNP5 locus was present in 21% of the probands compared to 13% of the normolipidemic pedigree founders, whereas the rare allele at the APOC3$^{c\ 386C>G}$ locus was present in 29% of the probands and 15% of the normolipidemic pedigree founders. Importantly, the results from this case-control study and the PDT complemented each other. For the example, the frequencies of the rare alleles at the SNP5, SNP6, SNP3 and APOC3$^{c\ 386C>G}$ loci in FCHL probands and affected FCHL sibs were remarkably similar (i.e. 0.1200, 0.1144, 0.1111 and 0.1486, respectively versus 0.1114, 0.1156, 0.1296 and 0.1566). Likewise, the frequencies of the rare alleles at the SNP6 and APOC3$^{c\ 386C>G}$ loci were similar in the pedigree founders and unaffected sibs (0.0694 and 0.1024, respectively versus 0.0511 and 0.1048) (Table 2). Thus, the case-control data support the evidence that the rare allele at SNP5 (APOA5$^{c\ 56G}$) and APOC3$^{c\ 386G}$ alleles (or alleles in LD) are preferentially transmitted in FCHL.

Probands with the rare allele at SNP5 (APOA5$^{c\ 56G}$) had higher mean triglyceride levels than probands homozygous for the major allele at this locus, and this was particularly evident in those individuals that were homozygous for this rare allele (n=5). Thus, mean plasma triglyceride levels in probands with the APOA5$^{c\ 56G}$ allele were on average 2.2 fold higher than in probands homozygous for the common SNP5 (APOA5$^{c\ 56C}$) allele, and ~1.8 fold higher relative to the heterozygote probands. By contrast, the APOA5$^{c\ 56G}$ allele had no major impact on triglyceride levels in heterozygote pedigree founders, and this was also the case when all individuals with the rare allele at the APOC3$^{c.386C>G}$ locus were excluded from the analyses (data not shown). Only one pedigree founder was homozygous for the APOA5$^{c.56G}$ allele, precluding an assessment of the impact of the homozygous state of this allele (or an allele in LD) on plasma triglyceride in the pedigree founders of white British families with FCHL.

The APOC3$^{c\ 386G}$ allele (or an allele in LD) had a modest impact on triglyceride levels in probands and pedigree founders. On average pedigree founders with the APOC3$^{c\ 386G}$ allele had plasma triglyceride levels that were 31% higher than pedigree founders without this allele (P=0.001), and this increased to a value of 38% (P=0.001) when we considered only those individuals with the common allele at the SNP5 locus (data not shown). Similar increases in plasma triglyceride levels were also observed in pedigree founders with the rare alleles at the SNP3 and SNP6 loci (data not shown). In a complementary analysis, increased frequencies of these rare alleles were observed in pedigree founders that had plasma cholesterol and triglyceride levels >75$^{th}$ percentile age-sex-specific values relative to the rest. This trend was not observed for the rare allele at the APOA5$^{c\ 56C>G}$ locus, indicating that this allele resides on a different APOA1/C3/A4/A5 haplotype than the rare alleles at the APOC3$^{c\ 386C>G}$ and SNP3 and SNP6 loci.

To further test for preferential transmission of the APOA5$^{c\ 56G}$ and APOC3$^{c\ 386G}$ alleles in FCHL, a second study repeated the PDT in families with haplotype data for the APOA1/C3/A4/A5 genomic interval. The distorted transmission of the rare allele at the SNP5 locus in FCHL was restricted to the 35 families that produced evidence for linkage of the chromosome 11q23 locus to FCHL (P=0.0133), suggesting that a major component of this observed linkage may be explained by this allele, or a polymorphism in LD with it or a linked allele. By contrast, the rare alleles at the APOA5$^{58892C>T}$, SNP6, SNP3 and APOC3$^{c.386C>G}$ loci were only modestly over-transmitted in the 35 families that had contributed to the nominal evidence of linkage of FCHL to chromosome 11q23 (P=0.0423, 0.12, 0.19, 0.079, respectively), indicating supporting that these alleles, or alleles in LD with them, may have contributed at most very modestly effects to the observed linkage signal.

The results of the case-control study, included genotype data from 181 white probands and 268 pedigree founders, and essentially mirrored the results of the PDT. Thus, the frequencies of the rare alleles at the SNP5, APOC3$^{c.386C>G}$, SNP3 and SNP6 loci were increased in FCHL probands versus pedigree founders. For example, the rare allele at the SNP5 locus was present in 21% of the probands compared to 13% of the normolipidemic pedigree founders (P=0.01), whereas the rare allele at the APOC3$^{c.386C>G}$ locus was present in 29% of the probands and 14.8% of the normolipidemic pedigree founders (P=0.01). The corresponding values for the rare alleles at the SNP3 and SNP6 loci were 20.5% and 6.4% (P=0.001), and 21.6% and 8.6% (P=0.001), respectively.

Probands with the rare allele at the SNP5 locus had higher mean triglyceride levels than probands homozygous for the major allele at this locus, and this was particularly evident in those individuals that were homozygous for this rare allele. Thus, mean plasma triglyceride levels in probands with the rare allele at the SNP5 locus were on average 2.2 fold higher than in probands homozygous for the common allele at this locus, and ~1.8 fold higher than those found in the heterozygote probands. By contrast, the rare allele at the SNP5 locus had no major impact on triglyceride levels in heterozygote pedigree founders, and this was also the case when all individuals with the rare allele at the APOC3$_{c.386C>G}$ locus were excluded from the analyses. Only one pedigree founder was found to be homozygous for the rare allele at the SNP5 locus, and this has precluded us from establishing the impact of the homozygous state of this allele (or polymorphisms in LD with it) on plasma triglyceride in the pedigree founders. Nonetheless, the inventors suggest that the rare allele at the SNP5 locus (or any polymorphism in LD with it) may have a major impact on plasma triglyceride levels in those persons predisposed to hypertriglyceridemia.

EXAMPLE 8

Modulating and Regulating APOAV Expression with Drugs

A. Human APOAV Gene Expression Induced by Fibrates Treatment

Fibrates are described at Miller D B, Spence J D. "Clinical pharmacokinetics of fibric acid derivatives (fibrates). *Clin Pharmacokinet* 1998; 34(2):155-62. To determine whether fibrates can modulate APOAV gene expression in humans, first, analyze APOAV mRNA levels in primary hepatocytes upon treatment with a fibrate such as fenofibric acid, the active form of fenofibrate, which is a prototype of PPARα ligands. Observe whether treatment with fenofibric acid at a concentration (100 μM) similar to that reached in plasma from patients treated with fenofibrate dramatically increases APOAV mRNA levels. These observations could demonstrate that fibrates induce the expression of the human APOAV, thus supporting the use of APOAV as a new target gene for fibrates. In general, a drug candidate may be tested in cells or animals and the effect of that drug on levels of APOAV mRNA and/or protein observed. Dug candidate which increase such levels have utility as agents which may lower cholesterol and triglyceride levels in appropriate subjects. As described in connection with Example 9, a drug candidate may also have insulin modulating properties which can be measured through the effect of a drug candidate on protein and/or mRNA levels of APOAV in a test animal or cell. Furthermore, which it is shown by the present work that increased levels of APOAV are associated with lowered levels of triglycerides and cholesterol, for individuals having deleterious alleles, lowering APOAV levels may be beneficial.

B. Fenofibrate Regulation of apoA5 Expression via PPARα Activation

Next, one could examine whether PPARα is involved in the regulation of apoa5 by fibrates. Apoa5 mRNA levels could be strongly enhanced in the liver of wild-type mice after treatment with fenofibrate mixed in diet (0.2% w/w). These experiments would show that apoa5 expression is induced by fibrates in vivo in mouse liver and its regulation may largely depend on PPARα activation.

C. Gene Regulation of APOAV by Fibrates at the Transcriptional Level

To delineate the mechanism of regulation of APOAV gene expression by fibrates, functional analysis of the APOAV promoter is necessary. Host cells, such as HepG2 cells, can be transiently transfected with a Luciferase reporter vector driven by the human APOAV promoter and challenged with a PPARα activator. Transcriptional activity of the APOAV reporter construct can be observed for increase in levels after addition of the activator. Co-transfection with PPARα may also have the effect of strongly stimulating APOAV promoter activity. Such results would indicate that the gene regulation of APOAV by fibrates occurs at the transcriptional level.

D. APOAV Responsiveness to PPARα or PPARγ

Transcriptional activation of APOAV gene by PPARα would suggest the presence of a peroxisome proliferator-activated response elements (PPRE) in the APOAV promoter sequence. Comparative sequence analysis of the murine and human APOAV promoters can be performed to reveal the presence of any regions of cross-species conservation containing putative PPREs with a high degree of homology between the putative PPREs and the PPRE consensus defined for PPARs.

To assess whether the putative PPREs mediate any PPARα or PPARγ effects, one should perform transfection experiments using a promoter construct containing mutated versions of any PPREs found. If mutation of any PPREs found abolishes activation of the APOAV promoter by PPARα this would indicate that the human APOAV promoter contains PPREs that act to mediate PPAR action.

EXAMPLE 9

APOAV Expression Levels and Their Effect Upon Human Insulin Levels

Significant differences in plasma triglyceride concentrations in APOAV genetically engineered animals prompted study to determine if alterations in APOAV expression led to changes in plasma glucose or insulin levels as well. Significant differences were also found for plasma insulin but not glucose levels. APOAV transgenic mice were found to have ~80% higher insulin levels than controls, compared to ~220% lower insulin levels in apoA5 knockouts compared to controls. P-values were calculated based on student T-tests. Plasma glucose levels were also examined and no differences were found. Their levels were 173, 166, 132, and 130 mg/dL in ApoA5 transgenics, littermate controls, ApoA5 knockouts, and littermate controls, respectively.

Table 7 Plasma Triglyceride and Insulin Concentrations in ApoA5 Transgenic, ApoA5 Knockout and Littermate Control Mice

| | Triglycerides (S.E.M.) | p value | Insulin ng/ml (S.E.M.) | p value |
|---|---|---|---|---|
| Control (FVB) | 152.9 (±6.3) | 0.000015 | 0.9 (±0.07) | 0.01 |
| APOA5 Transgenic (FVB) | 90 (±7.6) | | 1.6 (±0.29) | |
| Control (C57B16/129Sv) | 150.3 (±26.1) | 0.025 | 2 (±0.16) | 0.0000006 |
| ApoAV Knockout (C57B16/129Sv) | 245.9 (±41.0) | | 0.9 (±0.06) | |

The fact that both transgenic and knockout mice shown differences in insulin but not glucose levels indicate alterations in the function of insulin in these two models. For instance the finding of high triglycerides in APOAV transgenic (yet unchanged glucose levels) supports the hypothesis that these animals are insulin resistant.

These findings suggest that APOAV may plan an important role in metabolic syndrome, insulin resistance, obesity, and diabetes. In addition, they support that therapies directed at modulating APOAV levels or course of action may be useful for treating these common conditions in humans.

Thus there has been described in detail the making and use of the preferred embodiments of the present invention. In view of the present teachings, numerous alternatives and variations may be envisioned by one of ordinary skill in the field. Thus it is intended that the scope of protection for the present invention be limited only by the scope of the appended claims.

What is claimed is:

1. A method for determining an individual's genetic predisposition for elevated triglyceride levels, said method comprising:

(a) detecting at least one single nucleotide polymorphism (SNP) in an ApoAV gene of the individual, wherein the SNP is selected from the group consisting of $APOAV^{c.1259T>C}$ (SNP1), $APOAV^{IVS3+476G>A}$ (SNP2), $APOAV^{-1,131T>C}$ (SNP3), $APOAV^{c.56C>G}$ (SNP5), and $APOAV^{c.-3A>G}$ (SNP6);

wherein the presence of one or more SNPs indicates that the individual has a predisposition for triglyceride levels elevated at least about 20% relative to triglyceride levels in the absence of the SNP.

2. The method of claim 1 further comprising detecting a SNP in an APOC3 gene, wherein the SNP is $APOC3^{c.386C>G}$.

3. A method for determining whether an individual has a predisposition towards elevated triglyceride levels, said method comprising determining the level of APOAV gene expression in a sample from the individual, wherein elevated APOAV gene expression is associated with decreased risk of elevated triglycerides and lowered APOAV gene expression is associated with increased risk of elevated triglycerides.

4. The method of claim 3 further comprising determining the level of APOC3 gene expression, wherein lowered APOC3 gene expression is associated with decreased risk of elevated triglycerides and elevated APOC3 gene expression is associated with increased risk of elevated triglycerides.

5. A method for genotyping an individual comprising detecting a SNP from the ApoAV gene in a biological sample from the individual, wherein the SNP is selected from the group consisting of: $APOAV^{c.1259T>C}$ (SNP1), $ApOAV^{1WS3+476G>A}$ (SNP2), $APOAV^{-1,131T>C}$ (SNP3), $APOAV^{c.56C>G}$ (SNP5), and $APOAV^{c.3A>G}$ (SNP6).

6. The method of claim 5 comprising detecting at least 2 SNPs selected from the group consisting of: SNP1, SNP2, SNP3, SNP5, and SNP6.

7. The method of claim 5 comprising detecting at least 3 SNPs selected from the group consisting of: SNP 1, SNP2, SNP3, SNP5, and SNP6.

8. The method of claim 5, wherein the presence of said SNP indicates that the individual has a genetic predisposition for insulin resistance.

9. The method of claim 5 comprising detecting SNP5.

10. The method of claim 9 further comprising detecting a SNP from APOC3.

11. The method of claim 9 wherein said SNP from APOC3 is $APOC3^{c.386C>G}$.

12. The method of claim 1, wherein the SNP is detected by:

(a) specifically amplifying a SNP from ApoAV comprising a SNP selected from the group consisting of SNP1, SNP2, SNP3, SNP5, and SNP6; and (b) detecting the amplified nucleic acids, thereby detecting the SNP.

13. The method of claim 12, wherein the SNP is specifically amplified using a pair of primers comprising the sequences selected from the group consisting of: SEQ ID NOS: 20 and 21; SEQ ID NOS: 24-25; SEQ ID NOS: 39 and 40; SEQ ID NOS: 41 and 42; SEQ ID NOS: 43 and 44; SEQ ID NOS: 45 and 46.

14. The method of claim 12, wherein the amplified nucleic acids are detected by sequencing.

15. The method of claim 12, wherein the amplified nucleic acids are detected by hybridizing an oligonucleotide probe to the amplified product.

16. The method of claim 14, wherein the probe is labeled with a detectable label.

17. The method of claim 14, wherein the probe is selected from an oligonucleotide comprising the sequence set forth in SEQ ID NOS: 28, 29, 30, 31, 32, and 33.

18. The method of claim 1, wherein the SNP is SNP5 and is detected by:

(a) contacting an antibody that specifically binds to a polypeptide encoded by SNP5 with the biological sample, thereby forming a complex between the antibody and the polypeptide in the sample; and (b) detecting the presence of the complex, thereby detecting SNP5.

19. The method of claim 18, wherein the antibody is labeled with a detectable label.

20. The method of claim 2, wherein the SNP comprises $APOC3^{c.386C>G}$.

21. The method of claim 5, wherein the SNP is detected by:

(a) specifically amplifying a SNP from ApoAV comprising a SNP selected from the group consisting of SNP1, SNP2, SNP3, SNP5, and SNP6; and (b) detecting the amplified nucleic acids, thereby detecting the SNP.

22. The method of claim 21, wherein the SNP is specifically amplified using a pair of primers comprising the sequences selected from the group consisting of: SEQ ID NOS: 20 and 21; SEQ ID NOS: 24-25; SEQ ID NOS: 39 and 40; SEQ ID NOS: 41 and 42; SEQ ID NOS: 43 and 44; SEQ ID NOS: 45 and 46.

23. The method of claim 21, wherein the amplified nucleic acids are detected by sequencing.

24. The method of claim 21, wherein the amplified nucleic acids are detected by hybridizing an oligonucleotide probe to the amplified product.

25. The method of claim 24, wherein the probe is labeled with a detectable label.

26. The method of claim 25, wherein the probe is selected from an oligonucleotide comprising the sequence set forth in SEQ ID NOS: 28, 29, 30, 31, 32, and 33.

27. The method of claim 5, wherein the SNP is SNP5 and is detected by:

(a) contacting an antibody that specifically binds to a polypeptide encoded by SNP5 with the biological sample, thereby forming a complex between the antibody and the polypeptide in the sample; and (b) detecting the presence of the complex, thereby detecting SNP5.

28. The method of claim 27, wherein the antibody is labeled with a detectable label.

* * * * *

UNITED STATES PATENT AND TRADEMARK OFFICE

CERTIFICATE OF CORRECTION

PATENT NO. : 7,238,475 B2
APPLICATION NO. : 10/229834
DATED : July 3, 2007
INVENTOR(S) : Len A. Pennacchio and Edward M. Rubin It is certified that error appears in the above-identified patent and that said Letters Patent is hereby corrected as shown below:

On the first page of the specification, in the second paragraph entitled:

STATEMENT OF GOVERNMENT SUPPORT after "during work supported in part" add

-- by the National Institutes of Health Grant No. HL066681 and --.

Signed and Sealed this

Ninth Day of February, 2010

David J. Kappos

*Director of the United States Patent and Trademark Office*

SEQUENCE LISTING

```
<160> NUMBER OF SEQ ID NOS: 48

<210> SEQ ID NO 1
<211> LENGTH: 1334
<212> TYPE: DNA
<213> ORGANISM: Homo sapiens

<400> SEQUENCE: 1

gagcagagca gataatggca agcatggctg ccgtgctcac ctgggctctg gctcttcttt     60

cagcgttttc ggccacccag gcacggaaag gcttctggga ctacttcagc cagaccagcg    120

gggacaaagg cagggtggag cagatccatc agcagaagat ggctcgcgag cccgcgaccc    180

tgaaagacag ccttgagcaa gacctcaaca atatgaacaa gttcctggaa aagctgaggc    240

ctctgagtgg gagcgaggct cctcggctcc cacaggaccc ggtgggcatg cggcggcagc    300

tgcaggagga gttggaggag gtgaaggctc gcctccagcc ctacatggca gaggcgcacg    360

agctggtggg ctggaatttg gagggcttgc ggcagcaact gaagccctac acgatggatc    420

tgatggagca ggtggccctg cgcgtgcagg agctgcagga gcagttgcgc gtggtggggg    480

aagacaccaa ggcccagttg ctggggggcg tggacgaggc ttgggctttg ctgcagggac    540

tgcagagccg cgtggtgcac cacaccggcc gcttcaaaga gctcttccac ccatacgccg    600

agagcctggt gagcggcatc gggcgccacg tgcaggagct gcaccgcagt gtggctccgc    660

acgcccccgc cagccccgcg cgcctcagtc gctgcgtgca ggtgctctcc cggaagctca    720

cgctcaaggc caaggccctg cacgcacgca tccagcagaa cctggaccag ctgcgcgaag    780

agctcagcag agcctttgca ggcactggga ctgaggaagg ggccggcccg gacccccaga    840

tgctctccga ggaggtgcgc cagcgacttc aggctttccg ccaggacacc tacctgcaga    900

tagctgcctt cactcgcgcc atcgaccagg agactgagga ggtccagcag cagctggcgc    960

cacctccacc aggccacagt gccttcgccc cagagtttca acaaacagac agtggcaagg   1020

ttctgagcaa gctgcaggcc cgtctggatg acctgtggga agacatcact cacagccttc   1080

atgaccaggg ccacagccat ctgggggacc cctgaggatc tacctgccca ggcccattcc   1140

cagctccttg tctggggagc cttggctctg agcctctagc atggttcagt ccttgaaagt   1200

ggcctgttgg gtggagggtg gaaggtcctg tgcaggacag ggaggccacc aaaggggctg   1260

ctgtctcctg catatccagc ctcctgcgac tccccaatct ggatgcatta cattcaccag   1320

gctttgcaaa aaaa                                                     1334

<210> SEQ ID NO 2
<211> LENGTH: 1879
<212> TYPE: DNA
<213> ORGANISM: Homo sapiens

<400> SEQUENCE: 2

gagcagagca gataatggca agcatggctg ccgtgctcac ctgggctctg gctcttcttt     60

cagcgttttc ggccacccag gcacggaaag gcttctggga ctacttcagc cagaccagcg    120
```

-continued

```
gggacaaagg cagggtggag cagatccatc agcagaagat ggctcgcgag cccgcgaccc    180

tgaaagacag ccttgagcaa gacctcaaca atatgaacaa gttcctggaa aagctgaggc    240

ctctgagtgg gagcgaggct cctcggctcc cacaggaccc ggtgggcatg cggcggcagc    300

tgcaggagga gttggaggag gtgaaggctc gcctccagcc ctacatggca gaggcgcacg    360

agctggtggg ctggaatttg gagggcttgc ggcagcaact gaagccctac acgatggatc    420

tgatggagca ggtggccctg cgcgtgcagg agctgcagga gcagttgcgc gtggtggggg    480

aagacaccaa ggcccagttg ctgggggcgg tggacgaggc ttgggctttg ctgcagggac    540

tgcagagccg cgtggtgcac cacaccggcc gcttcaaaga gctcttccac ccatacgccg    600

agagcctggt gagcggcatc gggcgccacg tgcaggagct gcaccgcagt gtggctccgc    660

acgcccccgc cagccccgcg cgcctcagtc gctgcgtgca ggtgctctcc cggaagctca    720

cgctcaaggc caaggccctg cacgcacgca tccagcagaa cctggaccag ctgcgcgaag    780

agctcagcag agcctttgca ggcactggga ctgaggaagg ggccggcccg gacccccaga    840

tgctctccga ggaggtgcgc cagcgacttc aggctttccg ccaggacacc tacctgcaga    900

tagctgcctt cactcgcgcc atcgaccagg agactgagga ggtccagcag cagctggcgc    960

cacctccacc aggccacagt gccttcgccc cagagtttca acaaacagac agtggcaagg   1020

ttctgagcaa gctgcaggcc cgtctggatg acctgtggga agacatcact cacagccttc   1080

atgaccaggg ccacagccat ctgggggacc cctgaggatc tacctgccca ggcccattcc   1140

cagctccttg tctggggagc cttggctctg agcctctagc atggttcagt ccttgaaagt   1200

ggcctgttgg gtggagggtg gaaggtcctg tgcaggacag ggaggccacc aaaggggctg   1260

ctgtctcctg catatccagc ctcctgcgac tccccaatct ggatgcatta cattcaccag   1320

gctttgcaaa cccagcctcc cagtgctcat ttgggaatgc tcatgagtta ctccattcaa   1380

gggtgaggga gtagggaggg agaggcacca tgcatgtggg tgattatctg caagcctgtt   1440

tgccgtgatg ctggaagcct gtgccactac atcctggagt ttggctctag tcacttctgg   1500

ctgcctggtg gccactgcta cagctggtcc acagagagga gcacttgtct ccccagggct   1560

gccatggcag ctatcagggg aatagaaggg agaaagagaa tatcatgggg agaacatgtg   1620

atggtgtgtg aatatccctg ctggctctga tgctggtggg tacgaaaggt gtgggctgtg   1680

ataggagagg gcagagccca tgtttcctga catagctcta cacctaaata agggactgaa   1740

ccctcccaac tgtgggagct ccttaaaccc tctggggagc atactgtgtg ctctccccat   1800

ctccagcccc tccctctggg ttcccaagtt gaagcctaga cttctggctc aaatgaaata   1860

gatgtttatg ataaaaaaa                                                1879
```

<210> SEQ ID NO 3
<211> LENGTH: 16000
<212> TYPE: DNA
<213> ORGANISM: Homo sapiens
<220> FEATURE:
<221> NAME/KEY: variation
<222> LOCATION: (14695)..(14695)
<223> OTHER INFORMATION: SNP1: polymorphic T or C
<220> FEATURE:
<221> NAME/KEY: 3'UTR
<222> LOCATION: (14538)..(15295)
<223> OTHER INFORMATION:
<220> FEATURE:
<221> NAME/KEY: exon
<222> LOCATION: (13598)..(14537)
<223> OTHER INFORMATION:
<220> FEATURE:

<221> NAME/KEY: variation
<222> LOCATION: (13555)..(13555)
<223> OTHER INFORMATION: SNP2: polymorphism G or A
<220> FEATURE:
<221> NAME/KEY: variation
<222> LOCATION: (12974)..(12974)
<223> OTHER INFORMATION: SNP5: polymorphism C or G
<220> FEATURE:
<221> NAME/KEY: variant
<222> LOCATION: (19)
<223> OTHER INFORMATION: SNP5: Ser or Thr
<220> FEATURE:
<221> NAME/KEY: exon
<222> LOCATION: (12968)..(13079)
<223> OTHER INFORMATION:
<220> FEATURE:
<221> NAME/KEY: exon
<222> LOCATION: (12805)..(12853)
<223> OTHER INFORMATION:
<220> FEATURE:
<221> NAME/KEY: 5'UTR
<222> LOCATION: (12797)..(12804)
<223> OTHER INFORMATION:
<220> FEATURE:
<221> NAME/KEY: variation
<222> LOCATION: (12802)..(12802)
<223> OTHER INFORMATION: SNP6: polymorphism A or G
<220> FEATURE:
<221> NAME/KEY: 5'UTR
<222> LOCATION: (12280)..(12285)
<223> OTHER INFORMATION:
<220> FEATURE:
<221> NAME/KEY: TATA_signal
<222> LOCATION: (12244)..(12249)
<223> OTHER INFORMATION:
<220> FEATURE:
<221> NAME/KEY: CAAT_signal
<222> LOCATION: (12213)..(12217)
<223> OTHER INFORMATION:
<220> FEATURE:
<221> NAME/KEY: variation
<222> LOCATION: (11674)..(11674)
<223> OTHER INFORMATION: SNP3: polymorphic T or C
<220> FEATURE:
<221> NAME/KEY: variation
<222> LOCATION: (567)..(567)
<223> OTHER INFORMATION: SNP4: polymorphic C or T

<400> SEQUENCE: 3

```
ctcaagtaat ccttctgcct cagcctcctg agtagctagg accacaggtg ccaccatacc     60

tggctaattt ttgtattctt tgcagagaca gggtctcgct acattgccca ggctggtatc    120

gaactcctgg gctcaagcga tcctcctgcc ttgccttctc aaagtgttgg gattacaggc    180

atgagccact gtgcccagcc tcaaaattta atgtataaag ttttccttaa tttttcttag    240

cacaaaaacc ctggccccca acaataccta gttttctcca ggccggagtc ccactctttt    300

accctttca gagagaataa gcatctggtt ttctgctgct ttgggggtac ccagccaagt    360

agagttgaag agaacagctg cttctcaaac agactctcga ccaactgcca tatttctagt    420

cccactgcca cccactcttc cagaagaatg ttgacactaa tgtcagagca tttggagagt    480

ttagtagtga aaatcagggg ccttcttggc tttctccact gctgcttcaa aattcatgtc    540

aggtgtgcct gtcaccaccg tttgacyatt tggaagcttt ccagcttccc aaatgttgtt    600

atttttgtct ccttttctat tttccctttg ggtttatgca ttttgtaaaa agtgcacttc    660

aatgccacgt tattgagatt tcagagaaca gcagaggcta atgcatgcaa ttaatccacc    720

gtccgttact agaagtcaat cggatgctct ttagtctctc ttccccatat actagtttaa    780

aagttatcca ttctttctat tcgttttatg ggttatcctt aaaattttaa tattcttgtc    840

tgacctaaca aagtctatag ataatcaata tccctatctt tctcccgaat aatgcaaagg    900
```

-continued

```
ctgctgaatg ctttcacttt gatctctcct ttcccatttc caggttgctt cggtctgata    960
ttttagttcc tcattacttt taacacctcc tccaaagtag tcccttcatc aatagatgtt   1020
tttgagccct ccctaccatg tgataagcac tggtctaggc actgggagta cagtaggaaa   1080
tgagataaac ttggccaggt gtagggtggc ttacacctgt aatcccaaca cttttgaggc   1140
cgaggcgggc agctcgcttg agcccatgag ttcgagacca gcctgggaaa catagcgaga   1200
cccccgtccc tacaaaaaaa tataaaaatt agctgggcat ggtggtgtat gcctgtggtc   1260
ctagctactc agaagactga ggtgggagga tcatctgagc ccagggtggt cgaggctgca   1320
gtgattacac cactgcactc catcctgggc aacggtgaga ccctgtctca aaaaacaaac   1380
aaacaaacaa gcaaacaaaa cccccacaaa ctaaactatg tgtaaataca tttttgttag   1440
gtagaactat atgaaattgc cactatttga ccaattttta gtgaaaacta gtctcataag   1500
tgtgtgtgtg tgtattttca ctaatgtttt ttggatttac ctaaacgttt actaatttca   1560
ttgctcccca tgtctccttc tatcctattc ctttttctg ggttctgttt ccttttcaga    1620
tttttagtag ttcttttcag tgaggatctg tgagtggtaa actctctttc tctgaaatta   1680
acttcttcct ctcaaataat agttcacctg agtataagtc ttggttggcc attaatttcc   1740
tttcagtctt tagaaggtac attgatgata aatcagttgc cggtttaatc atgcttcgtg   1800
tgtagatcat tagtctttct ctttggttga ttttaagata tccattgcct tcagtgttct   1860
gcagattcct gtgatgtgtc ctcatttggt tgtgtgttaa tttttcctac caagactcag   1920
gatgcttcct gtacctgagg attccggtca catcttgctt caatgtttga aatttctcag   1980
ccatcatctt ttgaatattg cctcttccac agtccctgtg ttctcttcgt ggaaatccta   2040
caggcatata ttggacctcc cattctgtcc tccatgtctc ttaccgtcta ttcataccct   2100
ccttttata tttaattttt ttgagacaga gttttgctct gtggcccagg acggagtgca    2160
attgcatgat cttggctcac ggcaaactct gcctcccagg ttcaagctat tctcctgcct   2220
cagtctccca agtagctggg attacaggca tgcaccacca cgcccggcta atttttgtat   2280
ttttagtaga gacggggttt caccatattg gccaggctgg tctgaaactc ctgacctcag   2340
gtgatccacc cacctcggcc tcccaaagtg ctgggattat aggcatgagc caccatgcct   2400
ggccaatatc acccgcctcg gcctcccaaa gtgctgggat tacaggcatg agccaccgtg   2460
cctggtcaat atcctccttt ttatttctgt gattctttct gtgtgatttt ctcagatcta   2520
ccttctagct tactaattct ctctccaact gtagctaaat gtgttttata ttataatgac   2580
tatatttttt tcacttatag atgttctatt taattctctt tctttttgac aaatagaact   2640
tatttcaaaa caaacaaaag gccaggcatg gtggttcatg cctgtaatcc cagtgctttg   2700
ggaggctgag gcaggaggat tgcttgagcc caggagttca aggccagcct gggcaacata   2760
gtgagatcct ttctctacca aaaaaataaa aaatcagctg ggtgttgtgg gacactcctg   2820
tagtcccaga aactacagat tcttgggagg cagaggctgg aggattgctt gaggcagagg   2880
ctggaggatt gcttgagcct gggaggttga ggctgcagtg aactgtgatc atgccactgc   2940
actctagcct gggtgacaaa gtgagatcct gtctcaaaaa caaataaaca aacaagcaaa   3000
gaaacaaaaa aatgcttaca caggttacta ctttcttgct gggatagttt taacactgcg   3060
ttaagcataa acacctttct ttctgaaatg tatttgagat gtatattgat ttttaaaaaa   3120
cccacacctc cattaaggtc tggtgatagc agtagaaaca atgtagagtg gctccacaat   3180
catatagatg tttttggtgc gttctgagat ggagtccagg aacaccaagt aaagactgct   3240
```

-continued

```
acctcacagt ttacatctga gttcttagaa gacaagactg aaggagaaca atttgtaaca   3300
agatttactt ggcccgggtg tggtggctca cacctgtaat cccagtactt tgggagcttt   3360
gggagtccga ggtgggtgga tcacctgagg tcaggagttc aagaccagcc tggccaacat   3420
ggaataaccc ccatctctac taaaaataca aaaattagcc aggcacggtg gcacacgcct   3480
gtaatcccag ctactcagga ggctgaggca ggagaatcgc ttgaacccaa gtgactgggt   3540
tgccgagagc cgagatcacg ccactgtact ccagccaccc tgggtgacag agtgagactc   3600
tgccaaaaaa aaaaaaaaaa aaaaaaaaat acttactgtt cagaaggaga agtcataatg   3660
ttgctttaaa gaacaggtca caaaagaaag actctagaag atcttctcac ttggtgcata   3720
tcaagtgtct atttgagacc catacacttg cttaatccat gtgtttaagg caaaagtgct   3780
gctgctgagc agtaaggaat aaggtacctg ctaaccttta ccaatctaca ttttaaaatc   3840
cttcttacta cacatccaga atgagtcagc aattcttgtg tattaaaaaa caaaaacaca   3900
aaacaaagta gaggggcaac tctcttaaaa atgcagctat ccgcaaacac tgtgatacaa   3960
aacgacagtc aaggaaaggg cagcacaaac aagttcacct ggaaggaatc tgttcaaagt   4020
ctctggattt aagaacaagt tccctaaaag ctcttactta cagaagaaat cggataataa   4080
atgtagctgg aatgatggaa ttctttaagt tttcattttg ttttgggcaa ctctgtggcc   4140
caggctggag tgcagtggct tgatcacggc tcactgcagc ctcaacctcc caggctctgg   4200
tgatcctccc acctcagcct cctgagtggc tgggactaca agcatgtgtg ccaccatgct   4260
aggctaattt ttgtatttta tttttagttt tttttttttt tttttttttt ttgtagagac   4320
aggttttgcc atgttgccaa ggctggtctc aaattcctgg gttcaagtga tcctcccatc   4380
tcagccttcc aaagagctgg gattacaggc atgagctact gcacctggcc tagaattttt   4440
taaaaatcac tatctggcaa ctctcaggat aatattcgat tcaggcaagg atcatcaatg   4500
aatgctaaaa ccattgggtg aaaaattgtt gcagaatggg atgctcacat ggcttcaaag   4560
tattgctcca caaattactt atcaataacg taaaaaacca aactttacta gccatggaga   4620
aatctggttg ttatcacttt aatggagtga tcaaacttaa catcactaaa tagagtgcaa   4680
cctccagcta ggatacagta agaagggcca gatatcacct agtatttttg ccaaaaatgt   4740
ttaaccttaa tctaatcatg agaaagtaat cactcaaatc cagaatgtgg gacattttac   4800
aagatgtcct ccttgcactc ttccaaaaaa aaatcaatgt catgaaaaca aacaaatggt   4860
ggggttgggg agaacggttc taaatttaaa aactaaagtg ggataacaac cagatgagat   4920
gtgttagagc ttgaatttac agagagagaa aaacaactat gaaagcattt tggggaaaat   4980
ctgaatatgt aggatatgtt agatgatatt aaggaattgt gttaattttc aaaggtatga   5040
taatgttttt ttcttttgta aaagagtcct tatttttcac aatgtatgtt gaagtattca   5100
gagtgaagtg tcatgttggc tataattatt tcaaatggtt ccacacacaa agcacatacc   5160
acatacacat atacatatac ctccaaccaa ctcaaaacat gttcaacact gaaactataa   5220
gatgccacca aacagggaag catgagtgtg tgttgcatct acccattgta tcaatccagg   5280
ttcagtcaga aaaacaaaag ccattccacg tatttcaagc atgaaaggct ttaaaacaaa   5340
aaattaaagg tttatccaac tcttggaagg gctggaggag tgaccacctt ggtttgcagt   5400
tcagaaggag tgactctcaa acgctcatta gtaagtggct acaaatggga agctcgcctt   5460
attatgcctg caatatcaat gcatgtgatt cctgggaagg tcacccagaa gctgctttaa   5520
actccaagcc tgtccatgct tctgtctgca accggcattg aaacataatg gcctctcctc   5580
ttccgtctca cgctggctga ctctaaccta ggctcatata gagaagggat tctagaaaat   5640
```

-continued

```
gtattaatag ttccaagtgt cccctctgca tctcataaaa gaccttagaa agggcactga   5700
taatgctatt tgcaaaaaga caatccagcg cagttgtatt ttacagcaca ggctctttaa   5760
gtttgggtta tcagcaaaaa accattagag tatgagaaat tcctttttaa attgtggcaa   5820
aatatacata acataaaaat taccattgta gctattgtac attgtagcta agtatatagc   5880
ccagtagcac taaatacatt tacactgttg tgcaccacta tctagctcca gaaactttta   5940
atcttcccaa acagaaactt gtacctatta accaatacct tctccttcct cacttctcct   6000
agaaaccaga attatacttt ctgtctctac aaatctgact attctggata cctcagaatc   6060
acagtatgtg tcgttctacg actggcttgt ttcacttagc atcatgtctt caagggtcat   6120
ccacgttata gcatgtgtca gatttccttt tcttttcttt tcttttttt ttttttgag   6180
acacagtctc gctctgtcac ccaggctgga gggcagtagc acaatctcag ttcactgcag   6240
cctctgcctt ccaggttcaa gcaattctcg tgcctcagcc tcccaagtag ctggaatgac   6300
aggcatgcac caccacacct ggctaatttt tgtattttta gtagagacgg ggtttacca   6360
tattggccag gctggtcttg cacttccggc ctcaagtgat ctgcccgtct cggcctccca   6420
aagtgctggg attacaggcg tgagccacta tgcctggccc ccgattgtca ttatttaagg   6480
ctaagtgata ttttgttgtc tgtatatacc acaatttgtt tattcattca tctgtcaatg   6540
gacatttggg ttgtttccac cccctggtta ttgtggataa tactactagg aacacgagca   6600
tacaaatatc tgctccagtc cctgctttta tcttttggat atatgcccag aggtggaatt   6660
gctgggtcat aaggtaattc tagattaaat tttttgaggg actgccgtat tgttctccac   6720
catagctgca ccattttacc tttccagcag cagcgtacaa gcggtccagc ttctccacat   6780
cttcacccac acttgctatt tttggctttt attttatttt ttaaaataac attctaatgg   6840
gtgttaagtg gtcagaaatg gttcttttag gagtagagat agaggccagg gggatggctc   6900
acacctgtaa tcccagcact ttgggaggcc taggtgggcg gatcacttgg ggtcaggagt   6960
ttgagatcag cctggccaac atggtgaaac tccatctcta ttaaaaatac aaaaattcgc   7020
tgggtgtggt ggtgtgcact cccagctact tgggaggctg agggaagaga atcgcttgaa   7080
cccgggaggc ggtagttgca gtgagccgag atcacaccac tgtatggcct ggtgacagag   7140
caaggctctg tctcaaaaaa aaaaaaaaaa aaaaaagagt agagatagaa aagcattgaa   7200
aacacagcct cagctcagct cagtctgcca tggtgggaag ccattaattc ttcactcttg   7260
aaaccttttc gtccttggtg tggcagaggc tgcaagtctc ctctgcaact ttattcttcc   7320
cttctttctc agttataaaa tccctgattt tagaaatatc tttattgaga tataattcac   7380
ataccataac attcactaca attgaatggt ttttagtata ttcacagatt tgtacaacta   7440
tcaccacaaa ctaagtttag aactttttc atcatcccac aaagaaaccc cacacccatt   7500
agcagttatt cactatttct ccccaatcaa cctcccctcc cctcaatagc cctaggcagc   7560
caccagtcta ctttctgtct ctacctattt gtcttttctg gacattttat acaaatgaga   7620
ttttacaaca tgtagtcttt tgtgactggc ttttttcccc tagcataatg ttttccaggt   7680
tcatctgtgg tgtagcaggt atcagtactt caacccttt tattgccaaa taatattcca   7740
ctatatggat aggtaacatt ttgtttatcc attcatcaat tgatggacat ttgggttgtt   7800
tccattttct tgactgttat gaataatgtt gccatgaaca ttaatgcaca agtttttgtg   7860
cagatgtgta ttttcatgtg tcttggtttt atacctagga atagaattgc tgagtcatag   7920
gagaactcct ccatgtttaa ccattaatga actgccgaac tgttttccaa agaaattgca   7980
```

-continued

```
ccattgtaca atcccaccag caatgtatga gggtagaatc cctgattttt aactgatcat   8040
tgaactcagg cccattcaaa acaaagatga catttcctaa ccttccttac aagtagttct   8100
gaccagtgag atgggagaag aagttaggtt ttgtccttaa aagaaaggag agtggctggg   8160
tgcagtggct cacgcctgta atcccagcac tttgggaggc cgaggtgggc ggatcacctg   8220
aggccgggag ttcaagacta gcctgaccaa catggagaaa cctcgtctct actaaaaata   8280
caaaattagc tgggcgtcgt ggcgcatgcc tgtaatccca gctactcagg aggctgaggc   8340
aggagaatcg cttgaacctg ggaggtggag gttgtgatga gccgagattg tgccatcgca   8400
ctctagcctg ggcaagaaga gcgaaactcc atctcaaaaa aaaaaagaaa gaaaggagag   8460
tacattctac actctcctct cctccaccct gcccccttc cagtggctgg atgtggacat    8520
ggtggtaagc tatcttagat catgtggaca agggaaacac atagggatat tagaacctcc   8580
agacagaagg aacttaggac cctggacagc tttgtggagc agtgctccca taccagcgtg   8640
aagttttgta tgggagaaaa catacatttc cagcttttgt aagccactgt tattttgggt   8700
ctctctcaga gcagccaaat atataattta actaatatat tttctttctg tgattcttct   8760
ttattttgat tatacttcta cttctctgcc cctcttttag gtgggaggtg ctgctccaag   8820
cactaactca gaatatagac cctctccctc ttgtaatagt gccagcttgg agttctttgc   8880
ttccactgta ggggaaggaa ggaaaaaata tggagaactc acatccactc ttcattgtcc   8940
tcaaacagaa gtaacccatt ttgttctgct cacagcccat tggccagaac taactgtatg   9000
gccccaatct aattgcaaag gagtctggga agtacagcac agcacatgga tctttggaaa   9060
gcgttaattt tctctgccaa aggcttcttt tgttgttgtt gttgtttgaa atggagtccc   9120
gctccgtcac ccgggctgga gtgcagtggc cctatctcag ctcactgcaa cctccacctc   9180
ccaggttcaa gcactcctcc agccttggcc tcccaagtag ctaggattac aggcgtgtgc   9240
catcatacct ggctattttt tttgtatttt tagtagagac agggttttac cgtgttggcc   9300
aggctggtct caaactcttg gcttcaagtg atccgcctgc ttcggtctcc caaagtgttg   9360
ggattacagg cgtgagccac tgtacccggc caatactggt gttttctgac ctcagcgttt   9420
ttcttttctc ctgccatgta ctctccctag agatttcatc tactcccaag tcttccactg   9480
ctcctatctg ctgatgactc ccaaaactca gtctccagcc gagacttctc tcctgggctt   9540
gagacatatg tatccaactg ccagaacatc tccagtggac agcctttggg cacaaggcca   9600
cactagcttg tgggtacaag taatcaccca aagtcaattt cagtggctct ccactcccac   9660
attttttcaa cccctggaaa tgttcccttc ccaaatactc tgagtctctc ttctcttttg   9720
atgactgtgg ttttgtgact ggatggtagc tcctgttgct ttttttcctt tcaaatgaat   9780
tttctcttag gaggcttctt agccattaag caaatagacc tcaactgggc ttgccctatg   9840
cctatctgaa acccagctta ggttcgagtt aggactcctg ttaatctgag ctctcacttc   9900
ctgtcccaac ctgcttattt tttttggtga aagaaaatat catcccccta gttgctcaga   9960
aacctgggaa tcattgggat tttttcctct ccttcacctt cctcatccaa tcagtcacca   10020
agtgctatca actctgctgc cttagtagcc ctcaatatat acttacctat caaccatcac   10080
tgctatgcca tacttcaggc cttcatttct cacttggatt attaaaatat ccctaaatag   10140
ttcctctgcc ttctctctgg ccaccctcct gagtgatctc tccatcatgt acctttcagt   10200
gactgcttgc acaagcccct ttgtgacttg gtcatagtct gctctcttga accaccagag   10260
ccaagcacct gggttctgat tctggttgca actcttactg cgtgatgatg gacaggccac   10320
ttgatctcct caaacctcag ttcctaaatc aaatgaatga ttgaattcag tcacttaact   10380
```

```
ttgtatgtag taggtaggca ctgtgcaaaa catactagtg gatatagaga tgaataagaa 10440
aaagcccctg cactcaaaga gctctcggat tcatcaacaa attattgtgc agttagatag 10500
taagtgctat aatccaggaa tatacagtgt tgtgtgaata atgtggaatc agtttatctc 10560
cagagcagaa aaaggtgaag gccgaagaag gcattcagag tgatactgga gctgtgtagc 10620
aggggctact actgttccct caaatccttt cttctcttct tcctgagtaa tagagtcctt 10680
tttcagctag gcatacagcc atccaaaata aaaactatat ttcccagcct ccttttcagc 10740
taagtgtagc catgtgacta agttgtggcc aatgggatgt cagtacaagt ggtaatggca 10800
atatctggga tgtgtcttta aaaggaagga acatgtcctt ctccttttcc tccttcctgt 10860
tccctgggag gtgaacttgg tagctggagg tgaagcagct ggaacttgga tatgagcgtc 10920
ttgttgatga taatagtgca acaagataaa agcagcccga gctggcctac atttacatga 10980
gaaggaaata agactccatt ttgtttaagc tattctcttg catatatata tacacatata 11040
tatcagctaa gtgtagccat gtgactaact tgtggccaat gggatgtcag tatgagtggt 11100
aagagcagta tcttgtatat atatatgtgt atatatacac acacacatat atatacatat 11160
atgtatgcaa gaatataaaa tatacatgtg tgtgtgtata tatatacaca catatatatg 11220
tcccttgcag ccaagtctaa ttctaactaa tacaaactaa ctctaaaaaa tgaatatata 11280
ttcaccaggg gataggctat ttcaagcaga gggaagcctg tataaaggct cagggaatgc 11340
tgtggtttta tgtggcagca gatgagactg gaaatgagtc aggatgagcc acagtggagg 11400
atgaattaaa tgggcaggag tgtggtagaa agacctgttg gaggctatga atgcaatcaa 11460
ggtgacagac aactggtgca atgatggtag tggaaatgga ggagagggga ttgattcaag 11520
atgcatttag gaccaagaat cgggagcttg tgaacgtgtg tatgagtact gtagacggag 11580
tgggtgtgtc atcagagaag atctgagcat ttgggcttgc tctcctcaga ggccctgcga 11640
gtggagttca gcttttcctc atggggcaaa tctyactttc gctccagttc ctggggctca 11700
gagtccctgg cccagatgcc tcttgccatc tcatcttcac cctgcctggc ttcccttgct 11760
tgttccagga ttgtttcata aagagggatg tggttggtct ttaaccctat gaatgctggc 11820
tgaggatgcc tgcggaacct gtagtgaagc tttcaggggc tgctcgggtt ctggctggta 11880
ggtgaacact gtccatcttg ccggctggga cacagtgact ctgggtagtt gtgtaagaga 11940
ggggcccttg gcagacaaac aggttcttct ctgttggtgg gccagccagc aggtcagtgg 12000
gaaggttaaa ggtcatgggg tttgggagaa actgggtgag gagttcagcc ccatcccccg 12060
taaagctcct gggaagcact tctctactgg ggcagcccct gataccaggg cactcattaa 12120
ccctctgggt gccagggaaa gggcaggagg tgagtgctgg gaggcagctg aggtcaactt 12180
cttttgaact tccacgtggt atttactcag agcaattggt gccagaggct cagggccctg 12240
gagtataaag cagaatgtct gctctctgtg cccagacgtg agcaggtgag cagctggggc 12300
agagggatgg gggtcacagt cctaagggag ggcattgcag gtggcctcag gggagagcct 12360
ggggtggccc ctaagacgtc ctcttggaac attttggcag agttgcctct tcgccctcat 12420
tatggctcag tttttccacc atgaaatggg agggagggag acaggtgggc aggggagagg 12480
tggtagaagt ggcctagaga actgttcctg gggtctggga cctttgcgaa ggggttagag 12540
caccacgctc cctgctatgt gactgaggta gcaagagcac gccctcttcc catgtttgag 12600
gaagacaccc tagcctcctt gactcaccta ggtcagtcct cttgagcccc aacagctctg 12660
tgctccccag cccaaggaag ggtaacaggg atttcgggca gttgcccctg cagaggcccc 12720
```

-continued

```
ctgggcaagt cccctgcgcc atgtcccttc gtctccttct tcccctaacc aggcctccct  12780

ccacctgtct tctcagagca grta atg gca agc atg gct gcc gtg ctc acc     12831
                           Met Ala Ser Met Ala Ala Val Leu Thr
                           1               5

tgg gct ctg gct ctt ctt tca g gtgggtctcc gaccctgact tcaacgtggg     12883
Trp Ala Leu Ala Leu Leu Ser
10                  15

ggtgtgggtg gaggctggcc agagggccct gtccaccctg ggggaggaga gcccaggccc  12943

tgattaccta gtccctctcc acag cg  ttt tsg gcc acc cag gca cgg aaa     12993
                           Ala Phe Xaa Ala Thr Gln Ala Arg Lys
                                       20                  25

ggc ttc tgg gac tac ttc agc cag acc agc ggg gac aaa ggc agg gtg    13041
Gly Phe Trp Asp Tyr Phe Ser Gln Thr Ser Gly Asp Lys Gly Arg Val
                30                  35                  40

gag cag atc cat cag cag aag atg gct cgc gag ccc gc  gtgagtgccc     13089
Glu Gln Ile His Gln Gln Lys Met Ala Arg Glu Pro Ala
            45                  50

aggggaaggg gtgtaggcga agggaggaga cagctgggcc atgccatgat gacctgcctc  13149

tgctgcctca acctctgtgg ccgctgctgg gacagaggaa aggagcggtg ctagctctgt  13209

ctgcagatcc cggccatcct gggctcttta gcgccctctg cctgcagccc ccgccttgac  13269

aactccgtag ctgttgcccc cttgctcact gaggcgcggg acctgggatc aatcgggagg  13329

acgcccgctg cagtccccag aatcaaagga tgatgtggcg catctatgtt tctttggaga  13389

gtgttgtagg tctggatttg tatgggcaat gtgtttgtgc ttcgtgcgtg agttgttact  13449

ggccagggct aggacaagag ccctcgaccc tggggccaac gccctgcgtc cttggttccc  13509

ccagaggatc agtgcgcgat gacttgggga caaaggagat gatggrggct agcagtctga  13569

cggcctggat atctgtcccc ttctccag g acc ctg aaa gac agc ctt gag caa    13622
                                 Thr Leu Lys Asp Ser Leu Glu Gln
                                 55                  60

gac ctc aac aat atg aac aag ttc ctg gaa aag ctg agg cct ctg agt    13670
Asp Leu Asn Asn Met Asn Lys Phe Leu Glu Lys Leu Arg Pro Leu Ser
        65                  70                  75

ggg agc gag gct cct cgg ctc cca cag gac ccg gtg ggc atg cgg cgg    13718
Gly Ser Glu Ala Pro Arg Leu Pro Gln Asp Pro Val Gly Met Arg Arg
    80                  85                  90

cag ctg cag gag gag ttg gag gag gtg aag gct cgc ctc cag ccc tac    13766
Gln Leu Gln Glu Glu Leu Glu Glu Val Lys Ala Arg Leu Gln Pro Tyr
95                  100                 105                 110

atg gca gag gcg cac gag ctg gtg ggc tgg aat ttg gag ggc ttg cgg    13814
Met Ala Glu Ala His Glu Leu Val Gly Trp Asn Leu Glu Gly Leu Arg
                115                 120                 125

cag caa ctg aag ccc tac acg atg gat ctg atg gag cag gtg gcc ctg    13862
Gln Gln Leu Lys Pro Tyr Thr Met Asp Leu Met Glu Gln Val Ala Leu
            130                 135                 140

cgc gtg cag gag ctg cag gag cag ttg cgc gtg gtg ggg gaa gac acc    13910
Arg Val Gln Glu Leu Gln Glu Gln Leu Arg Val Val Gly Glu Asp Thr
        145                 150                 155

aag gcc cag ttg ctg ggg ggc gtg gac gag gct tgg gct ttg ctg cag    13958
Lys Ala Gln Leu Leu Gly Gly Val Asp Glu Ala Trp Ala Leu Leu Gln
    160                 165                 170

gga ctg cag agc cgc gtg gtg cac cac acc ggc cgc ttc aaa gag ctc    14006
Gly Leu Gln Ser Arg Val Val His His Thr Gly Arg Phe Lys Glu Leu
175                 180                 185                 190

ttc cac cca tac gcc gag agc ctg gtg agc ggc atc ggg cgc cac gtg    14054
Phe His Pro Tyr Ala Glu Ser Leu Val Ser Gly Ile Gly Arg His Val
                195                 200                 205
```

-continued

```
cag gag ctg cac cgc agt gtg gct ccg cac gcc ccc gcc agc ccc gcg    14102
Gln Glu Leu His Arg Ser Val Ala Pro His Ala Pro Ala Ser Pro Ala
            210                 215                 220

cgc ctc agt cgc tgc gtg cag gtg ctc tcc cgg aag ctc acg ctc aag    14150
Arg Leu Ser Arg Cys Val Gln Val Leu Ser Arg Lys Leu Thr Leu Lys
        225                 230                 235

gcc aag gcc ctg cac gca cgc atc cag cag aac ctg gac cag ctg cgc    14198
Ala Lys Ala Leu His Ala Arg Ile Gln Gln Asn Leu Asp Gln Leu Arg
    240                 245                 250

gaa gag ctc agc aga gcc ttt gca ggc act ggg act gag gaa ggg gcc    14246
Glu Glu Leu Ser Arg Ala Phe Ala Gly Thr Gly Thr Glu Glu Gly Ala
255                 260                 265                 270

ggc ccg gac ccc cag atg ctc tcc gag gag gtg cgc cag cga ctt cag    14294
Gly Pro Asp Pro Gln Met Leu Ser Glu Glu Val Arg Gln Arg Leu Gln
                275                 280                 285

gct ttc cgc cag gac acc tac ctg cag ata gct gcc ttc act cgc gcc    14342
Ala Phe Arg Gln Asp Thr Tyr Leu Gln Ile Ala Ala Phe Thr Arg Ala
            290                 295                 300

atc gac cag gag act gag gag gtc cag cag cag ctg gcg cca cct cca    14390
Ile Asp Gln Glu Thr Glu Glu Val Gln Gln Gln Leu Ala Pro Pro Pro
        305                 310                 315

cca ggc cac agt gcc ttc gcc cca gag ttt caa caa aca gac agt ggc    14438
Pro Gly His Ser Ala Phe Ala Pro Glu Phe Gln Gln Thr Asp Ser Gly
    320                 325                 330

aag gtt ctg agc aag ctg cag gcc cgt ctg gat gac ctg tgg gaa gac    14486
Lys Val Leu Ser Lys Leu Gln Ala Arg Leu Asp Asp Leu Trp Glu Asp
335                 340                 345                 350

atc act cac agc ctt cat gac cag ggc cac agc cat ctg ggg gac ccc    14534
Ile Thr His Ser Leu His Asp Gln Gly His Ser His Leu Gly Asp Pro
                355                 360                 365

tga ggatctacct gcccaggccc attcccagct ccttgtctgg ggagccttgg         14587

ctctgagcct ctagcatggt tcagtccttg aaagtggcct gttgggtgga gggtggaagg  14647

tcctgtgcag gacagggagg ccaccaaagg ggctgctgtc tcctgcayat ccagcctcct  14707

gcgactcccc aatctggatg cattacattc accaggcttt gcaaacccag cctcccagtg  14767

ctcatttggg aatgctcatg agttactcca ttcaagggtg agggagtagg gagggagagg  14827

caccatgcat gtgggtgatt atctgcaagc ctgtttgccg tgatgctgga agcctgtgcc  14887

actacatcct ggagtttggc tctagtcact tctggctgcc tggtggccac tgctacagct  14947

ggtccacaga gaggagcact tgtctcccca gggctgccat ggcagctatc aggggaatag  15007

aagggagaaa gagaatatca tggggagaac atgtgatggt gtgtgaatat ccctgctggc  15067

tctgatgctg gtgggtacga aaggtgtggg ctgtgatagg agagggcaga gcccatgttt  15127

cctgacatag ctctacacct aaataaggga ctgaaccctc ccaactgtgg gagctcctta  15187

aaccctctgg ggagcatact gtgtgctctc cccatctcca gcccctccct ctgggttccc  15247

aagttgaagc ctagacttct ggctcaaatg aaatagatgt ttatgataga agtttgcctg  15307

gcgtgactct catttggacc atgtctgaaa gcagtggcct caccactatc cccaaagcac  15367

acccatcacc cactccattc ccttgctgct ctttctcatc cacccactcc cagtccaggt  15427

ctgtcaaagg gggtctggct gggctctgct tcagggatcc tggctagaca acggctgtct  15487

gtcacacctg gcaggagggc ctgggttacg ggcccttcct ctgcacctgc actgttcact  15547

agcctgctcc cccacaggac actgtgcatg gaatgcaggc tgtgtctgga agagctgtgg  15607

ccctggtgga cctaagattc ctgaggtggg ctgcctcctt tgttcctgct gttctagagt  15667
```

-continued

```
ttgaatggcc tctttttatg ccggactctc ttctggggac tcccctcact caggggcacc  15727

aatgctccct atagatcccc tgggaactga aactggggtg tggtggagga cgtggaaagg  15787

gtaaacacag ctccttgtct ttggacttcc ctgtccggcc ccctttcctc ccagctcagc  15847

ctactgtccc cgggttctca gcacctgcct gctccccaac cccatagcac agaccccaca  15907

catatgtagg ctcatcatgc ctgcaggctg gtcttccctg acaccgtgga ttttgacaat  15967

gttggcaaca gaactgggtt gtggacccag cac                               16000
```

<210> SEQ ID NO 4
<211> LENGTH: 16000
<212> TYPE: DNA
<213> ORGANISM: homo sapiens

<400> SEQUENCE: 4

```
ctcaagtaat ccttctgcct cagcctcctg agtagctagg accacaggtg ccaccatacc     60

tggctaattt ttgtattctt tgcagagaca gggtctcgct acattgccca ggctggtatc    120

gaactcctgg gctcaagcga tcctcctgcc ttgccttctc aaagtgttgg gattacaggc    180

atgagccact gtgcccagcc tcaaaattta atgtataaag ttttccttaa tttttcttag    240

cacaaaaacc ctggccccca acaataccta gttttctcca ggccggagtc ccactctttt    300

acccttttca gagagaataa gcatctggtt ttctgctgct ttgggggtac ccagccaagt    360

agagttgaag agaacagctg cttctcaaac agactctcga ccaactgcca tatttctagt    420

cccactgcca cccactcttc cagaagaatg ttgacactaa tgtcagagca tttggagagt    480

ttagtagtga aaatcagggg ccttcttggc tttctccact gctgcttcaa aattcatgtc    540

aggtgtgcct gtcaccaccg tttgaccatt tggaagcttt ccagcttccc aaatgttgtt    600

atttttgtct ccttttctat tttccctttg ggtttatgca ttttgtaaaa agtgcacttc    660

aatgccacgt tattgagatt tcagagaaca gcagaggcta atgcatgcaa ttaatccacc    720

gtccgttact agaagtcaat cggatgctct ttagtctctc ttccccatat actagtttaa    780

aagttatcca ttctttctat tcgttttatg ggttatcctt aaaattttaa tattcttgtc    840

tgacctaaca aagtctatag ataatcaata tccctatctt tctcccgaat aatgcaaagg    900

ctgctgaatg ctttcacttt gatctctcct ttcccatttc caggttgctt cggtctgata    960

ttttagttcc tcattacttt taacacctcc tccaaagtag tcccttcatc aatagatgtt   1020

tttgagccct ccctaccatg tgataagcac tggtctaggc actgggagta cagtaggaaa   1080

tgagataaac ttggccaggt gtagggtggc ttacacctgt aatcccaaca cttttgaggc   1140

cgaggcgggc agctcgcttg agcccatgag ttcgagacca gcctgggaaa catagcgaga   1200

cccccgtccc tacaaaaaaa tataaaaatt agctgggcat ggtggtgtat gcctgtggtc   1260

ctagctactc agaagactga ggtgggagga tcatctgagc ccagggtggt cgaggctgca   1320

gtgattacac cactgcactc catcctgggc aacggtgaga ccctgtctca aaaaacaaac   1380

aaacaaacaa gcaaacaaaa cccccacaaa ctaaactatg tgtaaataca tttttgttag   1440

gtagaactat atgaaattgc cactatttga ccaattttta gtgaaaacta gtctcataag   1500

tgtgtgtgtg tgtattttca ctaatgtttt ttggatttac ctaaacgttt actaatttca   1560

ttgctcccca tgtctccttc tatcctattc cttttttctg ggttctgttt ccttttcaga   1620

tttttagtag ttcttttcag tgaggatctg tgagtggtaa actctctttc tctgaaatta   1680

acttcttcct ctcaaataat agttcacctg agtataagtc ttggttggcc attaatttcc   1740

tttcagtctt tagaaggtac attgatgata aatcagttgc cggtttaatc atgcttcgtg   1800
```

-continued

```
tgtagatcat tagtctttct ctttggttga ttttaagata tccattgcct tcagtgttct   1860
gcagattcct gtgatgtgtc ctcatttggt tgtgtgttaa tttttcctac caagactcag   1920
gatgcttcct gtacctgagg attccggtca catcttgctt caatgtttga aatttctcag   1980
ccatcatctt ttgaatattg cctcttccac agtccctgtg ttctcttcgt ggaaatccta   2040
caggcatata ttggacctcc cattctgtcc tccatgtctc ttaccgtcta ttcataccct   2100
ccttttttata tttaattttt ttgagacaga gttttgctct gtggcccagg acggagtgca   2160
attgcatgat cttggctcac ggcaaactct gcctcccagg ttcaagctat tctcctgcct   2220
cagtctccca agtagctggg attacaggca tgcaccacca cgcccggcta atttttgtat   2280
ttttagtaga gacggggttt caccatattg gccaggctgg tctgaaactc ctgacctcag   2340
gtgatccacc cacctcggcc tcccaaagtg ctgggattat aggcatgagc caccatgcct   2400
ggccaatatc acccgcctcg gcctcccaaa gtgctgggat tacaggcatg agccaccgtg   2460
cctggtcaat atcctccttt ttatttctgt gattctttct gtgtgatttt ctcagatcta   2520
ccttctagct tactaattct ctctccaact gtagctaaat gtgttttata ttataatgac   2580
tatatttttt tcacttatag atgttctatt taattctctt tctttttgac aaatagaact   2640
tatttcaaaa caaacaaaag gccaggcatg gtggttcatg cctgtaatcc cagtgctttg   2700
ggaggctgag gcaggaggat tgcttgagcc caggagttca aggccagcct gggcaacata   2760
gtgagatcct ttctctacca aaaaaataaa aaatcagctg ggtgttgtgg gacactcctg   2820
tagtcccaga aactacagat tcttgggagg cagaggctgg aggattgctt gaggcagagg   2880
ctggaggatt gcttgagcct gggaggttga ggctgcagtg aactgtgatc atgccactgc   2940
actctagcct gggtgacaaa gtgagatcct gtctcaaaaa caaataaaca aacaagcaaa   3000
gaaacaaaaa aatgcttaca caggttacta ctttcttgct gggatagttt taacactgcg   3060
ttaagcataa acacctttct ttctgaaatg tatttgagat gtatattgat ttttaaaaaa   3120
cccacacctc cattaaggtc tggtgatagc agtagaaaca atgtagagtg gctccacaat   3180
catatagatg tttttggtgc gttctgagat ggagtccagg aacaccaagt aaagactgct   3240
acctcacagt ttacatctga gttcttagaa gacaagactg aaggagaaca atttgtaaca   3300
agatttactt ggcccgggtg tggtggctca cacctgtaat cccagtactt tgggagcttt   3360
gggagtccga ggtgggtgga tcacctgagg tcaggagttc aagaccagcc tggccaacat   3420
ggaataaccc ccatctctac taaaaataca aaaattagcc aggcacggtg gcacacgcct   3480
gtaatcccag ctactcagga ggctgaggca ggagaatcgc ttgaacccaa gtgactgggt   3540
tgccgagagc cgagatcacg ccactgtact ccagccaccc tgggtgacag agtgagactc   3600
tgccaaaaaa aaaaaaaaaa aaaaaaaaat acttactgtt cagaaggaga agtcataatg   3660
ttgctttaaa gaacaggtca caaaagaaag actctagaag atcttctcac ttggtgcata   3720
tcaagtgtct atttgagacc catacacttg cttaatccat gtgtttaagg caaaagtgct   3780
gctgctgagc agtaaggaat aaggtacctg ctaaccttta ccaatctaca ttttaaaatc   3840
cttcttacta cacatccaga atgagtcagc aattcttgtg tattaaaaaa caaaaacaca   3900
aaacaaagta gaggggcaac tctcttaaaa atgcagctat ccgcaaacac tgtgatacaa   3960
aacgacagtc aaggaaaggg cagcacaaac aagttcacct ggaaggaatc tgttcaaagt   4020
ctctggattt aagaacaagt tccctaaaag ctcttactta cagaagaaat cggataataa   4080
atgtagctgg aatgatggaa ttctttaagt tttcattttg ttttgggcaa ctctgtggcc   4140
```

-continued

```
caggctggag tgcagtggct tgatcacggc tcactgcagc ctcaacctcc caggctctgg   4200
tgatcctccc acctcagcct cctgagtggc tgggactaca agcatgtgtg ccaccatgct   4260
aggctaattt ttgtatttta tttttagttt tttttttttt tttttttttt ttgtagagac   4320
aggttttgcc atgttgccaa ggctggtctc aaattcctgg gttcaagtga tcctcccatc   4380
tcagccttcc aaagagctgg gattacaggc atgagctact gcacctggcc tagaattttt   4440
taaaaatcac tatctggcaa ctctcaggat aatattcgat tcaggcaagg atcatcaatg   4500
aatgctaaaa ccattgggtg aaaaattgtt gcagaatggg atgctcacat ggcttcaaag   4560
tattgctcca caaattactt atcaataacg taaaaaacca aactttacta gccatggaga   4620
aatctggttg ttatcacttt aatggagtga tcaaacttaa catcactaaa tagagtgcaa   4680
cctccagcta ggatacagta agaagggcca gatatcacct agtatttttg ccaaaaatgt   4740
ttaaccttaa tctaatcatg agaaagtaat cactcaaatc cagaatgtgg gacattttac   4800
aagatgtcct ccttgcactc ttccaaaaaa aaatcaatgt catgaaaaca aacaaatggt   4860
ggggttgggg agaacggttc taaatttaaa aactaaagtg ggataacaac cagatgagat   4920
gtgttagagc ttgaatttac agagagagaa aaacaactat gaaagcattt tggggaaaat   4980
ctgaatatgt aggatatgtt agatgatatt aaggaattgt gttaattttc aaaggtatga   5040
taatgttttt ttcttttgta aaagagtcct tatttttcac aatgtatgtt gaagtattca   5100
gagtgaagtg tcatgttggc tataattatt tcaaatggtt ccacacacaa agcacatacc   5160
acatacacat atacatatac ctccaaccaa ctcaaaacat gttcaacact gaaactataa   5220
gatgccacca aacagggaag catgagtgtg tgttgcatct acccattgta tcaatccagg   5280
ttcagtcaga aaaacaaaag ccattccacg tatttcaagc atgaaaggct ttaaaacaaa   5340
aaattaaagg tttatccaac tcttggaagg gctggaggag tgaccacctt ggtttgcagt   5400
tcagaaggag tgactctcaa acgctcatta gtaagtggct acaaatggga agctcgcctt   5460
attatgcctg caatatcaat gcatgtgatt cctgggaagg tcacccagaa gctgctttaa   5520
actccaagcc tgtccatgct tctgtctgca accggcattg aaacataatg gcctctcctc   5580
ttccgtctca cgctggctga ctctaaccta ggctcatata gagaagggat tctagaaaat   5640
gtattaatag ttccaagtgt cccctctgca tctcataaaa gaccttagaa agggcactga   5700
taatgctatt tgcaaaaaga caatccagcg cagttgtatt ttacagcaca ggctctttaa   5760
gtttgggtta tcagcaaaaa accattagag tatgagaaat tcctttttaa attgtggcaa   5820
aatatacata acataaaaat taccattgta gctattgtac attgtagcta agtatatagc   5880
ccagtagcac taaatacatt tacactgttg tgcaccacta tctagctcca gaaactttta   5940
atcttcccaa acagaaactt gtacctatta accaatacct tctccttcct cacttctcct   6000
agaaaccaga attatacttt ctgtctctac aaatctgact attctggata cctcagaatc   6060
acagtatgtg tcgttctacg actggcttgt ttcacttagc atcatgtctt caagggtcat   6120
ccacgttata gcatgtgtca gatttccttt tcttttcttt tctttttttt ttttttgag    6180
acacagtctc gctctgtcac ccaggctgga gggcagtagc acaatctcag ttcactgcag   6240
cctctgcctt ccaggttcaa gcaattctcg tgcctcagcc tcccaagtag ctggaatgac   6300
aggcatgcac caccacacct ggctaatttt tgtattttta gtagagacgg ggttttacca   6360
tattggccag gctggtcttg cacttccggc ctcaagtgat ctgcccgtct cggcctccca   6420
aagtgctggg attacaggcg tgagccacta tgcctggccc ccgattgtca ttatttaagg   6480
ctaagtgata ttttgttgtc tgtatatacc acaatttgtt tattcattca tctgtcaatg   6540
```

-continued

```
gacatttggg ttgtttccac cccctggtta ttgtggataa tactactagg aacacgagca   6600
tacaaatatc tgctccagtc cctgctttta tcttttggat atatgcccag aggtggaatt   6660
gctgggtcat aaggtaattc tagattaaat tttttgaggg actgccgtat tgttctccac   6720
catagctgca ccattttacc tttccagcag cagcgtacaa gcggtccagc ttctccacat   6780
cttcacccac acttgctatt tttggctttt attttatttt ttaaaataac attctaatgg   6840
gtgttaagtg gtcagaaatg gttcttttag gagtagagat agaggccagg gggatggctc   6900
acacctgtaa tcccagcact ttgggaggcc taggtgggcg gatcacttgg ggtcaggagt   6960
ttgagatcag cctggccaac atggtgaaac tccatctcta ttaaaaatac aaaaattcgc   7020
tgggtgtggt ggtgtgcact cccagctact tgggaggctg agggaagaga atcgcttgaa   7080
cccgggaggc ggtagttgca gtgagccgag atcacaccac tgtatggcct ggtgacagag   7140
caaggctctg tctcaaaaaa aaaaaaaaaa aaaaaagagt agagatagaa aagcattgaa   7200
aacacagcct cagctcagct cagtctgcca tggtgggaag ccattaattc ttcactcttg   7260
aaacctttc gtccttggtg tggcagaggc tgcaagtctc ctctgcaact ttattcttcc   7320
cttctttctc agttataaaa tccctgattt tagaaatatc tttattgaga tataattcac   7380
ataccataac attcactaca attgaatggt ttttagtata ttcacagatt tgtacaacta   7440
tcaccacaaa ctaagtttag aactttttc atcatcccac aaagaaaccc cacacccatt   7500
agcagttatt cactatttct ccccaatcaa cctcccctcc cctcaatagc cctaggcagc   7560
caccagtcta ctttctgtct ctacctattt gtcttttctg gacattttat acaaatgaga   7620
ttttacaaca tgtagtcttt tgtgactggc ttttttcccc tagcataatg ttttccaggt   7680
tcatctgtgg tgtagcaggt atcagtactt caaccctttt tattgccaaa taatattcca   7740
ctatatggat aggtaacatt ttgtttatcc attcatcaat tgatggacat ttgggttgtt   7800
tccattttct tgactgttat gaataatgtt gccatgaaca ttaatgcaca agtttttgtg   7860
cagatgtgta ttttcatgtg tcttggtttt atacctagga atagaattgc tgagtcatag   7920
gagaactcct ccatgtttaa ccattaatga actgccgaac tgttttccaa agaaattgca   7980
ccattgtaca atcccaccag caatgtatga gggtagaatc cctgattttt aactgatcat   8040
tgaactcagg cccattcaaa acaaagatga catttcctaa ccttccttac aagtagttct   8100
gaccagtgag atgggagaag aagttaggtt ttgtccttaa aagaaaggag agtggctggg   8160
tgcagtggct cacgcctgta atcccagcac tttgggaggc cgaggtgggc ggatcacctg   8220
aggccgggag ttcaagacta gcctgaccaa catggagaaa cctcgtctct actaaaaata   8280
caaaattagc tgggcgtcgt ggcgcatgcc tgtaatccca gctactcagg aggctgaggc   8340
aggagaatcg cttgaacctg ggaggtggag gttgtgatga gccgagattg tgccatcgca   8400
ctctagcctg ggcaagaaga gcgaaactcc atctcaaaaa aaaaaagaaa gaaaggagag   8460
tacattctac actctcctct cctccaccct gcccccttc cagtggctgg atgtggacat   8520
ggtggtaagc tatcttagat catgtggaca agggaaacac atagggatat tagaacctcc   8580
agacagaagg aacttaggac cctggacagc tttgtggagc agtgctccca taccagcgtg   8640
aagttttgta tgggagaaaa catacatttc cagcttttgt aagccactgt tattttgggt   8700
ctctctcaga gcagccaaat atataattta actaatatat tttctttctg tgattcttct   8760
ttattttgat tatacttcta cttctctgcc cctcttttag gtgggaggtg ctgctccaag   8820
cactaactca gaatatagac cctctccctc ttgtaatagt gccagcttgg agttctttgc   8880
```

-continued

```
ttccactgta ggggaaggaa ggaaaaaata tggagaactc acatccactc ttcattgtcc   8940
tcaaacagaa gtaacccatt ttgttctgct cacagcccat tggccagaac taactgtatg   9000
gccccaatct aattgcaaag gagtctggga agtacagcac agcacatgga tctttggaaa   9060
gcgttaattt tctctgccaa aggcttcttt tgttgttgtt gttgtttgaa atggagtccc   9120
gctccgtcac ccgggctgga gtgcagtggc cctatctcag ctcactgcaa cctccacctc   9180
ccaggttcaa gcactcctcc agccttggcc tcccaagtag ctaggattac aggcgtgtgc   9240
catcatacct ggctattttt tttgtatttt tagtagagac agggttttac cgtgttggcc   9300
aggctggtct caaactcttg gcttcaagtg atccgcctgc ttcggtctcc caaagtgttg   9360
ggattacagg cgtgagccac tgtacccggc caatactggt gttttctgac ctcagcgttt   9420
ttcttttctc ctgccatgta ctctccctag agatttcatc tactcccaag tcttccactg   9480
ctcctatctg ctgatgactc ccaaaactca gtctccagcc gagacttctc tcctgggctt   9540
gagacatatg tatccaactg ccagaacatc tccagtggac agcctttggg cacaaggcca   9600
cactagcttg tgggtacaag taatcaccca aagtcaattt cagtggctct ccactcccac   9660
attttttcaa cccctggaaa tgttcccttc ccaaatactc tgagtctctc ttctcttttg   9720
atgactgtgg ttttgtgact ggatggtagc tcctgttgct ttttttcctt tcaaatgaat   9780
tttctcttag gaggcttctt agccattaag caaatagacc tcaactgggc ttgccctatg   9840
cctatctgaa acccagctta ggttcgagtt aggactcctg ttaatctgag ctctcacttc   9900
ctgtcccaac ctgcttattt tttttggtga aagaaaatat catcccccta gttgctcaga   9960
aacctgggaa tcattgggat tttttcctct ccttcacctt cctcatccaa tcagtcacca  10020
agtgctatca actctgctgc cttagtagcc ctcaatatat acttacctat caaccatcac  10080
tgctatgcca tacttcaggc cttcatttct cacttggatt attaaaatat ccctaaatag  10140
ttcctctgcc ttctctctgg ccaccctcct gagtgatctc tccatcatgt acctttcagt  10200
gactgcttgc acaagcccct ttgtgacttg gtcatagtct gctctcttga accaccagag  10260
ccaagcacct gggttctgat tctggttgca actcttactg cgtgatgatg gacaggccac  10320
ttgatctcct caaacctcag ttcctaaatc aaatgaatga ttgaattcag tcacttaact  10380
ttgtatgtag taggtaggca ctgtgcaaaa catactagtg gatatagaga tgaataagaa  10440
aaagcccctg cactcaaaga gctctcggat tcatcaacaa attattgtgc agttagatag  10500
taagtgctat aatccaggaa tatacagtgt tgtgtgaata atgtggaatc agtttatctc  10560
cagagcagaa aaaggtgaag gccgaagaag gcattcagag tgatactgga gctgtgtagc  10620
aggggctact actgttccct caaatccttt cttctcttct tcctgagtaa tagagtcctt  10680
tttcagctag gcatacagcc atccaaaata aaaactatat ttcccagcct ccttttcagc  10740
taagtgtagc catgtgacta agttgtggcc aatgggatgt cagtacaagt ggtaatggca  10800
atatctggga tgtgtcttta aaaggaagga acatgtcctt ctccttttcc tccttcctgt  10860
tccctgggag gtgaacttgg tagctggagg tgaagcagct ggaacttgga tatgagcgtc  10920
ttgttgatga taatagtgca acaagataaa agcagcccga gctggcctac atttacatga  10980
gaaggaaata agactccatt ttgtttaagc tattctcttg catatatata tacacatata  11040
tatcagctaa gtgtagccat gtgactaact tgtggccaat gggatgtcag tatgagtggt  11100
aagagcagta tcttgtatat atatatgtgt atatatacac acacacatat atatacatat  11160
atgtatgcaa gaatataaaa tatacatgtg tgtgtgtata tatatacaca catatatatg  11220
tcccttgcag ccaagtctaa ttctaactaa tacaaactaa ctctaaaaaa tgaatatata  11280
```

```
ttcaccaggg gataggctat ttcaagcaga gggaagcctg tataaaggct cagggaatgc  11340
tgtggtttta tgtggcagca gatgagactg gaaatgagtc aggatgagcc acagtggagg  11400
atgaattaaa tgggcaggag tgtggtagaa agacctgttg gaggctatga atgcaatcaa  11460
ggtgacagac aactggtgca atgatggtag tggaaatgga ggagagggga ttgattcaag  11520
atgcatttag gaccaagaat cgggagcttg tgaacgtgtg tatgagtact gtagacggag  11580
tgggtgtgtc atcagagaag atctgagcat ttgggcttgc tctcctcaga ggccctgcga  11640
gtggagttca gcttttcctc atggggcaaa tcttactttc gctccagttc ctggggctca  11700
gagtccctgg cccagatgcc tcttgccatc tcatcttcac cctgcctggc ttcccttgct  11760
tgttccagga ttgtttcata aagagggatg tggttggtct ttaaccctat gaatgctggc  11820
tgaggatgcc tgcggaacct gtagtgaagc tttcaggggc tgctcgggtt ctggctggta  11880
ggtgaacact gtccatcttg ccggctggga cacagtgact ctgggtagtt gtgtaagaga  11940
ggggcccttg gcagacaaac aggttcttct ctgttggtgg gccagccagc aggtcagtgg  12000
gaaggttaaa ggtcatgggg tttgggagaa actgggtgag gagttcagcc ccatcccccg  12060
taaagctcct gggaagcact tctctactgg ggcagcccct gataccaggg cactcattaa  12120
ccctctgggt gccagggaaa gggcaggagg tgagtgctgg gaggcagctg aggtcaactt  12180
cttttgaact tccacgtggt atttactcag agcaattggt gccagaggct cagggccctg  12240
gagtataaag cagaatgtct gctctctgtg cccagacgtg agcaggtgag cagctggggc  12300
agagggatgg gggtcacagt cctaagggag ggcattgcag gtggcctcag gggagagcct  12360
ggggtggccc ctaagacgtc ctcttggaac attttggcag agttgcctct tcgccctcat  12420
tatggctcag tttttccacc atgaaatggg agggagggag acaggtgggc aggggagagg  12480
tggtagaagt ggcctagaga actgttcctg gggtctggga cctttgcgaa ggggttagag  12540
caccacgctc cctgctatgt gactgaggta gcaagagcac gccctcttcc catgtttgag  12600
gaagacaccc tagcctcctt gactcaccta ggtcagtcct cttgagcccc aacagctctg  12660
tgctccccag cccaaggaag ggtaacagg atttcgggca gttgcccctg cagaggcccc  12720
ctgggcaagt cccctgcgcc atgtcccttc gtctccttct tcccctaacc aggcctccct  12780
ccacctgtct tctcagagca gataatggca agcatggctg ccgtgctcac ctgggctctg  12840
gctcttcttt caggtgggtc tccgaccctg acttcaacgt gggggtgtgg gtggaggctg  12900
gccagagggc cctgtccacc ctgggggagg agagcccagg ccctgattac ctagtccctc  12960
tccacagcgt tttcggccac ccaggcacgg aaaggcttct gggactactt cagccagacc  13020
agcggggaca aaggcagggt ggagcagatc catcagcaga agatggctcg cgagcccgcg  13080
tgagtgccca ggggaagggg tgtaggcgaa gggaggagac agctgggcca tgccatgatg  13140
acctgcctct gctgcctcaa cctctgtggc cgctgctggg acagaggaaa ggagcggtgc  13200
tagctctgtc tgcagatccc ggccatcctg ggctctttag cgccctctgc ctgcagcccc  13260
cgccttgaca actccgtagc tgttgccccc ttgctcactg aggcgcggga cctgggatca  13320
atcgggagga cgcccgctgc agtccccaga atcaaaggat gatgtggcgc atctatgttt  13380
ctttggagag tgttgtaggt ctggatttgt atgggcaatg tgtttgtgct tcgtgcgtga  13440
gttgttactg gccagggcta ggacaagagc cctcgaccct ggggccaacg ccctgcgtcc  13500
ttggttcccc cagaggatca gtgcgcgatg acttggggac aaaggagatg atggggggcta  13560
gcagtctgac ggcctggata tctgtcccct tctccaggac cctgaaagac agccttgagc  13620
```

-continued

```
aagacctcaa caatatgaac aagttcctgg aaaagctgag gcctctgagt gggagcgagg  13680
ctcctcggct cccacaggac ccggtgggca tgcggcggca gctgcaggag gagttggagg  13740
aggtgaaggc tcgcctccag ccctacatgg cagaggcgca cgagctggtg ggctggaatt  13800
tggagggctt gcggcagcaa ctgaagccct acacgatgga tctgatggag caggtggccc  13860
tgcgcgtgca ggagctgcag gagcagttgc gcgtggtggg ggaagacacc aaggcccagt  13920
tgctgggggg cgtggacgag gcttgggctt tgctgcaggg actgcagagc cgcgtggtgc  13980
accacaccgg ccgcttcaaa gagctcttcc acccatacgc cgagagcctg gtgagcggca  14040
tcgggcgcca cgtgcaggag ctgcaccgca gtgtggctcc gcacgccccc gccagccccg  14100
cgcgcctcag tcgctgcgtg caggtgctct cccggaagct cacgctcaag gccaaggccc  14160
tgcacgcacg catccagcag aacctggacc agctgcgcga agagctcagc agagcctttg  14220
caggcactgg gactgaggaa ggggccggcc cggaccccca gatgctctcc gaggaggtgc  14280
gccagcgact tcaggctttc cgccaggaca cctacctgca gatagctgcc ttcactcgcg  14340
ccatcgacca ggagactgag gaggtccagc agcagctggc gccacctcca ccaggccaca  14400
gtgccttcgc cccagagttt caacaaacag acagtggcaa ggttctgagc aagctgcagg  14460
cccgtctgga tgacctgtgg gaagacatca ctcacagcct tcatgaccag ggccacagcc  14520
atctggggga cccctgagga tctacctgcc caggcccatt cccagctcct tgtctgggga  14580
gccttggctc tgagcctcta gcatggttca gtccttgaaa gtggcctgtt gggtggaggg  14640
tggaaggtcc tgtgcaggac agggaggcca ccaaaggggc tgctgtctcc tgcatatcca  14700
gcctcctgcg actccccaat ctggatgcat tacattcacc aggctttgca aacccagcct  14760
cccagtgctc atttgggaat gctcatgagt tactccattc aagggtgagg gagtagggag  14820
ggagaggcac catgcatgtg ggtgattatc tgcaagcctg tttgccgtga tgctggaagc  14880
ctgtgccact acatcctgga gtttggctct agtcacttct ggctgcctgg tggccactgc  14940
tacagctggt ccacagagag gagcacttgt ctccccaggg ctgccatggc agctatcagg  15000
ggaatagaag ggagaaagag aatatcatgg ggagaacatg tgatggtgtg tgaatatccc  15060
tgctggctct gatgctggtg ggtacgaaag gtgtgggctg tgataggaga gggcagagcc  15120
catgtttcct gacatagctc tacacctaaa taagggactg aaccctccca actgtgggag  15180
ctccttaaac cctctgggga gcatactgtg tgctctcccc atctccagcc cctccctctg  15240
ggttcccaag ttgaagccta gacttctggc tcaaatgaaa tagatgttta tgatagaagt  15300
ttgcctggcg tgactctcat ttggaccatg tctgaaagca gtggcctcac cactatcccc  15360
aaagcacacc catcacccac tccattccct tgctgctctt tctcatccac ccactcccag  15420
tccaggtctg tcaaaggggg tctggctggg ctctgcttca gggatcctgg ctagacaacg  15480
gctgtctgtc acacctggca ggagggcctg ggttacgggc ccttcctctg cacctgcact  15540
gttcactagc ctgctccccc acaggacact gtgcatggaa tgcaggctgt gtctggaaga  15600
gctgtggccc tggtggacct aagattcctg aggtgggctg cctcctttgt tcctgctgtt  15660
ctagagtttg aatggcctct ttttatgccg gactctcttc tggggactcc cctcactcag  15720
gggcaccaat gctccctata gatcccctgg gaactgaaac tggggtgtgg tggaggacgt  15780
ggaaagggta aacacagctc cttgtctttg gacttccctg tccggccccc tttcctccca  15840
gctcagccta ctgtccccgg gttctcagca cctgcctgct ccccaacccc atagcacaga  15900
ccccacacat atgtaggctc atcatgcctg caggctggtc ttccctgaca ccgtggattt  15960
tgacaatgtt ggcaacagaa ctgggttgtg gacccagcac                        16000
```

<210> SEQ ID NO 5
<211> LENGTH: 26656
<212> TYPE: DNA
<213> ORGANISM: Homo sapiens

<400> SEQUENCE: 5

```
tcgagctgtt ttacctaagc tttccactca tgattaacta atgaagatta caatgattac     60
atggtagaac ccatacacaa accactagac ctggcaccag gggttttgc aagaaagagg    120
gtaagattct agctacatgc gaacagccca aatactctga tcttaaactt acctcctttc    180
tggctaaagg caggaatttc aaaatctagc tcaggaatcc ttgtggcagc agagtcagtc    240
ttcaccactt ctctgttcat gtcctgggaa gaaaagaata cgttcagtac aaagagactg    300
cagaacagct tctcctcaag taataaccag accgtcccct tccatcagac cgcagcccag    360
ctgtctctcc ctctcgccac tccacagggt ccagactgct cctttcgaat agtacaggtg    420
gtgtgagcca ggctgtccaa atggtgagaa tactattcat aacaactact gctcatttca    480
taccctcaga caacatttac aaagcatttt cacaaatctt atctcacttg agctgatgac    540
aacaccagta ccattttaca aaagaaacta aggctaggag acataggggg atttatttaa    600
gatccgaccg cctggaccag agctctgacc ccagtaccga atctctctct agaatactga    660
ggtacctgct ctgaggtcct ctcacctcca gagccctgac agacaaagtg tagcgcactc    720
cctggtcctg gatcctgcct gccgactgga tctccgtgtt gttccagcca cagtgctcgc    780
aggaaaagga gctcactatt atttctctga agaagggaat cttggtgagc aggaggcgcg    840
tcatgccctg gtgaagtaga aagtagctaa ggaaaaaaat caatgaaact ccctttcccc    900
gccctactat ctccgggcgc tcctcggggt ccccggccgg gcccacctgg ctgggtctga    960
cccccggctc gtcccggcac aagccctacc cacccgccgc tcgcggccgc gcccccgcct   1020
cacattgcag taacagttca tgcatagcga ctcgatctcg gtgggctgct gctcctcgtc   1080
ctcggcgctg atgggccgga acaggtgatc aggggcaggc ggcggggccg gggcgggcga   1140
cggggcgacg gcagcccccg ggggccctgg ttccacagcc ccgctggccg ccatggccac   1200
cacgcgcaat tcagacctcg gcttcctact tccgccgctc tcgcggcccc acccctctcc   1260
cgtcacttcc gccagctgcc accaccccaa aaaaagccgc agactccggg cactcgggga   1320
acaatgtcgt caagggctcc cggttcccgg gtttatatgg ctcgaacctt acatcgccag   1380
ccggatccac ctcaactcag ccgtcacttc ccctaagacg tcctcttaga accagggcac   1440
ttttttgctc cttcacaata gctccaccgc acggggttct attggtccct acgtcggtct   1500
acaagagcct tgacgacaag gggctggact tgtccctgag gaatccctga gaaggtgcgc   1560
ccggagccgg gctgcttggt tccagtgttg ggccacatac tgcttgcgtg ctaggtcgcc   1620
cctccgggtg gctcagcctc ttcccctctc tcacaatccc tgaatccctc tgtccctttc   1680
tgttcttccc actccctatt ctgtcctcat cactaccttc cccaatccca gcctcaagta   1740
cacagccctc attttcactc ctacctcctc atccccatca tagcccttga cctatgcttt   1800
tccagtttcc taacaacaac aaaaacacct tttattattt ctacctttct agcacttcct   1860
ctctccaggt gctgggtcca caacccagtt ctgttgccaa cattgtcaaa atccacggtg   1920
tcagggaaga ccagcctgca ggcatgatga gcctacatat gtgtggggtc tgtgctatgg   1980
ggttggggag caggcaggtg ctgagaaccc ggggacagta ggctgagctg ggaggaaagg   2040
gggccggaca gggaagtcca aagacaagga gctgtgttta ccctttccac gtcctccacc   2100
```

-continued

```
acaccccagt ttcagttccc aggggatcta tagggagcat tggtgcccct gagtgagggg   2160
agtccccaga agagagtccg gcataaaaag aggccattca aactctagaa cagcaggaac   2220
aaaggaggca gcccacctca ggaatcttag gtccaccagg gccacagctc ttccagacac   2280
agcctgcatt ccatgcacag tgtcctgtgg gggagcaggc tagtgaacag tgcaggtgca   2340
gaggaagggc ccgtaaccca ggccctcctg ccaggtgtga cagacagccg ttgtctagcc   2400
aggatccctg aagcagagcc cagccagacc ccctttgaca gacctggact gggagtgggt   2460
ggatgagaaa gagcagcaag ggaatggagt gggtgatggg tgtgctttgg ggatagtggt   2520
gaggccactg ctttcagaca tggtccaaat gagagtcacg ccaggcaaac ttctatcata   2580
aacatctatt tcatttgagc cagaagtcta ggcttcaact tgggaaccca gagggagggg   2640
ctggagatgg ggagagcaca cagtatgctc cccagagggt ttaaggagct cccacagttg   2700
ggagggttca gtcccttatt taggtgtaga gctatgtcag gaaacatggg ctctgccctc   2760
tcctatcaca gcccacacct ttcgtaccca ccagcatcag agccagcagg gatattcaca   2820
caccatcaca tgttctcccc atgatattct ctttctccct tctattcccc tgatagctgc   2880
catggcagcc ctggggagac aagtgctcct ctctgtggac cagctgtagc agtggccacc   2940
aggcagccag aagtgactag agccaaactc caggatgtag tggcacaggc ttccagcatc   3000
acggcaaaca ggcttgcaga taatcaccca catgcatggt gcctctccct ccctactccc   3060
tcacccttga atggagtaac tcatgagcat tcccaaatga gcactgggag gctgggtttg   3120
caaagcctgg tgaatgtaat gcatccagat tggggagtcg caggaggctg gatatgcagg   3180
agacagcagc ccctttggtg gcctccctgt cctgcacagg accttccacc ctccacccaa   3240
caggccactt tcaaggactg aaccatgcta gaggctcaga gccaaggctc cccagacaag   3300
gagctgggaa tgggcctggg caggtagatc ctcaggggtc ccccagatgg ctgtggccct   3360
ggtcatgaag gctgtgagtg atgtcttccc acaggtcatc cagacgggcc tgcagcttgc   3420
tcagaacctt gccactgtct gtttgttgaa actctggggc gaaggcactg tggcctggtg   3480
gaggtggcgc cagctgctgc tggacctcct cagtctcctg gtcgatggcg cgagtgaagg   3540
cagctatctg caggtaggtg tcctggcgga aagcctgaag tcgctggcgc acctcctcgg   3600
agagcatctg gggtccgggg ccggcccctt cctcagtccc agtgcctgca aaggctctgc   3660
tgagctcttc gcgcagctgg tccaggttct gctggatgcg tgcgtgcagg gccttggcct   3720
tgagcgtgag cttccgggag agcacctgca cgcagcgact gaggcgcgcg gggctggcgg   3780
gggcgtgcgg agccacactg cggtgcagct cctgcacgtg gcgcccgatg ccgctcacca   3840
ggctctcggc gtatgggtgg aagagctctt tgaagcggcc ggtgtggtgc accacgcggc   3900
tctgcagtcc ctgcagcaaa gcccaagcct cgtccacgcc ccccagcaac tgggccttgg   3960
tgtcttcccc caccacgcgc aactgctcct gcagctcctg cacgcgcagg gccacctgct   4020
ccatcagatc catcgtgtag ggcttcagtt gctgccgcaa gccctccaaa ttccagccca   4080
ccagctcgtg cgcctctgcc atgtagggct ggaggcgagc cttcacctcc tccaactcct   4140
cctgcagctg ccgccgcatg cccaccgggt cctgtgggag ccgaggagcc tcgctcccac   4200
tcagaggcct cagcttttcc aggaacttgt tcatattgtt gaggtcttgc tcaaggctgt   4260
ctttcagggt cctggagaag gggacagata tccaggccgt cagactgcta gcccccatca   4320
tctcctttgt ccccaagtca tcgcgcactg atcctctggg ggaaccaagg acgcagggcg   4380
ttggccccag ggtcgagggc tcttgtccta gccctggcca gtaacaactc acgcacgaag   4440
cacaaacaca ttgcccatac aaatccagac ctacaacact ctccaaagaa acatagatgc   4500
```

-continued

```
gccacatcat cctttgattc tggggactgc agcgggcgtc ctcccgattg atcccaggtc   4560
ccgcgcctca gtgagcaagg gggcaacagc tacggagttg tcaaggcggg ggctgcaggc   4620
agagggcgct aaagagccca ggatggccgg gatctgcaga cagagctagc accgctcctt   4680
tcctctgtcc cagcagcggc cacagaggtt gaggcagcag aggcaggtca tcatggcatg   4740
gcccagctgt ctcctccctt cgcctacacc ccttcccctg ggcactcacg cgggctcgcg   4800
agccatcttc tgctgatgga tctgctccac cctgcctttg tccccgctgg tctggctgaa   4860
gtagtcccag aagcctttcc gtgcctgggt ggccgaaaac gctgtggaga gggactaggt   4920
aatcagggcc tgggctctcc tcccccaggg tggacagggc cctctggcca gcctccaccc   4980
acacccccac gttgaagtca gggtcggaga cccacctgaa agaagagcca gagcccaggt   5040
gagcacggca gccatgcttg ccattacctg ctctgagaag acaggtggag ggaggcctgg   5100
ttaggggaag aaggagacga agggacatgg cgcaggggac ttgcccaggg ggcctctgca   5160
ggggcaactg cccgaaatcc tgttacccct tccttgggct ggggagcaca gagctgttgg   5220
ggctcaagag gactgaccta ggtgagtcaa ggaggctagg gtgtcttcct caaacatggg   5280
aagagggcgt gctcttgcta cctcagtcac atagcaggga gcgtggtgct ctaacccctt   5340
cgcaaaggtc ccagacccca ggaacagttc tctaggccac ttctaccacc tctcccctgc   5400
ccacctgtct ccctccctcc catttcatgg tggaaaaact gagccataat gagggcgaag   5460
aggcaactct gccaaaatgt tccaagagga cgtcttaggg gccaccccag gctctcccct   5520
gaggccacct gcaatgccct cccttaggac tgtgaccccc atccctctgc cccagctgct   5580
cacctgctca cgtctgggca cagagagcag acattctgct ttatactcca gggccctgag   5640
cctctggcac caattgctct gagtaaatac cacgtggaag ttcaaaagaa gttgacctca   5700
gctgcctccc agcactcacc tcctgccctt tccctggcac ccagagggtt aatgagtgcc   5760
ctggtatcag gggctgcccc agtagagaag tgcttcccag gagctttacg ggggatgggg   5820
ctgaactcct cacccagttt ctcccaaacc ccatgacctt taaccttccc actgacctgc   5880
tggctggccc accaacagag aagaacctgt ttgtctgcca agggcccctc tcttacacaa   5940
ctacccagag tcactgtgtc ccagccggca agatggacag tgttcaccta ccagccagaa   6000
cccgagcagc ccctgaaagc ttcactacag gttccgcagg catcctcagc cagcattcat   6060
agggttaaag accaaccaca tccctcttta tgaaacaatc ctggaacaag caagggaagc   6120
caggcagggt gaagatgaga tggcaagagg catctgggcc agggactctg agccccagga   6180
actggagcga aagtgagatt tgccccatga ggaaaagctg aactccactc gcagggcctc   6240
tgaggagagc aagcccaaat gctcagatct tctctgatga cacacccact ccgtctacag   6300
tactcataca cacgttcaca agctcccgat tcttggtcct aaatgcatct tgaatcaatc   6360
ccctctcctc catttccact accatcattg caccagttgt ctgtcacctt gattgcattc   6420
atagcctcca acaggtcttt ctaccacact cctgcccatt taattcatcc tccactgtgg   6480
ctcatcctga ctcatttcca gtctcatctg ctgccacata aaaccacagc attccctgag   6540
cctttataca ggcttccctc tgcttgaaat agcctatccc ctggtgaata tatattcatt   6600
ttttagagtt agtttgtatt agttagaatt agacttggct gcaagggaca tatatatgtg   6660
tgtatatata tacacacaca catgtatatt ttatattctt gcatacatat atgtatatat   6720
atgtgtgtgt gtatatatac acatatatat atacaagata ctgctcttac cactcatact   6780
gacatcccat tggccacaag ttagtcacat ggctacactt agctgatata tatgtgtata   6840
```

-continued

```
tatatatgca agagaatagc ttaaacaaaa tggagtctta tttccttctc atgtaaatgt   6900
aggccagctc gggctgcttt tatcttgttg cactattatc atcaacaaga cgctcatatc   6960
caagttccag ctgcttcacc tccagctacc aagttcacct cccagggaac aggaaggagg   7020
aaaaggagaa ggacatgttc cttcctttta aagacacatc ccagatattg ccattaccac   7080
ttgtactgac atcccattgg ccacaactta gtcacatggc tacacttagc tgaaaaggag   7140
gctgggaaat atagttttta ttttggatgg ctgtatgcct agctgaaaaa ggactctatt   7200
actcaggaag aagagaagaa aggatttgag ggaacagtag tagcccctgc tacacagctc   7260
cagtatcact ctgaatgcct tcttcggcct tcaccttttt ctgctctgga gataaactga   7320
ttccacatta ttcacacaac actgtatatt cctggattat agcacttact atctaactgc   7380
acaataattt gttgatgaat ccgagagctc tttgagtgca ggggcttttt cttattcatc   7440
tctatatcca ctagtatgtt ttgcacagtg cctacctact acatacaaag ttaagtgact   7500
gaattcaatc attcatttga tttaggaact gaggtttgag gagatcaagt ggcctgtcca   7560
tcatcacgca gtaagagttg caaccagaat cagaacccag gtgcttggct ctggtggttc   7620
aagagagcag actatgacca agtcacaaag gggcttgtgc aagcagtcac tgaaaggtac   7680
atgatggaga gatcactcag gagggtggcc agagagaagg cagaggaact atttagggat   7740
attttaataa tccaagtgag aaatgaaggc ctgaagtatg gcatagcagt gatggttgat   7800
aggtaagtat atattgaggg ctactaaggc agcagagttg atagcacttg gtgactgatt   7860
ggatgaggaa ggtgaaggag aggaaaaaat cccaatgatt cccaggtttc tgagcaacta   7920
gggggatgat attttctttc accaaaaaaa ataagcaggt tgggacagga agtgagagct   7980
cagattaaca ggagtcctaa ctcgaaccta agctgggttt cagataggca tagggcaagc   8040
ccagttgagg tctatttgct taatggctaa gaagcctcct aagagaaaat tcatttgaaa   8100
ggaaaaaaag caacaggagc taccatccag tcacaaaacc acagtcatca aaagagaaga   8160
gagactcaga gtatttggga agggaacatt tccaggggtt gaaaaaatgt gggagtggag   8220
agccactgaa attgactttg ggtgattact tgtacccaca agctagtgtg gccttgtgcc   8280
caaaggctgt ccactggaga tgttctggca gttggataca tatgtctcaa gcccaggaga   8340
gaagtctcgg ctggagactg agttttggga gtcatcagca gataggagca gtggaagact   8400
tgggagtaga tgaaatctct agggagagta catggcagga gaaaagaaaa acgctgaggt   8460
cagaaaacac cagtattggc cgggtacagt ggctcacgcc tgtaatccca acactttggg   8520
agaccgaagc aggcggatca cttgaagcca agagtttgag accagcctgg ccaacacggt   8580
aaaaccctgt ctctactaaa aatacaaaaa aaatagccag gtatgatggc acacgcctgt   8640
aatcctagct acttgggagg ccaaggctgg aggagtgctt gaacctggga ggtggaggtt   8700
gcagtgagct gagatagggc cactgcactc cagcccgggt gacggagcgg gactccattt   8760
caaacaacaa caacaacaaa agaagccttt ggcagagaaa attaacgctt tccaaagatc   8820
catgtgctgt gctgtacttc ccagactcct ttgcaattag attggggcca tacagttagt   8880
tctggccaat gggctgtgag cagaacaaaa tgggttactt ctgtttgagg acaatgaaga   8940
gtggatgtga gttctccata ttttttcctt ccttccccta cagtggaagc aaagaactcc   9000
aagctggcac tattacaaga gggagagggt ctatattctg agttagtgct tggagcagca   9060
cctcccacct aaaagagggg cagagaagta gaagtataat caaaataaag aagaatcaca   9120
gaaagaaaat atattagtta aattatatat ttggctgctc tgagagagac ccaaaataac   9180
agtggcttac aaaagctgga aatgtatgtt ttctcccata caaaacttca cgctggtatg   9240
```

-continued

```
ggagcactgc tccacaaagc tgtccagggt cctaagttcc ttctgtctgg aggttctaat   9300
atccctatgt gtttcccttg tccacatgat ctaagatagc ttaccaccat gtccacatcc   9360
agccactgga aagggggcag ggtggaggag aggagagtgt agaatgtact ctcctttctt   9420
tctttttttt tttgagatgg agtttcgctc ttcttgccca ggctagagtg cgatggcaca   9480
atctcggctc atcacaacct ccacctccca ggttcaagcg attctcctgc ctcagcctcc   9540
tgagtagctg ggattacagg catgcgccac gacgcccagc taattttgta tttttagtag   9600
agacgaggtt tctccatgtt ggtcaggcta gtcttgaact cccggcctca ggtgatccgc   9660
ccacctcggc ctcccaaagt gctgggatta caggcgtgag ccactgcacc cagccactct   9720
cctttctttt aaggacaaaa cctaacttct tctcccatct cactggtcag aactacttgt   9780
aaggaaggtt aggaaatgtc atctttgttt tgaatgggcc tgagttcaat gatcagttaa   9840
aaatcaggga ttctaccctc atacattgct ggtgggattg tacaatggtg caatttcttt   9900
ggaaaacagt tcggcagttc attaatggtt aaacatggag gagttctcct atgactcagc   9960
aattctattc ctaggtataa aaccaagaca catgaaaata cacatctgca caaaaacttg  10020
tgcattaatg ttcatggcaa cattattcat aacagtcaag aaaatggaaa caacccaaat  10080
gtccatcaat tgatgaatgg ataaacaaaa tgttacctat ccatatagtg gaatattatt  10140
tggcaataaa aagggttgaa gtactgatac ctgctacacc acagatgaac ctggaaaaca  10200
ttatgctagg ggaaaaaagc cagtcacaaa agactacatg ttgtaaaatc tcatttgtat  10260
aaaatgtcca gaaaagacaa ataggtagag acagaaagta gactggtggc tgcctagggc  10320
tattgagggg aggggaggtt gattggggag aaatagtgaa taactgctaa tgggtgtggg  10380
gtttctttgt gggatgatga aaaaagttct aaacttagtt tgtggtgata gttgtacaaa  10440
tctgtgaata tactaaaaac cattcaattg tagtgaatgt tatggtatgt gaattatatc  10500
tcaataaaga tatttctaaa atcagggatt ttataactga gaaagaaggg aagaataaag  10560
ttgcagagga gacttgcagc ctctgccaca ccaaggacga aaaggtttca agagtgaaga  10620
attaatggct tcccaccatg gcagactgag ctgagctgag gctgtgtttt caatgctttt  10680
ctatctctac tctttttttt tttttttttt ttttgagaca gagccttgct ctgtcaccag  10740
gccatacagt ggtgtgatct cggctcactg caactaccgc ctcccgggtt caagcgattc  10800
tcttccctca gcctcccaag tagctgggag tgcacaccac cacacccagc gaatttttgt  10860
atttttaata gagatggagt ttcaccatgt tggccaggct gatctcaaac tcctgacccc  10920
aagtgatccg cccacctagg cctcccaaag tgctgggatt acaggtgtga gccatccccc  10980
tggcctctat ctctactcct aaaagaacca tttctgacca cttaacaccc attagaatgt  11040
tattttaaaa aataaaataa aagccaaaaa tagcaagtgt gggtgaagat gtggagaagc  11100
tggaccgctt gtacgctgct gctggaaagg taaaatggtg cagctatggt ggagaacaat  11160
acggcagtcc ctcaaaaaat ttaatctaga attaccttat gacccagcaa ttccacctct  11220
gggcatatat ccaaaagata aaagcaggga ctggagcaga tatttgtatg ctcgtgttcc  11280
tagtagtatt atccacaata accagggggt ggaaacaacc caaatgtcca ttgacagatg  11340
aatgaataaa caaattgtgg tatatacaga caacaaaata tcacttagcc ttaaataatg  11400
acaatcgggg gccaggcata gtggctcacg cctgtaatcc cagcactttg ggaggccgag  11460
acgggcagat cacttgaggc cggaagtgca agaccagcct ggccaatatg gtaaaacccc  11520
gtctctacta aaaatacaaa aattagccag gtgtggtggt gcatgcctgt cattccagct  11580
```

-continued

```
acttgggagg ctgaggcacg agaattgctt gaacctggaa ggcagaggct gcagtgaact  11640
gagattgtgc tactgccctc cagcctgggt gacagagcga gactgtgtct caaaaaaaaa  11700
aaaaaagaaa agaaaagaaa aggaaatctg acacatgcta taacgtggat gacccttgaa  11760
gacatgatgc taagtgaaac aagccagtcg tagaacgaca catactgtga ttctgaggta  11820
tccagaatag tcagatttgt agagacagaa agtataattc tggtttctag gagaagtgag  11880
gaaggagaag gtattggtta ataggtacaa gtttctgttt gggaagatta aaagtttctg  11940
gagctagata gtggtgcaca acagtgtaaa tgtatttagt gctactgggc tatatactta  12000
gctacaatgt acaatagcta caatggtaat ttttatgtta tgtatatttt gccacaattt  12060
aaaaaggaat ttctcatact ctaatggttt tttgctgata acccaaactt aaagagcctg  12120
tgctgtaaaa tacaactgcg ctggattgtc tttttgcaaa tagcattatc agtgcccttt  12180
ctaaggtctt ttatgagatg cagaggggac acttggaact attaatacat tttctagaat  12240
cccttctcta tatgagccta ggttagagtc agccagcgtg agacggaaga ggagaggcca  12300
ttatgtttca atgccggttg cagacagaag catggacagg cttggagttt aaagcagctt  12360
ctgggtgacc ttcccaggaa tcacatgcat tgatattgca ggcataataa ggcgagcttc  12420
ccatttgtag ccacttacta atgagcgttt gagagtcact ccttctgaac tgcaaaccaa  12480
ggtggtcact cctccagccc ttccaagagt tggataaacc tttaattttt tgttttaaag  12540
cctttcatgc ttgaaatacg tggaatggct tttgtttttc tgactgaacc tggattgata  12600
caatgggtag atgcaacaca cactcatgct tccctgtttg gtggcatctt atagtttcag  12660
tgttgaacat gttttgagtt ggttggaggt atatgtatat gtgtatgtgg tatgtgcttt  12720
gtgtgtggaa ccatttgaaa taattatagc caacatgaca cttcactctg aatacttcaa  12780
catacattgt gaaaaataag gactctttta caaaagaaaa aaacattatc atacctttga  12840
aaattaacac aattccttaa tatcatctaa catatcctac atattcagat tttccccaaa  12900
atgctttcat agttgttttt ctctctctgt aaattcaagc tctaacacat ctcatctggt  12960
tgttatccca ctttagtttt taaatttaga accgttctcc ccaaccccac catttgtttg  13020
ttttcatgac attgattttt ttttggaaga gtgcaaggag gacatcttgt aaaatgtccc  13080
acattctgga tttgagtgat tactttctca tgattagatt aaggttaaac atttttggca  13140
aaaatactag gtgatatctg gcccttctta ctgtatccta gctggaggtt gcactctatt  13200
tagtgatgtt aagtttgatc actccattaa agtgataaca accagatttc tccatggcta  13260
gtaaagtttg gttttttacg ttattgataa gtaatttgtg gagcaatact ttgaagccat  13320
gtgagcatcc cattctgcaa caatttttca cccaatggtt ttagcattca ttgatgatcc  13380
ttgcctgaat cgaatattat cctgagagtt gccagatagt gatttttaaa aaattctagg  13440
ccaggtgcag tagctcatgc ctgtaatccc agctctttgg aaggctgaga tgggaggatc  13500
acttgaaccc aggaatttga gaccagcctt ggcaacatgg caaaacctgt ctctacaaaa  13560
aaaaaaaaaa aaaaaaaaaa actaaaaata aaatacaaaa attagcctag catggtggca  13620
cacatgcttg tagtcccagc cactcaggag gctgaggtgg gaggatcacc agagcctggg  13680
aggttgaggc tgcagtgagc cgtgatcaag ccactgcact ccagcctggg ccacagagtt  13740
gcccaaaaca aaatgaaaac ttaaagaatt ccatcattcc agctacattt attatccgat  13800
ttcttctgta agtaagagct tttagggaac ttgttcttaa atccagagac tttgaacaga  13860
ttccttccag gtgaacttgt ttgtgctgcc ctttccttga ctgtcgtttt gtatcacagt  13920
gtttgcggat agctgcattt ttaagagagt tgcccctcta ctttgttttg tgtttttgtt  13980
```

-continued

```
ttttaataca caagaattgc tgactcattc tggatgtgta gtaagaagga ttttaaaatg  14040
tagattggta aaggttagca ggtaccttat tccttactgc tcagcagcag cacttttgcc  14100
ttaaacacat ggattaagca agtgtatggg tctcaaatag acacttgata tgcaccaagt  14160
gagaagatct tctagagtct ttcttttgtg acctgttctt taaagcaaca ttatgacttc  14220
tccttctgaa cagtaagtat tttttttttt tttttttttt ttttggcaga gtctcactct  14280
gtcacccagg gtggctggag tacagtggcg tgatctcggc tctcggcaac ccagtcactt  14340
gggttcaagc gattctcctg cctcagcctc ctgagtagct gggattacag gcgtgtgcca  14400
ccgtgcctgg ctaatttttg tatttttagt agagatgggg gttattccat gttggccagg  14460
ctggtcttga actcctgacc tcaggtgatc cacccacctc ggactcccaa agctcccaaa  14520
gtactgggat tacaggtgtg agccaccaca cccgggccaa gtaaatcttg ttacaaattg  14580
ttctccttca gtcttgtctt ctaagaactc agatgtaaac tgtgaggtag cagtctttac  14640
ttggtgttcc tggactccat ctcagaacgc accaaaaaca tctatatgat tgtggagcca  14700
ctctacattg tttctactgc tatcaccaga ccttaatgga ggtgtgggtt ttttaaaaat  14760
caatatacat ctcaaataca tttcagaaag aaaggtgttt atgcttaacg cagtgttaaa  14820
actatcccag caagaaagta gtaacctgtg taagcatttt tttgtttctt tgcttgtttg  14880
tttatttgtt tttgagacag gatctcactt tgtcacccag gctagagtgc agtggcatga  14940
tcacagttca ctgcagcctc aacctcccag gctcaagcaa tcctccagcc tctgcctcaa  15000
gcaatcctcc agcctctgcc tcccaagaat ctgtagtttc tgggactaca ggagtgtccc  15060
acaacaccca gctgattttt tatttttttg gtagagaaag gatctcacta tgttgcccag  15120
gctggccttg aactcctggg ctcaagcaat cctcctgcct cagcctccca aagcactggg  15180
attacaggca tgaaccacca tgcctggcct tttgtttgtt ttgaaataag ttctatttgt  15240
caaaaagaaa gagaattaaa tagaacatct ataagtgaaa aaaatatagt cattataata  15300
taaaacacat ttagctacag ttggagagag aattagtaag ctagaaggta gatctgagaa  15360
aatcacacag aaagaatcac agaaataaaa aggaggatat tgaccaggca cggtggctca  15420
tgcctgtaat cccagcactt tgggaggccg aggcgggtga tattggccag gcatggtggc  15480
tcatgcctat aatcccagca ctttgggagg ccgaggtggg tggatcacct gaggtcagga  15540
gtttcagacc agcctggcca atatggtgaa accccgtctc tactaaaaat acaaaaatta  15600
gccgggcgtg gtggtgcatg cctgtaatcc cagctacttg ggagactgag gcaggagaat  15660
agcttgaacc tgggaggcag agtttgccgt gagccaagat catgcaattg cactccgtcc  15720
tgggccacag agcaaaactc tgtctcaaaa aaattaaata taaaaaggag ggtatgaata  15780
gacggtaaga gacatggagg acagaatggg aggtccaata tatgcctgta ggatttccac  15840
gaagagaaca cagggactgt ggaagaggca atattcaaaa gatgatggct gagaaatttc  15900
aaacattgaa gcaagatgtg accggaatcc tcaggtacag gaagcatcct gagtcttggt  15960
aggaaaaatt aacacacaac caaatgagga cacatcacag gaatctgcag aacactgaag  16020
gcaatggata tcttaaaatc aaccaaagag aaagactaat gatctacaca cgaagcatga  16080
ttaaaccggc aactgattta tcatcaatgt accttctaaa gactgaaagg aaattaatgg  16140
ccaaccaaga cttatactca ggtgaactat tatttgagag gaagaagtta atttcagaga  16200
aagagagttt accactcaca gatcctcact gaaaagaact actaaaaatc tgaaaaggaa  16260
acagaaccca gaaaaaagga ataggataga aggagacatg ggagcaatg aaattagtaa  16320
```

-continued

```
acgtttaggt aaatccaaaa aacattagtg aaaatacaca cacacacact tatgagacta  16380
gttttcacta aaaattggtc aaatagtggc aatttcatat agttctacct aacaaaaatg  16440
tatttacaca tagtttagtt tgtgggggtt ttgtttgctt gtttgtttgt ttgtttttttg  16500
agacagggtc tcaccgttgc ccaggatgga gtgcagtggt gtaatcactg cagcctcgac  16560
caccctgggc tcagatgatc ctcccacctc agtcttctga gtagctagga ccacaggcat  16620
acaccaccat gcccagctaa tttttatatt tttttgtagg gacgggggtc tcgctatgtt  16680
tcccaggctg gtctcgaact catgggctca agcgagctgc ccgcctcggc ctcaaaagtg  16740
ttgggattac aggtgtaagc caccctacac ctggccaagt ttatctcatt tcctactgta  16800
ctcccagtgc ctagaccagt gcttatcaca tggtagggag ggctcaaaaa catctattga  16860
tgaagggact actttggagg aggtgttaaa agtaatgagg aactaaaata tcagaccgaa  16920
gcaacctgga aatgggaaag gagagatcaa agtgaaagca ttcagcagcc tttgcattat  16980
tcgggagaaa gatagggata ttgattatct atagactttg ttaggtcaga caagaatatt  17040
aaaattttaa ggataaccca taaaacgaat agaaagaatg gataactttt aaactagtat  17100
atggggaaga gagactaaag agcatccgat tgacttctag taacggacgg tggattaatt  17160
gcatgcatta gcctctgctg ttctctgaaa tctcaataac gtggcattga agtgcacttt  17220
ttacaaaatg cataaaccca aagggaaaat agaaaaggag acaaaaaataa caacatttgg  17280
gaagctggaa agcttccaaa tggtcaaacg gtggtgacag gcacacctga catgaatttt  17340
gaagcagcag tggagaaagc caagaaggcc cctgattttc actactaaac tctccaaatg  17400
ctctgacatt agtgtcaaca ttcttctgga agagtgggtg gcagtgggac tagaaatatg  17460
gcagttggtc gagagtctgt ttgagaagca gctgttctct tcaactctac ttggctgggt  17520
acccccaaag cagcagaaaa ccagatgctt attctctctg aaaagggtaa aagagtggga  17580
ctccggcctg gagaaaacta ggtattgttg ggggccaggg tttttgtgct aagaaaaatt  17640
aaggaaaact ttatacatta aattttgagg ctgggcacag tggctcatgc ctgtaatccc  17700
aacactttga gaaggcaagg caggaggatc gcttgagccc aggagttcga taccagcctg  17760
ggcaatgtag cgagaccctg tctctgcaaa gaatacaaaa attagccagg tatggtggca  17820
cctgtggtcc tagctactca ggaggctgag gcagaaggat tacttgagcc cacgagttag  17880
agaccgcagt gagccatgat catgctactg ctctctagcc tgggcgacag aatgagaccc  17940
catctcaaaa ataaattttt ttaaaagact cctcagttca ccatctttcc ccatattgaa  18000
aatggaacaa cattctccct gagaaatttg gctggcccaa ggaaataagc ctaaagaaac  18060
tgacttttgg gggttccctg ctctccagat ggtccctcct aaattgaacc atggactcag  18120
gatttcacat cagcttcttc taatttatgc agctttcttc taatttactg tggggttttt  18180
tcggtgtttt ttgttttgtt ttgtttttttg agacagggtc ttgctctgtc atccagctgg  18240
agtgcagtgg tgtgatcata gctcactgca gcctcaaact cctgggctca agtgatcctc  18300
ccacctcagc ctcctaagta gctggggcta caggcatgac caccacacct ggctaacttt  18360
ttaatttttt gtagaggtgg gggtcttgac atgttgctca ggctggtctt gaaatcctgg  18420
cctcaagcga tccccctgcc tcagcctccc aaagtgctgg gatttcaagc atgtgccact  18480
gtgcctggct aagaatactt aaaggtgaag tgagaagttc acatgatgtc atatcaggag  18540
gtacacaatg gctacttgtc ccactaatag caatccttag ttttttcact tcgtgaggtg  18600
gtcactagca gacctcttgg ttggaaagat aggttatttc cctttgtaat taacaagtaa  18660
cagaattggg atactttggc atcttaaaat accttggcaa cctgatgaac atagcataca  18720
```

-continued

```
ttcaagattt ttgcctgaat taattattac attagaagag ttgcagaatg agaatgttct  18780
aattctacta tttcttttat atatttcagc tgatgttatt ctatgaagaa aagctccctc  18840
atcagtgaag atgaactgca cttctttcta aagaggcaat gtcagacggg cacggtggcc  18900
tataatccta gcactttggg aggccgagga gggtggatca cctgaggtca ggagttcgag  18960
accaacctgg ccaacatggt aaaaccctgt ctctacttaa aatacaaaaa ttagccgggc  19020
atggtggcac atgcctgtaa tcctagctac atgggaggct gaggcagaag aatcgcttga  19080
acctgagagg cagaggttgc agtgagctaa gattgtacca ctgcactcca ggctgggtga  19140
cagagtgaga ctctgtctca aaaaaaaaca aaacaaaacg aaacaaaaaa acagttgaca  19200
gtagttgttt ttgtagagtg aaaaatagag gtgggggttg agatactgct gctattttaa  19260
actaacttgt agatctgttt gactcttttt taaaaaacaa ttttttggag agatgaagcc  19320
ttgctatgta gcccgggctg ctctcaaacc cctggcctca agtgatcccc ctgtctcgac  19380
ctcccaaagt gctggggtta cagacataag tcaccacacc tggctctgtt tgactcttta  19440
tgtgcagttt gaacttttta actgaatttt ttaaaaggtg tgaaattagt ctttaaagga  19500
acacaaaacc aacagagaag caagcaggaa gatacaagaa gcaaagaaat atcatagtaa  19560
aatgaaaata caaaataata tgacataaat aaaacagtaa tcactatcaa attaaataga  19620
ttaagtgagc ccacaaggca ttgtctctgg gactagtccg ctgggtcgaa gtcctgccac  19680
ttattggttc tgtgaccttt ggcaaattat ttaacttctc tgtgattcca tttctttctt  19740
ttgttttctt tctttcgttt ttttttttga gacagagtct cactctgtca ctcaggctgg  19800
gtgcagtggt gcaatcacca atcacaactt actgcagcct ccacctcctg ggcccacgcg  19860
atcctctcac ctcagtctcc tgagtccctg ggaacacaga catgtgccac cctgccaagc  19920
taatttttaa atttttttgta gcgattgggt ctcactatat tgcctaggct ggtctcagac  19980
tcctgagctc aagtgatcct cccgccttgg cctcccaaag tgctgggatt acaggcatga  20040
gccactgcac ccagcctcaa actctgtaaa aggggaataa tgataatact tgcctcatag  20100
ggcttgtggg aaataatgct ttattactgt aggttaaaaa gcacacaaac atgcttgaca  20160
cagtaggtgc tacatcagtt tactattgtt gttgttttca gattggattt tataaaaact  20220
ctacttattt gcaatttata agaggcatac ctaaaatata atgtcagaga aaggttaaaa  20280
agtggagcca gggaaggaat ttaagaagac ataccagacc aatagtaatc aaaagaaagc  20340
aggtatgcaa tgtaacatca gaacaaataa gctttgctta tttggattga tagggataga  20400
taggattgat agggataaag cagatcatta tttaatgatc aaagaagaaa tttggctggg  20460
cgtggtggct cacacctgta atcccagcgc tttgggaggc cggggcaggg ggatggatca  20520
caaggtcagg agtttgagac cagcctgacc aaagtggtga aaccctgtct ctactaaaaa  20580
tacaaaaaat tatccgggtg tggtggtgca tgcctgtagt cccagctact caggaggctg  20640
aggcaggaaa atcatttgaa ccggggaggc agaggttgca gtgaactgag atcgcaccac  20700
tgcactccag cctgggtgac agaataagac tctgtctcaa aaaaaaagaa aaaagaagaa  20760
gaagaataaa ttcactggga agataaaaca attctgaacc tgacaacata gtctcaaaat  20820
acgtaaagca aaaagccact gagtcccaaa gagaacttga caaatttggt aggagatttt  20880
aataccattt cctcaaactg atggaatcac agaaaaaaaa tataagaaca agtcagcaaa  20940
cttgatatgg aaagaacagc atccccacct gagagtcagc agcctccatg caggaggacc  21000
gaggggaagc cagggagcag ggcagcctga gccaaggcca agcccagttg aggacaggaa  21060
```

-continued gtggaaggag gcacctagga aggctgaaga tgcagaggag tgtgttccag aggcagtggg 21120
aaaactggga gggaatagtt ctcgggatgt tggatagaga gaataagcaa agaacaatgc 21180
aggaagaaga gtggggtggg aggccgtgac cttgctagag agccttatgt tttgggctat 21240
gaccagggct gacagaagtg tgaggcatgg cgggttcaga agagagatca atgatgcatc 21300
gcacatctct aaagctgatg aaggcagcaa ttggcactga ggccaacctg gttgggactc 21360
agagaggtgg gacacatatt gtgtgccagg caccctgcca catcttggag agaataagac 21420
acaaaccctc atctagtggg ttggggaaat gatgcagggc tcagtgtggc tagcgcgttg 21480
gggtgggaag cagcctgggc acgcccacaa ggctctctgc cttccagaat ctggcccagt 21540
tgggtttgaa aagatttaat gacaatgagc tctctatgga cctaccttgt gcccagtatt 21600
tacctttctt atctgtaacg ctcaagtcaa tactctaagg taggaattgt tatcctcatt 21660
ttatttacag agaaactgga gttcagagag attcttgccc aaggtcttgc cctgggccaa 21720
ttccaggtct atctaactcc aaagtccatg ctcagtacac tgtctcctgc ttgggagcaa 21780
agagaggact ttgctcctaa gaccagaccc ataccacaaa gagcctcaac acttaactac 21840
tgggagaaaa caccgtccta agtaaaaagc caggtgctct tcccttacc ccaggggggtt 21900
taggatttgg gagaaagagg cctgatggaa tataggggta ccaggtccat gtgttaactg 21960
atctgggtac aagaacagta actcaaggcc agccagggaa agaacagcca agccgaggca 22020
cagctgccaa gtcatcacct ctcgttcctt gtcccaccat gccttgtctc agcacgaaca 22080
taaccccctc agtttccctc ttctcctgtc tcctgcatag gcagaaccag ttctgagtga 22140
tagccaggac agcaggtcct cgggtcctca ggcttgccac tacaacctgt ttaccctgcg 22200
cagaccatga tccatcaggt cgagaaatgc cccactgcta gatgtttgtg tcaaaaatgc 22260
ctgccggtgg tgcaacagct gggtgggacc agtgacgtgg acttgagtgc cacaaaatgt 22320
accgaacaca ttctgagtca acatagtgat ggtgtgccaa ctccagataa agattttcat 22380
tattatttgt ttgggttttg tttatatgta ctcctcttca tcaccaaaga tttgaggcta 22440
cagaaaatga aaattgaaat ggtaataaaa gagaggggct tgcagagagg accacaggat 22500
ggggaaaata gaaataatcg cagaaaatca tgacccgatg aagagcacaa tcatagaagc 22560
actaacagat gacaaggttg ccagatcttc accattggtt ttgggtttcg tgaaaacccg 22620
cgaagagagg gattcagtca attacatatt ttttttcctt ctttctttta tttttatttt 22680
ttattttttc ttgaaatgga gtctcattcc gtcaccaagg ctggagtgca gtggtgcaat 22740
cttggctcac tgcagccttc acctcctgag gttcaagcca ttctcctgat tcagcttcct 22800
gaatagctgg gactacaggc atgaaccacc atgcctggct aatttttgta tttttagtag 22860
agactgtcac acgcgagaca gggtttcacc atgtttgcca ggctctcgaa ctactgacct 22920
caagtgaccc gcccacagca gcctcccaaa gtcctggaat tacaggcatg agccaccgtg 22980
cctggcttgt tttaattttt tattataaac aacactgtga tgaacatcca catagctaaa 23040
tgcatgcatt ccatgatcat tttcttaaga taattttttt cttattattt gtgtatttat 23100
ttatttattt ttgagacgga gtcttgctct gtcacccagg caagagtgca gtggcacaat 23160
ctcggcttac tgcaacctcc acctcccagg ttcaaacaat tctcctgcct cagcctctta 23220
agtagctggg atacaggcac aagccaccaa gcccagctaa ttttgtattt ttagtagaga 23280
cagagtttcg ccatgttggc caggctggtc gccaactcct gacctcaggc aatcgcctgc 23340
ctcggcctcc caaagtgctg ggattacagg cgtgagccac ctcacctggc cttaagatac 23400
atttttgaag ggaagaacat tttctgtcca agtacattcc tgttcacaaa cccttttcca 23460

```
taacactgga gacttcctgg ggaggttgga accaatggct tagactccaa aggaatgaat  23520
gtaccataaa gctttcagca atcttctgtc aatgctactt gtatagactt ccagacaaac  23580
attgaagatt gaatgcatgc atctaatttc acttttttttt cctgaaatcc tcctgaaact  23640
ataatgaaga aatgtttggg aaaagatgta gccaggcact gtggcttatg cctgtaatcc  23700
tagcactttg ggaggccaag gtgggcagat cgcttgagtc caggagtttg agactagcct  23760
gggcaacatg gcgaaaccct gtctctactg aaaaaataca aaaaatcagc caggcatggc  23820
agacctgtag ttccagctac tcagggggct gaggtgtgag gatcacttga gcctgggagg  23880
tagaagctgc cgtgagccct gattgtgcca ctgaactcca gcctgggcga cagagtgaga  23940
ccctgtctca aaaaacaaaa aaaaaaaaaa aaaaaaaaag agacgggatc gggaaaagga  24000
agaaaagacc acagcacaat tttggatgtt agaaagcaaa tggaccagtt gtaactgatt  24060
tagccggcct tgggaatgct ggtcatgagc tggcagtgag aaaagatgag ttccagcctg  24120
acttacaccg ctggattctc aaaaggcgaa gagatgatag tagggctcct gccagcccac  24180
gctgcacctg tgtgtgcaat agaaacagcc tccccttttct caagacactc tacagccgtc  24240
tgccagaaat ttgacatgat aaatatacaa atctgtcatg tctaccctgt gagggaggtg  24300
gcctcagaat gatacagtgc acagcttgca cagccatata tgactgtcct gaattgggac  24360
accagtttct actgaaagta gaggtgacgg aggaggctgt cataaaacat gaaagattgg  24420
ttgaaactat ttaaggagca gttagagctt tagcttccct gtctcacctt agtagaagac  24480
tggaagttta ttctcttgaa cgtcaggcag agttgagggc aggagacctg tactagcaag  24540
aggattaaat caaagtatac cctctgaaat gctgaatcac cctcctgctt cttccacttg  24600
gccccaggga cactgtattc aggcctttac cctccaggca gaagaatgaa agacatttct  24660
taggggaata tgtccagctc aagaggtaag acccaaagat tttcacaatg gggttcccca  24720
gctaaacatc tcagtggatc accctgcagt gacattcata gtcaataagt actacgcacg  24780
tattggagct tcaaatcacc tttaaaatct cccattcttt tctttttttct ttttgagaca  24840
gagtctcgct ctgtcaccca ggctggagtg cagtggtgcg atctcggctc actgcaagct  24900
ctgcctcccg ggttcacgcc attctcctgc ctcagcctcc tgagtaactg ggactacagg  24960
cacctgccac cacgcctggc taattttttg catatttagt agagacagag tttcaccatg  25020
ttagccagga tggtctcgat ctcctgacct cgtgatccac ccaccttggc ctcccaaagt  25080
gctgggatta caggcgtgag ccaccgctcc cagcccaaat ctcccactct taaacttaag  25140
caaccaagga ttaccagtca tttgaggaaa gattctaaca tgaaagatag agacccaaaa  25200
caaacaaata tttaaaaagg aagttagaga aaactgagaa tatacagaaa gaagaacatt  25260
gaaaaatgcc attaataaca tcagagaatg aaaagattac attgattaaa caagaacagg  25320
atagtataaa aagaccttca cagaataaca ataacaaaaa ctcttagaaa ttaaaaaaaa  25380
gatagtagaa ataaaaactg aatagagagt aaagaaatag ttcagaaagg gagagcatgt  25440
agagattgaa gtaagaacaa agataagaaa atgagaggat ccacgccggg cgcagtggct  25500
cacgcctgta atcccagcac tttgggattt aatataaata tattaaatat tttaaataat  25560
ataattttaa ataatataaa tatattaaat atattaaata tttaaatata ttaaatattt  25620
aaatatatta aattcattca gtcaacaaat atttattgaa tacctactaa gttctagtca  25680
tcatgctagg cactgactgt tcaagaataa acatagacaa gacttctgcc ctttcagaaa  25740
ccagccaaga ttcttcaacc caaggcagct gtgaagtata acacatctct ggctcaattt  25800
```

```
tctccatatg gtttggggtt ccatgaatga gtctgtggga agatttcctg tacgtagaat  25860

gcatgcataa aggaataatt attctatggt tcgaaagaga aaaaaagtaa gatcaaagtg  25920

tagaagctat gttaagaaag attccagttt aatgattttt gaaagagcag taaaaataag  25980

accaagatgt ggaagctgta ttgagaaaga tccaatttaa ttctaataat ctttaacaga  26040

attgcccaaa gatagaatga attgttttga gagatggtac agttagctgt cagtgggagt  26100

gttcaatact aagcaagatt cactcgctca accattgagt gatgaccaca tgcaggcact  26160

gtgctaggct ctctgtattt tcagtaagct attgttgtac aacaaagcac cttaaaacag  26220

tgtcttagaa caacagtaaa tgtttatgat ctctcacaaa gtctgtgggt cagcagcttg  26280

gctgtgtgtt tctggttcag agtctgtcat gaggttgcat ctgaaggctt ggctgaggct  26340

ggaggatctg tttccaaggt gaatcacttt acatggctgg caagttggtg ctagctgttc  26400

ggaaggggct tcagttcccc cctgtgttga cctcttcaca gggctgcttg cacgtcctcc  26460

caacatggca gctatcttcc ctcagaatga gtgatccaag agaaatcaag gtaggtgcca  26520

caatgccctt tatgacttag acttagaagt gaaataccat gacatagcct attgatcaca  26580

catcagccac cattgtgagg gctagctacc acatcctgca aatacaatga tgaacaaaca  26640

aatggtgtgc ctgagc                                                  26656
```

<210> SEQ ID NO 6
<211> LENGTH: 263744
<212> TYPE: DNA
<213> ORGANISM: Mus musculus
<220> FEATURE:
<221> NAME/KEY: misc_feature
<222> LOCATION: (750)..(850)
<223> OTHER INFORMATION: gap of unknown length
<220> FEATURE:
<221> NAME/KEY: misc_feature
<222> LOCATION: (1584)..(1683)
<223> OTHER INFORMATION: gap of unknown length
<220> FEATURE:
<221> NAME/KEY: misc_feature
<222> LOCATION: (2154)..(2154)
<223> OTHER INFORMATION: gap of unknown length
<220> FEATURE:
<221> NAME/KEY: misc_feature
<222> LOCATION: (2358)..(2457)
<223> OTHER INFORMATION: gap of unknown length
<220> FEATURE:
<221> NAME/KEY: misc_feature
<222> LOCATION: (3208)..(3307)
<223> OTHER INFORMATION: gap of unknown length
<220> FEATURE:
<221> NAME/KEY: misc_feature
<222> LOCATION: (4044)..(4143)
<223> OTHER INFORMATION: gap of unknown length
<220> FEATURE:
<221> NAME/KEY: misc_feature
<222> LOCATION: (4809)..(4908)
<223> OTHER INFORMATION: gap of unknown length
<220> FEATURE:
<221> NAME/KEY: misc_feature
<222> LOCATION: (4921)..(4921)
<223> OTHER INFORMATION: gap of unknown length
<220> FEATURE:
<221> NAME/KEY: misc_feature
<222> LOCATION: (5652)..(5751)
<223> OTHER INFORMATION: gap of unknown length
<220> FEATURE:
<221> NAME/KEY: misc_feature
<222> LOCATION: (6469)..(6469)
<223> OTHER INFORMATION: gap of unknown length
<220> FEATURE:
<221> NAME/KEY: misc_feature
<222> LOCATION: (6477)..(6477)
<223> OTHER INFORMATION: gap of unknown length
<220> FEATURE:
<221> NAME/KEY: misc_feature
<222> LOCATION: (6482)..(6482)
<223> OTHER INFORMATION: gap of unknown length
<220> FEATURE:
<221> NAME/KEY: misc_feature
<222> LOCATION: (6487)..(6487)
<223> OTHER INFORMATION: gap of unknown length
<220> FEATURE:
<221> NAME/KEY: misc_feature
<222> LOCATION: (6489)..(6490)
<223> OTHER INFORMATION: gap of unknown length
<220> FEATURE:
<221> NAME/KEY: misc_feature
<222> LOCATION: (6523)..(6622)
<223> OTHER INFORMATION: gap of unknown length
<220> FEATURE:
<221> NAME/KEY: misc_feature
<222> LOCATION: (6637)..(6637)
<223> OTHER INFORMATION: gap of unknown length
<220> FEATURE:
<221> NAME/KEY: misc_feature
<222> LOCATION: (7410)..(7509)
<223> OTHER INFORMATION: gap of unknown length
<220> FEATURE:
<221> NAME/KEY: misc_feature
<222> LOCATION: (8177)..(8177)
<223> OTHER INFORMATION: gap of unknown length
<220> FEATURE:
<221> NAME/KEY: misc_feature
<222> LOCATION: (8248)..(8347)
<223> OTHER INFORMATION: gap of unknown length
<220> FEATURE:
<221> NAME/KEY: misc_feature
<222> LOCATION: (8358)..(8358)
<223> OTHER INFORMATION: gap of unknown length
<220> FEATURE:
<221> NAME/KEY: misc_feature
<222> LOCATION: (8967)..(8967)
<223> OTHER INFORMATION: gap of unknown length
<220> FEATURE:
<221> NAME/KEY: misc_feature
<222> LOCATION: (9057)..(9057)
<223> OTHER INFORMATION: gap of unknown length
<220> FEATURE:
<221> NAME/KEY: misc_feature
<222> LOCATION: (9105)..(9204)
<223> OTHER INFORMATION: gap of unknown length
<220> FEATURE:
<221> NAME/KEY: misc_feature
<222> LOCATION: (9980)..(10079)
<223> OTHER INFORMATION: gap of unknown length
<220> FEATURE:
<221> NAME/KEY: misc_feature
<222> LOCATION: (10092)..(10092)
<223> OTHER INFORMATION: gap of unknown length
<220> FEATURE:
<221> NAME/KEY: misc_feature
<222> LOCATION: (10827)..(10926)
<223> OTHER INFORMATION: gap of unknown length
<220> FEATURE:
<221> NAME/KEY: misc_feature
<222> LOCATION: (11701)..(11800)
<223> OTHER INFORMATION: gap of unknown length
<220> FEATURE:
<221> NAME/KEY: misc_feature
<222> LOCATION: (11816)..(11816)
<223> OTHER INFORMATION: gap of unknown length
<220> FEATURE:
<221> NAME/KEY: misc_feature
<222> LOCATION: (11827)..(11827)
<223> OTHER INFORMATION: gap of unknown length
<220> FEATURE:
<221> NAME/KEY: misc_feature
<222> LOCATION: (11829)..(11829)
<223> OTHER INFORMATION: gap of unknown length
<220> FEATURE:
<221> NAME/KEY: misc_feature
<222> LOCATION: (12565)..(12664)

<223> OTHER INFORMATION: gap of unknown length
<220> FEATURE:
<221> NAME/KEY: misc_feature
<222> LOCATION: (13327)..(13327)
<223> OTHER INFORMATION: gap of unknown length
<220> FEATURE:
<221> NAME/KEY: misc_feature
<222> LOCATION: (13440)..(13539)
<223> OTHER INFORMATION: gap of unknown length
<220> FEATURE:
<221> NAME/KEY: misc_feature
<222> LOCATION: (13554)..(13554)
<223> OTHER INFORMATION: gap of unknown length
<220> FEATURE:
<221> NAME/KEY: misc_feature
<222> LOCATION: (14133)..(14133)
<223> OTHER INFORMATION: gap of unknown length
<220> FEATURE:
<221> NAME/KEY: misc_feature
<222> LOCATION: (14213)..(14213)
<223> OTHER INFORMATION: gap of unknown length
<220> FEATURE:
<221> NAME/KEY: misc_feature
<222> LOCATION: (14293)..(14392)
<223> OTHER INFORMATION: gap of unknown length
<220> FEATURE:
<221> NAME/KEY: misc_feature
<222> LOCATION: (14559)..(14559)
<223> OTHER INFORMATION: gap of unknown length
<220> FEATURE:
<221> NAME/KEY: misc_feature
<222> LOCATION: (14900)..(14900)
<223> OTHER INFORMATION: gap of unknown length
<220> FEATURE:
<221> NAME/KEY: misc_feature
<222> LOCATION: (15119)..(15218)
<223> OTHER INFORMATION: gap of unknown length
<220> FEATURE:
<221> NAME/KEY: misc_feature
<222> LOCATION: (15231)..(15233)
<223> OTHER INFORMATION: gap of unknown length
<220> FEATURE:
<221> NAME/KEY: misc_feature
<222> LOCATION: (15919)..(15919)
<223> OTHER INFORMATION: gap of unknown length
<220> FEATURE:
<221> NAME/KEY: misc_feature
<222> LOCATION: (15922)..(15922)
<223> OTHER INFORMATION: gap of unknown length
<220> FEATURE:
<221> NAME/KEY: misc_feature
<222> LOCATION: (15962)..(16061)
<223> OTHER INFORMATION: gap of unknown length
<220> FEATURE:
<221> NAME/KEY: misc_feature
<222> LOCATION: (16757)..(16757)
<223> OTHER INFORMATION: gap of unknown length
<220> FEATURE:
<221> NAME/KEY: misc_feature
<222> LOCATION: (16809)..(16809)
<223> OTHER INFORMATION: gap of unknown length
<220> FEATURE:
<221> NAME/KEY: misc_feature
<222> LOCATION: (16810)..(16909)
<223> OTHER INFORMATION: gap of unknown length
<220> FEATURE:
<221> NAME/KEY: misc_feature
<222> LOCATION: (17660)..(17660)
<223> OTHER INFORMATION: gap of unknown length
<220> FEATURE:
<221> NAME/KEY: misc_feature
<222> LOCATION: (17681)..(17780)
<223> OTHER INFORMATION: gap of unknown length
<220> FEATURE:
<221> NAME/KEY: misc_feature
<222> LOCATION: (17898)..(17898)
<223> OTHER INFORMATION: gap of unknown length
<220> FEATURE:
<221> NAME/KEY: misc_feature
<222> LOCATION: (18183)..(18183)
<223> OTHER INFORMATION: gap of unknown length
<220> FEATURE:
<221> NAME/KEY: misc_feature
<222> LOCATION: (18408)..(18408)
<223> OTHER INFORMATION: gap of unknown length
<220> FEATURE:
<221> NAME/KEY: misc_feature
<222> LOCATION: (18498)..(18498)
<223> OTHER INFORMATION: gap of unknown length
<220> FEATURE:
<221> NAME/KEY: misc_feature
<222> LOCATION: (18527)..(18626)
<223> OTHER INFORMATION: gap of unknown length
<220> FEATURE:
<221> NAME/KEY: misc_feature
<222> LOCATION: (19299)..(19299)
<223> OTHER INFORMATION: gap of unknown length
<220> FEATURE:
<221> NAME/KEY: misc_feature
<222> LOCATION: (19306)..(19306)
<223> OTHER INFORMATION: gap of unknown length
<220> FEATURE:
<221> NAME/KEY: misc_feature
<222> LOCATION: (19369)..(19468)
<223> OTHER INFORMATION: gap of unknown length
<220> FEATURE:
<221> NAME/KEY: misc_feature
<222> LOCATION: (19485)..(19485)
<223> OTHER INFORMATION: gap of unknown length
<220> FEATURE:
<221> NAME/KEY: misc_feature
<222> LOCATION: (20163)..(20163)
<223> OTHER INFORMATION: gap of unknown length
<220> FEATURE:
<221> NAME/KEY: misc_feature
<222> LOCATION: (20214)..(20313)
<223> OTHER INFORMATION: gap of unknown length
<220> FEATURE:
<221> NAME/KEY: misc_feature
<222> LOCATION: (21029)..(21128)
<223> OTHER INFORMATION: gap of unknown length
<220> FEATURE:
<221> NAME/KEY: misc_feature
<222> LOCATION: (21869)..(21968)
<223> OTHER INFORMATION: gap of unknown length
<220> FEATURE:
<221> NAME/KEY: misc_feature
<222> LOCATION: (22077)..(22077)
<223> OTHER INFORMATION: gap of unknown length
<220> FEATURE:
<221> NAME/KEY: misc_feature
<222> LOCATION: (22643)..(22742)
<223> OTHER INFORMATION: gap of unknown length
<220> FEATURE:
<221> NAME/KEY: misc_feature
<222> LOCATION: (23471)..(23570)
<223> OTHER INFORMATION: gap of unknown length
<220> FEATURE:
<221> NAME/KEY: misc_feature
<222> LOCATION: (24291)..(24291)
<223> OTHER INFORMATION: gap of unknown length
<220> FEATURE:
<221> NAME/KEY: misc_feature
<222> LOCATION: (24311)..(24311)
<223> OTHER INFORMATION: gap of unknown length
<220> FEATURE:
<221> NAME/KEY: misc_feature
<222> LOCATION: (24317)..(24317)
<223> OTHER INFORMATION: gap of unknown length
<220> FEATURE:
<221> NAME/KEY: misc_feature
<222> LOCATION: (24326)..(24326)
<223> OTHER INFORMATION: gap of unknown length
<220> FEATURE:
<221> NAME/KEY: misc_feature
<222> LOCATION: (24338)..(24437)
<223> OTHER INFORMATION: gap of unknown length
<220> FEATURE:

```
<221> NAME/KEY: misc_feature
<222> LOCATION: (25114)..(25215)
<223> OTHER INFORMATION: gap of unknown length
<220> FEATURE:
<221> NAME/KEY: misc_feature
<222> LOCATION: (25943)..(26042)
<223> OTHER INFORMATION: gap of unknown length
<220> FEATURE:
<221> NAME/KEY: misc_feature
<222> LOCATION: (26151)..(26151)
<223> OTHER INFORMATION: gap of unknown length
<220> FEATURE:
<221> NAME/KEY: misc_feature
<222> LOCATION: (26810)..(26909)
<223> OTHER INFORMATION: gap of unknown length
<220> FEATURE:
<221> NAME/KEY: misc_feature
<222> LOCATION: (27604)..(27604)
<223> OTHER INFORMATION: gap of unknown length
<220> FEATURE:
<221> NAME/KEY: misc_feature
<222> LOCATION: (27609)..(27709)
<223> OTHER INFORMATION: gap of unknown length
<220> FEATURE:
<221> NAME/KEY: misc_feature
<222> LOCATION: (27809)..(27809)
<223> OTHER INFORMATION: gap of unknown length
<220> FEATURE:
<221> NAME/KEY: misc_feature
<222> LOCATION: (28423)..(28522)
<223> OTHER INFORMATION: gap of unknown length
<220> FEATURE:
<221> NAME/KEY: misc_feature
<222> LOCATION: (28557)..(28557)
<223> OTHER INFORMATION: gap of unknown length
<220> FEATURE:
<221> NAME/KEY: misc_feature
<222> LOCATION: (28779)..(28878)
<223> OTHER INFORMATION: gap of unknown length
<220> FEATURE:
<221> NAME/KEY: misc_feature
<222> LOCATION: (29124)..(29224)
<223> OTHER INFORMATION: gap of unknown length
<220> FEATURE:
<221> NAME/KEY: misc_feature
<222> LOCATION: (29230)..(29230)
<223> OTHER INFORMATION: gap of unknown length
<220> FEATURE:
<221> NAME/KEY: misc_feature
<222> LOCATION: (29910)..(30010)
<223> OTHER INFORMATION: gap of unknown length
<220> FEATURE:
<221> NAME/KEY: misc_feature
<222> LOCATION: (30746)..(30845)
<223> OTHER INFORMATION: gap of unknown length
<220> FEATURE:
<221> NAME/KEY: misc_feature
<222> LOCATION: (31528)..(31528)
<223> OTHER INFORMATION: gap of unknown length
<220> FEATURE:
<221> NAME/KEY: misc_feature
<222> LOCATION: (31542)..(31542)
<223> OTHER INFORMATION: gap of unknown length
<220> FEATURE:
<221> NAME/KEY: misc_feature
<222> LOCATION: (31561)..(31561)
<223> OTHER INFORMATION: gap of unknown length
<220> FEATURE:
<221> NAME/KEY: misc_feature
<222> LOCATION: (31566)..(31567)
<223> OTHER INFORMATION: gap of unknown length
<220> FEATURE:
<221> NAME/KEY: misc_feature
<222> LOCATION: (31586)..(31685)
<223> OTHER INFORMATION: gap of unknown length
<220> FEATURE:
<221> NAME/KEY: misc_feature
<222> LOCATION: (31891)..(31891)
<223> OTHER INFORMATION: gap of unknown length
```

<220> FEATURE:
<221> NAME/KEY: misc_feature
<222> LOCATION: (31983)..(32082)
<223> OTHER INFORMATION: gap of unknown length
<220> FEATURE:
<221> NAME/KEY: misc_feature
<222> LOCATION: (32776)..(32875)
<223> OTHER INFORMATION: gap of unknown length
<220> FEATURE:
<221> NAME/KEY: misc_feature
<222> LOCATION: (32893)..(32893)
<223> OTHER INFORMATION: gap of unknown length
<220> FEATURE:
<221> NAME/KEY: misc_feature
<222> LOCATION: (32902)..(32902)
<223> OTHER INFORMATION: gap of unknown length
<220> FEATURE:
<221> NAME/KEY: misc_feature
<222> LOCATION: (33574)..(33673)
<223> OTHER INFORMATION: gap of unknown length
<220> FEATURE:
<221> NAME/KEY: misc_feature
<222> LOCATION: (34308)..(34407)
<223> OTHER INFORMATION: gap of unknown length
<220> FEATURE:
<221> NAME/KEY: misc_feature
<222> LOCATION: (34447)..(34447)
<223> OTHER INFORMATION: gap of unknown length
<220> FEATURE:
<221> NAME/KEY: misc_feature
<222> LOCATION: (34549)..(34648)
<223> OTHER INFORMATION: gap of unknown length
<220> FEATURE:
<221> NAME/KEY: misc_feature
<222> LOCATION: (35325)..(35424)
<223> OTHER INFORMATION: gap of unknown length
<220> FEATURE:
<221> NAME/KEY: misc_feature
<222> LOCATION: (36100)..(36199)
<223> OTHER INFORMATION: gap of unknown length
<220> FEATURE:
<221> NAME/KEY: misc_feature
<222> LOCATION: (36700)..(36799)
<223> OTHER INFORMATION: gap of unknown length
<220> FEATURE:
<221> NAME/KEY: misc_feature
<222> LOCATION: (37380)..(37380)
<223> OTHER INFORMATION: gap of unknown length
<220> FEATURE:
<221> NAME/KEY: misc_feature
<222> LOCATION: (37412)..(37511)
<223> OTHER INFORMATION: gap of unknown length
<220> FEATURE:
<221> NAME/KEY: misc_feature
<222> LOCATION: (38304)..(38403)
<223> OTHER INFORMATION: gap of unknown length
<220> FEATURE:
<221> NAME/KEY: misc_feature
<222> LOCATION: (38808)..(38907)
<223> OTHER INFORMATION: gap of unknown length
<220> FEATURE:
<221> NAME/KEY: misc_feature
<222> LOCATION: (38966)..(39065)
<223> OTHER INFORMATION: gap of unknown length
<220> FEATURE:
<221> NAME/KEY: misc_feature
<222> LOCATION: (39899)..(39899)
<223> OTHER INFORMATION: gap of unknown length
<220> FEATURE:
<221> NAME/KEY: misc_feature
<222> LOCATION: (39902)..(39903)
<223> OTHER INFORMATION: gap of unknown length
<220> FEATURE:
<221> NAME/KEY: misc_feature
<222> LOCATION: (39906)..(39906)
<223> OTHER INFORMATION: gap of unknown length
<220> FEATURE:
<221> NAME/KEY: misc_feature
<222> LOCATION: (39916)..(40015)

<223> OTHER INFORMATION: gap of unknown length
<220> FEATURE:
<221> NAME/KEY: misc_feature
<222> LOCATION: (40417)..(40516)
<223> OTHER INFORMATION: gap of unknown length
<220> FEATURE:
<221> NAME/KEY: misc_feature
<222> LOCATION: (41297)..(41396)
<223> OTHER INFORMATION: gap of unknown length
<220> FEATURE:
<221> NAME/KEY: misc_feature
<222> LOCATION: (41993)..(41993)
<223> OTHER INFORMATION: gap of unknown length
<220> FEATURE:
<221> NAME/KEY: misc_feature
<222> LOCATION: (42106)..(42205)
<223> OTHER INFORMATION: gap of unknown length
<220> FEATURE:
<221> NAME/KEY: misc_feature
<222> LOCATION: (42262)..(42361)
<223> OTHER INFORMATION: gap of unknown length
<220> FEATURE:
<221> NAME/KEY: misc_feature
<222> LOCATION: (43651)..(43750)
<223> OTHER INFORMATION: gap of unknown length
<220> FEATURE:
<221> NAME/KEY: misc_feature
<222> LOCATION: (43822)..(43921)
<223> OTHER INFORMATION: gap of unknown length
<220> FEATURE:
<221> NAME/KEY: misc_feature
<222> LOCATION: (44097)..(44196)
<223> OTHER INFORMATION: gap of unknown length
<220> FEATURE:
<221> NAME/KEY: misc_feature
<222> LOCATION: (44953)..(45052)
<223> OTHER INFORMATION: gap of unknown length
<220> FEATURE:
<221> NAME/KEY: misc_feature
<222> LOCATION: (45710)..(45710)
<223> OTHER INFORMATION: gap of unknown length
<220> FEATURE:
<221> NAME/KEY: misc_feature
<222> LOCATION: (45900)..(45999)
<223> OTHER INFORMATION: gap of unknown length
<220> FEATURE:
<221> NAME/KEY: misc_feature
<222> LOCATION: (46123)..(46222)
<223> OTHER INFORMATION: gap of unknown length
<220> FEATURE:
<221> NAME/KEY: misc_feature
<222> LOCATION: (48473)..(48473)
<223> OTHER INFORMATION: gap of unknown length
<220> FEATURE:
<221> NAME/KEY: misc_feature
<222> LOCATION: (48514)..(48613)
<223> OTHER INFORMATION: gap of unknown length
<220> FEATURE:
<221> NAME/KEY: misc_feature
<222> LOCATION: (50619)..(50619)
<223> OTHER INFORMATION: gap of unknown length
<220> FEATURE:
<221> NAME/KEY: misc_feature
<222> LOCATION: (50635)..(50636)
<223> OTHER INFORMATION: gap of unknown length
<220> FEATURE:
<221> NAME/KEY: misc_feature
<222> LOCATION: (50800)..(50899)
<223> OTHER INFORMATION: gap of unknown length
<220> FEATURE:
<221> NAME/KEY: misc_feature
<222> LOCATION: (50963)..(51062)
<223> OTHER INFORMATION: gap of unknown length
<220> FEATURE:
<221> NAME/KEY: misc_feature
<222> LOCATION: (52796)..(52796)
<223> OTHER INFORMATION: gap of unknown length
<220> FEATURE:
<221> NAME/KEY: misc_feature
<222> LOCATION: (52798)..(52799)
<223> OTHER INFORMATION: gap of unknown length
<220> FEATURE:
<221> NAME/KEY: misc_feature
<222> LOCATION: (52803)..(52804)
<223> OTHER INFORMATION: gap of unknown length
<220> FEATURE:
<221> NAME/KEY: misc_feature
<222> LOCATION: (52806)..(52806)
<223> OTHER INFORMATION: gap of unknown length
<220> FEATURE:
<221> NAME/KEY: misc_feature
<222> LOCATION: (52808)..(52811)
<223> OTHER INFORMATION: gap of unknown length
<220> FEATURE:
<221> NAME/KEY: misc_feature
<222> LOCATION: (52826)..(52826)
<223> OTHER INFORMATION: gap of unknown length
<220> FEATURE:
<221> NAME/KEY: misc_feature
<222> LOCATION: (53011)..(53011)
<223> OTHER INFORMATION: gap of unknown length
<220> FEATURE:
<221> NAME/KEY: misc_feature
<222> LOCATION: (53398)..(53497)
<223> OTHER INFORMATION: gap of unknown length
<220> FEATURE:
<221> NAME/KEY: misc_feature
<222> LOCATION: (53578)..(53677)
<223> OTHER INFORMATION: gap of unknown length
<220> FEATURE:
<221> NAME/KEY: misc_feature
<222> LOCATION: (56930)..(57029)
<223> OTHER INFORMATION: gap of unknown length
<220> FEATURE:
<221> NAME/KEY: misc_feature
<222> LOCATION: (57040)..(57040)
<223> OTHER INFORMATION: gap of unknown length
<220> FEATURE:
<221> NAME/KEY: misc_feature
<222> LOCATION: (57073)..(57073)
<223> OTHER INFORMATION: gap of unknown length
<220> FEATURE:
<221> NAME/KEY: misc_feature
<222> LOCATION: (57165)..(57165)
<223> OTHER INFORMATION: gap of unknown length
<220> FEATURE:
<221> NAME/KEY: misc_feature
<222> LOCATION: (57204)..(57204)
<223> OTHER INFORMATION: gap of unknown length
<220> FEATURE:
<221> NAME/KEY: misc_feature
<222> LOCATION: (57207)..(57207)
<223> OTHER INFORMATION: gap of unknown length
<220> FEATURE:
<221> NAME/KEY: misc_feature
<222> LOCATION: (57237)..(57237)
<223> OTHER INFORMATION: gap of unknown length
<220> FEATURE:
<221> NAME/KEY: misc_feature
<222> LOCATION: (57241)..(57242)
<223> OTHER INFORMATION: gap of unknown length
<220> FEATURE:
<221> NAME/KEY: misc_feature
<222> LOCATION: (57244)..(57244)
<223> OTHER INFORMATION: gap of unknown length
<220> FEATURE:
<221> NAME/KEY: misc_feature
<222> LOCATION: (57248)..(57248)
<223> OTHER INFORMATION: gap of unknown length
<220> FEATURE:
<221> NAME/KEY: misc_feature
<222> LOCATION: (64615)..(64714)
<223> OTHER INFORMATION: gap of unknown length
<220> FEATURE:
<221> NAME/KEY: misc_feature
<222> LOCATION: (75186)..(75186)
<223> OTHER INFORMATION: gap of unknown length
<220> FEATURE:

<221> NAME/KEY: misc_feature
<222> LOCATION: (75416)..(75416)
<223> OTHER INFORMATION: gap of unknown length
<220> FEATURE:
<221> NAME/KEY: misc_feature
<222> LOCATION: (75247)..(75346)
<223> OTHER INFORMATION: gap of unknown length
<220> FEATURE:
<221> NAME/KEY: misc_feature
<222> LOCATION: (75420)..(75420)
<223> OTHER INFORMATION: gap of unknown length
<220> FEATURE:
<221> NAME/KEY: misc_feature
<222> LOCATION: (75428)..(75428)
<223> OTHER INFORMATION: gap of unknown length
<220> FEATURE:
<221> NAME/KEY: misc_feature
<222> LOCATION: (75440)..(75441)
<223> OTHER INFORMATION: gap of unknown length
<220> FEATURE:
<221> NAME/KEY: misc_feature
<222> LOCATION: (75443)..(75446)
<223> OTHER INFORMATION: gap of unknown length
<220> FEATURE:
<221> NAME/KEY: misc_feature
<222> LOCATION: (82978)..(83077)
<223> OTHER INFORMATION: gap of unknown length
<220> FEATURE:
<221> NAME/KEY: misc_feature
<222> LOCATION: (96874)..(96973)
<223> OTHER INFORMATION: gap of unknown length
<220> FEATURE:
<221> NAME/KEY: misc_feature
<222> LOCATION: (127516)..(127615)
<223> OTHER INFORMATION: gap of unknown length
<220> FEATURE:
<221> NAME/KEY: misc_feature
<222> LOCATION: (178685)..(178784)
<223> OTHER INFORMATION: gap of unknown length
<220> FEATURE:
<221> NAME/KEY: misc_feature
<222> LOCATION: (178795)..(178795)
<223> OTHER INFORMATION: gap of unknown length
<220> FEATURE:
<221> NAME/KEY: misc_feature
<222> LOCATION: (178806)..(178806)
<223> OTHER INFORMATION: gap of unknown length
<220> FEATURE:
<221> NAME/KEY: misc_feature
<222> LOCATION: (201692)..(201692)
<223> OTHER INFORMATION: gap of unknown length

<400> SEQUENCE: 6
atatcgatca gctatgacct gattactaat tatggccact gtgctctaaa gagtagaaat 60
aaggtgccca gccgaggtaa gagtcccctc agagaaagac tcttgggaga gtttgctgga 120
atttaagtgt gcaggggtgt tagcttggtt ctgctagtat tctgtgcgcc taagcaaaac 180
aaaacaaaac aaccctaaac agaccctagg accatttggg gggagaggtg aagcatgtgg 240
aaaggcgatt ggtgggtgag aagtcaccta caaaatagac agcagtcgac aggtggcacc 300
caggacactc ctggtcacac cacggggtcc tagagtccag atttgcccgg ctgtcatcag 360
aaagtcgcag tggaaaccgt cagcagtact aaggaaatgt gtaaactgtg gggctgagag 420
tcagagcctc cagcccgtcc tcctctgtcc tgactgcgag atctagactc tattctcatc 480
gtcctcttgt gtgatagaag ggcaatggac actggccctc tgcagcatct tgtgacgatc 540
cgagcatttg tgttcgtaca gactgcctct gtgtgtgtgt gtgtgtgtgt gtgtgtgtgt 600
gtgtgtgtgt gtgtgtgtgt gtgtgacaca gagagagaca catataccga gatagagaca 660
gacacagaga ccacttgata actaagtatg ctgtatactg tacatggtgc tgcgtacatt 720
tttatctcaa ggattatagt ttacctgagn nnnnnnnnnn nnnnnnnnnn nnnnnnnnnn 780

-continued

```
nnnnnnnnnn nnnnnnnnnn nnnnnnnnnn nnnnnnnnnn nnnnnnnnnn nnnnnnnnnn    840
nnnnnnnnnn gtgagtatca gctatgacct gattacgaat tatggccact gtgctctaaa    900
gggatacaca tctttaatcc tgcactcggg aggcagacgc aagtggatct ctagagcttg    960
aggcctgcct ggtctacaag tgagttcctg gtcagccagg gatacatgaa attctgtctc   1020
aaaaaaaacc aaaataataa attaattaaa aataaataaa atttatttat tgtatgtatt   1080
tgatttattt atttatttac ttacttactt acttattttt gtgacgggct tgcagccttg   1140
gctgtgggga aagtggaaat aaacctggtg gaggaacaag tgggaaggag agtgaagaga   1200
cataggcttc atcctggcac accatgagac aactcacagg accagagggc agagtggtgg   1260
ctccttcccc tggccttcac agaaatcttc ctggatgaca ggcacctgcc ctacaggctc   1320
atgatcagat gggacagatt cagctaaaca acacatgttg cacccagatt tgtccctgga   1380
tacataaacg taccctaatt ggctgaaaaa ctgcatatca gcatatgtac taaacagtaa   1440
agttagagct ggacctcgat gctggtcttc agatccaaat cccagggaat tttggggact   1500
cggcttcact ccccacccta tttcccgccc ctgttccaca cttgggtgtc ctgaagtaac   1560
tctgtaggca agttgactta aagnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnntaactat tcgacaacta ctatgacctg attacgaatt atggccactg tgctctaaag   1740
ggaatcacag tagtcctcct gcctcagcct cccaaacact ggaattataa gtgggtacca   1800
ctaccacatt gacttaagca atgaacctca gagctgtatg tgctaaaagg gttacggtgt   1860
gtggattttt aaatctcggt ttacaaagag aaaccgagca ggagcagcca ctccagtggc   1920
ttgagcagag gctaatccat gggtagggct gactcgcgag cctgggtgct ttgctcctgc   1980
ctcactgatg attcctgacc tttcttctca tgtcttctgg aacacaatcg cccttctggg   2040
acatggagcc gccttccttc cccaagaaac aattcatcgt tgttctgcta gcatcccaag   2100
acatttgaca agcggcagca actgggctga aagctgagtc taggatgagg tagntatttt   2160
aaagaccctg tgtttgttaa cttgcctttt ctccctccgc ccgtctgccc cccccccccc   2220
tcttctctgt ctctctctgc ctctgtctct atctttctcc cccacccccct caaggtttca   2280
cgtagcccac gctttcttca aactccctaa atagtacacg aatcctcctg cctctgcctg   2340
ccaagtgctg taattacnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnncta   2460
ttgataatac agctatgacc tgattacgaa ttatggccac tgtgctctaa agggctgcag   2520
agatggctca gtggttaaga acactgactg ctcttacaga agtactgagt tcaattccta   2580
gcaaccactt ggtggctcac aaccatctgt aatgggatct gatgccctct tctagtgtgt   2640
gtctgaagac ggctgcagta tactcatata aaaataaata gatagataat aaatctttaa   2700
aaacaaacaa acaaaagaaa tcaaagtcat aacagaaaga gaccactaag ggctagagag   2760
atggctcatt caggaaatgc ttgcgatgca agcaagggga cctgagttta agattcccca   2820
aagctaaatg taatgacaaa tgtttctaaa tccggtgctg gggagaagga ggcgggtgtg   2880
gaagtgtgct ggccaggcat ccccgattaa tcaggggggta acaggctcca gtaagagacc   2940
ctgtgttcat aggtagctag aaggataaca cttaaacaat tcccagtgaa atccgttggc   3000
ttacatatac acacagatac atgcccactt gtacacacat gaacatacac acgtgtggtg   3060
gcacacacaa aagaaattgg tacacttgat acagcagtta cacccaacac agcagaagcc   3120
```

-continued

```
atatgggtgg agcctatggt catttatttt ctcactccta agctacttca ctttaatttg   3180
gttagtgtct ttttctaccc cgacagcnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnngta ttgacgagca tgttgacctg attacgaatt atggccactg tgctctaaag   3360
aaatgttggt ccctttgaag gaatgctttc tgatcagtgc tttatttgtt tgttagtttt   3420
ttttaataac ttctgactca cgagagctct ttccagaggt gtcgtctgag ggactctgct   3480
gtaggccatc aggctggggg cagagacggc ttcgtggatc taactccttc agtgcctctc   3540
agcacatcct ctacttgacc ttcttttcca cttgtacatg aacgcaggcc ctttgagaag   3600
acactgggat ctacctgtgt gcattaaggg ctgcctttct ctctaatggc tggagctaga   3660
tagagtcgaa ggcaacttgt gagcaacaat caaactctgg gagcagaagt gcaatgaaaa   3720
gaaatgggaa gatggcctga catcacctca gcccaactgg cagaaaacca gtcttatgta   3780
tgacccaagc caagagtgat gtgcttctcc aaacagaagg gagactccac ttcaactaca   3840
ctcttcagga cacagactcc ccaacaggta acaggataga tgattaatat taatgagatg   3900
acacatctca ttaatctact cttcccggga agacagccac ctctccagat gccagtacta   3960
aaaagacctc gatgtatgtt cagattggaa tctggctcta cctcacccag cctgtgtcga   4020
catgaagagg gcatgggaaa gtcnnnnnnn nnnnnnnnnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnatatagt agaacacctc tatgacctga ttacgaatta tggccactgt gctctaaagc   4200
tggtaaatct ggcatcatct acctgcctat tatcattttc ttgtggtctg catcttgtgg   4260
tccagtaact gggagtgctt ttgttgtttg ggggtcctgt tgctttggct gaacactggg   4320
tgttctagat gacagactgg ggtacctgag gtttctgata tacctcccac ctcaaagctt   4380
ctgtctgctt tgttcctttt caacacttgg attgactcca tccatattct taggatttgg   4440
gtcctctctt ctgggcaaaa cagcctggca aattctggga tctccctagt ttgaactgaa   4500
gtctctacac ctcttttctt agccaaacac agccattcaa ctccattaat tcttagctga   4560
ttgcccactg tgttgttcgt ggatgcgagt tgttttacaa acaatatagc aaatgttggt   4620
ccctttgaag gaatgctttc tgatcagtgc tttatttgtt tgatagtttt ttttaataac   4680
ttctgactca agagagctct ttccagaggt gtcgtctgag ggactctgct gtaggccatc   4740
aggctggggc agagactgct tcgggatcta actccttagt gcctctcaca catactctac   4800
ttgacttcnn nnnnnnnnnn nnnnnnnnnn nnnnnnnnnn nnnnnnnnnn nnnnnnnnnn   4860
nnnnnnnnnn nnnnnnnnnn nnnnnnnnnn nnnnnnnnnn nnnnnnnnta gattcgtcga   4920
ngaacatcta tgacctgatt acgaattatg gccactgtgc tctaaaggct cccatcatgt   4980
ggttgctggg agttgaactc atgacctctg gaagagcaga caatgctctg agctgctgag   5040
ccactctagc ctccaattac agtatatttt gataaatgtc atagtagtaa gacaaggttc   5100
agaaagataa aaaccccgga aaatatctga atttgccttt tcttgaatat gcacgtgtgt   5160
aggccagaga acaatcttga ccatcaccct caggatcatc ggcttagcac tcgatcaggc   5220
tagactgcca gcaactccag cactcaggag actgggcgag atggttcttt agtttaaaat   5280
cagcctgggt tatagaaaga gactctgtct caaaacaata tattttgatt tttgaaaaca   5340
tatatgtgtg tgttctaagt tatagtataa agtatgtttt tttatcatgg ctgtagtaaa   5400
aattcttgaa tttcagtgct ttagacacat tagcagtaaa ctttatggca atgttaaact   5460
gctgaaacat ttttaaacta taaaatgata tcatcagatt tgtgcgtttg tatgcgtgta   5520
```

-continued

```
cctggaggtt tgcatgtgag gtgtattttt attattcgtg tctgccaagg tcacgcagaa   5580
acatggagaa gacaagggat ggaactcagc attcacagat ttgacaaagt ctaactttag   5640
ctaagagaag annnnnnnnn nnnnnnnnnn nnnnnnnnnn nnnnnnnnnn nnnnnnnnnn   5700
nnnnnnnnnn nnnnnnnnnn nnnnnnnnnn nnnnnnnnnn nnnnnnnnnn ntgtacggca   5760
tcagctatga cactgattac gaattatggc cactgtgctc taaagccttt aaaaatccaa   5820
aattctgtta tgcctctcta gccagttaga gacagacagc agcaatgtgc aatgacatta   5880
tttctataat aacaagtaca gatataaaag aatcctcagg aagctgtaga gaagccgaag   5940
actcttcaag ataatgtgac attatctgaa gtgcaggagg gcacaccgag acgtgggctg   6000
gggacagcac aacatggaga actagctcct ttatgtgctc aatcaaaaag ttccccaaca   6060
tttggtctga tacagattga ctcatcccta ctcacccgtc gcgtgggcgt gatcctgttc   6120
caggccagag atcgcacggc tgatgagtcc ttcaacagtg gtcagagctt gtggtaaatg   6180
aaacatgaga caagtgagtg ctgacgtgct atcacttgtc tgtgtgaccc tcaacacttt   6240
ccctgaactc tgcaggcctc cttctcctca tctataaagc tctaaactaa gcacaccgtg   6300
gtctgtctca ctactggact cttaagagat ttaattagac gggcagtggt ggtgcacgcc   6360
tgtgatccca gcacttggga ggcagaagca ggcagaattt cgagtgtgag gccagcctag   6420
tctacaaagt gagttccatg atagccaggg ctacataggg aaaccctana aaccacnaaa   6480
cnaaacnann acaaactaaa gagagagaga gataactatc tcnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nntctatccc tcttagncaa cagctatgat cctgattacg   6660
aattatggcc actgtgctct aaagagctag cagtcttatg tcatctccag gcttaaggtc   6720
agatatgatc accaaccccg tgcagctggt ttgcacagcc caggctgcct ggccccttta   6780
aacaggcgga aaggaaggag gcagattggg agggtggtcg gataagtctc aaccccactg   6840
cagtgtagcg gcttccattt cttatgaata aagtgggtag gacctgcccc tcccctgaag   6900
gtttgttgta gaaatgaaat ggtagtgtct aaaagcatga ggtgccgcat gcgcacaccc   6960
cttgtaaaca gtcctcactg tgatagctaa actaggtgac cttctagact ggaatggaga   7020
cccagtgtcc tcagaatccc aaaagggctg cttgctaagt tcctgccacc cccaaacact   7080
cacttcaaag agacccagtg tcacaaaaca agtcttgcac attatagagt aaaagactaa   7140
tgttcagaga gtgccagtgg ctgccccgga tcacgacaaa acacacttgc aggccagctt   7200
tccattttcc acgttgctgg caccggcaaa gcctctgccc agtgttggga agctctttcc   7260
catatgcatt ggcacagccg agcagctggg ctatggtctc tcttgaaatt caattagggg   7320
ttctctttct gtcaccaaga gccagaagtc tcattgttca cacacggcaa actttcctta   7380
cccaaacctt ggtttaatgt cctggtgtgn nnnnnnnnnn nnnnnnnnnn nnnnnnnnnn   7440
nnnnnnnnnn nnnnnnnnnn nnnnnnnnnn nnnnnnnnnn nnnnnnnnnn nnnnnnnnnn   7500
nnnnnnnnnc atcgatatga tcctgattac gaattatggc cactgtgctc taaagatccc   7560
tactcacccg tcgtgtgggc tgatcctgtt ccaggccaga gatcgcacgg ctgatgagtc   7620
cttcaacagt ggtcagagct tgtggtaaat gaaacatgag acaagtgagt gctgacgtgc   7680
tatcacttgt ctgtgtgacc ctcaacactt tccctgaact ctgcaggcct ccttctcctc   7740
atctataaag ctctaaacta agcacaccgt ggtctgtctc actactggac tcttaagaga   7800
tttaattaga cgggcagtgg tggtgcaggc ctttgatccc agcacttggg aggcagaggc   7860
```

-continued

```
aggcagattt ccgagtttga ggccagccta gtctacagag tgagttccag gacagccagg   7920
gctacatagg gaaaccctaa aaccaacaa aacaaaacaa aacaaaacaa aagagagaga   7980
gagattaact ataacttttt actcacatta aaacatgaaa atccactata attaaatgac   8040
caaacacaag ccactaggcg tgacctggac caagctttga aagaaaatag gaaacatctc   8100
agcttgtgaa cagctcacac acctcacaca cctgatctta aaactcacct cccttctggc   8160
tggaagcttg gatctcnaaa tccacctcgg ggatcttgtg gtggcagagt ctgtctttac   8220
cacttctctg gtcatgtcct ggacagannn nnnnnnnnnn nnnnnnnnnn nnnnnnnnnn   8280
nnnnnnnnnn nnnnnnnnnn nnnnnnnnnn nnnnnnnnnn nnnnnnnnnn nnnnnnnnnn   8340
nnnnnnntcg tctggtanga acagcagtat cgaccatgat acgacttatg gccactgtgc   8400
tctaaagtcc catctcacca tcgaagtcac atgtatgact ggtcccatag cttgtctgca   8460
aatgcgccat gacactctat tacacttggg cctcagcttc ctagcagaac caaaataaaa   8520
tcccacatcc tggcatgtgc aaccggccct ggccattcct gtcaccgtca ctccgttctc   8580
tctcccttct tagccctggc catgctgacc ttctcctttt gactcgcctc ttctctctct   8640
ggccttgcat tatcttcctt cggcttagaa ggctttgact actctgctta aatcagccta   8700
tcacatcaca cagattgcat ctttcaaggt ccttattaag agttgtgtgt ctctcctcat   8760
cagaatgata ttgaaaggga cagtttcttc tgctgctgca tccccaggac ctcaaccagt   8820
gactacacag tcagcagctt atccatattt gctgacagag cctctgcaag tctctcctct   8880
acaatgtccc tcaagcctta cctcaaatgt tctatcttga gtaaagcatt tatgtctatg   8940
tgagcactag catgaagtct gaatcangaa agctattgag ggtctttttt tctttagtgt   9000
cccaggcttc tttatttaag ttgatagtga cagcgtaatc tacatgagca ctcaacntca   9060
tcatcatcca tcaccttgcg catctgatcc tcctcagcta atgannnnnn nnnnnnnnnn   9120
nnnnnnnnnn nnnnnnnnnn nnnnnnnnnn nnnnnnnnnn nnnnnnnnnn nnnnnnnnnn   9180
nnnnnnnnnn nnnnnnnnnn nnnntttttt attattagaa atcagcttga tcctgattac   9240
gaattatggc cactgtgctc taaaggtttc catcccttgt ttagagattg aaaacattta   9300
aacaattgtt agctgtgtac atgggtacac acgcgctatg gcatgtatgt ggagttatgg   9360
catgtatgtg gaggtgaggg acaactttca ggagttggct ttctcttccc tttctaaggc   9420
tcaaactcag gtcatggggg tttactctct gccacctctg accttgggcc gagactttaa   9480
ggcctgtgat caatcaggag cagatggcaa gcgcctctct tcactaacag aatcttgata   9540
tttccacccc actccctctt ccacaccagc actctccccc catgtgtttt cctgtctgtt   9600
aaattctctt tctccccttt tggatttttt tttttagacc tgaaaatgag gtttctccaa   9660
atctaagctc ccacccacgc ttttcaaagg tcttgtgggc tccacttccc ttctgtgccc   9720
tcctgtctgc tttcctgagt gatgttccca agcctcaagt cacaagaagc tatcacttga   9780
ccagctcttc tgagtgccca gctgaggctc acttctctgt caagtggaag tggctaaagt   9840
gccacaagca ccgcccgtgt gggaagactc agcttgattc tatcttcatt gctttctgta   9900
gaagtggaag gaacttgagc gaagtgccga tctttcttga cctgtgccct ctgcagccta   9960
cccacaagct ggtgatagan nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnnnnnnnt  10080
ctttttcttt tntttagcgc aacagttttg accatgatta cgaattatgg ccactgtgct  10140
ctaaagagag gtttgttctc tcatcctacc atttgggttc tagggtttta actgatgtca  10200
tcaggctggg tgactttgtt cactgagtca tcttggtggt ctttcaatgt tttctgagtt  10260
```

```
caggctctgg agtcgactcc ctgtgtttgc acgtggatcc cacacagtct gtgctgtgtg  10320
gtcttggatg agtcttcgtt gtgaagattc tgtgagatag tctggctccc cttaggttcc  10380
tcgttgaata ttagctatgt acgggttctc tctgtgtacc attgacccat tggtcctcat  10440
cttgctttac ctaatcatgc ctggtccagc ctgtgctgtg cccaaaggtc agaactgatg  10500
ggggatgagt cacgtaggac atctcagcta cagttccacc tcctgaacct gcagactgag  10560
tctctcaagt gccagcagcg tgggacaggt ccagaggtgc ttgcccactc ataccctctc  10620
tgagaagacc tgtgttacct aagtttgttc aagggtggtt tccagtgacg ggctgtcaga  10680
tatgcataga tatctgagtt gtccaggggt tcagaagttg gctctgagct aagagactgg  10740
gtcatcgtac acacatgtgt ggctagcact cacgtatgca ccagccccta cagggagttg  10800
tattgcctcc tgcgcgttat aatcatnnnn nnnnnnnnnn nnnnnnnnnn nnnnnnnnnn  10860
nnnnnnnnnn nnnnnnnnnn nnnnnnnnnn nnnnnnnnnn nnnnnnnnnn nnnnnnnnnn  10920
nnnnnncata ataattagtt taacagtcgt accatgatac gaattatggc cactgtgctc  10980
taaagaacaa aaagaagaaa tggtggacaa ttttcggcag gagtcacgca gacgtcttat  11040
cagctgccat gtagaactga tgagaattga tctacagact gatcctgtga gcaagcagca  11100
gtgaaagaaa gaaaacagtt attcaagaac atctatgaaa attcagtaag caatgagggt  11160
ctagattctt gagccagccc tatgcatggc accacagcct ctctgactct cccatgccct  11220
cctcatgtgc acacaggctg ggtgaggtag agacagattc caatctggac atacatcgag  11280
gtcttcttag tactggcatc tggagaggtg gctgtcttcc cgggaagagt agattaatga  11340
gatttgtcat ctcattaata tttatcatct ttcctgttac ctgttgggga ggctgtgtcc  11400
tgaagagtgt agttgaagtg gagtctccct tctgtttgga gaagcacatc actcttggct  11460
tgggtcatac ataagactgg gtttctgcca ggtgggctga agtgatgtca gggcatcttc  11520
ccatctcttt tcattgcact tctgctcccc acatttggat gttgctcaca agttgccttc  11580
gactctatct agctccagcc attatagaga aaacagacct tatgcacaca ggagatccag  11640
tgcttctcaa gggctgcgtc atgtctagtg gaaagaacgt cagtataaga tagcatgaga  11700
nnnnnnnnnn nnnnnnnnnn nnnnnnnnnn nnnnnnnnnn nnnnnnnnnn nnnnnnnnnn  11760
nnnnnnnnnn nnnnnnnnnn nnnnnnnnnn nnnnnnnnnn ttgctgcggt ttttanagac  11820
atcagtntng accatgatta cgaattatgg ccactgtgct ctaaagttga tggttatatt  11880
aagtgcttgg caccatcaga ccttctgaat aactctggcc caaggttcct cattttttcct  11940
ttccaaaaca ggttttgtta cctgctccaa atcacccagt agaagtatca ggaaactagg  12000
atgcaaaccc aggtctgggc ttatgacaca cagaggacgc cttggaaggg agggagaagg  12060
ccagagcagc tgggaccacc cacagcatgt tccagtccat cccacgggaa ctttacccat  12120
tctgaggcag aggggtttga cttgcagacc tgaggcagag gctacagcca gtatgtgaaa  12180
tcttttggaa ggaatccctg aactactcta ctctgagatt ccctccttag ggaggctcta  12240
agtctccaag ggcagggaaa attcattcca gagactgcag cctcctgtgg ctggctgtcc  12300
ccataaaacc actggggtcc tctgatgggt tcatttcttt gccccagcga ccaccagctt  12360
tgtcatagac aggcaagcca cccatcaaga ggctcctggg caaagcctgt tccaccttgg  12420
ctgccaaggc tcgttcatat cccgtggcat ctattataca gctctggagt caacagattt  12480
atccataggt ggagaaaact ccggcgcaaa catgagtact ttacagtggg acagagtggc  12540
ttacttttgt atagataaga caaannnnnn nnnnnnnnnn nnnnnnnnnn nnnnnnnnnn  12600
```

-continued

```
nnnnnnnnnn nnnnnnnnnn nnnnnnnnnn nnnnnnnnnn nnnnnnnnnn nnnnnnnnnn  12660
nnnngatttg agacagcagc ttcgacctga ttacgaatta tggccactgt gctctaaagt  12720
gggaattgaa ctcaggacct ctggaagagc agctagtggt cttaaaccgc tgagccatct  12780
ctccagcccc agttgccaat gtttttgtta tgtgtagatg ctgttattca gcctcccttc  12840
cagagaaaac ctcaccatat accatgacca ctaaaagggg tcatgtagtt cagtgacgat  12900
atgtcttccc agagtggtga gggcctatgc tcacttgcca ggatgggaga gctgggtagc  12960
tgtgtagagt gggctgagta cggtggccag tttttgcact tggaaggtca gagggttgag  13020
agttcaaaac cacagccttg cccatatagc aagtttgaag tcagcctggg ctatatgaga  13080
atatctaaaa acaaaacaaa acaaaacaaa acaaacaaac aaacaaaaac cacagatcat  13140
ctctaaaatc ccattatgga aagtgagttt tcaagctaag aggaactttt gagaccatct  13200
atttgaggtt ctaccatgaa cttccttcta gataagggcc tgttgagagt ggaaggaatt  13260
tgctgtgtcc tttatctctc agccttagat gcaaggatgg accttgcgcc caggtctctg  13320
catttgngac tccaggcagg aatgtactct gcccatctcc cttagaaact ccccaactcc  13380
ctaaaaccag cttggaatct gtctaccaga tcagggagtg ggctggatta caagctggtn  13440
nnnnnnnnnn nnnnnnnnnn nnnnnnnnnn nnnnnnnnnn nnnnnnnnnn nnnnnnnnnn  13500
nnnnnnnnnn nnnnnnnnnn nnnnnnnnnn nnnnnnnnnt gttgttgctt tttntagcta  13560
cagctttgac ctgattacga attatggcca ctgtgctcta aagggcgcca taggtctgta  13620
accctgtaag tactggctct tctcaggctg tcacagtggc catggtggga caagtaaggc  13680
cagcccaggc tctagccagt cctggacact gtccctctgg ccagctggct agtgcagaag  13740
gcgctgggga gttaagtaaa ggcagggccc gcagtggaca gacaagcagt gttcattggc  13800
tggccagtca ttcagtaagt ggggcggttg ctggtcacag gatttggggg gtgggttctg  13860
cccacactta gtaaaggctc gagggagcca cttgtctact ggggcagccc ccctgaggct  13920
ggggagctta ctaaccccaa cagtgccagg agaaggggaa aaggtgagtg tgctagtaac  13980
cagctggggt catccttctt tgaccctcca cgtggtgttt gctcagagga attgttgtca  14040
gactccctgg cgcctagagt ataaagtaag agtggctgct ctctgtgccc agaaccggac  14100
aggtgagctt acatggcaca gggatggtgg ggngtgggtg gcagaaaagg taggagagag  14160
ctgcagatca agctagcaga aattgtgtgt accagtcctc attcctaaaa gcngctcggc  14220
agacagaaga caggcgaacc gaggagctag attgcatttg agtggtgggt catctctcta  14280
ggcagtctga gtnnnnnnnn nnnnnnnnnn nnnnnnnnnn nnnnnnnnnn nnnnnnnnnn  14340
nnnnnnnnnn nnnnnnnnnn nnnnnnnnnn nnnnnnnnnn nnnnnnnnnn nntacatcat  14400
cgcttgacct gattacgaat tatggccact gtgctctaaa ggctgatcag ccccacctcg  14460
ctctcttact gcttactctc ttacttgtct ccctcttacc cctcactctc accttctctc  14520
ccctctcttt gtcttctctc ctctcttctc tctctttgnt ttctcctctc ttctcctctc  14580
ctctcttctc tccctcttac tctctttctc tctagtctct ctctctctct tctctctttc  14640
tccctgcatt tctataataa agctcttaaa ccatagagag tctctgctca tcaaggctgc  14700
atgcactctc gtaggtattg ggaacatctt ccctcatccc tctctcctat aaccctggtg  14760
gctttagcaa agtagctcca gggtccccag gtagggctgc ccctggccgt cccctgaaga  14820
gagggtcaga ggcttggatg cccatccagg gatgagtgga aaggtagcag ccctcccaca  14880
cctgacaaac cagagaatan gtaaaactct ggtggggcat gggtctatct cccccctctt  14940
cattccccag gccccctttt ttagctccca cacaatactg acttccaggc agctaggatg  15000
```

```
aaagtcttag agcccatgct cacagtgata catctattcc acaaagccac acctcaaata  15060
gtgcacttcc tgggccaaca tatcaaacca tggcactgag atggtcttct ctgcccacnn  15120
nnnnnnnnnn nnnnnnnnnn nnnnnnnnnn nnnnnnnnnn nnnnnnnnnn nnnnnnnnnn  15180
nnnnnnnnnn nnnnnnnnnn nnnnnnnnnn nnnnnnnntt gccgtggttg nnngacatct  15240
ataagccatc attacgaatt atggccactg tgctctaaag tttattattc cactgcactg  15300
taacttcgtc tcagtgggga actgttgtac atgggggaac tgttgcttct ggctcacaaa  15360
ggtatctgcc atcacattta catcttacat cacacgggca cataacacat aattaaaaag  15420
aaattccttt aaaaatccaa aattctgtta tgcctctcta gccagttaga gacagacagc  15480
agcaatgtgc aatgacatta tttctataat aacaagtaca gatataaaag aatcctcagg  15540
aagctgtaga gaagccgaag actcttcaag ataatgtgac attatctgaa gtgcaggagg  15600
gcacaccgag acgtgggctg ggacagcac aacatggaga actagctcct ttatgtgctc  15660
aatcaaaaag tttcccaaca atttggtctg atacagaatt gactcattcc tactcacccg  15720
tcgtgtgggc tgatcctgtt tcagccagag atccgcacgg ctgatgagtc cttcaacagt  15780
ggtcagagct tgtggtaaat gaaacatgag acaagtgagt gctgacgtgc tatcacttgt  15840
ctgtgtgacc ctaacactgt ccctgaactc tgcacgcctc cttctcctca tctataaagc  15900
tctaaactaa gcacaccgng gnctgtctca ctactggact cttaagagaa taaattagac  15960
tnnnnnnnnn nnnnnnnnnn nnnnnnnnnn nnnnnnnnnn nnnnnnnnnn nnnnnnnnnn  16020
nnnnnnnnnn nnnnnnnnnn nnnnnnnnnn nnnnnnnnnn natatacgat atgatcctga  16080
ttacgaatta tggccactgt gctctaaaga ccctacggag ggcagtagat attgaagaaa  16140
gctattctgc tttaagctag aacacctcag tgtggttgac atgaagggta tggagagtta  16200
ctgcccgggt cctggcactg tactgctccc cctgcccctc cagagattac ctgctgcaac  16260
tgcttgatgc tgctgctgtt gcccattttt tccaggtgag ctttgaaggc ctggatgctt  16320
gcagccccgt ctgagaaccg gcgcacgggg gagaaacgct ccgtagggag atgcacggtg  16380
ttggagtcct tgtaggtgga gctgaatata tgggaagaga cggttagcag ccaggactcg  16440
gggggttatg accaatcaca cgggaccatg ggtctacatg aatacagaga cagtggatgc  16500
atgaggagcc ctgcacatgg tactccgtgt cacttcctgg agtggctgtc cccctgagtg  16560
gactacaggc cctcatctcc cacctccact tacactcagt tggtcctact tcctcagcct  16620
gctgcagtcc tggggtcaac tacatccggg tcttatataa acatactaga gcagggtgcg  16680
aagtccgcag acggccagga ctggctgaac cacacaggct tggctcttat agtcacatca  16740
tttatttcta ttgtagntgc atttggggag cggtgtgtgg ataatgttgt gcaagctatg  16800
ggttctaann nnnnnnnnnn nnnnnnnnnn nnnnnnnnnn nnnnnnnnnn nnnnnnnnnn  16860
nnnnnnnnnn nnnnnnnnnn nnnnnnnnnn nnnnnnnnnn nnnnnnnnnt tgtggtattt  16920
gcgatcagta tgacctgatt acgaattatg gccactgtgc tctaaagtca agacgggaat  16980
tacagatagg tgctaggaat tgaacccagg tcctctggaa gagcagctcc tgagccatct  17040
ttccagtcat ggtctttatt attctttaca tcttttacca gtgcacactt gaatcatatg  17100
ttggtcattt gtaacttaca ggttggctga gttttacaca ccttccaaat gctgacgttt  17160
ttattataca ccatcagaaa attacttgag tggtagattg agaaagttct ctaaatacat  17220
gtagaatatt ttcccattct tttgattctc cctagtgact gatgccctta atatacattc  17280
agcaattact tgggatgatg gtgctttata aaactctgtt aggctaaggt ggcttgagag  17340
```

-continued

```
tttacagaac tgtcctgata ccttagttgt tttctctcag ttgctgttat gtctcagctg  17400
cgttgggtcc agaattccca tctgatggct tgcatgtctg cactgagatt tcccatctgc  17460
tcacccattt aaagactgtt ttctcatttt gtaaaaatat ttataaatgg tgttttgaag  17520
gtttgtctgc tgattacaac attctgctca ccacaaactt gctttttggt aataacctgt  17580
cccctgcctc cctctctgtg aggaccgaca gggtctcact ctgtatgtca gtctgattta  17640
gagcttgcta tgtagcccan actgatcaca gactcagcac nnnnnnnnnn nnnnnnnnnn  17700
nnnnnnnnnn nnnnnnnnnn nnnnnnnnnn nnnnnnnnnn nnnnnnnnnn nnnnnnnnnn  17760
nnnnnnnnnn nnnnnnnnnn tgtgtttggc tttgcaaact gctatgacct gattacgaat  17820
tatggccact gtgctctaaa gttctcgcca agtgtcttca ggtgggtttt ggccctggtg  17880
tggtactcgt tcaactangg ttgctcttga gctcagccag gcgctgggcc aggctctcgc  17940
gcatctgttc gctgtggggc gctagctgtg tgcgcagaga gtctacgtgt gtgcgcatgc  18000
ggtcgcgaaa ttcctcagcc acaggggaca gtctcccttg cagctcctgc agcttctggc  18060
gcgcgctctc ctgcagctcg gcgcccagag gcgccacctt ctggcggtag agctccacat  18120
cctctttcca tttcttctgg aattcgtcca ggtagggctg caccttctgt ttcacttcct  18180
ctnagtcctt gttcatctcc tgtctcaccc aatctgtttc tttctccagg ttatcccaga  18240
agtcccgagt caatgggccc agccgttcct gcagctgact aacggttgaa cccagagtgt  18300
cccagttttc caggagattc acgctagagg gggaagagag cggctgagag acgagcccag  18360
gcatcatgcg ctgcccctgg tctgcagatc catgcacatg atagctgngt gccacctgtc  18420
ccctaatgtg caggggctat ggggctaggt tccccgaaca tgcgacccgt ctaactcact  18480
ggcttctctt tacatttntc tgtgacacat gcggggaggg agccagnnnn nnnnnnnnnn  18540
nnnnnnnnnn nnnnnnnnnn nnnnnnnnnn nnnnnnnnnn nnnnnnnnnn nnnnnnnnnn  18600
nnnnnnnnnn nnnnnnnnnn nnnnnnatta aagttatcat ctatgacact gattacgaat  18660
tatggccact gtgctctaaa gaaatccaag taggccctca ctccctcttc gctctctcag  18720
aatgcgtttt tgagtttgct ggcaggcaca ttggcctgtg cattgtctga aagactcagg  18780
gcagcgtgga gtgtgagcca cgtttgtggg tgacatgtct gagtcacagc gctttctgcc  18840
ccttcccagg aatagcccta atgcctttcg tagctcacga tgctgccgtt cccccctttt  18900
gtgttttagg attctatttg tcctcctcag ccctccccac ctcttcaggt tgcctgtgaa  18960
aaccaaccag ccctcctcac ccaccagctc cagaggtaat gaactactta gcctcttcct  19020
gcattgttgg ctggctggac ggtgtggctc ccttgtctga cgcatgggga cgcttgactg  19080
acttgagcat ttgggatagt cttctagaag aacagggaag ccgagttaga gtttgaaggg  19140
cttactagaa tgctgactat ttcctgagct ccatgaacac agtggcctga catccatcga  19200
aggccaggcc agtgagtgct gagttggtgg caggggaagg actggtagac tgaggtgtgg  19260
gcaagctgtg gtggcctgct accgcagttg tccgcccana ctacanactg tctgtctgca  19320
tggattgtct gggctgatgt tactgcagat gttctgtcac tcagaagcnn nnnnnnnnnn  19380
nnnnnnnnnn nnnnnnnnnn nnnnnnnnnn nnnnnnnnnn nnnnnnnnnn nnnnnnnnnn  19440
nnnnnnnnnn nnnnnnnnnn nnnnnnnnct atcaacaatc cgctntgaca ctgattacga  19500
attatggcca ctgtgctcta aagatttatt tttatatgag tatactgcag ccgtcttcag  19560
acacacacta gaagagggca tcagatccca ttacagatgg ttgtgagcca ccaagtggtt  19620
gctaggaatt gaactcagta cctctggaag agcagtcagt gttcttaacc actgagccat  19680
ctctgcagcc cacgactttg atttcttagg taaaaatctt tatgacattt atcacctctg  19740
```

```
gttgagtctg taggccataa atcttttcct atcctctgaa aagggactgc tggctgtctc  19800
catctattat tcaaggcgat gctttaagct ggacatccag tgctcacctg taatctcaac  19860
atttgggagc ccgaggcaga agaattgaaa attctccaac ctggtctcaa tctcccaccc  19920
caaaagtaat attttaccat ctgtatattt gaaagagcat agtgaattgt aggttcatgt  19980
atgcttaccc ttggaagtgt aaatgaaaga tttctaaaca ttgcagatat aaccttgcct  20040
ctaagatact ggtcattctg aaatcatttc ttcccggggc ttgttttctg tatacagtca  20100
gcatatctac aattatgctt ttccctgtat gtcacctcaa gtatccgatc caagatgctc  20160
tgntaaatca ccgtgtgcca tgtttgcatg caagcaatgt acaagtacag gtgnnnnnnn  20220
nnnnnnnnnn nnnnnnnnnn nnnnnnnnnn nnnnnnnnnn nnnnnnnnnn nnnnnnnnnn  20280
nnnnnnnnnn nnnnnnnnnn nnnnnnnnnn nnnttatcat caatatgacc tgattacgaa  20340
ttatggccac tgtgctctaa agatctagcc ctatcagctc taccagcccc ccagaccccc  20400
cactagactg aggacagctg tttgtctgtt gcagagtgtg agcacttgat ccgccacatg  20460
ctggtgttag atccaaataa gcgcctctca atggaacaga tctgcaggca caagtggatg  20520
aagctcggag atgcagaccc caactttgac agggtaagcc ggacccttgc ctcagggaac  20580
tcctgattaa ctccttctct tcttcagtgg ttgtgatctg cctaggacct aaagagatga  20640
gcagtaggaa ccagctgctg gctaagacca gtggcaggtg aattcacagg gagccgcggg  20700
atccagcaag gctgtggaga cagtgatact gggcattacc acagaaatca tagtttgctt  20760
ttgacttctg agacagcata ctcccagttc tgcaggtcac tgccaccaga gtgcctttct  20820
tgtcttgagt gcgctccctt caacagcttc tgtcacatac tgctgcaccc cattatgatc  20880
actctcgtac ccccacgagc tcacgaagca gcccctgacg gttttggtca gcccatagct  20940
gattgccaga actgtcttgc ttagacttcg tatgacaccc acagaatctg cagcagtggg  21000
gccatacaac agctttggca atgtgtatnn nnnnnnnnnn nnnnnnnnnn nnnnnnnnnn  21060
nnnnnnnnnn nnnnnnnnnn nnnnnnnnnn nnnnnnnnnn nnnnnnnnnn nnnnnnnnnn  21120
nnnnnnnncc cttcgtcagc atcatctatg acctgattac gaattatggc cactgtgctc  21180
taaaggaaga tgatgtcctc tgttgctgtc taggctgtgg gtctcagtac tagctcaggg  21240
gactatctta gttgccccag agcgcctcct tcatcctcac cttctttgtg aatgccctgt  21300
ctataccttg ctgcttgcag gttctcatag atagggctca tgtaggggtc agatatcacc  21360
cagccatggg ccctgctcct atctcaggat tactaacgat aggtccagag ggcaagagga  21420
ggcctgtgga ggagttgggg aggggcaagg ccttgggttc catgtgacct ttgtccttct  21480
ctcactaatc cctgcccagc tactgcagag gagactgttg ggatcacagg tggaggtcag  21540
tgtgggggca tgtaaccttc actctgcccc ctcccacccc acttcctccg atgctccaca  21600
gtggcaccac agattcccca ttccattcta ctggaaggct ttcaggcggc ttctgtgaca  21660
gagcctgtca ctggctctag gctgtaaagc aggcctgagt ccaagcttgt ccctgtcttt  21720
ttctgtctca ccgactcatc tagtgagccg gtagctcacc cttggcggcg gcagtggacg  21780
agaaaagcat gggcaatctc agaaggattt ctcaactcct ctggcagatg gctgcatgga  21840
cgttctgcct caggctctga tctggacgnn nnnnnnnnnn nnnnnnnnnn nnnnnnnnnn  21900
nnnnnnnnnn nnnnnnnnnn nnnnnnnnnn nnnnnnnnnn nnnnnnnnnn nnnnnnnnnn  21960
nnnnnnnnct tgattttggg atcatcttcg acatgattac gaattatggc cactgtgctc  22020
taaagagtcg agctgaggtc tgaaccccga agtcataatt caccttcatg acacggnagg  22080
```

-continued

```
cattccctta tgctcctgga actctggccc ctgcgtaagc cccccacatg cccccataag  22140
agaagcatgg tcagtagtca cgtaggcaat ggtccaagct tctgaccttc aggctgaact  22200
cctccccagt tacctagcaa cagtaaagac cataaaaagg gctgatcagc cccacctcgc  22260
tctcttactg cttactctct tacttgtctc cctcttaccc ctcactctca ccttctctcc  22320
cctctctttg tcttctctcc tctcttctct ctctttggtt tctcctctct tctcctctcc  22380
tctcttctct ccctcttact ctctttctct ctaggctctc tctctctctt ctctctttct  22440
ccctgcattt ctataataaa gctcttaaac catagagagt ctctgctcat caaagctgca  22500
tgcactctcg taagtattgg gaacatcttc cctcattcct ctctcctata accctggtgg  22560
cctttatcaa agtagcttca gggtccccaa gttaggcgtg ccctgggcgt gctctgaaga  22620
gaggtcacaa gctggatgtc ctnnnnnnnn nnnnnnnnnn nnnnnnnnnn nnnnnnnnnn  22680
nnnnnnnnnn nnnnnnnnnn nnnnnnnnnn nnnnnnnnnn nnnnnnnnnn nnnnnnnnnn  22740
nntggtataa gagatcagta tgacctgatt acatattatg gccactgtgc tctaaagatc  22800
cagtaaaaaa cgccctgttc ctaagccagt gtaagaggca aagaaaggag ggcccttggg  22860
cctggctggc cagtctgtct agtttaattg gtgggttcca cgccaatgag agatgctgtc  22920
tcaaaggagg tggacaagtt ctctgaggtg acaccaagac tgtcctccag cctgacacac  22980
aggaaagcag caggcttgct tgcacagcgc ctgcctgccc ttcatggtgg ccagccttcc  23040
ttcctcttcc tgctcactct agtgaagacc ccagggtagt gaggagaagc tggagaggaa  23100
acaaggaacc agcagacagc tgggggtgct ggccacacac tccccaaccc tggcagcaca  23160
agccccatca ttgggtgcta attaaatccc cctaatgagg aaaacggatg caggagctgg  23220
ctcctccggg gcctccccgg ccccacgccc ttgcctctcc atcggactta tcgctcgtca  23280
caggatgttt acaataattt ttaatttgtg caattattaa tcacttttct atctccctca  23340
tttgcataat aattagacat ctcactgttt gggatgcctg ggaatgacag ggtttaaatt  23400
gaatttagat ttaatattct attttctgct ttttcccttc acacgctata aagccagatt  23460
ggcaccagag nnnnnnnnnn nnnnnnnnnn nnnnnnnnnn nnnnnnnnnn nnnnnnnnnn  23520
nnnnnnnnnn nnnnnnnnnn nnnnnnnnnn nnnnnnnnnn nnnnnnnnnn ttatctatac  23580
gcattacact gattacgaat tatggccact gtgctctaaa gtactgctgt gaacagatac  23640
catgaccaag acaactctta taaggacaac atttaagtgg ggctggctta caggttcaga  23700
ggttcagtcc attatcatca aggtgagaac atgacagcat ccaggcaggc atggtgcagg  23760
aggagctgag agttcaacat ctacaattta aggctgctag cagaatactg tggggaattg  23820
caggcttgtc tccagtcgag ctgaggtctg aaccccgaag tcataattca ccttcatgac  23880
acggtaggca ttcccttatg ctcctggaac tctggcccct gcgtaagccc cccacatgcc  23940
cccataagag aagcatggtc agtagtcacg taggcaatgg tccaagctta tggagccgtg  24000
tagtcccagc ccctacaagt caggccagga gggtcagtgc agccttgcag ctaacctggt  24060
ctacattgta agtcccagtc taaccacagc tacaaggcaa gacacagcct taaaaaacca  24120
gcatgccaga ttgaatgcca aagtgaatga aatggctgat gggtggcaga ggctcttcat  24180
gggcaaggtt ggcattggtt ggcaaggatc agcatcagca ttgtggatag tggggtgctt  24240
cctctgtcca ctggactcgt tgctgccaag gtcactaaca agctcttgtt ngataaatca  24300
gtaggcattt nttatcntta tttttntgga tggctcannn nnnnnnnnnn nnnnnnnnnn  24360
nnnnnnnnnn nnnnnnnnnn nnnnnnnnnn nnnnnnnnnn nnnnnnnnnn nnnnnnnnnn  24420
nnnnnnnnnn nnnnnnnccc ctttttttgat cactacgacc tgactacgac ttatggccac  24480
```

-continued

```
tgcgctctaa agagtggggg ccaatcttgt ctcactaaaa ttttgacttg ggcggcagag  24540
actcactggc tgcaccacgc acaaagacaa ctagaggaag atctgcactt tggttctgca  24600
aaccacatca ttcagaaaac acaggatgac tctgttctca atgtgagcaa tcagagactt  24660
tctacatcca gtttgaaaag actggtttga gatggtggct catcccggat tggacctgca  24720
tgtagaacct cctgcaagac tcacctcaca cttcctaagg agacctttgt tggcagctcc  24780
cagaatctgc aatgagcatc catttctcct tcagcctttg aaatcacaca taaagataag  24840
gttatgcaga taatctgaat atttctggga atattgaaga atcctatagt cggttataaa  24900
gggatattgg aatctggaag aaaacgggtg attccgaaag gtctgaactc tgccattatg  24960
cgtggagaag aacagaactg aagaactgcc aacagggtta gtctcctgcc tcatttaaga  25020
acgttgtgga gaatcttcat ctgtaaagac aactttctct cctgatcctc acgccttctt  25080
gcctcaagtt gatgttgatt atccgcacgt taannnnnnn nnnnnnnnnn nnnnnnnnnn  25140
nnnnnnnnnn nnnnnnnnnn nnnnnnnnnn nnnnnnnnnn nnnnnnnnnn nnnnnnnnnn  25200
nnnnnnnnnn nnnnntttga atacggatgg ccagctccat gtgctctcag gtgtgtatgt  25260
gtgtgtgtgt gtgtatgtgt gtgtgtatgt gtgtgtatgt gtgtgtgcgc gtgtatgtat  25320
gtgtgtatgt gtgtgtgtgt atgtgtgtgt ctgtgcgtgc gtgtgtgtag tgtgtgcgtc  25380
gtatgcgtgc gtgtaccgcg tgtgtgtgta ctatgtgtgt catgcccgcg tgcgcccccg  25440
tgtgcccgcc cgccgccccc cccatccccc atccccatcc cctgcctata cccggccatc  25500
cccccacccc ctctccacac cccagtctcc ctcctcccac ccccaccccc cgacccatac  25560
cccacccccc ccaccctccc cacccaactc cccctccccc ccttaccccc tcccactccc  25620
cctctttttc cccccaccac actaacaccc ccctgccccc ccccctgacc tccccccctc  25680
cctccccccc accccccgct ccccgcctat tttcccctct accccccccc cccgtcccca  25740
cctcgatccc cccccccccc ttcccctggc gccacccccc ccaccccccc cccccttgaaa  25800
cccccacgta cccccccccc tccccccat cccctcccca cccccccctcc ccaataacta  25860
ccctcgcctc cccccacctc tccacccctt cctccctacc cccaattgac ccccctttcc  25920
ccccctcctc ccctgcctca cgnnnnnnnn nnnnnnnnnn nnnnnnnnnn nnnnnnnnnn  25980
nnnnnnnnnn nnnnnnnnnn nnnnnnnnnn nnnnnnnnnn nnnnnnnnnn nnnnnnnnnn  26040
nnttagcaaa catcttgaca ctgattacaa ttatggccac tgtgctctaa agaggcatgg  26100
aggaggggc attatgtggg tatgtaggtg ctcttgctaa ggacgtctta ngcccaaggt  26160
gtcccctctg ctgtgccatc ctctggctgt gcccggatga tatcagaaca gagggggtgg  26220
agctatggcg gaggaggaaa aggcagatgg ctcagatggg aaggcctggc tgctgtgtgt  26280
tccttagatc cagagaggcc actagcctca ctgttcacat ctccaggatt ctgtttggac  26340
cactccatgc aggagacgcc ctcaccccaa cccccgcctt catcccatat gtcttctcag  26400
acttgggcca tctcctccac cagttggccc aagcttttga atgccaatat gatttggggt  26460
tttgttttgt tttgtttttt gaaacatttt ttattctggg gggttttaga tgagaactat  26520
ctggtaaaat ttatatgagt gttcaaaata aaactaaacc ctgaaattgg aaatactgat  26580
cccaagcatt tccgatgaag gacagtctgt ctgcactgga gttcggtggc agaggcagcc  26640
tagcaagaga agctgctagc ttctagcagc acagctctac agcatggcca tagggagggt  26700
gctgagcctc agagaaagct tcgcagatgc ttggatggaa ggaagctgtc tgggtaggtc  26760
tcagtactgt ggttatgctg accttgctct agggaccgga gactgaaacn nnnnnnnnnn  26820
```

-continued

```
nnnnnnnnnn nnnnnnnnnn nnnnnnnnnn nnnnnnnnnn nnnnnnnnnn nnnnnnnnnn  26880
nnnnnnnnnn nnnnnnnnnn nnnnnnnnna tggccactgt gctctaaagc agcccatgga  26940
atgaccccag cccatggaat gacctcagcc catggaagga ccccagccat ggaaggaccc  27000
cagcccatgg aaggacccca gcccatggaa ggaccccagc catggaagga ccccagccat  27060
ggaaggaccc cagcccatgg aaggacccca gcccatggaa tgactccagc ccatgggagg  27120
accccagcca tgggaggacc ccagccaatg gaaggacccc agcccatgga atgaccccag  27180
cccatggaat gaccccagcc catggaagga cctcaggcca tggagtgacc ccagcccatg  27240
gaaggaatgg tgttgcccac acttaggctg ggtcttccaa ctcccttaac ctaatgtaga  27300
taatccctca ctgatgtgac cagagatttg tttccatggt gattctaaag cccatcgagt  27360
agacaatcaa gattagccac cacagtctct gaggacaaga tgcctgcatg cagaagtgtc  27420
tctccctatg ccatctaaga tggctgccag ataactgtga acttaattat aatgtcatcc  27480
ccacactaaa cgacatactc cagtgtcttg acagttgaca attgctgtga tgacaactag  27540
aaagaaccat ccaaggagcc aaaggaggtg gccccagaat tcctgggaaa gctctatcca  27600
ctcncagann nnnnnnnnnn nnnnnnnnnn nnnnnnnnnn nnnnnnnnnn nnnnnnnnnn  27660
nnnnnnnnnn nnnnnnnnnn nnnnnnnnnn nnnnnnnnnn nnnnnnnnng attatcatgt  27720
tgacctgatt acgaattatg gccctgtgct ctaaggggca ctccatcgct tctgcggggg  27780
ggaataaagt cgcttacctt tatcctcgnt gtgcctacgc ttacagttca aagacctgct  27840
ataccaacct cccctcggct ggtgcgatgc gtggttatgg cgcgccacaa gtcgtatttg  27900
ccggtgagtc tatgcttgat gacgccgcga cagcgttagg tattgatcct gttgaaattc  27960
gtttacgcaa cgccgcccgc gaaggagatg ctaatccgct cacgggcaaa cgtatttaca  28020
gcgcagggtt gccggagtgt cttgaaaaag gccggaaaat ctttgaatgg gaaaaacgcc  28080
gtgcacaatg ccagaaccag caaggcaatt tgcgccgcgg cgtttgcgtc gcctgtttta  28140
gctacacctc taacacctgg cctgtcggcg tacaaatagc aggcgcgcgc cttctgatga  28200
atcaggatgg aaccatcaac gtgcaaagcg gcgcgacgga aatcggtcag ggtgccgaca  28260
ccgtcttctc gcagaggtgg cgagatctgt gtgggtgccg gtcagcgacg ttcgcgttat  28320
ttctactcta gataccgacg atacgccgtt cgatccctgc gcattatgct cacgctagag  28380
ctatgttgcc gcgcctgcgc tgcgcactgc gcactatgat tcnnnnnnnn nnnnnnnnnn  28440
nnnnnnnnnn nnnnnnnnnn nnnnnnnnnn nnnnnnnnnn nnnnnnnnnn nnnnnnnnnn  28500
nnnnnnnnnn nnnnnnnnnn nnaaattaat gtggagactc agcgccaacc tccatgngct  28560
ctccagagga agaggaactt atgagggtta gaagggggct gggggctgt gatcaggata  28620
taaaatgaat acatacatta atgagaaaag tgatattata cttctaaagt gttgtaaatt  28680
aatactggtt cttttagaat acaggagttt aagtttgcca atctgccttt cacctctatt  28740
tggccgtgtt aattgctgtc agcacagaga attccgcgnn nnnnnnnnnn nnnnnnnnnn  28800
nnnnnnnnnn nnnnnnnnnn nnnnnnnnnn nnnnnnnnnn nnnnnnnnnn nnnnnnnnnn  28860
nnnnnnnnnn nnnnnnnnct tcgtgccgct tctccctggt ttccgacacc ttggccggtt  28920
tacccgggaa acactggtcc cgcctttttc tccccttctg ggaaaacggt gtgggggctt  28980
ttcttaataa acttcaacgc ctggtgaagg tattcttaaa atttcggggg agtaaggggt  29040
ggtttcggct tttccaaact ttgggcttgt tggttcaaca caaacccccc cccggttcag  29100
aacccgaccc cggtgtggtc cctnnnnnnn nnnnnnnnnn nnnnnnnnnn nnnnnnnnnn  29160
nnnnnnnnnn nnnnnnnnnn nnnnnnnnnn nnnnnnnnnn nnnnnnnnnn nnnnnnnnnn  29220
```

```
nnnntttggn atcgtgactg gccaactcaa tgtgctctaa agccacaatc tccagcaacc  29280
agcccaaagt cgggcccata caagacattt aatatttgtt gaattcaccc ggaggccagc  29340
ataagcttct aaagcatgcg ggagtaattg aaactcatta gagtttcttt gggtcaaatc  29400
aatgcataga ggtattaaaa ggttatttgt atacattcaa accatacaca atccttatag  29460
accactagtg gcaagtctgg gagaggttca tggattatat gcacacacat acacacatgt  29520
cctcgcacac ataagtaaat gtagttttaa agttaaagga agatattata agatttaggc  29580
ctaaattgaa tctttgcaat gattggtttc tttttctttt tccttttttt ttttttttttg  29640
gggggggggg ggggggggaa gcaagggttc tcaggataat tttggctggc ctggatctca  29700
ctttattaac caagctgact ttgaacttac cgagacctac cttgctctga gtgagtgtga  29760
gctggcacct tctggatgcc attggtttct tctttgggac ctcttaggac agacctggtc  29820
cttgacaaga actttgcagg ctgtggggaa caaaaagctt ttgtgctttt tttttaacct  29880
ccctttaaaa tccaagggct ttctaaattn nnnnnnnnnn nnnnnnnnnn nnnnnnnnnn  29940
nnnnnnnnnn nnnnnnnnnn nnnnnnnnnn nnnnnnnnnn nnnnnnnnnn nnnnnnnnnn  30000
nnnnnnnnnn tctccttttc cttagaatac tgtatcagcc tgattacgaa ttatggccac  30060
tgtgctctaa aggaatcttc ctggtttctt tgccacactg accacgaatc catttcactg  30120
ggatgagttt atatcatttt ttagaaagac atatcaaagg tgagaaggtc agtacaggtt  30180
tgataaaaac ctatcaaact tttatagtca caagtttgac ttcccctaaa tggtacccgg  30240
aagcctcttc cagcagactt cccaccaaaa ggtatttata gcaataaaag tgattgaaat  30300
tgaaacgttt ggtacagcgt ccattattaa aacgctgctc aagaatgtgc ccctagtggt  30360
acagctatgg taagtcccac cattcataca ggtgttcttc cttactctgg cgctgatgct  30420
gccagggtag gatcatgtta catcggcctg tggcttctca gctgagacag cgtgggctgc  30480
aggctgttgc accgattcgt cgtctcaaga aaagcacagc cagcccgaga tgcacgcact  30540
ctcccctgga gcctcttaaa gctcaagtct ttaagtccag gagttcaaaa agtccgcgtc  30600
ctaaagcttc gcttgtggct cacccatacg gttcgcgttg aagaattgtg tccccacgcc  30660
gagctgttgc cgcgccttcg cgctgccatg gcggcagctc cggcactcac catactgata  30720
tctggagcga tactttctgg gaccannnnn nnnnnnnnnn nnnnnnnnnn nnnnnnnnnn  30780
nnnnnnnnnn nnnnnnnnnn nnnnnnnnnn nnnnnnnnnn nnnnnnnnnn nnnnnnnnnn  30840
nnnnnatggc cactgtgctc taaagcagcc ctaagtttag cagcttactg aaggtgctat  30900
tttggataga aagttgaaac tctgggggct aattccattc tcacactcca cccccaggtc  30960
tactaaatgc ttatcagctt aaagagagta ctagatagga tacaaagtgt ggctcaccct  31020
ctctgtgggg cagtatcatg gtctaacagt attattaccg tatggtccat tgaactgggt  31080
cgaattagtc cctcatttcc acacttctct tcattagagc ttgagcatga cctcatttat  31140
agatggaatc tttgtggtgt taccagttaa gatgagccta tattcagtta aggtggtgtt  31200
gaattcagtg tggctgatgt ccctggaaga aggggcaatg gcatgcaggg ggaaagttta  31260
agcttctggg aggtgagtgt cagcagcaac acaactgcac atctcatttc caggatgggt  31320
tccttctgct tccctgcctt aggggaatgc ctggtttgtt ttatgtcagt gatgatgaaa  31380
aacatgatgg gacaaagatg tcatgacttt agaagaaggg catggaacat tagaggctga  31440
cttgtcagag cctggagacc agccttttca cggttctaga atgaaacagc tcctgtggtc  31500
agagccagag ttttgtcttt cactttgnga ctatttctct gntctccctg atttccata   31560
```

-continued

```
naccanngct ctccatcttc tcctcnnnnn nnnnnnnnnn nnnnnnnnnn nnnnnnnnnn  31620
nnnnnnnnnn nnnnnnnnnn nnnnnnnnnn nnnnnnnnnn nnnnnnnnnn nnnnnnnnnn  31680
nnnnncttgg aaagcatccc ttcgggcggc cttttctttg tttcccgaac ccctggcccg  31740
agtttacccg ggaataacct tgtggcccgc gtctttttct ttctcccttt caaggaaaaa  31800
ccgtggggcc ggctttttct ttaattaagc tctacacggc cttgggaagg ggttattctc  31860
ttaaagtttc ggggaggtaa ggggtatcgt ntccccettt ccacaaactt tggtgggctt  31920
gtgggtagac aacacaaaac ctcctccctg tttttaaaac ccccccaaac ccgcgtttgg  31980
ctnnnnnnnn nnnnnnnnnn nnnnnnnnnn nnnnnnnnnn nnnnnnnnnn nnnnnnnnnn  32040
nnnnnnnnnn nnnnnnnnnn nnnnnnnnnn nnnnnnnnnn nnatggccac tgtgctctaa  32100
agtctccctg catttctata ataaagctct taaaccatag agagtctctg ctcatcaagg  32160
ctgcatgcac tctcgtaggt attgggaaca tcttccctca tccctctctc ctataaccct  32220
ggtggcttta gcaaagtagc tccagggtcc ccaggtaggg ctgcccctgg ccgtcccctg  32280
aagagagggt cagaggcttg gatgcccatc cagggatgag tggaaaggta gcagccctcc  32340
cacacctgac aaaccagaga ataggtaaaa ctctggtggg gcatgggtct atctcccccc  32400
tcttcatccc cagggccccc ttttttagct cccacagaat actgacttcc aggcagctag  32460
gatgaaggtc ttaaagccca tgcccacagt gatacatcta ttccaacaag gccacaccaa  32520
gatgagccta tattcagtta aggtggtgtt gaattcagtg tggctgatgt ccctggaaga  32580
aggggcaatg gcatgcaggg ggaaagttta agctttggag caatactgat tagaattaga  32640
atcctagctg tgctacttat agcctgagtg gtccagggca agagatgttc atctcagccg  32700
ggcgtggtgg cacacgcctt taaatccagc actcgggaag cagaagctag cggatttctg  32760
agtttgagcc agcctnnnnn nnnnnnnnnn nnnnnnnnnn nnnnnnnnnn nnnnnnnnnn  32820
nnnnnnnnnn nnnnnnnnnn nnnnnnnnnn nnnnnnnnnn nnnnnnnnnn nnnnnttctt  32880
ctcctttgta tancatcatt tngacctcga tacgaattat ggccactgtg ctctaaagtc  32940
tgcataacaa ggggacataa ggaactcctt ggtcacctac ccccaattct caaaactctg  33000
tgacagtgat aaaggaatgg tctgtgtatg atgtagtaat ctcattttca ctagaaatgc  33060
gtcacatggt agtctcctgc tgtcactcac agactcacag actcatgttt gaagaatggg  33120
aagcttccac ttggcactgg agcggaaggc ctccatctgc tttacctctt ctggacgctc  33180
atccacaaac tcagccacct gcaggagtag gggcactaca gtgaggaaac ccacaggacc  33240
cagccaagga tcacttgtct caagaaccca gagccatagc ttacaggcag agaactgcct  33300
gcttctcctt gtgatcgcat gactgacttc tactgcccat catgagacta tcataccaaa  33360
cagtgctagc cgaagatcaa aaattcaaaa ccattttctg ctgaaaatgt atcatgtcca  33420
caccactgca cagtccaaac attaagttgg gagcaggtgt ggtggcgcac gcctttaatc  33480
ccagcacttg tgaagcagaa gcaagtggca atctgaattc aatgacagcc tggtctacag  33540
agtgagtttc aagatagcca gcgctacaca gagnnnnnnn nnnnnnnnnn nnnnnnnnnn  33600
nnnnnnnnnn nnnnnnnnnn nnnnnnnnnn nnnnnnnnnn nnnnnnnnnn nnnnnnnnnn  33660
nnnnnnnnnn nnncagcgca ctgggggtca gagcccccaa tcggaccatc agcccttcac  33720
cagacctgtc ccaagccctt agtgtcgtcc tttgacagtg gtgtcggtgg tgctggcctc  33780
ggttctgctg ctttgagtgg tgaacgtgct ttgcgaattt tgtgggagtg atgggattta  33840
tgtggaagag ctgggctttg tgggtggtgt tcttaccttc tgggtagtca ggctgacacc  33900
atgtgtacta tcctgaagta gtttggactc ttctgaatgg aaggcgggaa gaagaaagat  33960
```

```
ctgggttggc atctgatgga gagatggtct ggttatttcc caagctttgg tgtatcaatg  34020
ttattcattt agtaaatgtt tggtgtctct ggtgccagtc ccactaaagg acagagtcct  34080
tgcactgccc tgtgcaggtg atctgtgctg agacagaagt tgtgaaatgg gctaccttcg  34140
ctggtgctga agctaccaac acttccggga ttccaggcag caccttcctt gccaattcaa  34200
gagtcacttt ggaaggtgcc aagatgaagg ggtgaatggt agtgagagaa atgcctatga  34260
tacgcactat cttcactctc tgtcacacca caccttctac acaccccnnn nnnnnnnnnn  34320
nnnnnnnnnn nnnnnnnnnn nnnnnnnnnn nnnnnnnnnn nnnnnnnnnn nnnnnnnnnn  34380
nnnnnnnnnn nnnnnnnnnn nnnnnnnatt atttatacgg atggcaagct catgtgctct  34440
aaagctncca agacagcaat tgcacctttc agaacagcat caatgtccaa acatgagcca  34500
ggtcctccca aatggcaggc gcatcagtct ttagagcaca gtggccatnn nnnnnnnnnn  34560
nnnnnnnnnn nnnnnnnnnn nnnnnnnnnn nnnnnnnnnn nnnnnnnnnn nnnnnnnnnn  34620
nnnnnnnnnn nnnnnnnnnn nnnnnnnnaa atttaagatt acgcatggcc agctccatgt  34680
gctctaaagt tgaaacctaa tgtatagcac atggtaatgg tgtaggtatt cttgcctagg  34740
tgagaggctc cattctgatt ctagagttcc tgtccccttc aggtccctgc agtttccctg  34800
tctcaggatt ccaagcacac gcctgtaatc ctgttttatg ccgtgtttga gatcaatctc  34860
tggactatgt atattttagg taagtacagc ttacaaccct tctttaacga cccatgtgct  34920
gggacagagt gggaagcttt ttccatgact gggactacag actcagaagg tggccccagt  34980
cttcctgagc aatgacgtgg ctgcttttta gtttctattg gctatatggg ctcttctctg  35040
accctaatga caaggtacaa tagcttgtag gtggtgactc agtttcaggt tgttatgtta  35100
acttcgtgtt ggttcagatg ggggagtgag gcccgtggct tttaaccaga tattaagaga  35160
taactaacat tctaactttg tcttcaaact ggtactggtt tattaatttg ggtggctttc  35220
tttgtttcta gatttaaatt aagttggctc tctgtgtgtg tggtcatctg cttaaggtat  35280
agaatgaaac ttggacttgg tgtatactta acaagggcct ttgannnnnn nnnnnnnnnn  35340
nnnnnnnnnn nnnnnnnnnn nnnnnnnnnn nnnnnnnnnn nnnnnnnnnn nnnnnnnnnn  35400
nnnnnnnnnn nnnnnnnnnn nnnngtgtgt agtacgtgat gggcaagctc catgtgctct  35460
aagttccacc gcctttgcaa gctagatctc cctttcttct cttaatggcg actcgcaagc  35520
tcgaaagcag ccacctcagt ggtgagccaa ctgttggccg gttaggcaag cttatcttcc  35580
ttcttccaga gttccagcgt ggcactaatt atgtccctgt ctgctcagag ttcacctgcc  35640
tcagctgatt acctgctgct cacaagaagc acaatgagaa ccctgtatgg agctgatctg  35700
agtggctagt tgcaagtgtt ccctccgatt ggcacacatg tgtactgaat ttcctcacaa  35760
cccatctgct ttcgccttct ggaggaggct gcattccact atcccaccct accccaagaa  35820
gactggaaga aacaagatca agccatggct ggcgaccttg ggaaacatga cctggggagc  35880
tagggacagc catcaaatgg aatggcttag atgccagtca ttaaggaata cagaaggaca  35940
tcaactctct tggtggccgc ttccctggaa tcagctaatt tatctaatta gagttagagg  36000
gaaactctgg ttctctcttc cacggaaaga attcttaata acagagcctt accaaagact  36060
tgcttggaga atactttaag aattactttc cacaccccgn nnnnnnnnnn nnnnnnnnnn  36120
nnnnnnnnnn nnnnnnnnnn nnnnnnnnnn nnnnnnnnnn nnnnnnnnnn nnnnnnnnnn  36180
nnnnnnnnnn nnnnnnnnnt caaagtctgt ggtgctgagg agacttctgt ggcaaaggcc  36240
acatgatcct gggtggaaag tggtatgggg gctccaagct ttgaggtggg aggtatatca  36300
```

-continued

```
gaaacctcag gtaccccagt ctgtcatcta gaacacccag tgttcagcca aagcaacagg  36360
acccccaaac aacaaaagca ctcccagtta ctggaccaca agatgcagac cacaagaaaa  36420
tgataatagg caggtagatg atgccagatt taccagaaga aaacataaag atgatcacag  36480
acacagaggg gctcaccagt gaagcaacaa cggtaaaggc aggaatcata atgtcacttc  36540
agataaagaa tatcaacagg agacattgtt ttaaaaaatt attgggctgg gaaataagta  36600
aatcattaga aagtctccgc aacagagttg aactgcctga aagaagaaac acaaactcaa  36660
ggatagatca gtaagattgc tttagagcac agtggccatn nnnnnnnnnn nnnnnnnnnn  36720
nnnnnnnnnn nnnnnnnnnn nnnnnnnnnn nnnnnnnnnn nnnnnnnnnn nnnnnnnnnn  36780
nnnnnnnnnn nnnnnnnnnt catcccagtt ccagaaagac aaatatggta tgtatattct  36840
cacatatgga tattagcagc accctactac ttggttccag tgataaccaa gctacaatcc  36900
ataaaaccac aaagattagg catagagtaa aaaacctgag agaccagaca gccctcctta  36960
ggaagaggaa actgaataga taattatgga tgggtcccag tgggtgactg gaacaggagg  37020
atcaagttgt ggaggagaca agggggggaat atggggagaa acaactcaaa ttaagaaaca  37080
tttgaaggga tttctggaag cctaatacag tagaagcttg gtgtgacctt tgctgtacat  37140
aaccagtgtc tctctcccag gacttctcct taattttgta gccactcttc ccactgccac  37200
taatacctca agccagtcag cctgtggttc tgcctgtggc ctacttgagc tgtgtggacc  37260
gagaacgtac cctctggctc accccctcct cttgggatgt ttctttctgc tttagcgctc  37320
acacatgcct taaaccacta cttattttgc tcctttagag cgcagtggcc attttcgtgn  37380
cgtggtcatg atgctaaagt agcccgccgc cnnnnnnnnn nnnnnnnnnn nnnnnnnnnn  37440
nnnnnnnnnn nnnnnnnnnn nnnnnnnnnn nnnnnnnnnn nnnnnnnnnn nnnnnnnnnn  37500
nnnnnnnnnn natggcccgt gtgctctaaa gccaaaacaa aacaaaacaa actatttgat  37560
ttactgtaat ttggctctcc tagtctctga taaatcatgt ttgttacaaa ccatgtttgt  37620
tttgttttgt ttttaaggtt tatttatttt tattatgtct aaagtgctct gcctgtatgt  37680
attcctgcag gccagaagag ggcaccagat ctcattatag atggctatgt tggaaattga  37740
actcaggacc tccatagcca tctctccagg cccagaccag tgtttttgag tgaagcttaa  37800
ccggcctctg tgtactcaac tttgtgaatt aagaacaact tttttctttc ttcttctctt  37860
ttcttttctt ttcttttctt ttcttttctt ttcttttctt ttcttttctt ttcttttctt  37920
ttcttttctt ttcttttcct ttcctttcct tttcctttc tttccttcct tccttccttc  37980
cttccctgga aaaaaaggtc cgatggtaaa tggaccttta aagcgattgg agcttttttg  38040
aagaaacaca cataactgtt gccctgctga taaaaacctt tgatccttgg ggctttaacc  38100
tctgccttag attcgcccgg ggcttgtgca aaaaacatag aaatttccac ggggcttttt  38160
tctacctttt tttttccaat cacagctttt ctccaaagtt tttactctct agccaacttt  38220
gagagacccg ataattggct tcttgcgcgc cctttcaagg gtgctgcgaa tttattattt  38280
aggttcttgt gccgacttta aatnnnnnnn nnnnnnnnnn nnnnnnnnnn nnnnnnnnnn  38340
nnnnnnnnnn nnnnnnnnnn nnnnnnnnnn nnnnnnnnnn nnnnnnnnnn nnnnnnnnnn  38400
nnnatggcca ttgtgctcta aagccctccc cagccctggc tccccattcc tgctagcact  38460
accccttgtt gggtacatat tcccagaagg ggctggcacc attgaaggcc tgcgcctttc  38520
tgtgaccctt tgccagtctg agaagctttc tactgactac tgagtggaga ggaaagaggt  38580
ttatttgttc tcatcttttc acagaatctt tgatatacga tagaaaggtt cacaaaaatg  38640
agccagttaa attactgtgt cagtcgctcc tgaacactga ctggtgcctt ctcacactgc  38700
```

-continued

```
tgcgtcaatg gccacctacc agaacctcta tctccaacct ctctcaccca agctgctgaa  38760
gctagtagct tactgatcac caggggttta gttcagggtc tgatacannn nnnnnnnnnn  38820
nnnnnnnnnn nnnnnnnnnn nnnnnnnnnn nnnnnnnnnn nnnnnnnnnn nnnnnnnnnn  38880
nnnnnnnnnn nnnnnnnnnn nnnnnnntct tcctcttctt ttacggtcgg gccaagctcc  38940
atgtgctcta gagcacagtg gccatnnnnn nnnnnnnnnn nnnnnnnnnn nnnnnnnnnn  39000
nnnnnnnnnn nnnnnnnnnn nnnnnnnnnn nnnnnnnnnn nnnnnnnnnn nnnnnnnnnn  39060
nnnnncgata cgaatatggc cactgtgctc taaagagctc cttcagtggc tcctccccag  39120
cactaagccc ccaaaagacc caaatacagc tgatgcccat cctcaagtag attcaggaag  39180
ctggcagact gctacaaagg cgttgcccct acgccaatct tctcccaccc acctcattag  39240
tccgatgccc acaattctca cagttggtgg ccatgatgat aacctcttta aagtggggga  39300
tttctggaag atggagttaa agaagtctat ctgcttcaag gaaaacaccc ccaccccca c 39360
ccccaaggaa aagcaaagcc aagtcccaca caaacagatg caggacccaa gagtacaata  39420
aacgggcctg tgctcacaaa cacggagacc tggccacact cagaagccag gtatgcagta  39480
tgtagcttca ttaaaggttc atcctcacca ctgaggataa agcactggct ttccctgaag  39540
ggaaggctcc cgtctgtaat ataacgttca tgcccgagtc agctgaagag caacccaatt  39600
gcctgctgaa agatacggac aagcttatgc tggcctccgg gtgaattcaa caaatattaa  39660
atgtcttgta tgggcccgac tttgggctgg ttgctggaga ttgtggcctc tatctttaat  39720
aaactctaag tccacaggcg aaggaaaaca tgaagttcgc tgtactacag agacctctag  39780
cacagttggg aatataacgc atcatggagt gagcccctga tgccactgtg tcagcagcaa  39840
gggacaggga gaatgtccag gctttagagc attggagctt gccaatccgt actcagagna  39900
annganaccc cctacnnnnn nnnnnnnnnn nnnnnnnnnn nnnnnnnnnn nnnnnnnnnn  39960
nnnnnnnnnn nnnnnnnnnn nnnnnnnnnn nnnnnnnnnn nnnnnnnnnn nnnnnatggc  40020
cactgtgctc taaagtcctt tctcttcaac ctccagtcgg tccccctgcc tccacccaca  40080
cgctgttccc gtcactttcc tcagaacttc cctctgccct tcaccgtgac cagttcagcc  40140
tcctcccttg tctccacaca aaacttctgc catcctcgat ccacttacct ctcaggcaca  40200
gggggatgtc tgcctataat cacggcactg gggaggctga ggcaggagaa ttgtaagttt  40260
gaggccagtc tgggctgctg tgggaggtcc tatctcaaac aacaaaacta agaagagaaa  40320
aagaagctgc caagcttggg ccaactggtg gaggagatgg cccaagtctg agaagacata  40380
tgggatgaag gcgggggttg ggtgagggc gtctccnnnn nnnnnnnnnn nnnnnnnnnn  40440
nnnnnnnnnn nnnnnnnnnn nnnnnnnnnn nnnnnnnnnn nnnnnnnnnn nnnnnnnnnn  40500
nnnnnnnnnn nnnnnngacc atgattacga attatggcca ctgtgctcta aagctctgga  40560
aagagctctc ctgagtcaga agttattaaa aaaaactaac aaacaaataa agcactgatc  40620
agaaagcatt ccttcaaagg gaccaacatt tgctatattg tttgtaaaac aactcgcatc  40680
cacgaacaac acagtgggca atcagctaag aattaatgga gttgaatggc tgtgtttggc  40740
taagaaaaga ggtgtagaga cttcagttca aactagggag atcccagaat ttgccaggct  40800
gttttgccca gaagagagga cccaaatcct aagaatatgg atggagtcaa tccaagtgtt  40860
gaaaaggaac aaagcagaca gaagcttcaa gcagtggtga gctagtgaaa tgcccatgga  40920
gtcctacttg ttttagtaac atacaaggca gattaatcag ggctggggaa aggatgtcac  40980
ggtccagaca ctgagttcac caaggatgct tgcagacacc tgttctctct gcacttcagc  41040
```

-continued

```
ctctgaatgg aaacccagca ccggtattat ctcccctcac atcggacgcc tacactttca  41100
gtattttcag gcaatagaca ggtttccgtc acccagggat gttcttcgag ctgtctttct  41160
gcatgaaacc atttctttct cattatagca agaatatccc aggttcaagg tgtggcaccg  41220
ttttccggac tctcaggcag tgaagtcggc cccagctctt tagagcacat ggagctggcc  41280
agtccgtacc acagagnnnn nnnnnnnnnn nnnnnnnnnn nnnnnnnnnn nnnnnnnnnn  41340
nnnnnnnnnn nnnnnnnnnn nnnnnnnnnn nnnnnnnnnn nnnnnnnnnn nnnnnntgat  41400
gaatccccta atgattttgg taaaaatcat taagttaagg tggatacaca tcttgtcata  41460
tgatcaaatg gtttcgcgaa aaatcaataa tcagacaaca agatgtgcga actcgatatt  41520
ttacacgact ctctttacca attctgcccc gaattacact taaaacgact caacagctta  41580
acgttggctt gccacgcatt acttgactgt aaaactctca ctcttaccga acttggccgt  41640
aacctgccaa ccaaagcgag aacaaaacat aacatcaaac gaatcgaccg attgttaggt  41700
aatcgtcacc tccacaaaga gcgactcgct gtataccgtt ggcatgctag ctttatctgt  41760
tcgggcaata cgatgcccat tgtacttgtt gactggtctg atattcgtga gcaaaaacga  41820
cttatggtat tgcgagcttc agtcgcacta cacggtcgtt ctgttactct ttatgagaaa  41880
gcgttcccgc tttcagagca atggtcaaag aaagctcatg accaatttct agccgacctt  41940
gcgagcattc taccgagtaa caccacaccg ctcattgtca gtgatgctgg ctntaaagtg  42000
ccatggtata aatccggtga gaagcttggt tggtactggg taagtcgagt aagaagaaaa  42060
gtacaatatg cagaccttag agcgcaaact ggaaacctat cacacnnnnn nnnnnnnnnn  42120
nnnnnnnnnn nnnnnnnnnn nnnnnnnnnn nnnnnnnnnn nnnnnnnnnn nnnnnnnnnn  42180
nnnnnnnnnn nnnnnnnnnn nnnnncttgt tacgcgctgc tgggctccat gtgctctaaa  42240
gctttagagc acagcggcca tnnnnnnnnn nnnnnnnnnn nnnnnnnnnn nnnnnnnnnn  42300
nnnnnnnnnn nnnnnnnnnn nnnnnnnnnn nnnnnnnnnn nnnnnnnnnn nnnnnnnnnn  42360
ntttcgtcta cacctataag atctctttcc attgaggagt tcctcgggat catgatctcc  42420
cgcctcccta agcagacggc gcgaaggatc gaccatagct gcgtggtaaa caccgacgcg  42480
tactcttcat atatacgcac ggcgcgataa cggaggaacg ggtgtgctct tgcgggaatg  42540
ttcagataat caacgggttt gtcgccgcca atgtccatag tgcgcacaat aatgctgcgt  42600
ccgttggcgg attccagcgc ctgacaaaaa atgttgtaca actcgctttc gcccggtgcg  42660
ctggtgcgat ccatatagag catttcagtg cggaacaaac caacgctttc cgcaccattg  42720
ccgaatgcgg cctgcgcttc cacggagtga gcgatgttag cggcaatttc aatgcggata  42780
ccgtcagcgg tacgggcttg ttgggtcagc cagacacgct gttgctcacg cagggcgtcc  42840
tgtacgcggg cttcttgctg ataataacga gctacggctt cccctggctc aaccacaatc  42900
gccccggcgt cgccgtcgat ataaatcgtt tgttgctgcc acggagtaag ggcatcaata  42960
tccacaccaa ccagcgttgg aatgttgaac gaacgggcaa ggatcaccgc atgtgaggtg  43020
gtgccgccgc ttttgagcaa caatcctttg aggtgatttt tatccagttc gaggaactgg  43080
ctgggggtca gttcatcagc catacaaatg gcgggctgcg tcagtttgcc cggtgccggg  43140
aagcgttgct caccgtagat ttgctggagt aactggaagc agacgtcgcg tacgtccagg  43200
gcacgttctt gcaagtagct gctgctggaa cgggaaaact cttcgcaaaa gtgattcgcg  43260
ctggcaacaa ttgcttcggc gcagcttaat ccggcgctga cgcctgccag taaatgttcg  43320
cgcagggaag tatcgccagc ctaggatcgg ggagctttca gaatcgcgct ggtagcaccg  43380
tcgctatcca gcaaacgaaa ctcaatgttt tttagtacca gcgtcaggcc gttttccagt  43440
```

```
gcggattgct ctgcgtcaac gcctttggct gcgggaagat tacccagcgc attgagatct  43500
aaaaaaaaga tctgcgtcgg aatgccgcct gcactatcgg tgcacaccgc gcgggcgctg  43560
gataattgcg gattcagatt ggtcagtgat acccggagat gtttcagttc gccagattta  43620
acttctgtca gcggcgcatc gcagtgtgtg nnnnnnnnnn nnnnnnnnnn nnnnnnnnnn  43680
nnnnnnnnnn nnnnnnnnnn nnnnnnnnnn nnnnnnnnnn nnnnnnnnnn nnnnnnnnnn  43740
nnnnnnnnnn aaggacaatt ctataaattc ctctgatcgc gcatggcgca actccaatgt  43800
gctctaaagc acagtggcca tnnnnnnnnn nnnnnnnnnn nnnnnnnnnn nnnnnnnnnn  43860
nnnnnnnnnn nnnnnnnnnn nnnnnnnnnn nnnnnnnnnn nnnnnnnnnn nnnnnnnnnn  43920
ntagcccccct tcctaaatgc tcatagcact gacaggcaac ctctaggctc aggatccctc  43980
ttgcctggca tgcacctgta tgatcttcat gtctctctta tgtcaaatgg ctaattctct  44040
tttgtatcat acctgctggt ctctcgggca tccttacttt agagcacagt ggccatnnnn  44100
nnnnnnnnnn nnnnnnnnnn nnnnnnnnnn nnnnnnnnnn nnnnnnnnnn nnnnnnnnnn  44160
nnnnnnnnnn nnnnnnnnnn nnnnnnnnnn nnnnnncata caaacaatca tgacctgcat  44220
tacaattatg gccactgtgc tctaaagaag agcaaacagt aagagtccca caatgtgctc  44280
tggcctaatg gcacagaggg taacaaaccc cacttatgag acaattcttt tgtcacctat  44340
gtataagaaa agagcaagca ccaggaatat tctatagtta aatagatctc aagaagtaag  44400
attgaatcac agtgacctag actatagact gagaccgtct caaaggttta aaaaaaagaa  44460
aggaaggaaa ggaagacaca ggggatggag gagaagatgg gagagccttg tttatggaaa  44520
gtcaggagaa cagagaaata gtcacaaagt gaaagacaaa actctggctc tgaccacagg  44580
agctgtttca ttctagaacc gtggaaaggc tggtctccag gctctgacaa gtcagcctct  44640
aatgttccat gcccttcttc taaagtcctg acatctttgt cccatcatgt ttttcatcat  44700
cactgacata aaacaaacca ggcattcccc taaggcaggg aagcagaagg aacccatcct  44760
ggaaatgaga tgtgcagttg tgttgctgct gacactcacc tcccagaagc ttcccactct  44820
gtcccagcac atgggtcgtt aaagaagggt tgtaagctgt acttacctaa aatatacata  44880
gtccagagat tgatctcaaa cacggcataa aacaggatta caggcgtgtg ctctttagag  44940
cacagtggcc atnnnnnnnn nnnnnnnnnn nnnnnnnnnn nnnnnnnnnn nnnnnnnnnn  45000
nnnnnnnnnn nnnnnnnnnn nnnnnnnnnn nnnnnnnnnn nnnnnnnnnn nnatggccac  45060
tgtgctctaa agagagagag gggaaacaat aagtagacat acttgtgagg ggggacctat  45120
tttcaataaa gacagaaaag gggaaacacc ttccttaaca atgagtcaca tctgtccttt  45180
aactccatct tcctctatgc tgggatcttg ctgggaggag tgacatcttc atccttgcca  45240
cactgtatct gtatttctgt ctgtcactca tccaattgaa gtttatctca tttttttttt  45300
tttttgggcg ggtggcctga actcatatgt agaccatgtt gtccacaaat cacagagtaa  45360
gtgacacctc tctgcctctg cctctgtctc tgccccctct gcccctctgc ccctctgccc  45420
ctctgcccct ctgcctctcc tctgcctctc tgcctctctc tctgcctcta tggctcatct  45480
ctatgcctct ctgcctctct ctctgcctct ctgcctctct ctctgtctgt ttggctctga  45540
gacagggttt ctgtatgtat ctctgacttt ctggaactca ctttgtagac tatgctgctc  45600
ttgaactctc aaagatccac caatctccac tttgtgtgtg ctgggattaa aggcatgtgc  45660
catcacacct ggcataaatt aatgttttta aactcactta tcattgcttn gctaagaaag  45720
aatgagcctc gggaaccttc aaccttagtg ggagccattc tctgtcagtg ggtccctcac  45780
```

-continued

```
aggatcacta gtattctacc tgtctctatg cctttataca agcttatttg gtcacctttt  45840
aaaaaattgt tgccacccat caaaactaac ttgggccaat ctggggctat tttaatggtn  45900
nnnnnnnnnn nnnnnnnnnn nnnnnnnnnn nnnnnnnnnn nnnnnnnnnn nnnnnnnnnn  45960
nnnnnnnnnn nnnnnnnnnn nnnnnnnnnn nnnnnnnnng cgccaaagct tgcatgcctg  46020
cagccgcgta acctggcaaa atcggttacg gttgagtaat aaatggatgc cctgcgtaag  46080
cggggcacat ttcattacct ctttctccgc acccgacata gannnnnnnn nnnnnnnnnn  46140
nnnnnnnnnn nnnnnnnnnn nnnnnnnnnn nnnnnnnnnn nnnnnnnnnn nnnnnnnnnn  46200
nnnnnnnnnn nnnnnnnnnn nntttaggtc gcgactgcca gctccatgtg ctctaaaggc  46260
tagatctctt agttaaagga cttttcacag gttattggat attttcaaca gaacatgcta  46320
tggcattctc tctctctctc tctctctctt tctctctctg tgtgtgtgtg tgtgtctgtc  46380
tgtctgtctc tgtgtgtgta tctgtgtgtg tttgtgtgtg tgtgtgtgag tgtgtgtgtg  46440
tgtgtgtgtg tgtgtgtttg gttggttttt caagacagtt tctctgtgta gccctggcta  46500
ccctggaact cactctctct gtagaccatg ctggccttaa actcacagag acccacctgc  46560
ctctgcctcc caagtactag gattaaaggc gtacaccacc ccacccagct agtatacact  46620
cttccctgct gagccatttc ttgtcccaag gctgacattt ataatctgtt aactgtcatg  46680
atgtaaagtt gggttaaagg tatcaatgac gctggctcag gtaaacctag taccttactc  46740
taaggtacta agaatatact tttaaaactt gctataatgg ctatggaacc accaaattgt  46800
ttttcagtct tgaggatagc ctgatctcta atattataga gtctattaca ggtgagggct  46860
ttttgagagg ggtgtgtgtg tcgggggggg gggttaccct ctattctagc cacttctcta  46920
ttgatcattt ttcttggtgg aaacttcata ttacctataa aaattaatat tttagttcta  46980
agaagagcag atgcagatat aaagatttat gtgccatggt aagtgactca agtatgcttt  47040
tttgtgttcg attataggac tttaaaaaat aagagaagct aggatggaca gagctctaca  47100
tgaggccaat cttccacagt gtagtgtctg ctccagtcta aggattggtt gctaagactc  47160
tgctttttga cacactcttc aaacacagga aatgcttctg atgcttatct tcatgtgtgt  47220
ttgctaatgt gcatgtaatc ttatgcaggg ggagttgaaa aggaacgtgt taagtgttat  47280
aattctggaa aagtaccatc aagccctgag aacccttttc caatgtgtac tttctgtttg  47340
tgtgtggttt tgtgtggagg agggcagggg tccaagacag ggtttctctg tgtagccatg  47400
gctatactgg aactggatct ttatgccaga ctggccttga actcagagat ccaaatccct  47460
ctgcctccca ccgagggagt gtgccaccac tgccaggcac atatgtactc gttgtgtgca  47520
ccctcatcac agcaggctca ggcttaaagt ggtttaggct caggtgctag tgtgcttcat  47580
tgatgtgcac aggagtgtgc cttattcccc ttcagctctg ttcaggcttt gttggttcat  47640
ttgttttaga tgtacttaca tatgtaaata aatgttttgc ctgcaggtct acccgtgcac  47700
cacatgcaca cagatacctg atacctgtgg aggtcagagg aagtcctcag acctagagtt  47760
ggattaacaa tggctctgag ccatgtgcac tgctgagcta tctctcaagc ccctctgttt  47820
actttttaac tgttaactga tgcatactcg cttgcttcct taagctgcct gaggggctct  47880
gccagcatct tgggtgggta ctgactctac tcttgttcac cacagaccac ttggtagccc  47940
atggaagaat ggcagagaag gaagctcgac ggaagttcaa acagatcgtc acagcggtgt  48000
atttttgtca ctgtcggaat atcgttcatc gtgatttaaa agccgaaaac ttacttctgg  48060
acgccaatct gaatatcaaa atagcaggtg aggtgtgtgt gcacgtgcgc atgtgtgtgt  48120
gtgtatgtgc tgaagacagg agtcatggtt aaagtaggga cagtttaggc ttttttaaaa  48180
```

-continued

```
atgagagctg gggcttgttc atgctggagg cacttttctc actgagctca cccccactcc  48240
agacttcact ttaataacct gaaaattaat aaacttccaa aggacatttt aaaatatagt  48300
attagctaga actctttaag aagaaagaaa aaggtagtat ttcaaattct attactttga  48360
taaatccttt gtcaataatg tagagtagac tatttttttt atagcaagaa agaaaactgc  48420
tgaaatgatg tgctcagctt cttctgccta agctgtttgc actgccccag ccncagacac  48480
agccacagcc ccaacacccc accgcgcaca tccnnnnnnn nnnnnnnnnn nnnnnnnnnn  48540
nnnnnnnnnn nnnnnnnnnn nnnnnnnnnn nnnnnnnnnn nnnnnnnnnn nnnnnnnnnn  48600
nnnnnnnnnn nnntctcgat caacagctat gatcctgatt acgaattatg gccactgtgc  48660
tctaaagcca cataaagacc caacaaaaaa agagaattac agtgatctcc cttatgaaca  48720
tagatgcaaa ttttctcaat aatatactta caaactgaat ccaaggacac agcaaaaaca  48780
tcatccacca tcatcaagta gtcttcatcc caaagattca gggatggttt gacatatgta  48840
aatcgataaa tgtaatccgc catataaaca gactgaaaga aaacacacac acacacacac  48900
aatggttatc tcattagaca tagaaaggcc ttttaaaaga atccaacacc ccttcatgat  48960
aaaagtcctg gaaaaattag ggatacaagg agcatacata aacacaataa agaaagttta  49020
cagcaaacct atagccagca tcaacttaaa tggagaggaa acacaaagca actcccctaa  49080
aatcaggtac aagccaaagc tatccactct cttcatacct actcaataca tgacttgaag  49140
tcttagctag atcaataaga cacctggaag aaaccaaggg ataccaatta gaaaggaaga  49200
agtcaaacta cctttatttg caaatagtat atttaagtga ccctaaaatt tccaccagga  49260
accaacctcc tacagctgat aaacactttc agcaaagtag tggatacaaa attaactcaa  49320
aaaaaaaaaa aagaaagaca gtaagatgct tcctttatcc tactgcagac attcgctcaa  49380
ctgtgttcat tgctgctctg ctcctaatag tcagaaactg ggaacagcct agacgtccct  49440
caacagatga atggaatata tatatattta cacaatggaa tattacttag ccattaaata  49500
attaaatcat gaaaatcaca ggtaaatgga tggagctaga ataaaatcat cctgagtgag  49560
acatcccagg tccagaaaga caaatatggt atgtatattc tcacatatgg atattagcag  49620
caccctacta cttggttaca gtgataacca agctacaatc cataaaacca caaagattag  49680
gcatagagta aaaaacctga gagaccagac agccctcctt aggaagagga aactgaatag  49740
ataattatgg atgggtccca gtgggtgact ggaacaggag gatcaagttg tggaggagac  49800
aagggggggaa tatggggaga aacaactcaa attaagaaac atttgaaggg atttctggaa  49860
gcctaataca gtagaagctt gctaagatag atccatatat gaaggcagtc caaatggaat  49920
caccaaatat tggaagatac aaggccctaa ctaaacatct ctgtcaccaa atgaagcttg  49980
tacatttaat tgagttattg tacaaaggag accctatgcg aacctttcaa caacccaggc  50040
tgctgctaag actacaggtg gatcttcaca aactgacagc gaggccccat tgctgaggct  50100
aatacccaca caactcgtag aacatgaaca agtcaagccg gtgcctacac ggagccttca  50160
cacctacatt ccagtccttc tttggtgcag gaaggtacgg tgcatgctac caaagagaaa  50220
tataaacacc aagccagcca tagcctcaca tgagagtcag agcctctcct ttcttctttt  50280
taatctcctc ttatttttat tttattttat tttattttat ttacatcttt ctctccttct  50340
catgtacatt atggcttcca gtctagtgtt tttatgggat tcatgagtgt gccaccaaag  50400
ggtctctgtg tctgtatcta tttcttgtgc cttgggttct tttctgtctg cttgttttgt  50460
cttattttga tgtgttaatt tttgttttct tattttattt tattttattt tattttattt  50520
```

-continued

```
tattttattt tatcttatta gtatccctta gaagattgtt tactaatgag agacagaaag  50580
ggggtagatc tggatgggag gggaggtggg agagcactnc aatgggaacc ttcanntacc  50640
taccttcgat ccagaactat tttcaataca aactcactac ggaaacacct ccgttcaaag  50700
tatcacatcg tcctttactc ctctttcttc tactggactt gctggacgaa gactcctctt  50760
ccttgccact gatccagttc tgacgccccc tccactaaan nnnnnnnnnn nnnnnnnnnn  50820
nnnnnnnnnn nnnnnnnnnn nnnnnnnnnn nnnnnnnnnn nnnnnnnnnn nnnnnnnnnn  50880
nnnnnnnnnn nnnnnnnnnc ctcccccccct ttttgtatca tcgtaccagc cagctccatg  50940
tgctctaaag cacagtggcc atnnnnnnnn nnnnnnnnnn nnnnnnnnnn nnnnnnnnnn  51000
nnnnnnnnnn nnnnnnnnnn nnnnnnnnnn nnnnnnnnnn nnnnnnnnnn nnnnnnnnnn  51060
nntgagcttc aggaaccagt gccccaatta ctgtaaggtg gtggcaagcc aataaataaa  51120
tgtgtgccac acagatgaac tgtgctgcaa ggaggaggtt atttgaaatg ccaggaacac  51180
atgacacagc tttaatcaca acaaccattt cagacaagta gtaaggggct gggacttcag  51240
gctcagagag atgaacatct ctctcttttt tttttttttt tttttgggtt ttttgagaca  51300
gggtttctct gtgtagccct ggctgtcctg gaactcactt tgtagaccag gctggcctca  51360
aactcagaaa tccgcctgcc tctgcctccc gagtgctggg attaaaggcg tgtgccacca  51420
cgcccggctg agatgaacat ctcttgccct ggaccactcc agctataagt agcacagcta  51480
ggattctaat tctaatcagt attgctccaa agcttcctgg atgccagcaa aacccatatg  51540
cattgaagac aaagtgctaa tttaagagga agctgctgaa gtgtgaatga cttactatga  51600
atgctctcac ttacttaaga taacatttcc cagttgttag ttcagtttta aaagggataa  51660
tttttatctg tcccagccaa cttctaaata aatgagacag agactataag atttatttaa  51720
ccaccgccgg gtggtgtctc gaaaaaccaa aaaccaaaaa caaaaaaaaa aaagagagag  51780
agagagattt acttaaccca gctttacttt atggtacagt atctgagcat ttattagtct  51840
gttttaatcc tgcgagctaa cctggctacc tctcaggtgt attctcatgg tgtctctgtg  51900
accctttcct tatagacacc cgacccctgc tgggattgga agtccagcct tattctctcc  51960
cccaatcagt cattggatga tcagctttta ttgacaaatc agaaaatgaa tggggagcaa  52020
tgtttacata gcattgaaat aagagattat tagaataagc attgcagtgc catgtctgga  52080
ttgcaaccag atatgggggc agaaaatcag cattggaata acaaaggata atctttacac  52140
agtgcacaat aacattatgc ccacatccaa tggtgccaac aggcatgaaa cccaggaatt  52200
cccacaaacc aatttattta tgccatggag cattcaagga ctgccagtag ggcaggcagt  52260
ggtgagggca aaattgtgta accattgaat gctacaccgt gaggtccatg ttccattgag  52320
aacttttatc ttgttaaatt ctagatcttc acggacatta acatagcaca tactgtgtgc  52380
cagcttgctg tcacctttaa aacatatgtt attttaacca catacattct ttgtatcctt  52440
ctaaacaaaa ctagtattct cccatcaaac tggttcatta ttattattat tattattatt  52500
attattatta attattgtta ttattagact atgaagacta gtactctgct caaactttac  52560
attggaggca gataaccaca ccactgtgct tatctgatca ctgatcaaac aaataggagc  52620
cattttcttc ccagttaatt cctcatttgt tagtctgtag ttttgctttc ttaatatcat  52680
acatagctag tttatgtttg taatctgtac aggatgcctg cagaagccac tgtgcatttc  52740
cctcagagcg ccattggctc tcttctcttc tcttctcttc tcttctcttc tcttancnnc  52800
ccnncncnnn ncccccctcc ccttcnctcc ccctttctca tttttttttt cctattaact  52860
tattatcatt tccttcccta catcaaacat ttaaacacct ttcctgattt tcccttttaa  52920
```

```
catatcaaaa actttctcta attcaacagt taaccccaaa cacctcattt cacccctctt  52980
tttaaacaca cccactttcc ccataattca naggggcact taacaatttt ttccccaaaa  53040
tgacccaaat ggccaccatt tcccattcct ccgctattgg gtggtcgctc tcaaaaacgg  53100
aggcctgttt gggccccaag cttcttaaaa acatggcact tctaaatgag atcctctctc  53160
cgcgacaata acctcagcgg gattggttaa tagcacccca cctcttcccg ttaacgcccg  53220
tggagtaaga ggggaccaca tatggaccca ccctcttttg gggggatgat ttaggcgctt  53280
gagcgcccca taaaccccga atatatgtgc ctctcttttg tccgcgggtt caacttcata  53340
agccagcgcc ttttaaggac tcggagtcgg tcatgcgctc tcttttatta tagagacnnn  53400
nnnnnnnnnn nnnnnnnnnn nnnnnnnnnn nnnnnnnnnn nnnnnnnnnn nnnnnnnnnn  53460
nnnnnnnnnn nnnnnnnnnn nnnnnnnnnn nnnnnnnata taatagaata aaataataat  53520
aagtttttaa taagcggttt ggtcaagctc caatgtgctc taaagcacag tggccatnnn  53580
nnnnnnnnnn nnnnnnnnnn nnnnnnnnnn nnnnnnnnnn nnnnnnnnnn nnnnnnnnnn  53640
nnnnnnnnnn nnnnnnnnnn nnnnnnnnnn nnnnnnntga ctatcagcta tgacctgatt  53700
acgaattatg gccactgtgc tctaaagctc tgcctagcta acttgtgcat tcctttctta  53760
ctggtggtta cttgttgctg tgacctgtca gcatttgtct gacagatgca agtgcatctc  53820
ctgctgatta gcagacagag agtgtatagc aactataaat agaaaatagg tggttttttt  53880
tgttctttga cagtttctat taatacattg tatgtccaga ggaaaataaa gtagtttgtg  53940
ctgaaactga agtattgttt gaatgtaacc gccttgcaca gccaaggact cataagctgt  54000
cctcagattt ccctgtaagc agggcaggag ttgagagttc agatttatat cttgttccag  54060
gtcaaagcac ctgagcaagg ccctgccagc tgtggtgctt ctgtctctta gaggcagacc  54120
tatcctttta agtcctagga atagtgtgtt tccatcccgg tctcagactg acggctgtgc  54180
ttgtgttctg aagctcacat agtcttccac tgtgttgggc cttggcatga cacagcaggc  54240
aagagtcaaa ggctttcttt atggctggag actaagccag gcactgtgac tcgtcctgcc  54300
ttcgcctgtc aaaggacatt actgtgcagg aaaccatggt tttcctttgt cttcatgtca  54360
gttgtggcta ttcccataga attaggtaat gtggaaagac ctggcaatgt caaaccttct  54420
tttgtaatta cctttttttt ttgtagcttc aatgaaatga actgtaaaca gcatatactg  54480
aagctctcag aactcagaca tgtgacatgg gatttgaagg cagcctggat gcattgcaag  54540
accctgtctt ataaaaaaaa aaagtgcatt gcaacaggcc tcttagctcc ttactgttgg  54600
tgaaacaaat tagcacaaac tccaaggctg caagcacggt ggtgttctaa gtcagctctg  54660
gaggtcagta gaataaaaaa catccggtta gcagctgtgg ttcctggagg acctaggggg  54720
aaagcccaga ttcttgcctt ttttaccttg tagagcgaac ctgcctttct tggcgcaggc  54780
cccgtcttca cagcacttcc caaacttcat ggttccattg tggtgactgt tctcctgatt  54840
cctggtacta aaaggagccc tgtcattaca tcaggtcctc ctagataatc caagactacc  54900
tccacagttt cctgatattg acttggtcac ttccatagag agctcctttg acattcacga  54960
ggataggatg cttgccacat gggtgtgttg gaggacacaa gccattccca tgccatcccc  55020
agagcccttc ccatgccatc ggattattaa gtagttgaaa gaaagccctt ctttatattt  55080
tataattgta ttctgcatat gtgacctaag tttaaagtgg tttttttttt ttttttttgg  55140
ttttgtattg tgttgtgttg ttttatgctt ggttcatgat ttttacgtca gggccattct  55200
gattaagtta aggaaaattc ctgtgtcaat tagttttttc tggagaaacc aaaaataaaa  55260
```

-continued

```
gcaaaggtca ttgataattg agactaaaat tactgaaaaa ttagtggaag gtgatttttt  55320
tttttttttt tttttttttt ttttagtttt tcgagagagg gtttctctat agccctggct  55380
gtcctggaat tcactttgta gaccaggctg gcctcgaact cagaaatcca cctgcctctg  55440
cctcccgagc actgggatta aaggcgtgcg ccaccatgca gaaggtgatt taaaaaaaaa  55500
aactggaggt ggggactgga gagatggttc agtggttaag agcactgact gttcttccag  55560
aggtcccgag tttaattccc agcaacaaca tggtggctca caaccatctg caatgggatc  55620
tgatgccttc ttatggtgtg tctgaagaca gctgcaatgt attcatataa ataaaaacat  55680
aaataaatct tttaaaaaat ttttttggta agtcattaaa acaaatccaa gcagttgcag  55740
taagaatgta cccactggag tgtgagtgaa gctgctggga cgctggcagc cagccctgtg  55800
ccctctgtgt tctaacacat aggctttggc acagttttaa agttcagttt aagtgtttac  55860
attagtattt gttttcagag caaaacaaag actaaattgg gactgtagtt catggttgcc  55920
tacagtgcta aatgtttatc tttgggtgac tgctcatgcg ctcttttttt ttccatgccc  55980
ccattatgtg gtttctcagt cattgctcga gcttggggtg tttgcacaag tattagatgg  56040
gattctcatt tacacttgcc ctatcttcct tgaacctaat ggatcactag gagaaatgcc  56100
tttactgaag tccaagtaga acccgagtaa cttcagagtg gactgggtga taagtaatga  56160
aatcaatttt atttctaaga gtgtaaagca actattagag ccctgttcct gtcagtggtc  56220
attttggata ccatattcga agccttagga agaagctact gtatatgaaa gacatatatt  56280
tacaagagag aaaatgagct ttttggttgt gtgtgtgtgt gtgtgtgtgt gtgtgtaaga  56340
atcatcttat atagctcagg ctggcttcca actcaagagc ctcctacttc agtctctcgc  56400
taggttataa tgtggtcata caccaccatc tctgccattc tgggggtggg gaggggaaaa  56460
gagtgttaat aaaccaagcc agagatgtta tcagtcctgg aacgcctatc ttagccacta  56520
gtgaggctaa agtagcagaa ttttaagttt gaggccagcc tggacaacgt ttggagaccc  56580
tatctcaaga aatgaaagtg ctaggcagaa tgcttaccta ctttcaggtc ctgagttcaa  56640
tacaaaaaaa aaaaaaaccc caaatcctca gtctttactc cctcatcttt aaattatgtg  56700
tgttaaggaa caacttattt tggactaata cagattttaa ttatgaaatg taagcagtta  56760
acatttttat gccaggtatt tatacaaggg gcttttgttt taaaagcatt ctggtagctc  56820
agctactaca ggtatttgct ggcaagttcg atgacctgtg ttccattccc agcacccatg  56880
tactgcgagg aggaaactga tgctgacaag ttagctgtcc tctgatctcn nnnnnnnnnn  56940
nnnnnnnnnn nnnnnnnnnn nnnnnnnnnn nnnnnnnnnn nnnnnnnnnn nnnnnnnnnn  57000
nnnnnnnnnn nnnnnnnnnn nnnnnnnnng ggagaagagn agagaagaga gaggagagag  57060
aaaaagggaa ganaagggag gagaaagaag aggagagaag ggagaagaaa aggaggaaag  57120
aagaaaggag gagagaacaa ggagaggaga aggaagagag ggagnaagaa aaaggagaga  57180
agggagaaag gggagagaag aganggnagg aagagaagga gggagggaag gagggangga  57240
nngnaggnag ggagggaggg agggagggag gaaggaagga aggaaggaag gaaggaagga  57300
aggaaggaag gaaggaagaa aacttcagat caaaacaaga gttcagagaa tttcaaatgt  57360
gaccaagaaa gctaaggttc tacttagatt agaaggcaag gaaaactgcc ttatgtctca  57420
caatgtagga agccagtctt cttcaactct tcgactcaca aattctcttt tgttcttttc  57480
cttttccaac atttaaaagc atttagttag ttagttgggg ttgggggggc atgacttggt  57540
atgcccaagg acaacttgtg ggagtcactc tctccctccc tccctcatgc aagctccaac  57600
tcacactgta gtaccccaga gcttaccatg ggtaccagct accaggctgg ccttgagctt  57660
```

-continued

```
gaagcaatct tattcctctg cctgccaaat gcttcaattt cagatgtggg ctaccatacc  57720
caggtacaaa ctccttttaa aacagtattg tcttaaaacg tcccaagaaa gacattaaaa  57780
aacaaacaat aataacaccc ccccccccca gttctgttgt ttttgcttga tttacgatca  57840
aatggtttag gcctgtagta catggaaatc agtctcaatt ctcctaccca ttcttcaaca  57900
aagaaacaaa cagtctagtt aaggggcttg gtaaggtggc acatatgtaa ttccagaaac  57960
ccaagcaggg gaatcttgag tgtgaggcta gcctctattt gataaaagaa aaacaaaagt  58020
ccttcataaa tttcaagcag agtcatgata ccattaacag cacccacact aacttattta  58080
tgaaaaggat tcatttcagt tggatataaa agctgcataa acacggaaat taattaatta  58140
caataggtaa atgcttttaa tgactcggca ttttgagtgg acatactaga acctaaacca  58200
ccaagtcagt ttatctgaat tatttttgtg ttttgttttt gcaaatgata aaatgcatta  58260
gcaagcatgg ggccatgatt tataataaac aaacaaaata aataatatta tactatacca  58320
agaatgcact acagtatgta tacatttata gatatatggc tactagtata taatgtctga  58380
attgattatg tctgtctaca tcatgtgtgt atgttcatct gtctatactc aagtgttttt  58440
taaaagtctg gctttaaaaa aataataagt aaataaataa attaattaaa aacaataata  58500
agtctggctt ttgagcctta ccagcatgtc ttgatgctgt gataaaaagt gtaactaagc  58560
cgggcgtggt ggcgcacgcc tttaatccca gcacaggcag aggcaggtgg atttctgagt  58620
ttgaggccag cctggtctac aaagtgagtt ccaggacagc cggggctata cagagaaacc  58680
ctgtctcgaa aaaccaaaaa aaaaaaaaaa aaaaaaaaaa aagtaactaa tgaatctcat  58740
gaggtgaatc ttgaagcact gcataattaa tcctttattc tcattcattt gaacatcaat  58800
attagtgttc cctattcctt atatagtcca ggggttcata acatataaat ttaacaaaat  58860
acaaggaaaa tctacctcct ggtgagatta ccatggcaat cactaccaca agcgagcaac  58920
gaaacgtgct gagtgaggag cctgtccatc agcccctgcc cgaaggtgca cacacttaaa  58980
ccactcagag gctctcagag gagggtggga agacctacag aactactcca ttaattagct  59040
cctaagaaaa ggcaagggaa aatcgatacc attttgggag agagggtagt tgaaacaggg  59100
tctcatttat cccagggtgg tcttgaacta gctgcacagc aaatgatgtc agcctatgcc  59160
tgaccacttc ttcctttctc cccatcttcc cttctttaga gtgtattata cgcagcaccc  59220
tacctctgag ctatatccac tgtcttttat tatctttttt tgagacatca tgaagcaaag  59280
gattaagtgt ttctggtcat ttcagggtat ggcattgctc tcgactcacc ccagcccgtt  59340
gtcctttccc tctgctgtgt ggggaccaca gtggaaaaat atgacaagca gctctgtctg  59400
cactggaaga ggccttacac agtcattctt gacacctcac aacacacaac tacactgaca  59460
agaaacaatg ttccaatgtt aactctatac tctttccata aaaacatata tattcatata  59520
aatacataca gatatataca tacatatata tctctcaaat aattttgaat aaaagaatat  59580
tgatattcac ttacattgtg ctattcttag gaacaagatt taagagaaat gattttaatt  59640
aaaaaattta tttatgtatg tgtatgtatc tctgtgcttg aggactgtgg tgccctcagg  59700
ggccagagga gtgtttcaga ttctctgcag atggagctgt aaacaactgt aagtcactca  59760
atgcaagtgt gacaaccaag cacggggcat ttgcaagagc agtgcacgca catctttaac  59820
ttctaggcca tctctctgat cctcgaaaag atcatttttc agagtgtttt cctactattt  59880
gtattattta ttaaaattaa tttatgcctc atgtgggcat acatgtaggt acatgcagct  59940
atgtacttgt gggaagccaa aagagtggct ccccaaagcc agagctacaa gtgtgagcca  60000
```

-continued

```
actttgttac atggctgctg ggaccccgac tccagtcctc acggttgcat ggcaggcact  60060
cttaaccact gaaccatctc cagtttccaa tttttcacat tttactttcc aaccacttag  60120
catgtaccag aatcacttag caccgtctac atgagtgtca catgccattc cagggacaca  60180
gcaaaagtta gggtcaatta tgacctgaat ttaggaggtc acaacggtct tctctggctc  60240
tcaacttcct ggcctatcag cctgaaaggt gtgatgggta acccaaataa agtgttgggt  60300
cagggataag gaaggactct ctggggacag ccgggcagtc ccaaaatcac agcacagagc  60360
agccgttctc agcaaccagg gattccaccc tctgaactct cttctggatt gcaaaaggtc  60420
agtgcactga ctcacaaagt gtttggattt ttaataaaca ccactctttc aatctcactg  60480
cgccgaggcc cgaactttcc actgtctctt aaacccatgc actctggaaa ccctccccga  60540
agggccagct tttctgtagt taccctgaag gtccttgctg tctcctgact gccaacgaaa  60600
acactaacac gggagtggaa actgtcttgt ggagcccatt ctgggagtgg acatttaaag  60660
gggaaagttt ccaacttcct ttggttaaag aaaataagtt tccacaattt tcaaaacatt  60720
ctcataatgt ctgaaacttg aaagctcttt tctttaggga gtaagtcagc tatgtttagc  60780
tttttttttt agacattctt ttttttaaa catagacatc tcactactta atctttggga  60840
acaagattta aatggctttc aaactgcagt gtattgacca ttaaacaaga acataccatt  60900
tactgttgat ggctaaacat aatttttatt gctgacaatt atttgatgag aagttccttc  60960
tccatggctc agacacccta ttgctaccat gtcctggaaa tcattggctt ttcctggttt  61020
tttgcccttg ccacctcccc gtgtctgtga cttccgcgtt tttaactggt ccttttatct  61080
tcttgccctt ctttctcccc aaatcttttt ctatctgtag tgaaggttcc ttattatgtc  61140
ttaatagtca agcaatttca cagtttagtg acaaaaaaaa aaaaacctcc catttcttac  61200
acatggtttc catatcattt aaaaagaata ttgcatctac ccacatgcat ccacatgtgc  61260
tgtggcacat gtgtagagct cagaacttgg gagtcagttc tttccttctt cctagtttcc  61320
gagacagtct tgattctgtt acgctgtgaa ctccaggcca gttgaccgaa tagctttcca  61380
gtgattctcg tgtttctgcc tcccatctca ccatagaagt caaatgtatg actggtccca  61440
tagcttgtct gcaaatgtgc catgacactc tattacactt gggcctcagc ttcctagcag  61500
aaccaaaata aaatcccaca tcctggcatg tgcaaccggc cctggccatt cctgtcaccg  61560
tcactccgtt ctctctccct tcttagccct ggccatgctg accttctcct tttgactcgc  61620
ctcttctctc tctggccttg cattatcttc cttcggctta gaaggctttg tctactctgc  61680
ttaaatcagc ctatcacatc acacagattg catctttcaa ggtccttatt aagagttgtg  61740
tgtctctcct catcagaatg atattgaaag ggacagtttc ttctgctgct gcatccccag  61800
gacctcaacc agtgactaca cagtaggcag tttatcccata tttgctgaca gagcctctgc  61860
aagtctctcc tctacaatgt ccctcaagcc ttacctcaaa tgttctatct tgagtaaggc  61920
atttatgtct atgtgagcac tagcatgaag tctgaatcag gaaagctatt gagggttttt  61980
ttttctttag tgtcccaggc ttctttattt aattgataag tgacagctta atcaacatga  62040
gcactcaact tcatcttcat ccatcacctt gtgctcctat cctcctcagc aaatgaagaa  62100
cttcatcccg aagccctggt ggcacagcct ccaagttctc ttggtctagc tctttccctc  62160
tctctgttcc ctacatccac tggcagggag agtgccccag tttaaaacgc atgggacagc  62220
ctagagcagt gacagaaatc tctagagggg aagacttcat cctcaggaaa aggagcctaa  62280
gagtagagta tggtgaaatg agggccccta cagcctgagg caccaaaatg ggggccttgt  62340
ggcagaggaa agaacacaga ccgccccagg gaaagaagac ctgtacctca gacccctctc  62400
```

```
ttgggaacag tcaatgcttg attatttgcc tgccgaacca cgttcccctg ctcccccaca  62460
tgcacttctc catgcttcta cttcttttct gtgcctgcac tgcactaggg tctctgctgt  62520
gcaaatctcc caaagggttg tcttttccat ccacttctcc agcaatggcc tggggtcaaa  62580
tgttcctgat gctgagctga aggacctcat ttagctgaat accttcccaa agagaatgcc  62640
cagggtgagc cctacattgg tctgagggta cctcacggtg ctcctcttct gcttgagggg  62700
cctggcaagt tgttctagtt ctttctgcag gactttgacg tcctgggact ccttgggact  62760
ggattccacc ttctccaact tcacagctct gaggtggaca gtacaggacc cagggaagag  62820
atcctctcag gtgctcccca ttctagctcc tgcatggcac tcaggcttca atctccaggc  62880
caacttaggg tattggtccc aggccaactt ggggttcaca atatgttatc cttccacagg  62940
actcaatgga aagatcccca acacctccaa acttggtcca acctctggtc cagttccagg  63000
cccacttgga gggcctaagg cgctcagcta tgtctcaggg catgcccagc ctggctctag  63060
ccctcctaac ttcatcagtc ccacctggta gggatgagaa ggtaaagtct aaagccaggt  63120
gtctgaccat ggggaagcat gggtacctca ggcagaggcc tgattactga gattcttgta  63180
cacgtacaaa gtggggtgag gcagcagaca gcgtgtactt acagatcctg tgcattccca  63240
gtaagctgga attttacaca ctacagtgtg ttcttcggtc tatggaagta tatggtgatt  63300
acactgcttc actaatgggt tggaacgtat ctcttgttac atgatctata taattcagta  63360
gctgaagaga ttaaacacta tcagccaggg atcatcctct gccatgtgct gtggactgaa  63420
agttaggctg cgcttccttc ctctatctgc tttattacag aatcgcacac atctgaaaca  63480
tggaaactga agggttaaaa gcgaataatc cctcctttc cccagcctca ggtacatgat  63540
gaggtttgca tggatgcggg tcataaatcc attttggacg ttaaaaccgc tggaagatga  63600
aagggttctc atgtttttgg aacacactgt atttacatat acaaaggcat taaacgatac  63660
atgggaaagg ccctgtgtgg cacgactctg gtattctcta actgccagca ctctgaatgt  63720
ttgcggcccc agagaacctc ggatccctgt gggcaggagt cacgtttccc tttcccgctc  63780
tgttgctgct gagccacctg aacaagaagc ctttaaagac aatggacaag accccagctg  63840
acccggcaga tcctcagctc cagatgttgc ttttgcctgc aaatactgga gcctcactca  63900
caacaaacac tcactgaaga gagtctacgg aagacagctt tgttactgcc attagcatga  63960
atttctaaat tccacaacca ggaagaaaaa cccaactata tagtgaattt ttcttctctc  64020
tagaaacaga taaagaaaaa tgaaaagaca taaaaaacca tgaagtgtag aattacagct  64080
gactcttctg atagctatcc acatgcctac cctcacacca agggaccata ttcttcacca  64140
gggctagcac tagactagca gggacacata gacagcttat gtagtaagct atctgtagta  64200
tcaactacta aacacatatt gataggaagt ccctcaaaaa gcaaatataa tacaaatgaa  64260
accagaactt actcatcttc cacagtggac acagtttatt tgagatagga tcctactctg  64320
tagtcttggc tggcctcaaa ttcattatgt ggctaagggt agccttgaat tcccagcagt  64380
tatcctgcct ctgcattcaa gtgttaacag ttacccacag gaacagcttg ggtgtgctgg  64440
atcccagtag gcagaggcag gcaggactgg tctacatata gttccaggcc agccagaacc  64500
atacagtgag accctgcccc caatttcttt cttttataac tatttattta ttggggaggg  64560
caacacatgt atagtgtgtg catggagatc agagctttag agcacagtgg ccatnnnnnn  64620
nnnnnnnnnn nnnnnnnnnn nnnnnnnnnn nnnnnnnnnn nnnnnnnnnn nnnnnnnnnn  64680
nnnnnnnnnn nnnnnnnnnn nnnnnnnnnn nnnntcttta gtacgcattg gcaagctcca  64740
```

-continued

```
tgtgctctaa agaaggccca cgctaggcga cgaggggaat ccacttacat ggcacagtct  64800
agaagatata tagagtgcat tgtgaaagca agggacatac atgattctag agtgtaaaaa  64860
tgatgtacac tcacagacac acagaagaca cacacacaca cacacacaca cacacacaca  64920
cattattatt attatacgta tataactact aagaaagatc agtcaagcca ggtgtggcaa  64980
caatgctatc atcctagtac ctgggaggct gaggcagggg acatcttgtt tgaggccagc  65040
tttgggccac ctaggaagag actttgaaat cactaaaaat agacaaagca aacaaccctt  65100
aaaagatctg ttataatgtt ttgtttccta tacgcaaatc tttaaagtgg ttcccttaaa  65160
aacaaaaaca aatacaaaca aacaaggaac ccagcacagt tacttgcaac ttaataggga  65220
aaaaaaggag aggacaataa gactctatgc tggaggtaag agacagcttc acacagaggc  65280
cagaatggaa cggagagctt atacccagca tacttaggct gctggtgaga tccatggtgg  65340
gggtggggga aatctctgaa tagaaagtcc ctgactgaag acagcagtgt tccacagctg  65400
cccaggaact ggacgttcat cacaggcagg acactacatt ttaagcgatc ccgctctatc  65460
agtacctgtt gcctgacccc ccccattccc ttaagagggg cctaattatt ctaataatat  65520
gttttagttg ctaaacttga cctaattaaa gagctttgag gaggccgctc ttcttgagaa  65580
acacaagagt aactcttctg aagggctacc atcagaagct cagaagctca ctgggccatg  65640
ccacccacta attaaaatgc ccaagagaca ttcgtctggc agtaaacact aattaccaaa  65700
acacatcaaa gcttctcaaa caagacagaa tgattcattt tgtgatttcc aaaataaggg  65760
attttctttc atttaaaaaa aaaaaaaaaa aaaccttctt tacaaatgtc taagtacctt  65820
atttttctaa aatagttgga aaattctcaa acttgttata gagttcaggc tagtgtagtg  65880
cagcctagtt ctgttttatc tccacaatga cacattggtt gtccttggat aaaacattta  65940
tactgccaac agcctcacct ccccttgctc tgttaaatgg aagccaactg tcacaagcca  66000
ggaccaatga aaaagctcct gcatttgggg ataaacttgt actcttaaga gttaccatat  66060
ataacaaatc ttgaattttc aacatttaaa aatacactta ttacatgttc actcagcgcc  66120
atggcgggga agagttaaga attttgtgaa gagctccaag ctctccaaca gctgcctgtg  66180
ctgctcagaa ccctcatcac tctggggtcc gggcggaagg catcagtggc agcatactgg  66240
gtagcctgga atacgcacac cacccagaac tgcgactaca aacatccaca cactactgct  66300
gtaactgtgg gtgtagctgt ggctgtcact taagcagctg cggcacatca ggcttcccca  66360
agtccagcac ttgactctgc tgctcctcgc tgggctctgt gctcctctcc tccagctctg  66420
tcttctgggc tcatgtgcat tcacacctta gcctcagctt ttattttcat gcactgggct  66480
ccccccaccc attagtttgc tctcagtcta atatcaggtg ggtgtgccag gaaaccaatg  66540
gcctgcagtt tcattccctg tagaaacctg cctttcagtg gtctgctgac aaatggttgc  66600
tttatgttcc tacagactca gtgggcagga agcaaatatt caagtccaga tgggatattt  66660
aacctctgag ggagaaaccc agaacagtag ccagcctaca cttacacagt cagaggatct  66720
gaatctacag tggggcactt tcacacagtg aaacagtcaa agaaaagcag tctggacttc  66780
agcaggattc cagctagaag taacttcctc caggccattt ggtgagctag ctctcctgtg  66840
tcttggctac caatgccagc cctgatagag tctcaactgt acccagacct tggcttctga  66900
tcagcttctg attcttgccc ttccttccct cagcagacat caaggagaca cctgctatgt  66960
aaagtctgcc atgccgacct ttcccagcac taactggcag cttattgttg aaatgtggtg  67020
ctgatttaag tgttctttac tgtaacatgg ctccagccag ctaaaacaga aatgcatttc  67080
cttccctttt gaagtcttat caaaagtggg gcagaggatc tcttcccact taccagtcat  67140
```

-continued

```
ggcaggtcac ttgccatggg tcctcaggtg ctcgcccatg aagtctttca aacatcagtg  67200
gcactctgag gctcacatac cctctgaggg tgacagaata atgaatggag tctgcagttc  67260
aaaaacacta cagcactagc acacagacct gcctcagaat tcactctcac tctgtcccag  67320
tctactgggg caccaagtgg aggtgggata tgctgtggat attcaagttc gaacctttca  67380
aagaataaaa cacacaggcc agtttttgct tgcctagacc agcagcctca ctggcgtctt  67440
agaggtatgc cactaataga acagaggaag ggagctaaca tttcttaaaa taagtcactt  67500
ttccactctg tgcagactgt ctccttcttc agagctgatg gaaaccacgg caggtcaagc  67560
aatgggcaaa actgtttcct gagatggaag gtgagcgcag cctcacctct gctggtcttg  67620
tgtggtggcc tgaaaccatg tctgcccttg caaactaacc agagccagca accctttaga  67680
gtgctacttg gttctatcat ttgttcttcc tacagccctg gaaacaactt cctgtttatc  67740
aagcaaatgc ttctttccaa aagagccagg gtgaggccaa aataactcaa gctgcccgca  67800
agcaggttaa tgagagtgct cactttgctc tcctattgtc ctcagacgtg aaggtcaggg  67860
tgccgcaggg tagaggaagc aggcttggtg ctctgtttcc tggcagaaac acacagaggg  67920
cttctgggcg tgctaggggt tctttttaca gtctgtctag cttgccagtg gtccgtgttg  67980
tacatttctt ctcccagact cacaatccaa cacagcaacg caatctatga gctccacccc  68040
ccaaaattcc cagaagccag caacttctca cgctggtttc caccctgtct agcatcacca  68100
attggggtga acagccacca gatttcaaga tctcttgata acatgcctaa gtattatctc  68160
caattctgcc caaggctttc tgcatctgtt ctctaaacag tcacaagtca ctgggaagag  68220
aatacaaaca ggtccccagt accttcctca atggctaagt cttacacaat tagagaagag  68280
aagcaaggcc cagaatctga tatgggtgtg atatgtatcc gtgtcgtttt agcacacatg  68340
cagatacaca accttctcac tgtaatcagg atgcagaatt actgccagtt tttcttcctg  68400
gggagttact ccttggtgag aatgtctgca catgtgcaca caagtaagcc tgtcttactt  68460
aactcctggc tccaaaagat acagagatat tctactaccc caaagttctc cctactactc  68520
tgtcatgttc taacagatac agtgctcttg ccttaggacc gctgttctct cctgactttc  68580
tcccagcaac atgtgaactt tgatcgcatt acagccttct ccgagtcctc ccttgactgc  68640
cctttgattt tatcttagtg tgggtgttat actggcatgc ttctctgtgt atcacgtgtg  68700
tgcctggtga ccacagaagc cagaagaggg agtcagagcc tctagaacta gagtcacaga  68760
aggtagtgag aaaccacgtg gatgctaaga attgaactct ggtccccctt caagagcggc  68820
aggggctgtt aacaactgag ccaactctcc actgctcctc tggccccaga cttttcacac  68880
tttatcatct tctgactaat tacacatcta tgtagtttgt gtgttgtttg tctctcctac  68940
taacaagtgt caacagggat ttgtgtcttc tgtattcatc actgcttctt gtacttgtgc  69000
actagctggc acatgtgaag tacttgacat gtgtatgttg ttcagagaac agtggcatgg  69060
gaaatgcaac cagtacaaat gtggatgcag gacccaccca ccaacagagt tctgaccata  69120
tattttttta aactcacttt gccactaagc aggttttgta aactaagggc attttctgtt  69180
ctttttaaat acttttgata cctagcccat ttacatgatt acatgaagca tgactgattt  69240
tcacagggct ccgtatctct aaatccaaag gcctgtttgc ttgtgataag gcacctcctc  69300
ctatcccaaa agtcttttaa taaaatgtta attgtggttt cctgcagtag aaacagatgc  69360
ctctcatact gtcccagtgt atcagcacag gttggctagt ctgaatgatg cttctattct  69420
tgagttccta cacgtagaaa aaaatatcat gcggtgtgct tccgtttgtg taggaggaac  69480
```

-continued

```
agaaaagcaa tgttaaatga ataatgttaa tttaacatta aataaatatg actgcttacc  69540
gaggtaggac ttatccctct cctagtgttc tctcctttag atagggactg tttaactcta  69600
aatctaagac agagaatgtt caaggaaggt ctagaatctt gttcaaaggc aaaggagtta  69660
ttgagaagtc aactggatgt ggttccgaag tggaataatt tgagtagtga gagaataatg  69720
acacaggaca gggaggcagc tcagtgatag agaggagaga gaaagggaga agatggtgat  69780
ggagaagaag aagaaaacct cagtggacta aagcacacca gccacattcc agtccatgga  69840
ctcacagaaa agaaacaaac aactcaagtg ggtcccactg gacactatta gggtaccaac  69900
ttgcttgaaa tctgaccttg ctacaatctc tagttttttt aaagcaaagt tctttaaaac  69960
tgataaatgt agaaagcatg aaagaattag aaaactacca gtttgcaaca tttggggtga  70020
actttgctct gagacatggt cttcctgtgt aacccaagct gacctgaatc aagcttgcca  70080
tggaaccttg tctagacaca gactctgatg atcccatccc agcctcggca gtgtcaggac  70140
tagaaggacg tgctatttgg accaggcgtc actttgtatt ttagcatgga accatgtctc  70200
taggtgacca tgtgagagga gcagcttcaa aaactggcta aggtcagaaa gggattacag  70260
ggacacagct aaacctgcag gttatctgaa catcactaaa gtggaaacca gtcactatcc  70320
aaaacttgaa gtgaaccaat ggaagaggtg tgcagaatcc tgcctctcca ccagggaatt  70380
ccacctacat ttaagcaaac tgtaaccaca actggcactt tacgagaaag tgcgagagct  70440
aagaggacat gtttcatgat gagagacatg aacagccaaa tttagtactt acacatctta  70500
caagacagtc cagctttttt ctttaacatt tatttattta ttttatttat ataagtacac  70560
tctagctgtc ttcagacaca ccagaagagg gcatcagatc ccattgcaca tggttgtgag  70620
ccatcaccat gtggttgctg agaattgaac ttagaacctc tgaaagagta gttggtgctc  70680
ttaaccactg agccatctct ctagcccaac agcccagctt cttaagcaag agactacaaa  70740
ggaaaaggaa caaacaaaaa tgatgtggca agtggggaaa gaagggcttc cagattataa  70800
agacatagta agacaggcat gtatcaagcc caagcatgct gtaaacaggc ttcatgggcc  70860
gttctggtgg gagttgggat gaccaaatta ccacgacaaa cagaagatag tgaaggcctg  70920
gctcccgagt ttcagaggag aatgagaact agattagaaa ctgggctaaa ggccatttta  70980
tgatatccta gcaaggaatc tggctatttt ctccatgtgt tgagaactga gagaggctgg  71040
acgtaagagc aatggactaa ttcatctggt agaagaaacg taaatacaga atagcatgca  71100
ggctgtgaca tggctgcttc ttacagttct catccaggtc atctgtgagg gagtatcaaa  71160
aggcaaagca gaaagatatg aaattgtgca ctttgagagg aaaggagttg gagtttaacc  71220
ttactaaaag acagggctac aggattttta aagagattac agcaatctcc actgcaacta  71280
caggagctag gtatgcccta agggcaagac cttagacact ggagactcca ctgtataaac  71340
ttgaaaattc atttgaaaga agaaaccctc aacagagtaa gtcactgaag gaacccctcc  71400
tcctcctgga aaacagatcc ctaggatgt gtttcgccat tagtacacag agactgatac  71460
aactgtggtc cccagaggcc atgctccatc cactttgagc tggtagcaga cattgatgga  71520
attagtcaca caatactgag ttctcaggca tgagagacac gggactgtgg gggtccaaag  71580
atttaagtca cagttgaaga gtgttgctga ggccaggcca tgtgtggcaa gggagaggtt  71640
cctgtaagaa agtcctgaag gggcactggg tgaagctctg aacgtgaagc cagaatagca  71700
atgaagagac actgggaatg ccagggccat gggacaggca ctgaggaaag ctgcaggcac  71760
ctggcagagc cggccgggag agaagccgtg tgatagacag aactgttgaa gggctggggg  71820
ttagccataa cttgtggtac tcgggtggcc ccatcacaat ccccagatgc aggccacaga  71880
```

-continued

```
gcttgaagac ttggtgtttt tactgctagg ttttggtctt gctttgaccc aattgctctg  71940
ttctatgctc cattttcttc tttcaaaata tcaatgttta ctcagagctg ctgtgtattt  72000
gacgtgggtg atttgtttat gattttatag ggatttacag ttaggaggcc accttgagtc  72060
ttctgtgact ctaggacttt gggctttcca atatcgttaa aaagcccagg agacttcaga  72120
agttggactg aatattcaca ttgtagagag ccacgaacca agctaaggaa taaaaggtga  72180
tggcttgaaa gtgctatgtt gaaaggctct gggatcacct tggagacaaa tttctgggca  72240
tatctgtaag gaactttcta gattaagtta cataaaatgg gaagtccagc ctaaggacag  72300
agggacccac accagcattc cccagtgcct gcctaccaac tctgggacac tgtgacagtg  72360
cctgtgctta ctatgctccc tgccatgatc aaatgtaaat tggaataaac catcaagttg  72420
cttcttgtcc aggattttgt tacagaaaca agaaaagtag taacacagaa ggacaaaggg  72480
gaagaaaact ggaaagagca tcaaaattag caagaaggta ttcggatgca tacatgtaat  72540
tgcaatcgtg tggggtagag aggcaagagg attgcaagtt tgaggctatc ctgagctata  72600
catttaaaat ttaaaaatca gaatggcaat tctactcaga gccatggtca agcccctggc  72660
tgtatgcaca caacgttaac actcggaggt gggcttagca gagagcagca gccaggagtc  72720
actcagaggt tccacccaga agatcctgga gttctccttc aagttaaaaa gagcagcttt  72780
gttgaatatt ccagaaaact atccctctgg agtaagggct acataagagt aaggataaaa  72840
tggaaaccac aaactggagc tgcgacaggt tcagtttaat cacctgacag aaccaagtgc  72900
tactgaaggc aacaaccaca atcactgcag tgatcgcccc tcctgcccaa cacacagtaa  72960
aaatgacaga acggaaaaag cagaactggt aggatggttg gcaggcagag gtgcttgctg  73020
tcaaggctgg tattcacatg gtggaggggg gaactggtac ctacaagctg tcctctgatc  73080
tccgtgtgtg ctctggcaca cacacacaca acaaatgaaa caagtgtttc aaatagtctg  73140
tgaaaacagg ggcaaaaaga ctgagagacg tggatgaaca aagacttagc tatgattgct  73200
ttgctaaaga acactcacga aaaggagagc gaagggataa aaagagcctt taaggtaaga  73260
cactcactaa acctcgtcta aagctgcaaa atatcttaaa ccaagaagct actagaagct  73320
gggtggggag tacagcattt gggagcctga ggaagaagat taagtgttcc aggttagttg  73380
gggctaacaa ctagtgagac tgtctcaaaa acaaaagcaa aaagcaaaca gtattagtgc  73440
tctttttttt gttttgtttt gtttttccag acaggatttc tctgtatagc cctggatatc  73500
ctagaactca ctctgtagac attagtgccc ttaagaaagg tgttgtgatt aagctgttta  73560
aaatccttta cacataagaa aaactgtaag tatttatgac taaaaaaaaa tgttccttga  73620
atttaacttg aaatattcaa aactgaaact atagaacagt tggggaaaag aaacaacagc  73680
accagcataa tgctggcgat tgtcagccct gggtgttggg ggagcggggt ttaccacgag  73740
acccttctcc tgtacgtcta gttgaacatg cttacagtaa aaaggggttt tcactggtac  73800
atcagtgctc actagtatca gcatcaggac cgaagcatgg gaactcaagg gtccatcacc  73860
agatgaacac atgaaatgtg tcactgatga gtctgacaca tgaacatcat aagtgacata  73920
agctggtccc acaaggacaa atacggggtg attccattta tataagtccc taaagtagtt  73980
aagctcaaaa catcaggaag ggtgatgctt tgggggaact gtagggtggc agaatagtgg  74040
ccagtgatta acacctcgag tttccattct acagaatgca aagtttcaga tgacaggact  74100
gcagtgtcat tattaatgtt actgaaaatg gttaaaataa ttctgtgtac tgaatatttt  74160
acaactttaa aaaaatggaa tgctggctgg aatatcttca agacattttg aagatatact  74220
```

-continued

```
gaaatgtgac atattaattt caaataagaa attaaaaact gtagatatca ataaaggtta  74280
taattaaata tcttttcatg tctttattac tagaccaagg aaaactacat tttcctaaaa  74340
gggttaaaac atagtttgaa aaaactctca ggaaaagtgt gtatgtatac agatttatat  74400
tgacacatac acatgtatat ttatgtacac acacaaaaca gaaaaaaatt cctttcgaac  74460
atacatatac taaattcagc aaaaaatgtt tggcttgggt atgatgccag cactcagaag  74520
acaaggggat ggtgaactca atgtagaata ggctacacaa tgagacctta tctcaaaaac  74580
cttccatgaa aaaaataaat attttaaaaa cccacaaata gtgactgatg agactgtgca  74640
agcatgagga tccaagctca tatccttagc acccatgtaa aatgttgctt ttggtacatg  74700
ccagtaatct gaccccttgg aaggtggaga ctggaggatt cctgaagctc actaccagag  74760
tcctactgaa atcgtgagtt acaggtccaa tgagagactg tatttcaaaa ctatggtaga  74820
gagaaagaaa agcagccaac atcattctct ggcctcggcg tgcactgagc tcacatggta  74880
caaataacat cttgatcaga aaactgtcca tgacaggatc ccccatggag gagctagaga  74940
aaggacccaa ggagctgaag gggtttgcag ccccatagga ggaacaacaa tatggactaa  75000
ccagtatccc cagagctccc tgggactaaa ccaccaacca aagagaacac atggggggac  75060
tcatggctcc actgcatatg tagcagacaa tggccttatt gggcatcaat gggaggaaag  75120
cccttggtcc tgtgaagttc tgtgcccctg aataggggat gccagggcca ggagtgggag  75180
tgaggngttg gtgagctggg gagcaggtag ggggtggggt tctcagggtt acctaggagg  75240
agagacnnnn nnnnnnnnnn nnnnnnnnnn nnnnnnnnnn nnnnnnnnnn nnnnnnnnnn  75300
nnnnnnnnnn nnnnnnnnnn nnnnnnnnnn nnnnnnnnnn nnnnnntaaa cccctgtaga  75360
gcattctccc ctctcttcta catcctcttc ctccattact attacaatgc tgtgcntgtn  75420
ttttgttngt gtttggggtn ntnnnngggg ggcgtccatg tagtacatct attatgacca  75480
tgattacgaa ttatggccac tgtgctctaa aggtagtgtg tgtgtgtgta gtatgtgtgt  75540
atgtgtgtgt gtgtgtgtgt gtgtgtgtgt gtgtgtgtgt gtatgcaggt atggacatgt  75600
catgcatata tgtggagatc agaggacaac tttgggaaag tcaggtctct ctcctcccac  75660
catggttgca ggacttaaac tcaaatcacc aagcttgtgc agcaaaatgc cctcccccca  75720
ggaccgcctc ccactcccca ttttttttctt ttaagaaatt aagacccctt tgtcctctac  75780
ttcatcttgt gccttcttct ctatgctcag gtttaggctt attttttttt tttaatttaa  75840
ttttgttttg tttgagacag tttcgctgtg tagcccaggc tggccttgga atcacagtag  75900
tcctcctgcc tcagcctccc aaacactgga attataagtg ggtaccacta ccacattgac  75960
ttaagcaatg aacctcagag ctgtatgtgc taaaagggtt acggtgtgtg gatttttaaa  76020
tctcggttta caaagagaaa ccgagcagga gcagccactc cagtggcttg agcagaggct  76080
aatccatggg tagggctgac tcgcgagcct gggtgctttg ctcctgcctc actgatgatt  76140
cctgaccttt cttctcaggt cttctggaac acaatcgccc ttctgggaca tggagccgcc  76200
ttccttcccc aagaaacaat tcatcgttgt tctgctagca tcccaagaca tttgacaagc  76260
ggcagcaact gggctgaaag ctgagtctag gatgaggtag ttattttaaa gaccctgtgt  76320
ttgttaactt gccttcctcc ctcccgccct cctgcccccc ccccccctct tctctgtctc  76380
tctctgcctc tgtctctatc tttctccccc accccctcag ggattcacgt agcccaggct  76440
ttcttcaaac tccctaaata gtacaggaat cctcctgcct ctgcctccca agtgctgtaa  76500
ttacagttgt gtcccatcat gcctggaatt tctgtctgtg tgacagcgtc tcatactaca  76560
gcccatgctg gcctaggatt tacagcagtc ctgcctcagt ggagtgctgg gcttacaggc  76620
```

```
ttctggtgtg atttcccaga atttattcag gcagtccttt tctccaggtg ttccttttgt  76680
gaggccaaat tctggagctg acctgggaaa gcaggcagag agattatggg tccaagatgg  76740
agctgagttg ctgccatgcc tgggggtgac tggggctcac cgtcttacct gcttggcttt  76800
tcttactcag ttgagaatgt atttgtctca ggtttgatgc aactgttctg gggcttacaa  76860
acttcactct ttcagaaaac aagggcatgt atgctacctt cgtgttgact tgatcctcaa  76920
atggctcctg tgaacccagg gacagagtca gctgataaaa gacaaacccc cccctcctct  76980
gcatcacagt ctgagcccat ttcttagtta agaaatcaca ggactttatt ctgccccagg  77040
taaaaatggg ctctctaggg ctccatagat gatcagtggc taagagtggg tgtgtctttt  77100
gcagaggaca catgagcttg ggtcccagca cccacattga acagcttaca aaccatccaa  77160
ctccggctcc tgagaatcag gcgtctctga cctctgagat cacctgcatt caaatgtaca  77220
tattcccaca cagatacaga cacacacgca catggacaca cacataaata cacatacata  77280
catatgtagt aataataata ataattaata ataatagata taaaaatggg atctctagtg  77340
cttagtaagc aaggttagga aatagtcttg ttcaaaattg ctctgatggc aagtgagata  77400
ttagcttagt tggtaaggcc acctactacc tggtgatggg tgtagagaga tgattagtgg  77460
ttaagagcac aggctgccag ctcacaaatg tctgttactc cagttccagg ggatctgatg  77520
cctcttctgg cctccacagg caccaggcac acattgcaca gacataatac atgcaggcaa  77580
aacacccatg catataaaat aaaataatac agaaaatatg tatttgtttt taagattatg  77640
cagttcctac cgggagcttt tcgttacttc caaagcgccc ttgggactga gttctccagt  77700
cttggaagat ctgcttgctg gtcacttcag attgtaacct gccttggaag accccagctg  77760
tgttgggggg acacctattc ttccctttt tctccaggag cttgagaggt ggcagagagg  77820
gcatctggga aagagtgaca gctttaacag cacttgtcag ctgggcagca cggagtggct  77880
atggactaga gaaagccaga aatgcgtttc tgcatttccc aagagaatca aaggggtggc  77940
aggccccatt gttctctttc ccctgacgga ggagttagga ccctaccctt cccagacagg  78000
atatctctgt gtagcctgac tgtcctggta ctcactctgt agaccaggct ggtgtcaaac  78060
tcacggagat ctgcctgcca aattctggct tttttttttt ttttaacagc atcttgtagc  78120
ttaagccaat ttgtagccaa ggaaggatga ctttgaactt ctgaccctcc tgcttccacc  78180
ttccacgtgc tgagtccaca gacactcacc actatacccg gtttttatag tactggaaat  78240
ggaacctagg gcttcacgct tattaagtaa acactgccat ttgagcccca gccctggtta  78300
cctcttgacg ggaaagcttg cgcactttac cctggctgtt gtagcatcat taaacttggc  78360
agttctcttt gtccccacaa aggctgtccc atgctttgtc tggctcttct catgatgtgc  78420
atgggtcata gaccaccaac cggattctgt tcccttctgc ctcgacacgt gctgtgcgga  78480
ttggctgcac agggaacaga agattctact gggggtgctc tccctccccg agccaaccca  78540
ggtgacctga acggaagggc cccgtgacgt gacgtgacgt gggcttgcct ccttgccctc  78600
tgtttgtggg tctgcctaaa tgaaacaata tattttcggg tactttcaag tgagaatttc  78660
tttattgctt ctctagaaag aaaaaaaaat taaatttatt ttatgttact ttttcgtatc  78720
tctcagttct catgctgtga tttagcaggg agagcgagtc acctgctgcc acaggttagg  78780
agcacaggga acacactgtc tcccctgacc cccagcacct aggggccgca ggttgagata  78840
gggggtctgg gggaaaggga gtttggaagt ttgtttggaa gtttgtggct tcttttgtca  78900
ctagactcgt gatcgggtca ctttgagatg gacatcacct cttcaatcta cagctgtggg  78960
```

-continued

```
acacttgcaa ggcacatggt agtgcccctg ggttcaaggt gggcttccta attgggtagg  79020
gatgaggtaa aggactgtca ggggccatag agggccatag caggtctaag atagtctgta  79080
ctcccgtgag accagtaagc ctgggtcttc ctagcttgca tgggggtggg ggtgggggac  79140
actatgtctt ccaggaatgc acaggggaca gggctgacct tgaatttagg atcctcactc  79200
ccctaccagt ttgtcctttc tcaaatctca ggtgacatca aaggtcaggt taaagttgaa  79260
ctagagggaa gtctaaaatt cctgaagaac acgccctttg ctctactaaa gagctgtttc  79320
tctgagatga cagatggggg acttcatata gtacctgcgc ctgggaaata ggcccctcct  79380
ttccctactc ccacccacac agccctgcct cctgggcatg agttcggtct cagctctgcc  79440
tactcacatg actccctgac tgctcttgtc tagaccaggg aagagggcat gactccacac  79500
taggacttgg gtgtcctggt cctggctgtc atactccaca tgtctcagct gtcctcttgg  79560
tgttgctctt ctgccctggg tgtgacctgg aagtattgtg tatgtagctg agggcggact  79620
tgaacttctg ctcttccttc gtctacctct caagcgttgg gattacaggt gttgcatcaa  79680
tcaccatgcc tgctttatgc aatgcccggt ctgtcatggc cctggtgggg acagaatgac  79740
atggctcctg cccctgggac agggccagca ggcatgggcc tccatgattg ttgatagctg  79800
ctatgggcat aaggcttatt tgtatgaata atgtacatat tttaccttcc tccagccagg  79860
acaatcagag acagcatgtg tctgcgaggc aaaggtgtgg ctagtgtcag caaaatggta  79920
aacactggga ccttcaagac agcccttaag gctgggttca aaaacatata acttctcaaa  79980
aaataaggat gcaatatata tgaggggctt catgaatcta aagaaccaaa agcgggtgtg  80040
ctgtgagctg gcttgtcaga aaaagagatc ctaagatgga gaaagagaga ttagggagtg  80100
gtgagcacag gaggttccac ccagtacatt ttttggtttg tgcttacaag ggcagacaga  80160
ttcctgagtt caagctcagc ctgggacaga gctaatttag acccaagtgt agtagaaaag  80220
gtaatttcag gatgggttcc cacccaacta gtttatgctg gtctgtgatt agcagaggcg  80280
ggcaggtctc tgaattcttt cgaaatgtta aaagaaaatg tgtgcttgcc atctcctaag  80340
aacttagggg ccggggttat gggatactgg ttcataggat aatcaaatgg aacctgggta  80400
aataactggg ttgatatgta aaataaaaga ctgggcttag gatctgcaag agaggagcta  80460
tctggagaat gttttagaat agcaagagaa agaactgtct gcagcaacaa agagaggtag  80520
cagcagcagc agcagcagag agagagagag agagagagag agagagagag agagagaaac  80580
ctgtctggag atctccagag aaagcagatc agagagagag gaagcggact agagagaaag  80640
caggctggag agctgtcttg agcagaacat atctgctagc ttcttcctac aatctgactt  80700
cttgagtcac tttcaccact cccagacacc ccttctctca ggaccccctc caagccaagg  80760
ctggtccttg gcaaggcaat aatggacttc acgaatgcta gacaatcaat ctgtccacta  80820
agctacatcc gagcctcagt cagccccttc attttagatt tacttattta ttttatgtat  80880
atgagtatac tgtagctagc tgtcttcaga cacaccagaa gagggcattg gattccatta  80940
cagatggttg tgagccatct gtaatggtgt gtgtgggtgc tgggatttga actcaagact  81000
tctggaagag cagttagagc tcttaaccgc tgagccatct ctccagccca gcccctccct  81060
tcattttaaa agcctggacc gcagggtcaa aacaagaagg agggaaggca gaggagggac  81120
ggtaggcagt ttggcaccct gcagagtgat cctggctagc cccttggagc ctggcaatgc  81180
ctgaaggagt gtgctgaagg ggaggaacca agcgtgcgct ctgtgttgta ttctactggg  81240
ttggtggccc caccactggg atctgactgg gacagagatg ctcctgcatg ggactcaaca  81300
agggctctgg ggacaagggg ctcagacttc cctttatgtt caatgccatc ttccacccca  81360
```

```
cccccaccca taagtcctac ctgaatggga aagctcagcc tcagggtttg tcacggtcca  81420
gggcttgaac cactctctct ggtttttgct gaatggcatc cccccaggct tgtggcactg  81480
gctgtgtaca ctggaactca tgctccctaa tggagcctcc tcgagcagct gcaggcggta  81540
tttcacgtct gttggggaga tttcctcctc ttccagatcc tcagggacag ctctgtgctg  81600
ctgctgctgc tcctgctgct gctgggaggt tcactcggtc agaggggcca ttactgggtt  81660
aagtagggga agtgagtgtg gatgtgtgtg tgtgatgggg agagaagtct cctaaacact  81720
tgccagtgtc ccctagaaag ttacttgtct gagctacaat gtccttactt gcaaagtcaa  81780
taaaatatgc ccgctttctg ggttccctag gagagcagag ctaagggctt agcattatgc  81840
ttggcctgag taagtggcta atcgtctctt tctcttaaaa tatttatgat cctgccagac  81900
agtgctgcgt tggtggcaca cggggagact tggttggagc ccttagcttt acctgaccac  81960
tggaggcgct gtcctcaagt ccagtgggaa cagccaggga ctctcgctgg atggaattgg  82020
ataaagagtc atcaagcaag aaggatcttc tgggtccagg agagagaatc tctagagtag  82080
ggaaaagaac tgaggaccat ctcagccctc ctgcctgtgg gccgctttta gctctccatc  82140
accctcccag gggaaagcaa ggaagggagg ggcaatgtcc agatgggtcc agttttaatt  82200
tatttgagat tagattagtc tgagacctgg agtggaaggg ttagagtgga atggggctgg  82260
ctctctgcat ttaggggcac atggcaaagg caaccttcct tccttcctcc cttccttctt  82320
tccttccttc cctctttcct ccatccttcc ttcctccctc catccccatc tgtcttctac  82380
tcttcctcct ccctccctcc ctccctccct gccttccttc tttttgaga gacccataga  82440
acccaacgat agctaggccg taactatcta cataactaca tgcagtccat gattaattga  82500
gcctcctgtc tgtgccgccc gaccgaggga acgacacgac aggcgctgat gcattcatag  82560
atgtaaaccc gaacgccctg caagctaggc acttacgttc aagacctaca tacctaccta  82620
cctacataca cagatataca atccaatcat tggattggtt ctttctttcc aactagcctc  82680
cctttaactg tgggcattga ttaacctacg acaatacaag atggatcctt tgtcccctgc  82740
taggccaatc aaaaacaccc tgtccacaaa ctttgaaaga ataacagaag ccaccccttc  82800
tttttctagc gggcgaaaag aacaaaaaaa ccaccccaac gctttcggtt cctttccttt  82860
ttttggctcg gagcccgcaa tacctcccca atcacccctt ctagaaagcc cctcctgggt  82920
cttccctaac tgccctggaa agcaaatgaa agggagcgct cgggctggga acataatnnn  82980
nnnnnnnnnn nnnnnnnnnn nnnnnnnnnn nnnnnnnnnn nnnnnnnnnn nnnnnnnnnn  83040
nnnnnnnnnn nnnnnnnnnn nnnnnnnnnn nnnnnnnaat atagacgatc tttatgacca  83100
tgattacgaa ttatggccac tgtgctgtgg agccaatccc agcatgggtc gggtgtctat  83160
aaggaaaggg tcacagagac accatgtgaa tacacctgag aggtagccag gttatgctcg  83220
caggattaaa acagactaat aaatgctcag atactgtacc ataaagtata gctgggttaa  83280
gtaaatctct ctctctctct tttttttttt tgtttttggt ttttggtttt tcgagacacc  83340
acccggcggt ggttaaataa atcttatagt ctctgtctca tttatttaga agttggctgg  83400
gacagataaa aattatccct tttaaaactg aactaacaac tgggaaatgt tatcttaagt  83460
aagtgagagc attcctagta agtcattcac acttcagcag cttcctctta aattagcact  83520
ttgtcttcaa tgcctatggg ttttgctggc atccaggaag cttttgatca agtgctgggt  83580
ttaagagcac atgataggaa gtttgaggga atatatctca agaaattata ttgggggagt  83640
tttgaattat gaatttagtg atttgccaaa cttactagct tctcaattct attggaacat  83700
```

-continued

```
taggcagagc cacactgtca tggctgccct tttacaacgc agtgctaagc cgcaatattc  83760
atttcaccga gtcagctaat agagcaaaca acacgcatgc agtgatgcac tccacttctt  83820
ccaggtcaaa cttcccatct gcttcctttt ctctatacac tcaaatagca aagataaaca  83880
tgtttctccc ctaagtcaaa acctcacaca actaaaataa gtgagcagga gaaatggcca  83940
ttcattctct gcttgacttg gaatatgtgc gtgctgtgct ggacaccaca ttaaacaata  84000
agagcaggtc acagctgtaa tgccatctgt ccatcagtcc attttcattc cctccttctt  84060
tcattcagct gatctataaa tagttagtgc ctatgcagtt tctgtgggaa ctattctgag  84120
aattggcaag caccaaaaat tacaaaatcc tggcttggga tatggttcag tatctcttgc  84180
ctatcatgtg taagggcaat gttgactctc tagaaccaaa aatacaagac aaactcttta  84240
ctgtcaagat gtactttggt aaggtcagat gtaaacaagt gagggccagt tagatggctc  84300
agcaggttag gaaacatgat gacctgcgtt cagtccctgg aacccatatg aagacagggg  84360
aggagaaatt ccataaagtt gtccaatgac ttcaatgtgg atgcatggca tgcacacaga  84420
gcataaaaat gctacacact aatgagtgac tgagtatatg tcaattggtt ataaagacta  84480
ataagaaaag taaagaaaaa aatgagatac agaatagtaa gccagtagga aaaataaagt  84540
ttagttaaag ttgtctcaaa tgaggaaatg caggaaagat tctcaagtaa gtggaacaaa  84600
gatgtgggac gagagttgca gaaagaaatg ggacaatatc tagaccttac agtggaggac  84660
agaggacagc caaatgtgga aggagcagga gagcattggg agctacagtt ggagacaggg  84720
ttgtgtgttt taagccctcg taagacactt ggtgagcgag gcacaagagc tgggtgagat  84780
ggcagcacta gcacgatgtc cagagtggtt cagtctccgg tcccctaggc aaggtcagca  84840
taaacacagc tactgagacc taccaggcag cttccttcca tcccagcatc tgcggagctt  84900
tcctctgagc tcagcacccc tcctatggcc atgctgtaga gctgtgctgc tagaagctag  84960
cagcttctct tgctaggctg cctctgccac cgaactccag tgcagacaga ctgtccttca  85020
tcggaaatgc ttgggatcag tatttccaat ttcagggttt agttttattt tgaacactca  85080
tataaatttt accagatagt tctcatctaa aaccccccag aataaaaaat gtttcaaaaa  85140
acaaaacaaa acaaaacccc aaatcatatt ggcattcaaa agcttctgat ttgaaagcat  85200
ttcccagtgc aggctcctgg tcaggcattc cccatgtgaa gcacgggctc atcaccgctt  85260
ctagatcagc gacatagaag cacatctgca taactgccag caactacaga ggaaagcaag  85320
cagtaccact cactctgcgc ttgatctcag caacttatcc agcacatttc acaccgggaa  85380
cgatagagaa atcagcagtg agacttgctc ttctctgctt ttcaagcaca ctacgtctta  85440
gaagtccaga gtctacacat ggcacactac caattaaaca ctgaactgac tgactatggc  85500
caaagtaaaa tacttttagt tctttcaaaa tagggtgcaa ttaaatatga aagcactgta  85560
cagtatggaa tcagaatgtg gccttgcccg gagaaaagat ctaacctccc cttggctttg  85620
tggtggggtc tttattagcc tggagcctca gtcgtgttag aaggtctaat aataatgtag  85680
gaacactagg aagaccaacc atatgaaatt aagcttggga ctctgggaca tcatgtcaat  85740
tgtcctgaaa attgaggtca acagtatgga caatcaatca atcaatcaac caaccaacca  85800
accaaccaat aaggcacaca taaaataaaa atgtggatgc aaaggctgag cctccctgta  85860
acaatattct gtgcatattg tcacacactc atcccaagac aaagcacacc caggcaaagg  85920
acaatgaaga ctctgcaccc agcacttgtg ggcctgccgg ctttacaccg cccttggctg  85980
gtttcaccga catcctctcc ctggaagagg gcacagcagt gagttctgag agtcttccag  86040
cagtttatca cacccgaatg gctctggggg atttctcaac ttacacttgg tgccagagtg  86100
```

-continued

```
cgagtgatct tggagaaagt gctttctcta tggcagctca cccctgcccc agcaaaataa  86160
aaaatctctt gtacaatgct ctggctgcca ttcaaatgcc actgtaaact aacctaaatt  86220
cacagttcag ttccacagct gaccttgctc catttccaaa gagcaacagc agcgtgtgaa  86280
cagcagctca catgctggga gccatattcc tggactttat ctggccttct ggttcccaac  86340
acacttggtt ttcaatttca cgtagacctc cagcctttcc tattctaatg cgtgatcatt  86400
taaactggtc atacttgtat aactactgcc gctgaagcac agacatcaca agaaaaaaac  86460
atacatgtct tcttttaaaa tcacaaaatt cctcctttga ccccatcggt tctccttgtg  86520
atgtacctat ttgtgggcct ttgtatttag gctacatttg aaagtccttg aggtttttgg  86580
acatgtgagt tactattttt tcaaaatgtc tgctattttc atagccattt tttcttacag  86640
tttctgcctc tgtctctaca ccctcctaat actgtcactg tgcacggaat atgctctgtc  86700
tcctacagtg cagaggatac tctgcctgtc tcctcccact gtgcacagga tgctcctgac  86760
tgtctcctcc cactgtgcac aggatgctcc tgactgtctc ctcccactgt gcacaggatg  86820
ctcctgactg tctcctccca cagtgcacag gatgctcctg actgtctcct cccactgtgc  86880
acaggatgct cctgactgtc tcctcccact gtgcacagga tgctcctgac tgtctcctcc  86940
cactgtgcac aggatgctcc tgactgtctc ctcccactgt gcacaggatg ctcctgactg  87000
tctcctccca ctgtgcacag gatgctcctg actgtctcct ctcactgtgc acaggatgct  87060
cctgactgtc tcctcccact gtgcacagga tgctcctgac tgtctcctcc cactgtgcac  87120
aggatgctcc tgactgtctc ctcccactgt gcacaggatg ctcctgactg tctcctccca  87180
ctgtgcacag gatgctcctg actgtctcct cccactgtgc acaggatgct cctgactgtc  87240
tcctcccact gtgcagagga tgctcctgac tgtctcctcc cactgtgcag aggatgctcc  87300
tgactgtctc ctcccactgt gcagaggatg ctcctgactg tctcctccca ctgtgcagag  87360
gatgctcctg actgtctcct cccactgtgc acagaggatg cgccttacag tctcctccca  87420
ctgtgcacag gatgctcctg actgtctcct cccactgtgc acaggatgct cctgactgtc  87480
tcctcccact gtgcacagag gatgctcctg actgtctcct cccactgtgc acaggatgct  87540
cctgactgtc tcctcccact gtgcacagga tgctcctgat tgtctcctcc cactgtgcac  87600
aggatgctcc tgactgtctc ctcccactgt gcacaggatg ctcctgactg tctcctccca  87660
ctgtgcacag gatgctcctg actgtctcct cccactgtgc ataggatgct cctgactgtc  87720
tcctcccact gtgcacagga tgctcctgac tgtctcctcc cactgtgcac aggatgctcc  87780
tgactgtctc ctcccactgt gcacaggatg ctcctaactg tctcctccca ctgtgcacag  87840
gatgctcctg actgtctcct cccactgtgc acaggatgct cctatctgtc tcctcccact  87900
gtgcacagga tgctcctgac tgtctcctcc cactgtgcac aggatgctcc tgactgtctc  87960
ctcccactgt gcacaggatg ctcctgactg tctcctccca ctgtgcacag gatgctcctg  88020
actgtctcct cccactgtgc acaggatgct cctgactgtc tcctcccact gtgcacagga  88080
tgctcctgac tgtctcctcc cactgtgcac aggatgctcc tgactgtctc ctcccactgt  88140
gcacaggatg ctcctgactg tctcctccca ctgtgcacag gatgctcctg actgtctcct  88200
cccactgtgc acaggatgct cctgactgtc tcctcccact gtgcacagga tgctcctgac  88260
tgtctcctcc cactgtgcac aggatgctcc tgactgtctc ctcccactgt gcacaggatg  88320
ctcctgactg tctcctccca ctgtgcacag gatgctcctg actgtctcct cccactgtgc  88380
acaagatgct cctgactgtg tcctcccact gtgcacagga tgctcctgac tgtgtcctcc  88440
```

-continued

```
cactgtgcac aggatgctcc tgactttatc ctcccactgt gcacaggatg ctcactgtct  88500
atctcctcac gctctgcgca caggatgctc ctgattgtct cctcccactg tgcacaggat  88560
gctcctgact gtctcctccc actgtgcaca ggatgctcct gactgtctcc tcccactgtg  88620
cacaggatgc tcctgacttt ctcctcccac tgtgcacagg atgctcctgt ctgtctcctc  88680
ccgctgtgca ctggatgctc aagataaaat cctcccactg tgcacaggat gctcctgact  88740
gtctcctccc actgtgcaca gaatgctctt gactgtctct tccaatggcc cagggatgct  88800
cctgactgtc tcctcccact ggccaaagaa tgtccctgac tgtctcctcc cactgtgcac  88860
aggatgctcc tgactgtctc ctcccactgt gcacaggatg ctcctgactg tctcctccca  88920
ctgtgcacag gatgctcctg actgtctcct cccactgtgc acaggatgct cctgactgtc  88980
tcctcccact gtgcacagga tgctcctgac tgtctcctcc cactgtgcac aggatgctcc  89040
tgactgtctc ctcccactgt gcacaggatg ctcctgactg tctcctccca ctgtgcacag  89100
gatgctcctg actgtctcct cccactgtgc acaggatgct cctgactgtc tcctcccact  89160
gtgcacagga tgctcctgac tgtctcctcc cactgtgcac aggatgctcc tgactgtctc  89220
ctcccactgt gcacaggatg ctcctgactg tctcctccca ctgtgcacag gatgctcctg  89280
actgtctcct cccactgtgc acaggatgct cctgactgtc tcctcccact gtgcacagga  89340
tgctcctgac tgtctcctcc cactgtgcac aggatgctcc tgactgtctc ctcccactgt  89400
gcacaggatg ctcctgactg tctcctccca ctgtgcacag gatgctcctg actgtctcct  89460
cccactgtgc acaggatgct cctgactgtc tcctcccact gtgcacagga tgctcctgac  89520
tgtctcctcc cactgtgcac aggatgctcc tgactgtctc ctcccactgt gcacaggatg  89580
ctcctgactg tctcctccca ctgtgcacag gatgctcctg actgtctcct cccactgtgc  89640
acaggatgct cctgactgtc tcctcccact gtgcacagga tgctcctgac tgtctcctcc  89700
cactgtgcac aggatgctcc tgactgtctc ctcccactgt gcacaggatg ctcctgactg  89760
tctcctccca ctgtgcacag gatgctcctg actgtctcct cccactgtgc acaggatgct  89820
cctgactgtc tcctcccact gtgcacagga tgctcctgac tgtctcctcc cactgtgcac  89880
aggatgctcc tgactgtctc ctcccactgt gcacaggatg ctcctgactg tttcctccca  89940
ctgtgcacag gatgctcctg actgtctcct cccactgtgc acaggatgct cctgactgtc  90000
tcctcccact gtgcacagag gatgctcctt acagtctcct cccactgtgc acaggatgct  90060
cctgactgtc tcctcccact gtgcacagga tgctcctgac tgtctcctcc cactgtgcac  90120
aggatgctcc tgactgtctc ctcccactgt gcacaggatg ctcctgactg tctcctccca  90180
ctgtgcacag gatgctcctg actgtctcct cccactgtgc acaggatgct cctgactgtc  90240
tcctcccact gtgcacagga tgctcctgac tgtctcctcc cactgtgcac aggatgctcc  90300
tgactgtctc ctcccactgt gcacaggatg ctcctgactg tctcctccca ctgtgcacag  90360
gatgctcctg actgtctcct cccactgtgc acaggatgct cctgactgtc tcctcccact  90420
gtgcacagga tgctcctgac tgtctcctcc cactgtgcac aggatgctcc tgactgtctc  90480
ctcccactgt gcacaggatg ctcctgactg tctcctccca ctgtgcacag gatgctcctg  90540
actgtctcct cccactgtgc acaggatgct cctgtctgtc tcctcccact gtgcacagga  90600
tgctcctgtc tgtctcctcc cactgtgcac aggatgctcc tgattgtctc ctcccactgt  90660
gcacaggatg ctcctgactg tctcctccca ctgtgcacag gatgctcctg actgtctcct  90720
cccactgtgc acaggatgct cctgactgtc tcctcccact gtgcacagga tgctcctgac  90780
tgtctcctcc cactgtgcac aggatgctcc tgtctgtctc ctcccactgt gcacaggatg  90840
```

-continued

```
ctcctgactg tctcctccca ctgtgcacag gatgctcctg actgtctcct cccactgtgc  90900
acaggatgct cctgactgtc tcctcccact gtgcacagga tgctcctgac tgtctcctcc  90960
cactgtgcac aggatgctcc tgactgtctc ctcccactgt gcacaggatg ctcctgactg  91020
tctcctccca ctgtgcacag gatgctcctg actgtctcct cccactgtgc acaggatgct  91080
cctgactgtc tcctcccact gtgcacagag gatgctcctt acagtctcct cccactgtgc  91140
acaggatgct cctgactgtc tcctcccact gtgcacagga tgctcctgac tgtctcctcc  91200
cactgtgcac aggatgctcc tgactgtctc ctcccactgt gcacaggatg ctcctgtctg  91260
tctcctccca ctgtgcacag gatgctcctg attgtctcct cccactgtgc acaggatgct  91320
cctgactgtc tcctcccact gtgcacagga tgctcctgac tgtctcctcc cactgtgcac  91380
aggatgctcc tgactgtctc ctcccactgt gcacaggatg ctcctgactg tctcctccca  91440
ctgtgcacag gatgctcctt acagtctcct cccactgtgc agaggatgtt cctgattgtc  91500
tcctcccact gtgcagagga tgctcctgac tgtctcctct cactgtgcac aggatgctcc  91560
tgactgtctc ctcccactgt gcagaggatg ctcctgactg tctcctctca ctgtgcacag  91620
aggatgctcc tgactgtctc ctcccactgt gcacaggatg ctcctgactg tctcctccca  91680
ctgtgcacag gatgctcctg actgtctcct cccactgtgc agaggatgct cctgactgtc  91740
tcctctcact gtgcacagag gatgctcctt acagtctcct cccactgtgc agaggatgtt  91800
cctgattgtc tcctctcact gtgcacagga atctcctgac tgacaccaac tctggaagct  91860
gcctttagtt ccttcttctc atctctgtac ttgagtgtgg caatcttact gatctatcct  91920
tgagtttgtg tttcttcttt caggcagttc aactctgttg cggagacttt ctaatgattt  91980
acttatttcc cagcccaata attttttaaa acaatgtctc ctgttgatat tctttatctg  92040
aagtgacatt atgattcctg cctttaccgt tgttgcttca ctggtgagcc cctctgtgtc  92100
tgtgatcatc tttatgtttt cttctggtaa atctggcatc atctacctgc ctattatcat  92160
tttcttgtgg tctgcatctt gtggtccagt aactgggagt gcttttgttg tttgggggtc  92220
ctgttgcttt ggctgaacac tgggtgttct agatgacaga ctggggtacc tgaggtttct  92280
gatatacctc ccacctcaaa gcttctgtct gctttgttcc ttttcaacac ttggattgac  92340
tccatccata ttcttaggat ttgggtcctc tcttctgggc aaaacagcct ggcaaattct  92400
gggatctccc tagtttgaac tgaagtctct acacctcttt tcttagccaa acacagccat  92460
tcaactccat taattcttag ctgattgccc actgtgttgt tcgtggatgc gagttgtttt  92520
acaaacaata tagcaaatgt tggtcccttt gaaggaatgc tttctgatca gtgctttatt  92580
tgtttgttag tttttttaa taacttctga ctcaggagag ctctttccag aggtgtcgtc  92640
tgagggactc tgctgtaggc catcaggctg ggggcagaga cggcttcgtg gatctaactc  92700
cttaggtgcc tctcagcaca tcctctactt gaccttcttt tccacttgta catgaacgca  92760
ggccctttga gaagacactg ggatctacct gtgtgcatta aggtctgttt ttctctctaa  92820
tggctggagc tagatagagt cgaaggcaac ttgtgagcaa caatcaaact ctgggagcag  92880
aagtgcaatg aaaagaaatg ggaagatggc ctgacatcac ctcagcccaa ctggcagaaa  92940
accagtctta tgtatgaccc aagccaagag tgatgtgctt ctccaaacag aagggagact  93000
ccacttcaac tacactcttc aggacacagc ctccccaaca ggtaacagga aagatgataa  93060
atattaatga gatgacaaat ctcattaatc tactcttccc gggaagacag ccacctctcc  93120
agatgccagt actaagaaga cctcgatgta tgtccagatt ggaatctgtc tctacctcac  93180
```

-continued

```
ccagcctgtg tgcacatgag gagggcatgg gagagtcaga gaggctgtgg tgccatgcat  93240
agggctggct caagaatcta gaccctcatt gcttactgaa ttttcataga tgttcttgaa  93300
taactgtttt ctttctttca ctgctgcttg ctcacaggat cagtctgtag atcaattctc  93360
atcagttcta catggcagct gataagacgt ctgcgtgact cctgccgaaa attgtccacc  93420
atttcttctt tttgtttgtt ttagggcttt gtttggttgg ttgatttttt ttttttttggt  93480
ttggttttct ggtttttgtt ttgtttgttt gtttgttttg agatagggtt tctctgcgca  93540
gccctggctg ttttgaacac tcccgtttgt tctttaacat gaaggcaaag ggaagcatat  93600
gccaaagctc tctatgctga ctcactacac tcacaccctt cacccaaaac tggaggtcaa  93660
acctagggac ttacaggggg ctggacttga aatatccata gcatgagccc tagtccatct  93720
tcacaactgt agaccttatt ctagaggccc tgggactgag tccaagaatg actgggttac  93780
ttgcctccag cagagggtct atggatgaac ctatccatcc ctgcactacg ccaggcctca  93840
caaccacctc cccaggccca cattaacctt tgctgaaatg gaatccaggg tctcatgcat  93900
gctaggcaag catattatca ctgaactccg cctccacccc tcagcacctc ccttcttgac  93960
taagtgcctc ttctcttatc gtgtacacag acactttaga aaatcagtgc cacacgagac  94020
agcttatcct tgtgcagtct cgttgtccgt ctgatttggg gtttgatttg atagtaacca  94080
aacccaggcc ttggcacaag ttaggtaagc tattctgtca cagagctcct ccacaaatct  94140
gtgtgaggtt ttagtaattt ctttgggtaa tatgtaattt cttctcttca actggatcat  94200
taaaaagtct actatgggcc aaggagatag atggctcagt aggtaaaaga gcttgccctg  94260
atggcctgat ggtcagagtt cagatccccc atgtgatagt ctccgtgtct ctacactgag  94320
atgggagaca ggagaatcac ccacaaggtt atgggacagc tagcctggta tagacagtga  94380
agtcgtagaa acaagaaaca cttggccaca aaacaaggtg gaaggcaaga agcaactcct  94440
acaagttgta ctctgatctt cacacacgtg tcctggcatg caaactccta catgcacaca  94500
gcaatattaa tcatgtcaat taacaatata ttcactcata taattatatg ctaggttgta  94560
atagataatt gtgtgatatt cccttttttaa aaaataccaa aactgtgttc tgtgtactca  94620
tgctacatat gcattaagct acatatacac aaagggttta tgaccaaaaa ggactgttat  94680
ctttcctttt aagatctgtt ttcttgccag gcatggtggc acatgccttt aatcccagca  94740
ctcaggaagc aaaggcaggt ggactgctat gaatttgagg tcagcctagt ctacagagtg  94800
agttccaaga cagacagcca aggctacaca gagaagtcct gtcttgaaaa gaaatcaact  94860
agaaaagggc agtgttccca aagcaggaca catgcactgt gcttgcttag agtgtcagga  94920
acattaagat gagccagcct ctgttattct aaggatatca gtgcccctct gtgaacaaag  94980
gccttactat gacttagcta acaggcagtt cgtggatcag atgctgtgct tcctttcagg  95040
acaaagttca taaaaggtgt taggtaacaa aagttgccca ctggttttgt gtgcatttgt  95100
gacccaatgt gaagcagtat cagtgaacca accgtgtgcc tgggtgtcag gcctccatgt  95160
attccccagt ggcatcaggc aacttctctc tcccagtctc tggcattctt ctattctcca  95220
ctctgtggac tcattaaacc aggaagatgt ctgtgctctc tatagcactg ctatactccg  95280
gtacggactt cacagcctgc attctcctag tctaagatac acatagattt ccatgattgc  95340
cttctattag atttcttcat ggaggaaaat cagtgtcttg atatggaacc attacctcca  95400
aagttactga ttggcttgta attatcatat gtactaaaag cctacactat tgtcttgata  95460
tacaatatta ttctgagatt ttaatgcact aatttctttg aaatgaagtg tttctttaaa  95520
cactgtatag tgtaaaataa gcataaacac cgccgtttaa aggtaagagg aagaaacact  95580
```

-continued

```
tggtcctcta ttaaaggggg gaaatagcag tgacaatgat acttttcctg taaaaagttg  95640
atggtttttt tttttgttgt tttttttctt tttttgagac aggatctctc caggtagcaa  95700
tagctgatct ggaactcact attgacatca ggctgattca gaattcacaa gatttctctg  95760
cctctacatg cagagtgtta gaattaaagg tatgcatcac catgtctggc ctagcctaca  95820
aattcaccca ccaccaccac atcacatagc tattaattaa aaaataatgt tcactttaaa  95880
agtgggaagc cctcctgaga gtctatagga gtaatgccag ctaagaatcc tagcaactgg  95940
agatataaag actgaagtag ccacctccta tagccagaca ggacatccag tggaagaaga  96000
aggacatcaa tccacccaca aaaccttcca cccaaaatct gtctgcctac aagatgtgca  96060
gggataaaga tggagcagag accgagggaa cagccaacca atgactggtc caagatgaga  96120
cccatcccat gggagagagc caaccctgac gctattaatg atcctctgct gtgcttgcag  96180
acaggagcct agcataactg tctcctgaga ggtttcatcc agcagtgcat tgagacaaac  96240
gcagagaccc acagccaaac atcaggcaga gctttgggag ttctgtggaa gagtgcggga  96300
taggattgag tgtgcgggag cagtcaagga caccacaaga agacctacag agtcaactaa  96360
cctgagccca tggaagctaa cagagactga accactaaca aagaacatgc atgggccagc  96420
ataggtgccc tacacattta tagcagacgt gcagctttgt cgtcatgtgg ctcccctaac  96480
aactatgtca gggctatctc tgactgagct gcctgccatt ggaaccctcc ccttcctcta  96540
gctgaactgc caggttgcac ctcaatggga gaggacacac acattcctgc ttctacttgg  96600
tgtcccaggg cagggccgta tacaaggggg gcttcccctt aggagaagag gaagggataa  96660
taggaagagg aacttatgag ggttagaagg gggctggggg gctgtgatca ggatataaaa  96720
tgaatacata cattaatgag aaaagtgata ttatacttct aaagtgttgt aaattaatac  96780
tggttctttt agaatacagg agtttaagtt tgccaatctg cctttcacct ctatttggcc  96840
gtgttaattg ctgtcagcac agagaattcc gcgnnnnnnn nnnnnnnnnn nnnnnnnnnn  96900
nnnnnnnnnn nnnnnnnnnn nnnnnnnnnn nnnnnnnnnn nnnnnnnnnn nnnnnnnnnn  96960
nnnnnnnnnn nnnctccatg tgctctaaag gcctctctac ctaactctct aactctctct  97020
ctgcctctct gactctctct gcctctctga ctctctgcct ctctctctgc ctctctgcct  97080
ctctgcccct ctgcctctct ctctgcctct ctgcctctct ctctctgcct ctctgcctct  97140
ctctctgcct ctctgcctct ctgcccctct ctctgcctct ctctctgcct ctctgcctct  97200
ctctctctgc ctctctctct ctgcctctct ctgcctctct tgcctctctt gcctctgctc  97260
ctctgcccct ctgcccctct gcctctctct gcctctctgc ctctctgcct ctgcctctgc  97320
ctcctctgcc tcctctgcct cctctggcct ctgcctctgc ctctaagtgc taggattaaa  97380
ggagtgggcc accatgtcag actatgagcc agccttcaaa tcccagtcaa acctggcccc  97440
ctctctgctc actgctataa acctctctcc tcagtcctac ccaaccaggg cctcagtctt  97500
ccacaggagc gcttatattg taatgtgccc gactcttcct ggcacagtgc ctggcacaca  97560
gaaaactcaa aattaactta gcatcaagag aagaaatgag atgtcctgtc acgttctgga  97620
tgcagaaact gcagtcggac aaagatgctt ggtttcccca aggccactcc tgcccagtgc  97680
cagaggcaag gccagagaat gatccagttg tgatccctgc tctggattct ctcactgacc  97740
ccatagctac ctaccaccac taaatcatag tgctccatat tggtaacttt tgttattctt  97800
ggttagttca ggccaagtct aaacgcactc tatagccctt taaactgtct tcctgtctcc  97860
acctctcaag tacagggatt atagggtata gcaccacacc caacccagta cttttattaa  97920
```

-continued

```
tcacagtatg taccacacac cccgaagaat gttggaatat agatgcaggc tgaaaagaac  97980
accagccgat tacctgccta agccctgccc cgaagcctac ccccacccca agttaaccac  98040
cacccccctct atgttaagca ctgcctccct ctgtttcctg tgtgtatcat ttttctgagt  98100
ctccctaaca ttgtatttct tgtcctctgc ttgtttggct agctgtgtgt ttgctactct  98160
gtttccagaa ctgcacagaa tccaccatct cgcttaccct tcttgctcgc cttccctgtg  98220
ctgtgaaccc agagcagctg cttactagaa aagccaacca caaaagcagg tggagccctc  98280
ccatcagaga gcaccagccc tctcctgaaa gccactttat tttaggcacg gagttaatag  98340
cgtacaaatg acatccacag taatgtggaa ttagcatatg tctttttttt tttttccagg  98400
aaagaatttt gtatgtgttt gaaaagtcaa cttgttcagg ccctttttctg acagggctgt  98460
tttgattcca gttgtctgac agcaggtgat ctgaccttgt gtttggaggc agaaaagagg  98520
ccccaggaga gttcaagaga aaacaggctc agaggactca caggcccctc cccctcttcc  98580
ccccacccca cccccctcct gccagccctt actgaggtgg ctttggccca tagctgccct  98640
agcccaggga cccagtggca gacagaagca gacctacttt ggtttccatg acaactgcag  98700
gcatcaggag gcggaccaag tgagccgcag ccaacaaggc agctggtttg aagggtgttg  98760
atctctctgc agaccagcaa ggcagaacct ctagggacca gcagcaacag aagccaaaaa  98820
ggagcctcta aatctggacc tgcaaaatcc ttagggacct gtctacacag ctcagccact  98880
cacctgccac catccttcac ctacccacct ggacaggcac accactgtgg atatatgctc  98940
atacctaaag catagcagac ttgtacccag acccacctcc acctacacaa atacagcctg  99000
ctacatctat tcacaccccg atgaaaagaa gcacagacca aaagatccag gcacacactc  99060
aagatgcgca cacccattta cacaggtgac acgcccagga agttcacctt atcacgagga  99120
cactctcaga tacatatacc cagattcaga acacaacctc taggtgccga cacacatgag  99180
gcacatgaac ccacgctttc tgaaccaact cagaaacagc attgctgttc ccgaggtgcc  99240
tcagctgaat gacagagtcc aacaaatgac atgcgggcac acataccctc cttctgcttc  99300
aggagccaag tccccccatgg agtccggccc ttaatcctct ttgtttatta gtgtttgtat  99360
gcacgcttcc tccagaaatg cttaaaggac aaaactctca gcatgctcct gttgttacaa  99420
attaaaaata aacagtgtac tgaagcaggg tatggtggca catgcctttg atcctggcac  99480
tgagaaggca ggggcaggtg gatcgtcagg agttcaaggc cagcctggtc tatctaaaaa  99540
gaatactact aataaactct tgctaactgt ctcacagagc cacatagctc tttaaagcac  99600
ccagtgcacc ccacactccc ataggcatgc tctacaatgc aaggtggggc ctgctgcttt  99660
gcacacccaa atggagggca atgcccagag catggagtag actcctaggc cacaggtcac  99720
ctcctgagcc agttataaca tctgacagac atagcctctg tccacagagg ccactgagag  99780
cctagggtcc cagaagcctc ctggaaggac attttgttcc tttgagttct ctgaaaatcc  99840
aaagacggct ggcaccatct cagtcttacc ccaactgtag cttgtgaatc aacatcaaaa  99900
tgagaaagac tgtcctacac ccatgtgcct gtctgtctgt ccttacagca ccgttggtta  99960
cagtcataat tgccaggcat gttggctgtg ttgtgtactc tcacactggt gatgaagata 100020
atctagaact tagaattctc aaggacatca cagaaaacca caaccaatca aaatgcagag 100080
ttggggagcc cattcaaaac agagacatct cgctgggcgt ggtggcacat gcctttaatc 100140
ccagcactcg ggaggcagag gcaggcggat ttctgagttc gaggccagcc tggtctacaa 100200
agtgagctcc aggacagcca gggctataca gagaaaccct gtctcggaaa aaaaaaaaaa 100260
aaaaaaaaaa aaaaaaacag agacatctct aagacaactc ctgcacctta ggctccggga 100320
```

-continued

```
tcactgcagg aaagggggcg ggaaaattgc taagagccag agcagcaggg ggtttgctgt 100380
gagaccgggt cacctagaaa cgtcagaagc tacacccata aagactctcc aacacgctgc 100440
ctagacatgg gttgaacaag gatgattgct accgcggagc gaggagaggc catgcagcct 100500
caaccccatg cagctaagac cggccgctaa ggaatgaatg ccaagaacag gagaaaggct 100560
tcctgggggga gagcacactg gttatccagc accaaacggt cagccctata aacacccatc 100620
cgagtatcat tatacaggct ggatggattt cattcatgta ttttggaata cacacataca 100680
gttacataac aaagatgaaa aaagaggtca tgaatttgaa agagagcgag gagaggcata 100740
tgggagtggg gtggagagaa gaaagggaag agggaaataa tataatctca aaaaaagaat 100800
gtgtgtgtgt gtgtgtgtgt gtgtgtgctt tttattctca gagttgttga gatagacaat 100860
cgattccaca ggttataatc tgatagctac tttttggttt tctcagtaat agtgactgtg 100920
gagtgcctga cagcacagtt tcatgtacac ctcatttgtg tccctgagta ggatgcagaa 100980
ggaggagaca gcgcagagct tagcaagacc cgggcctgag ggtttggaaa gtagctttgg 101040
aacttggaaa gatgtcagcc caggaaaggg agagaggagg cttcagggag gaagccactg 101100
atgacgtagg cctgaaagca caagtcagca tagtcaaata cagagctgga aagggccctg 101160
atgcccacgg agccagagca gagggtgtgg gcctgtgtag ctaggctcct ggagagagcg 101220
agcgggcagg taagagcaac agtaaactga gatctcccag actcgggtct ccagcctcaa 101280
gcaaaggatt ttgtcgctag tgaatcacca gctgtgggaa tgggtgatag ctgtgccatt 101340
gggctggtag tatagctccg gaggaagagt gcttgactaa gccctggctt ccatccccag 101400
tccctccaaa atttgtcatg gaggagcagg gctataaccc tcagctatca gagaggtgga 101460
ggcaggagga tcagaagttc aaggtcttct ttagatacaa agtgagttta aagccagcct 101520
gggctacatt ataccctatc tcaaaaccaa acaaccaatt aaggagagaa aggacagaag 101580
ataatgaaaa tatctcaagt agccagacag tagacatcga agcggggcca cctagggact 101640
tcatgtgtcc acgggggcag tagattttgc ccagtcatga acagagccag agtaccggtg 101700
acaccccaca tctagctcag agcctgaccc accaaaggct ttacataaat gttttctgaa 101760
ctgcgtggcg ccacggggtc acgcgaggaa aatggaatta agagtcgagt gacccgcagg 101820
gctagttcag gcctggtatt gactggttcc tggacctcgg ccggagattt aacctctcct 101880
gttctcgatt tccacgctgg taaagcgaat ccgataatgc cctgacctac atggcttagc 101940
tgctgcgggg ctgcagcagg atgcgggact cggcctggct ggagccatgc tggccgatcc 102000
ctccagcgct tgggactcac ctcgctccgg gaccagatgc aaggagagct ggctcagccg 102060
tcagcaatta cctgcgcccc cacccaacac ctgcgctcca ctttggagag ggcagatggt 102120
gcaactaact tctcagtacc gccccactcc cggcgccagc ctagaccaaa cgcagagcca 102180
gcgcgggcca gcgtgtagcc agttcaggac tccagcacca gagccccttc cgctcagcct 102240
cagcacagta cctccagctt cagctcctca ccagccctct aaactgtgaa cagggaagag 102300
agctgggccc ctgcttttct tataaactga ggatccgaga aatgaggtgg tttgcagaag 102360
gaggcaccag acagaagccc aagtctctcc aagtccgctg ctacgttatc tggagctgca 102420
ataattccaa ggactactct ggcaaagggg cctaagtgtt ccttggggac aggggcatgt 102480
ttgctatatc tgtatatctg tgtacgcgcg catgtgctca catacacaca cacactcaac 102540
ttgtgctcca agtaattcaa ggttagtgga gatctaagtc aagcctaaac caggattcaa 102600
tgattatatt tttaaaaaca ttaaaagagg cctggcatga tggctcagtg ggtgcttcct 102660
```

-continued

```
taaccagaag atctgagttg gattccccag aactcacaca gtggaagaag agaaccaact 102720
tttgcaaatt gtcctctggc agacatggtc tataaccccc acactcagac tgagtcagga 102780
ggattgctgt gagttcaagg tcagcctagg gtacttattg aaactttgac aaaagagaga 102840
gagagagaga gagagagaga gaggaaggaa ggaaagaaag aaagaaagaa agaaagaaag 102900
aaagaaagag aagaaagaaa aggaaggaag gaaggaagga aggaaagaaa ggaaagaaag 102960
aaagaaagaa agaaagaaag aaagaaagaa agggagaaag aaagaagaaa gaaaaggaag 103020
gaaggaagga aggaaagaaa aagaaagaaa gaaagaaaga aagaaagaaa gaaagaaaag 103080
aaaggaaagg aagaaaagga agaaaaggaa gaaagaaaga aaggaagaaa gaaagaaaga 103140
aagaaagaaa gaaagaaaga aagaaagaaa gagaaaatga gtgaaataaa ccagggagct 103200
gtcccaccat ggtggtgcac ttagaaggca gaagcaggca gatcttatga gttccaggcc 103260
agcttggtct acataattag tccctggaca gccagggcta tgtacataga ccctgtctct 103320
aaagaaacaa agctagagag atacatagtc aacaaaagcc ctgcctcgtg agaaagagaa 103380
cctgagtttg actcccagaa gtcacacagg gcttggcact tttctaatgc cagcactcag 103440
aaggacagat taaggtggat ccctgaggtc cactcactag ccagccgcca tagcctaatt 103500
ggtgaggtcc aaaaagcaag gtagtgaggc tggagaggta gctaagagta cttacagctc 103560
ttgtcgagac tcagagttca gttcaagcac ccataccagg tggctaacca cacctgtaac 103620
tccagttccc agggaccctc cgccccttga gcacctacaa acatgcaggc acacacacat 103680
acaaataaat aataagcgaa tcagaacata cacaaaatga catccaatgc taatacctga 103740
ctcctcttgt acacacacac acacacacac acacacacac acacacacac acaccacaga 103800
gagaatggtg agccgactct actactcttg gaactgttgg ttctcctgct tagaagggat 103860
catgaaacaa ctctaaaccc gctccggtga gtttactgtg ccctctttgg ctctcattac 103920
ctgagaccta tctgcctcct taacgatcca gttgaagcta gagagggttc agtggctaaa 103980
aggacttgtt gcacaaacac gaggacctga gtttagatct catcacccac ccataacaag 104040
ccaggcttgg tctcctgcct gcatacctgt catcccaaac tgtgaaggtg gtaaggcgga 104100
cacaggagaa tccctgggca tgatgtcagc cagactgact gaaaactttg agctctgggt 104160
ttgaggagaa accctgcctc aaaggagcaa agcagagtgc tagaggacag ttggcaccca 104220
cctttgacct gtgtgtgtac ctgtgtatac gtgtgtgagt ataccacaaa cacaatacac 104280
acactaataa acatatctat atataaacaa gaaatgcaaa gatacagttg tctctattgg 104340
aactacctag agcaaatcaa atgtcatcag tttccaactg gatccttttc acctcacaga 104400
accaactaca agaccaagca tcgatagagg agctagagaa aatacccaag gagctaaagg 104460
gaactgcaac cctataggtg gaacaacaat atgaactaac cagtaccccg gagctcttgt 104520
ctctagctgc atatgtatca aaagatggcc tagtcggcca tcactggaaa aagaggccca 104580
ttggtcatgc aaactttata tgccccagta caggggaaca ccagggccaa aaagtgggag 104640
tgggtgggta ggggagtggg gggaggggta tgggggactt ttgggatagc attggaaatg 104700
taaatgagga aaatacctaa ttaaaaaaat tatcataaaa aaaaaagacc aagcatgaga 104760
ccaaaggaga ctaactcttg gtcaagagca ggagaagcag gcaatatgct ctaaaatcaa 104820
ctgctctaga tgctggggat ccagaagtta tagctccagg taagacaaaa tgagggtgag 104880
caacaggctg gtaatggagg gaattgtgtg tgtcttctgg gagtggatag agctttccca 104940
ggaattctgg ggccacctcc tttggctcct tggatggttc tttctagttg tcatcacagc 105000
aattgtcaac tgtcaagaca ctggagtatg tcgtttagtg tggggatgac attataatta 105060
```

-continued

```
agttcacagt tatctggcag ccatcttaga tggcataggg agagacactt ctgcatgcag 105120
gcatcttgtc ctcagagact gtggtggcta atcttgattg tctactcgat gggctttaga 105180
atcaccatgg aaacaaatct ctggtcacat cagtgaggga ttatctacat taggttaagg 105240
gagttggaag acccagccta agtgtgggca acaccattcc ttccatgggc tggggtcact 105300
ccatggcctg aggtccttcc atgggctggg gtcattccat gggctggggt cattccatgg 105360
gctggggtcc ttccattggc tggggtcctc ccatggctgg ggtcctccca tgggctggag 105420
tcattccatg ggctggggtc cttccatggg ctggggtcct tccatggctg gggtccttcc 105480
atggctgggg tccttccatg ggctggggtc cttccatggg ctggggtcct tccatggctg 105540
gggtccttcc atgggctgag gtcattccat gggctggggt cattccatgg gctggggtcc 105600
ttccatgggc tggggtcctc ccatgggctg gggtcctccc atggactgga gtcattccat 105660
gggctggggt ccttccatgg ctggggtcct tccatggctg gggtccttcc atggctgggg 105720
tccttccatg gctggggtcc ttccatgggc tggggtcctt ccatggctgg ggtccttcca 105780
tgggctgggg ccattctgtg atatgctttc tgggattgaa taaaaaggag aacatgagtg 105840
agcacatgct ttcatctctt tctacttctt aactagagac acagcgtgaa cgttggcttc 105900
ttctgtccgt gctggtgtga ctttcccact agggaaggac tgtctcccct agcaccctga 105960
gctaaaacac acccttcctt tcctaagttg cgtttgtgca gtatttttgt agccgtcaca 106020
atcaactgat cccatgaccg agcaaggaga aaagcagcta ggctgtgtag gtcaactctt 106080
ctcacagccc agtctgctga agagggtaac ttactctctg acggaatggt taagctcctc 106140
ccccacccgc cagaagtcct gctgtgagct cctctccctc caccttgagt ttcagagttc 106200
agtgcaaatt tgagttctta gtttgtgtca aggagtgtgc taagacgctc cctcgacatc 106260
tcatcgctca ccccaggagg tggctcctca gtacccccca tttgacagat gaagctgggg 106320
agcaaaggac ctgggacaaa gagacttagc tcctctctgc taccctgcct gggctctcga 106380
ggagagagaa ggattcgtgc gctctctccc agctgctcca gcagaagggc tggaactagt 106440
gccgctgttc ttagagtcca aaccgctggc tttgcaccca ctcccacatg ttacgtacga 106500
tggcctgggc aagccacctg tcttgtctcc tgaccgtaaa agagagggca acggtgtcgc 106560
ccagcttctc tgtcataacg gggtgaact gagatgcact tgtctaagga cagaaagatt 106620
gcttagtagt tgagtggttg ctgctcttcc agaggacatg agttcaattc cctataacca 106680
catgcccctc ccccaccccc accctcacct ccacccccgc atgaaaatgc ctgtaactcc 106740
cgcctcaaag aatcggatgc cctcttctgg cctccgttag aaactgcatg catattgtga 106800
acccacaccg atacgcagta cacattaatt aaaagtaaat taagtctttt aaaaaggaga 106860
gatttgtcag ggtgaccctg agcccgatga cccccacgtt aatccactgc agccggagcc 106920
caggaaagtc gagcaaacga ggtgattcct gccacagctg ggagggggct gagtctctcc 106980
agattcatga gctaagttca agtcctcaga tctcccatca ggcctggagt cactctgtaa 107040
aatgatttgt gaagtgacaa gcaaaaatat attaccaatt taagagtgtg atttgcctgc 107100
aactttttaa tcctccggct gttgttgaat agattaaagt gtctgctttg atccatgcat 107160
ttagatggag acataaatat agccatcact tattttccca gccgcaggga tgggtgtcgt 107220
gctgtgtctc acaggcttcc gaccccgcca gggtacggca agagaatgac ctttttgcca 107280
ttcaaatctc tcttgcattt cagccctgac ttttcagctc ctgaccgggc ctatcagcag 107340
cctcctaatt cgatcactgc tcactccagg aaacagtcac caggaaggag gtccggcgca 107400
```

-continued ggcgggaagc agcggccgcg cagtgccctg gtgctgtgaa cttcccctgg ctcgccagag 107460
ccctgcaaaa ataaatctcc ggagaaatag attttgaaga ggaattcggc acatagatct 107520
tctgtcagcg gagcagactc tgcctcagcc gtttttcagg ctcgctgagt atccagaaat 107580
acatctattt ttacatggct ctctagcgag agttcctctt gcctggaggg gtaagaggcc 107640
gtggaaggag tcagaggatg ggagaggaga ggggtgcggg cactgactgg agaaggacag 107700
ggaggtgacc gtgcagtgct ggtcttcccg gttttcctgc atcctgcagg accttgggtt 107760
tgccaaccaa gtttgggttt gcctcgtcgc tatgaaggct ctgtgtgtcc cttggcccac 107820
cggacccatc ttagtaacag gcctgatgtc cccggagaag acaatacact acggcagttt 107880
ggcgcgcgcg cgcacaaaga gctgcagcac cgcccggggc tcactgtttt gttctcggcc 107940
tagctgtcgc ggtgaacagc aggagccatg gaccagatgg ctggagggag gtgcgagcgg 108000
atcgcactgg caggcaatta ggcctcaaac aatggcccgt gaaatgtcag aagtggcaag 108060
gaagggtcgt ggtggaacag cgggatgaca acgtaaggat ggcgccagga accccggaga 108120
cagttcctgc ttgctcccac aggcccctct ggcagaggga acactcaatg acccttctcc 108180
ccaatgccca cgcagactcc tctgaagata aagaaaaggc tgaggggaag ctatagtgca 108240
gatggtgagc cccaggtgta gatcgggtca gtagatgctg gcaccaaata aaacctgtca 108300
tgacgataca cacatgcgat cccagcactt aaagaggcgg gaggaggatc aggagttcaa 108360
gatcatccat ggccacatgt atagtgagtt cgaaggcagc cttagatata ggtgacttca 108420
aaagggggcg tgggagagag cgaaagaacc gggggggggg gggattgaaa gagaaacagg 108480
agaaggaaac agtgctggag aaggagcaat gagagaagac agggaaggga ggtgaggaga 108540
gagagtgtgg agaggagagg agtaggaacc gcccctcccg gtggctgcca gcaaccacga 108600
gaaccccaca cccactagat gctggggtta aagtgaggct aagagatggc gacacccacc 108660
cccttggcca ccacaactaa gaattatgta gagtaattaa tcaagagcta atgagaaatg 108720
tgttttctct cgcagcctag ccccacatca tattcttatt agcggaggtt attacaatag 108780
taatcagcgt gctccaggcg caaattgggt tttttgctcc actgccacca atttagaaaa 108840
ccattaatgg caagataagg cccccgtggc tcacaccggg ccaagcctgg gaacctgcag 108900
ccaactctct gctcatgaac ctacacgccc atgctccagg gggcgctcga gcaagcatcc 108960
tggctcttct gggacgacag agaagaaaaa gccaaccgct ttctaggagg tgctgtacct 109020
gcgggaccat agaactttct caaatgtgaa tcctatacaa cagtcacttg gatgagacaa 109080
cctcatggaa caaaacatta aagccaagtt tgccactaga gccagagcgc catatactgt 109140
gcccttgagt cctgcttcaa gccagtctgc tagaaacgct taggtgaatc tatagctctt 109200
aggcaggagg ttgcgatcag acacaagccc tggaacaagt ttctatcagt gaaaagagtg 109260
gagagttaag agtttggggt ttttcttata ataataataa taataataat aataataata 109320
atagccgggc gtggtagtgc acacctttaa tcccagcact tgggaggcag aggcaggcga 109380
atttctgagt tcgaggccag cctggtctac agagtgagtt ccaggacagc caggactata 109440
cagagaaacc ctgtctcgaa aaaccaaaac caaaacaaat aataataata ataaaaaaac 109500
ttgttattta cttatttgtg tgtataccac agcactcgca tgaagatcag aggacttctc 109560
tccttccacc atgaggggcc aagagattga actcacgttg tcagggtttg gaggcaagaa 109620
ccgtcatgtt tggcagcaaa gacctctacc tactgagccg tcaccatagc cctgctgaga 109680
tagtttcata acgataaatg cactctactt tttgatgatg ttctcagttc caaaattgtc 109740
tccctgtgtg cgtgtgtgtg cgcatgtgtg tgcgcatgtg tgtgcgtatg tgtgtgtgtg 109800

-continued

```
tgtgtgtatg tgtacttact catatgtctt tttatgtaca aaagataggt tccttcatgt 109860
atagttggag aagggctggg tgatctgact gggaggaaaa gaaagaaaac caggagtcac 109920
gtctcttctg ccccttgtg ggatcctgga tcaaactcag gttgtcagga ctgcatggca 109980
gggtctactt gctgagctgc ctcaccagtc ccctttcctt tttcaacatg tagaggccaa 110040
gtatgtccct ggttctacac agcagacaaa gagttaagaa gcaacagcta tactgcagtt 110100
aagtcctgcc ttttgtttgt ttggttggtt ggtttggttt tggtttgaga cagcctttct 110160
ctctgtagcc ctggctatcc tgaaactcac tctgtagacc aggctggctt tgaactcaca 110220
gagatccagc tgccactgcc tcctgagtgc tgggattaaa gatgtgcacc atcatcaccc 110280
agcttagtca tttctaccgg tcactattat ttagttagtg ttacttagtt ccttgaatat 110340
gttgtccaca aaaattctct caaataatta actacttcat cctgtggaat aaaagatttg 110400
agtgaggcag acctaagttt gaagtctgtc tacttatcac tggcttttgg tttgggattt 110460
tatttatata cgtgtgtgtg tgtgtgtgtg tgtgtgtgtg tgtgtgtgtg tgtgtgtgca 110520
tatgtgtata tgtgtatgca cacatgcatg caggtaccca ctggagccag aagagggtgt 110580
cagggcccct ggaattacaa gtagttgtga gccacacaat gtgggtgcta gatgtggctg 110640
ctagacatgt aagctagaca tgggatctag gaataaaatt cggaaataac aagcactcaa 110700
ccactgagct atccctccaa cctgtctgtc tagttttgag aaaagcatta gcctgctaaa 110760
gcctccattt cttcatctat agaatgggac tgtacctcca tgttctttga aagttccaaa 110820
gacatatccc tgtgtgcttt ggtaaataca gagcacctgg aagtctcagg cactatttga 110880
gatgcaatat atggagaaag gactcatctg ggatctccc taaggatgcc cgagagacca 110940
gcaggtatga tacaaaagag aattagccat ttgacataag agagacatga agatcataca 111000
ggtgcatgcc aggcaagagg gatcctgagc ctagaggttg cctgtcagtg ctatgagcat 111060
ttaggaaggg ggctacctcc agacaagctt gggccaactg gtggaggaga tggcccaagt 111120
ctgagaagac atatgggatg aaggcggggg ttggggtgag ggcgtctcct gcatggagtg 111180
gtccaaacag aatcctggag atgtgaacag tgaggctagt ggcctctctg gatctaagga 111240
acacacagca gccaggcctt cccatctgag ccatctgcct tttcctcctc cgccatagct 111300
ccaccccctc tgttctgata tcatccgggc acagccagag gatggcacag cagaggggac 111360
accttgggcc taagacgtcc ttagcaagag cacctacata cccacataat gccccctcct 111420
ccatgcctcc ttaacaggac taaggttcaa tgctgctaat taacaaacag caatcaactc 111480
agctaccccc ccccacccct tcaccagacc ccgacccccc cgcccccatg cttcctttcc 111540
ctcctgtgga gaaggcacag ctgagctgca ggcaggggca gagggtggga gcaggctgag 111600
gtagacacta gagatccggc agaggggtta cactcaatat tgagttgtaa attcaacaaa 111660
ctggagatct ctctaacgcc catctagatg agcatctggg ataacagaca tttctagcta 111720
gacggagctt ttgcctgtca catggagtgc cattagttta gtcctcagac agtccatcac 111780
aaccctcatt taacaatgat ttaacagtgt ccttggcccg ctctaacact aaggaaggca 111840
ctgtcatgta tgctcaggag gtcacacagg gcatagaggt gacattcaac caatagacag 111900
ggtgggtgga aatatagatg catataggtc aacaggcagg tgaagggaca aaggtggtgg 111960
tgggttagcc cattttacag aacaagaaac tgacataagc caggaatgat gactgacacc 112020
tgtactcccc acacttgggt ggctgaggcc agaggattaa tgtgggtttg aggtcaacct 112080
aggctccaga gagggtctca agtaaaaagt taaaatgtaa aggaaaaaag aaagggaagg 112140
```

-continued agggagggaa gaagggagga aaagagagga aataaaaaga gaaaagaaag tcgggcagtg 112200
gtgatgatac acactttttt aatggtgcac ttgggaaaca gaggtgggtg ggtctctgag 112260
ttcaaggtca gcctggacta cagacagcta gggctacaca gagaaccctg gaaaggagaa 112320
gagaggagag gggaggggag gggagggaga aagagagaga gagagagaga gagagagaga 112380
gagagagaga gagagagaga gagagagaga gagaagaaac tgagacaaag agaaaacatg 112440
acttactcta aactagacat ctagaggcag gtcagaagca ggtctcacca tccacccttc 112500
tgttctctgc attcccagaa gccagccccc acctctccaa tctcaggctg gctgccatga 112560
cacccgtctc tctgaaggct gagatgatga ggggaacccc agactccctg tgttccccct 112620
cctctggaac ccaaggcctc acataggggg cacagtatga aggtccttga gtttacagat 112680
ctccagagaa gccaggagtg ttaatcacac aggactgtct ttccaattgg aaacctgttc 112740
gttcttccat ctccaaagct gagacctgga agtgatgaac agtctggtga tctgtgttgt 112800
tatctgttgg accaggccat accaagctcc tacaaccaaa gctaatctaa atgaccctca 112860
tagccagagg ctgccccaac caggaccaga ggtagctaat aatctaaatg acctctatgc 112920
tatctgtgtg accaaaacca gaccagaccc ttaggccctt aagctagcac tggtaactca 112980
tgtgacatcc ctgccttacc tctcacctgt cccacttcct aagggcccag catgcctccc 113040
gcactcctgc tcctgtccct gaaccatgac agcctcacac caagttgagg tccctttgct 113100
ttcagtttgt ggcatcacct cttctcgact aagatctcat gggtctgggc aagcattggc 113160
tccccctctg cccagaatcc tttctttccc tctggtcttt ctaaagcttc aggtttctcg 113220
gctcagaatc cttttatctc cagtctaaaa gtcctaagtg ggccttccac acagtttggg 113280
ggtttcaggg acttgtgtgc atttgataaa aaaaaaaata gcccatggct agaggtattc 113340
ttgccccccc ccataaagct tggagccccc ataccacttt ccacccagga tcatgtggcc 113400
tttgccacag aagtctcctc agcaccacag actttgagtt cccttcccct gggcttggca 113460
tgataccaga accagtcctc tttccagcct gtctcctctt aaacaaagtc agagcctgag 113520
gccatcaagt ctttgcaggt attcacaatg acctctggac actacacaca acagatgtta 113580
tcaagctaag gctttggatt cagctggcca gtcaacctaa cctcctttat accttctgtg 113640
tacccaacat gggagacaga aaggtagaca aggtagagtc ctctgaagta ctagggttct 113700
tcccgttaca taggagagac cactgaaatc tatggttaac tcctgtctgt aatttaacaa 113760
ttaattggtc agtcaaggaa aagacaaaga taaaactcaa gggccttagc ttcttgggtt 113820
ggttcaaggg tttgcaatgt gtgcttcacc ttgtgatgtc atcagctccc tttcagatca 113880
gcctcttcct gatggggcca aatggcagag agagagctgc caaccggcag gcacatacct 113940
atggtaccaa gtatctgctt ttctcaaggt gcaaacaggg ctcctggcag aagaaggggg 114000
agggaagcca ggaagctaca gcctgtgcat gcaaatgaga cagctgcata attaattaac 114060
acccaacagt ttcattagga gacagagctt tgcactgact gtcttggttc agagaatagg 114120
atctagcact gttcaaagcc aaagtccgaa gctagagatg ctgcccacca ccgatgctgg 114180
ggacaatact tgttgctagg agaggttgcc tggggcagct ttggtcctat cttagacttc 114240
gtaccaggga ggatgagcct atgattgtca cataagtccc ctctgctcag gcctcaccca 114300
cacttaggtg tgggaaggga ggtgggcacc tcagagagcg gaaggggatg cccctggagc 114360
atctgtctga gctgtggctt cccccgaggg tcagtctttt ctacagctct gagaacagca 114420
gccttgtttc cagaatggtc tctaagcgct gtaggatact gtacggaatc caaagccaaa 114480
ccaggacagc taaatctcca gctcccttgt ccctccctca acaactaatg tttctctata 114540

-continued aaactgaggg aggaaggtag aggaataggc agctccttgc taaaccttct gggagcctct 114600
gtccccagcc ctaatcccat cctagcttgc atttctgttg ctgtgataaa cactgacaaa 114660
aaacaatttg ggggaaaggg gagtttgggc ttaaacttgt atttcacagt ctatcattca 114720
agaacatgag ggcatgagtt caaagcaggc acataaaggc aggagctgaa agagaggcca 114780
tggaagaaca ctctcaacag ctagctccca tgacctggtc tgtttgcttt cttgtacacc 114840
ccaagaccac ctgccaaggg gtggcactgc ccctgtgggc tggacccccct cccagcagtc 114900
actaatcaag aaaacatccc cctatccccc acagccttgc atacaggcat tctggtggag 114960
gcattttctc catcgaggtt ccctcttccc agatgaccct agcttgtgtc aagttgggaa 115020
gaaacagaac aaaaacttaa gcagctaagt ttcatggaca agaaacatca tctctcagaa 115080
ggaatcctag caaacctcat gacctgcctc cgctttcctt tctggaacca tctctgctcg 115140
ccacatacac cctgggttgt atccacatca gactacctcc attttccacc cccaccccca 115200
tgagtggcct ctcatgtctc tgctactcct tcagttatga aggccctctt gcccttctca 115260
cctacctgca gactcctctc ctcaggagag ccttccttga cgcacaccct ccctactcct 115320
ccacccccta caaagctagc tattttcttc cctcttttct gcataacata tgcaataatt 115380
attaatttac ttgattgact ctgaccataa gggagtcacc ccttgagggt agagactgta 115440
tcttccctgt ctctgcatca ttaagtcctg ggctacactt caaaagtttg ccagatgagt 115500
aagtgaataa atctgttaag ttgaaaacac ctgttataga tccttgactc tttatatttc 115560
aaccattcag aagtttattc cctcgctaaa cctatagccc tgcactggag aaagcgtagg 115620
gatgggaaag ggaccctcaa ggggactgag gtcatcagga agcaacaaca gtggctggtc 115680
ccggcaggat aagagcctag gttggatagc ataaagctct ccattgttcc ccatagctaa 115740
agcagctaaa agaaccccag gggccttcca acctctttgg ccatcagtct tccgcatgtc 115800
ctcacatccc aacttccagc aatttctccc tccagcccga tccaggcaca caacagacat 115860
agctctgcca gaatcacaga gccctcctcc aaagctcctg gcccttgttc tccagttttc 115920
ctggggtggc cagagaagac ccatcctcag tgccatggtt tgaatatgct tggcccagga 115980
agtggcacta tttggaggtg tggccttgtt ggaatagatg tatcactgtg ggcatgggct 116040
ttaagacctt catcctagct gcctggaagt cagtattctg tgggagctaa aaaagggggc 116100
cctggggatg aagagggggg agatagaccc atgccccacc agagttttac ctattctctg 116160
gtttgtcagg tgtgggaggg ctgctacctt tccactcatc cctggatggg catccaagcc 116220
tctgaccctc tcttcagggg acggccaggg gcagccctac ctggggaccc tggagctact 116280
ttgctaaagc caccagggtt ataggagaga gggatgaggg aagatgttcc caatacctac 116340
gagagtgcat gcagccttga tgagcagaga ctctctatgg tttaagagct ttattataga 116400
aatgcaggga gaaagagaga agagagagag agagactaga gagaaagaga gtaagaggga 116460
gagaagagag gagaggagaa gagaggagaa aacaaagaga gagaagagag gagagaagac 116520
aaagagaggg gagagaaggt gagagtgagg ggtaagaggg agacaagtaa gagagtaagc 116580
agtaagagag cgaggtgggg ctgatcagcc ctttttatgg tctttactgt tgctaggtaa 116640
ctggggagga gttcagcctg aaggtcagaa gcttggacca ttgcctacgt gactactgac 116700
catgcttctc ttatgggggc atgtgggggg cttacgcagg ggccagagtt ccaggagcat 116760
aagggaatgc ctaccgtgtc atgaaggtga attatgactt cggggttcag acctcagctc 116820
gactggagac aagcctgcaa ttccccacag tattctgcta gcagccttaa attgtagatg 116880

-continued ttgaactctc agctcctcct gcaccatgcc tgcctggatg ctgtcatgtt ctcaccttga 116940
tgataatgga ctgaacctct gaacctgtaa gccagcccca cttaaatgtt gtccttataa 117000
gagttgtctt ggtcatggta tctgttcaca gcagtagaat cctaagacac tcagttaaca 117060
aggatattcg cagttgatta tctgaggttt ctctgtaatt ggaaaagaaa gagcaacagg 117120
caaatgtcaa ttttggcttc cctgcctccc atccctgagg gatggaggga acaagagtcc 117180
tgtctactct caaggccttg ctccaaccag gtcttcttgc tcagcttttc tccataggct 117240
catactatac acacacacac accccccctca agggtgatat ttgggactta gccagcccca 117300
tggagcaagc ggcccacaag tccacagaca ctacagagag gttcagggac agtgagagag 117360
aaatgtattt ggtgtttgaa tgtgtgcaaa gggagggaca gcacccagac cccacaccac 117420
ctcgtctatg gagtcttatc ttcactgtgg tgttattcca cagctaagca cagccaacat 117480
gcatcagctt gtgaatttct agtcccaagt tcactgcccc cagagagact ttgtgatcag 117540
ggcctacaac tcttcttccc ttcacttccc tgggcccctc cctgaggagt tgaagcagag 117600
acagtgtgga aagcaagacc ctacctttag ccgccattct aatccagtgt ctaccactcc 117660
ttgggggaaa gatagcaggt gtcacaaggt ggtcacctct cctttccacc agaatgccac 117720
ctcctgggtg gaagtccaat gttaccttcc accctcacat acacatcact gagatcctgc 117780
cttctttcct gccacctctc cttcggtggt cagagatcat gtctttcttg cagatggcta 117840
tgacagcctc cagataggaa ccagtgggga ccccaccccc aactttgtct tcacaatgag 117900
gttgatgtga gcttgggggg gggggttcga gacagggttt ctctgtgtag tcctggctgt 117960
cctggaactc actctgtaga ccaggctggc ctcaaactca gaaatctgct tgcctctgct 118020
tcccaagtgc tgggattaaa ggcatgcacc accacatctg gcttgatatg agctttctaa 118080
gccaattcca atcatgcctt cccccaacat taaatttttt tttctaccca ggtcctcaat 118140
ataggactca aatctcccag aacaaatcat caacccctcc actccccgat gtggccttcc 118200
cccagtccct tgaccatctc tgaacttctt ttattctctc accccagggc cttagctcat 118260
gccattcctt catctctttt cctgtgttct caaggtcctg gacaccatgt accaactgca 118320
cctctagcac tccatacaga gaaacgaggt ctcgcctagc aaattgatgg ctgaaaatga 118380
ggcaaaggat gggtgggaaa gtcccatgga attgtagacg cttccccatc ttattcattt 118440
acctgtggca cttccattca aacccttgct gtacacaggc tgggcaaacc actgggctat 118500
ccccagccca actcttgtaa aaccgaacag atccagagag gtgaggcaaa ctcagccaag 118560
gccacacaaa gacttgtacc acatcccatc acccttggtt gtctcagaag agcccagaaa 118620
gaccctagcc agaagccgag gttggactga gaccctcagg atgagttcag ccagcagggg 118680
gcaggagtaa gccatggcca gtactaggct ctcgagaagg aaaactctgg ctaggaggca 118740
gaagcaggca gatttctgag tttgaggcca gcttacacct cccactgctc caagtctaac 118800
cttgggcttc ataacttcct gtggcctctc tggacaccaa gagccatttc cctaaggccc 118860
aggatttata gaggacagca aagatagcca gccactcaac cagccccagc cccatctgcc 118920
agagaccagg catccagacc ctggtagggg gaagctgtgg ctggtaaata aaaaaattta 118980
ttaagaatat gttagctgag ccgggcagtg gtggtgcacg tctttaatcc cagtacttgg 119040
gaggcagagg caggcggatt tctgagttca aggccagcct ggtctacaga gtgagttcca 119100
agtcagccag ggctacacag agaaaccctg tctcgaaaaa agaaagaaag aaagaaagaa 119160
agaaagaaag aaagaaagaa agaaagaaag aaagaaagga aggaaggaag gaaggaagga 119220
aggaaggaag gaaggaagaa aggaaggaga gagagagaga gagagagaga gagagagaga 119280
gagagagaaa gaaagaaaga aagaaagaaa gaaagagaaa gaaagaaaaa gaaagaaaag 119340
aaaagaaaag aaagaaaaga gaatatgtca gctggagtga agcaatggct cggtctgtaa 119400
agaatttgcc ttataaacac aaggacctga gttcaattcc cagaatccag taaaaaacgc 119460
cctgttccta agccagtgta agaggcaaag aaaggagggc ccttgggcct ggctggccag 119520
tctgtctagt ttaattggtg ggttccaggc caatgagaga tgctgtctca aaggaggtgg 119580
acaagttctc tgaggtgaca ccaagactgt cctccagcct gacacacagg aaagcagcag 119640
gcttgcttgc acagcgcctg cctgcccttc atggtggcca gccttccttc ctcttcctgc 119700
tcactctagt gaagacccca gggtagtgag gagaagctgg agaggaaaca aggaaccagc 119760
agacagctgg gggtgctggc cacacactcc ccaaccctgg cagcacaagc cccatcattg 119820
ggtgctaatt aaatcccccct aatgaggaaa acggatgcag gagctggctc ctccgtggcc 119880
tccccggccc accgcccttg cctctccatc ggacttatcg ctcgtcacag gatgtttaca 119940
ataattttta atttgtgcaa ttattaatca cttttctatc tccctcattt gcataataat 120000
tagtcatctc actgtttggc atgcctgtga atgacagtgt tttaaattga attaagattt 120060
taatattcta ttttcctgct ttcttcccct ccacacgcta atcaaagtca gatttggcag 120120
ccagagggag ggtacggagg aggttggcag gcactggact tggcccattc tgtgctcctg 120180
agaaccaacc gtgctgagaa cagggcctgt ggagaaggca acaagcaatc accctactcc 120240
aaacggaggc tgaaggggtt aacccagcca tagctaattg agcagaggta atgaggagtg 120300
gggaggggca gccagggagg aggggtgggg agggaggagg gtcacaggct cagcggcacc 120360
agagagcaag aaaagtgctt ttcatttatt ttcttttcca agtaggctgc ttttggtaag 120420
ggaacactag aggggacatg ataggccagc cattgatccc cagttagact aggttaactg 120480
tgaaggctct gagtcccgca agtggaggaa gcaggctgga gcagcctaaa atcccattca 120540
ttgcgtctct ctcaacgtgc aagacaattt tctggggttg actccctgtt cttctcccca 120600
cttctccaca caccaacagg tcctctgccc aagttgggtg cctcacgggt gaggaacaag 120660
aagtaaggga tttccaccga caagggacag cagacaggcc acgtgtcccc taagttagag 120720
gcagctgtgg ctctacagat cattttctaa ccctaaatcc ttcttctaat cacgccaggg 120780
attcagcctc agcctggagg agggcctgtt ctattgctgc ctccctttgg attgcctttc 120840
gtgttgccat ggtgatccct aggctaccca ggatacccat tgctgcccca gaattctctg 120900
cttgagcaga gcggctctcc cttcagcctg tttagaacac ctttcttttt actatgatat 120960
gctcaagctc tgcaaaaacc aacaccgctt tgtccataca ggtgagtcgg gatggacatt 121020
ggctcccaga gatgggctct gtgcaaacaa tatgaaggca ggtcagccat cacaggcaag 121080
gggctggaaa ccacactcca acacagccac caagctcttc ccccacacca cacaagggct 121140
ttcaactctg cacatgagga ccaaaatcag gaaagtcccc catgagggaa agaagaaaag 121200
gggtcttgtc aggaggagag ctaggctgga agggtttgaa cccctacctc cagtgggtcg 121260
cctccttctc tggatcccct ttggctcagg acatcccaga gcgtccttgc cctcctacta 121320
attcctgctg acacacatgg agaggctctg gcctcaaggc tggtccatct aggtgcccac 121380
acaacctagt gtctgcccaa aggaatagca acagcaataa gccatcagga tttaggaaag 121440
gcacagccca atctaggatg aacaggaaag caatgagaag ccaggccggg agctttgagc 121500
tgtgtcccca ggccaaacca gagaaagcac tcagtctctc agccccagac aggctaagag 121560
aatccagagt atcacctggg gacatcagca ctaaggaaaa cccagacttg tagataatca 121620

```
actctaacca gtacagcctt gtttctggat ccttatggcc ctggaatgag aagtggtaag 121680
gcccatagct agtgctatag cagcctctac tggccacctt tgccttctat gctgtgccag 121740
gagccctgca tcctagttgt ttgggatggt cctgtgaaca cctgttgtca ttaatgctga 121800
ggactcactc tcagaaatac cccagtacac acatgacttc agtagccttc agtcacagcc 121860
gagttccatg tcccagaatg ccttcaaggg catagagaaa taggtggtgc gttaagatct 121920
ctgaccccgg cagcaaagca tctttctcat cagaccacag gagtgaataa ttcagagtcc 121980
tctgtcctgg gccaggacta aggcttcttg acagcgccac cgtgaagaag atggaaagca 122040
ggtgtgtggt gagcaggagg gaggggcctt ggcctaaaga gggtagaagg gatgagatgg 122100
aagtatccag agggcaggaa gtgccaaggg tgtgacatgc tattgctgca tgtgtccagc 122160
agatggcaac atagagcagt ctgcatcagc tcttggaagg gacctgcctg agccaggact 122220
ggcttctgat gtcctgcagt gcagagcgcg ctctctctct ctctctctct ctctctcctg 122280
ttcttggtcc atttcccccc agatgagtcc ttaggtaggc taaactacaa aatcgctaaa 122340
gaatacattt cataagccct atgcctacct tcccaggaga ggaaaattgg aagagaagcc 122400
aggcctatta gctccatgga ttcctggagc cctctgtctt ttcccagtgc ctgcgtggtg 122460
caaagctcca agggaaccct ttttccctca cccactgggt cagggattct gagtccagag 122520
atgaagagac ctgtgtgagc tgagggaatg tctccacggt ctgtcattca gagatgttca 122580
tgccgattag cagcatggtg atgggcaatg tccacttacc atcaggatct gcagaatgtg 122640
aggatctagg aacggcagcc atagctgcta tctcatagag ctctatcagg cggagagaac 122700
ctgagctgct actgacagat ctccagcatc tcctccttct gagtcccctc caggtaaaac 122760
agaggccaga ctggaagtct cagaaggcac accctgccta cacaagcata ttactatcac 122820
aagcttgggt tgctgtccta gggccccagt cccagaccat taacttgctc tatggatcca 122880
agactctcta ggcatgtgga tagagacaat ttggagtctt aagttcccta ggcagaagga 122940
gatttttcag aaaaggaata atgaagatct tcaaatccag gaagatttga tgccttcaaa 123000
ggtgttcagc ccacacctac acatcattca cgaactagtc actgagtctt caagtccaca 123060
cttggttagt tggttcatct tgctttgtat tgaaggttgg cctcaagttc actatgttag 123120
ccccagctgg ccccaaactc ccaataatcc tcctgactca gcctcccaag ttgcagagat 123180
tacaagcata ggccaccaca cccaggtgca agctcactct tgcttgccca gttcttacct 123240
acagagaaag cttatgctgg cctccgggtg aattcaacaa atattaaatg tcttgtatgg 123300
gcccgacttt gggctggttg ctggagattg tggcctctat ctttaataaa ctctaagtcc 123360
acaggcgaag gaaaacatga agttcgctgt actacagaga cctctagtag agttgggaat 123420
ataacgcatc atggagtgag cccctgatgc cactgtgtca gcagcaaggg acagggagaa 123480
tgtccaggaa ggaaatgaca tttgagcagg gtgctgaagg ctaagagccg gaggattgga 123540
agtaaagacc atgctcactc agggtgtgtg tagtccaggg aggggcaggt aaagaagtcc 123600
cacaggctgt gaaggctctc aagcaaaggc tgaggatgct ggaccttaca taagggcttc 123660
tcccagaatc tgcttccagc aggtcattcc tgacctcggc cttctctctg gtgtctgcac 123720
tcctgcctct cccctccccg ttctcacaaa agccacagac tccctgcctc tgggcctggc 123780
aaagctactc cataaatatc tgattggaca gttccctgtg ctaatgtggc agttatgtga 123840
cccagcacac acaggaccat cagttagcct agctaatgag atctcttcta aggagctgga 123900
gagcaaagat ctgtatgcac cctggtcacc tcccacctgc agttcccacc cagctggtta 123960
tgaacccaag gaccccacaa tccccaaaca ggataaacgt cgtcttcgga gtcccgtgaa 124020
```

gctcaggaaa gactcaacca ggaagcagat tctgtgcagg gaacactgca aacgtctaaa 124080
gtagaactgg gtgacagggc cactctctag ctgtgacaag ctgggcattc acctagtaac 124140
ccaggtggct gcttgagtgg tgactttgcc acactttcac aaggaggctt taaactggga 124200
ctcagaagct aagttctggt taggcatggc ggctgctgcc tgtaatctta gcacactggt 124260
ggtggaggcg agagggtcag ggttcaaga ccgttcttgg ctacatagca agttcagagc 124320
cacataaaga aaggcacctg tggccaagct tgacaatccg agttccatgc ctgggaccca 124380
cgtggcagaa ggatagaggt gactcccaca agttgtcctc tgaccacaca cacacacaca 124440
cacacacaca cacacacaca ccataaaagt ttgttttaaa agcactgatt cacttagggg 124500
cagcaattat accccagcag ataaagcaca ttccttaaag ggctgactat cagagttcga 124560
tccctggagt ccacataatg gtagaaggag aaaaccaact caacagagct gtcccctggc 124620
ctccacacat aggctgtggc atgcacgttc cacatcatac acacatgcac aagaatggta 124680
aaatttacat tttaaaacta ctgactaacc tctgagcctg tgggaggtta cccagaccat 124740
gctccgatgg aggctccctg agcttgctga catccttcct ggctcacaaa agtgttagct 124800
cagctggaaa tttctacttg aaaacgagtt agtctgtttt tataagccct gggatgggta 124860
attcaaacaa atggtgaagc cacagggaga gacaattgaa aatggctagt gttgctccag 124920
aatggaatat acatttgtcc caagaggggt gacagagtgg ggagtgttca actgtggggg 124980
agtagcattt aacagataca gctctgggat cggtgcgggg actcatggct gcagtccctc 125040
tcctactcca tatctaggat tagtgaatca acactgtcat tccatgcacc agggtgggac 125100
actttgatca aataaagaac aacagactgg gaaggaaggc cgaatgaagt gcaacccagt 125160
gagtcatttt ccagactcaa ggccctattt tgtgattgca ggttctgaaa aggagtcagg 125220
taccggcaaa ccaacatcac tggcagaatg cagctcaacc ctctgtctca ggaaacttgg 125280
tgggtgtgca gggctgggcg gactggaagt aaggacagga aagacatatg aggggtcaga 125340
gcttggatat gctgtacacc ctcacagaca gacagacaga cagacagaca ggataaacag 125400
acacatacac acaggacagt cacacacaca cacacacaca cacacaccta tggttctgtg 125460
cataaatgta tagtgaacta tgactcactg tatagtcagt cacacgcgca caaagtggaa 125520
actcacagtt agacctgaga caagtaacag agataaggct cagcaatctc aaggcctgat 125580
tatttccaca gtcacccatt cccctagatg ctggtcataa caggctgttg ctggggacag 125640
agctgcctcc tgttcctctc ctgaagccag tataacatat agaaaagttc catggcagcc 125700
taagacaata acctcagagc taatttctgt atcactcagg agctggggaa cagaggacaa 125760
agtgagcagg cacagtgggt cacagccctc ccctcagcta tctctgtatg ctctgtgact 125820
gtgggtggct gtcctctggc catctcccaa cctgatatcc cacctcgtca aaccttcttt 125880
aaccccaaaa ttcctccctg cctctaatgc tggtagagga caccggcttt tgttctgtcc 125940
ccacagacct caacttacta ggtccctgct acagttgcag ttgcccacat actagcagct 126000
aacagcctaa gacatctgtt tctgtctgag gattcactca ctctcatcct gtctgcccac 126060
tctacttgac acataccaat caaaaatgcc cctttttggg ctggagagat ggttcagtgg 126120
ttaagagcac tgactgctct tccagagctc ctgagttcaa ttcccagcaa ccacatggta 126180
gctcacaacc atctgtaatg ggacctgatg ccctcttctg gtgtgtctct gaagatgcta 126240
cagtgtattc atataaataa aaataaatat ttttttaatg cccatttctt taacagctaa 126300
aggctatctt tcctttcttt actggtctct cttgagcctc aaacacctag ccttccactt 126360

-continued gggtctgata tctgaccaca aaaaatcagc tcacagaccc atccttcctt cctgtcacta 126420
tggaaccaga gtggcctctt caaggttctg ggatgtatac ttgtaacttt gatgaaagca 126480
aggaacaaaa gccccaatgt tctcctttct ctccccctta ggagacatgg acaacaccgt 126540
gcctactcca atgtcactga aaggttgtct tgcttgactc tccaggagcc cagtgtcagc 126600
catctctacc gtaagctacc cattcgccac agccacaaca ttcaaggcca aaagaaagaa 126660
ccaaaccaat cctggaatgt ctaactgttt ttgcagcttg ggatgtagct cagtttttag 126720
agcaagttcc tagcatgcag gacgtgctgg gttacatttg ctgaagaaac caggcctgta 126780
ctgtaatccc atcacttggg aggtagaggc aggaggatca gaaactcaag gctgcctttg 126840
gctatgtaca gagttcttgg ctaaccttag ctacataata aggctctctc aaaagaaaag 126900
gaaaaaaagg agggagggag ggagggagga acggatgcaa cgaaggaagg aatgaacgaa 126960
ctgtatgacc gaatgagggg acaaaaagac gggcaaccat cagggaaaag ggagtcaggt 127020
atgagccgct ttatcgctac cgtagccact gaccaactac ggactggtaa gcggggcggg 127080
ctaaccgtaa aaccatacct taatgccgac ctataagctg ccccccctaat ggagtggtca 127140
ccgccacgaa agatctaggg actggaagag gcttcagagg ggggagcccc gtaaaaaggc 127200
cggggtgacc gcggagttcc ataaggtccc ccccccctgg caaacttaag ataaatcgac 127260
ccccctagtc ctagggggcg gcaacccccc agggcttttc ctaatccccc cccgttcccg 127320
ctgaaagaac cttggctggc ccccgttccc ccctgagcgc taataggaag aaaggccgcc 127380
tctaccctga ggcacccagg gggctttttt aatgaacgta aaagctgagt tggcgcgtac 127440
aaaggaatcc ccaggcggga ccaggtgctc acaagcctgg atgcccccta aggcccggcc 127500
taaggacccc caagannnnn nnnnnnnnnn nnnnnnnnnn nnnnnnnnnn nnnnnnnnnn 127560
nnnnnnnnnn nnnnnnnnnn nnnnnnnnnn nnnnnnnnnn nnnnnnnnnn nnnnnatggc 127620
cactgtgctc taaagccgtg tcgactagac aggcctcaaa gtcacagaga tccacctgct 127680
tctgccttgc aagtactggg attaaaggtg tgcaccacta cacccaaaat tttgaagttt 127740
atgcagccta tggcactgct agcctcaatt gagaaaaggc atgccatact gccctctagt 127800
gaccagccta ggaaatgaca gccagctgca aacaaggcag acagtggtct ctggcattct 127860
aaggcagaga aacagtatac atcttaatca aggtcaacag gcacccagaa tagaatcttt 127920
attctcttgc tacacttcaa tctctgcttg aaaacatagc aatcccctta gaaattgtga 127980
gaccttaaaa ctgcagtgag gacgtaaacc tgcctgtgga gaagaccctg tacagaagag 128040
ctatgacgac aggctaggag tagaatgtgc tcacctctgc aggtatccaa ggggatggcc 128100
tgacggcctg aagattcctc ctggagtccc ttggaggtgt tttaacacct tttaaaacaa 128160
tttttaaaat tatacctcta tttccttgtt gtgtgtgggc aggtagggtg cacgccatgt 128220
ggcctatatg gaggtccgaa gacaacttgc aggagtcagc tccttccctc caccatgtgg 128280
aactggggga tcgaactctg gtcatttgac ttggcagcaa gcgccttttt cactgaacca 128340
tcttcctggt cttagaagtc ttgtcttttt taggggcaga gggtaattct acgcttaaag 128400
atatttgtag agtcagcaca atgtgttctt tcctctaagc ttaacatcct agtaacgaaa 128460
ggacatcaga aaatttagac agagcactgg gaatttgtat aaactaaaaa ctagatttac 128520
cattaggttt tccattaata atttgttttg gccgattttc gggttttttt tttttttaaa 128580
gacagggttt cgtgtagccc taggctgacc gccaagtcca agaaaacctt gaactcctga 128640
acctcctgcc tatacctccc aggtgatgag cgtatagcct catctggttt ctatggtgct 128700
ggagattgaa catagggtac tctagcaact gagctacatc cctagcccct tggcttctca 128760

-continued gaggacaaga tgagcaagag tggtttagag aacaaaccag cagctctggc cccagttcac 128820
aatctaactt gtagaatttt ttcatttcat aaatactgat catatacata atcatgttct 128880
ttctctctcc tccccctcga ccctcctaaa taacacggta ccaggcttgc tggctgtggg 128940
atttacaggt ataatcttct tacagaagta acagaagccc aaggacaaca cagctgctgt 129000
gagaagcctg tgctaacttc ccatgggggc cagggtgggg aggggccctc atttattccc 129060
taagggatag agcactgact gacttggatt ttgagatggt agcctaaatg agccttggaa 129120
cccccatctt cctgcctgtc tcccaaattc tggaattaca aatatgtcac catggtctgg 129180
cttctgtctt cactgttctt ttttaaatta cctttaattt tgtgtttgtg agcatgtaca 129240
cgtgtgagtg tgtgaaggct ccttccacca tgtgaatccc aggaaacaaa ctcaggttgt 129300
caggccattt cactgcccct gacttaaaaa aaaaattcca ccctaggaat tcatatcttt 129360
aacaacttcc ttagcaataa atagtacctg cgggctggag agatggctca gcagctaaga 129420
gcactgactg ctcttccaga ggtgctgaac tcttcttgag ttcaaatccc agcaaccaca 129480
cggtggctca caaccatctg taatgggatc tgatgccctc ttctggtgtg tctgaaagat 129540
gctatagtgt actcatatgc ataaaataaa taggtaaatc cttaaaaaaa atagtacctg 129600
tattactttc ttgattcctg ctgtccaaac tacatagaga tattcatcat gtaactaatt 129660
catacaggtt cctctgaagg gcatagccag gaaactactc tttttgtttt tttttttggt 129720
tttttttttt ttttatttga gacaaggtct ctctcggtcc aggctggccc atgatcctgg 129780
tctttctcca tctacctcac aaatactagg attagagtca tggatctttg taacaagtta 129840
atgcctcttc catgaaaatt acctacctca gaggttgtta gcagctagta acaataactc 129900
acaggaagat atctgcaaat catgcaatct ggctaaggga ccagttacca aaatacaaaa 129960
tctactttgt ttctttagtt tggggtaatg aaactgagac ttgcacatgg cagaagccta 130020
ggcaaacact ctaccactga gccatactcc caaccattcc agaaacaatt ctttacatga 130080
aagtgtgtac aagccgagta tggtggcaca cacctttaat cccagcactc agtaggcaga 130140
cacaggtgta cttctgttag cttgaggcca gttttctaca tagtaagttt ctgaacaacc 130200
agagctatac agtgagaccc tatctacaaa aataagaaaa aaatgtgcat atacatatat 130260
ttatacacat atgatgtaca tgtgtgtata catatgctgg gtccttatag atacatgaaa 130320
aatgggcgaa gtcccttaat agacatgaag atctataaag atgctcaaca tcaccatcca 130380
ttatggaaac cagcattgca gacttaccac ctcctatcca ccaggatagc tgtagtaaga 130440
acagaagtac agacaagatt gcagggaagc caaaactctc ataaactctt gggaagagac 130500
ctggcgctta ctcaacaagt cagagcatag atttccatag gactcaatgg ccccactccc 130560
gagtccgtgt atggatacac actgatagct gcagagtaga aaatgtttct ctttgcattt 130620
agctaaccgg gagtgaggca atgggctcac tggctgtcta ggtttgattg tctccatttt 130680
tctactttca cacttgtctt ttccttcctg ctttgtagag ttctgtcagg tagtcaatcc 130740
ttcgtgtctg caatccctcg ctgttacaca ttgccggtgt cttctcgatg tctgtagtca 130800
tccttaactc cgacatgacc tgctctgctg cacagagcgc ctggcttatg cagcagcccg 130860
agcaatgagg gtgaggtttg ccgtgagctg tcctcacact gtacagccgt cattgctccc 130920
accgggcttt actacctgtt tgagctcaga agcccagagc ccatctgagc cacactctag 130980
cttcgctgta cagttcacct gggtccttaa ttgcttcagg actgctgatg tggtatgaga 131040
caggggcctt cttcattttt gtccatataa cctaattttc tgagcctcag cggccacctt 131100

-continued tcccactaac atgtaacact accttatcac acatacagtc caatattcct gaacttggtt 131160
taacaccaaa ttctgatttt cacagaacac ttttacccac acaggtaaat taatgaaaac 131220
tgcaatcact caatactccc gagacaccca gaaatttcat acagctggaa ttcttcccaa 131280
gcagaatacc cagttaggaa atgattataa aaaaataaat atgtgtttat ttttaagaaa 131340
aaggaaaaca ctggccaaga acaaaccctg ggataaagaa gtcaccgtgt cctgcccaag 131400
ccagccacag acagtgaggg cacagccagg ttaggtgcct gtccaaaggt caggctgaca 131460
gcaacttgct ggtctgcgtc tcttagcagg actcctttag agctggatgt gagctggtgc 131520
taacagcacc acagcatcac atggcctcag gggtcacatg gcctgggggg ggggtggtgt 131580
cacatatcct ccacactcca cttgtaggca agctcctcca cagccttctt gctggcgagc 131640
ctggcaaagc gcttctgttc aaagccattg gatctgcaat caaaagagaa attctagtca 131700
gccaaaactc tcaacgttta ctttaaaagg aaggaagcca ggtggtggtg gcacatatct 131760
ttgactccag caatcaagag gcagaggcag gcagaggcca gtctggacta tagagagttc 131820
cagaactgcc agagctacac agagaaaccc tgtctcaaac aaacaaacaa aaaggaaagc 131880
tatttatagg aaaatattta aaccatatgc taaaaagtca aagcaacaaa acacacaaat 131940
taaccctctt ctcagtcccg gttcagactt acggacaact atcagacgct tagacaacta 132000
tttcaaacct ttattattct ctacaaagat tcaacacagc tcggcctggc ctgcatgggc 132060
tgcggagtta agttcatggt taagctggac aacttcacga agttttgcct caaaataagt 132120
agtaaactga agggacctaa ctcagtggca atggcagagc ccctaccagg ctatgagctc 132180
aacacacggt gcaaaaccaa agcacaactc acttgtggcc gatacccaca ggctcaattt 132240
aaccgttggt tacataagta ctgagttctc actggacatc cgggtgctac ggaagaatca 132300
gggcaggaaa atgaactgca caatacctgt gctgatgaac tcagacaagc gacacagaca 132360
tttaactaaa aagcaaaagc cagggctgaa aacgtggctc gggtgttaaa agcatttgtt 132420
gctcttgcaa acccaaaatg tgaacccctg gtaccattgg ataggctcac aatcaccttt 132480
aactctagcg ccaggggacc caagaccctc ttctggatta tagacactac tgacacacag 132540
acacacaact gcgactgaag agatggctca gcagttaaga acactggggt tcctctggaa 132600
agcccgtatg tcagctcact accatctgta actctagtcc cagggaatcc aaagctactg 132660
ctgccctgag ggtggtgcac agacacaaag ctaaaacacc cataaaaaca aacaaaatgg 132720
aagagttaaa ttaaaaaaaa aaaaaaaaaa accaaataaa aggaaaaact gttagaaaca 132780
tgtgtgggat atcaaagaaa cagaagtggg ggtggggaaa tatcagatga aggactaagc 132840
aagctaaaac acccataaag acaaacaaaa tggaagaatt aaattaaaaa aataaataaa 132900
taaataaaag gaaaaactgt tagaaacatg tgtgggatat caaagaaaca gaagtggggg 132960
tggggaaata tcagatgaag gactaagcaa gggcctttgt gggagtagcc ccaagctatg 133020
cctgaaagca gcagcaaacc cgcaggcaca gaaaaaagag ccctggtctt cgaaaggggt 133080
gacgggtgtg tgtgtggggt cggggggtca ctggcatggg cagagcctag agtgtgacaa 133140
atggtgtagc cacaagtcaa cactggaaag acaggtagag gccaaatccc tgtgagctta 133200
gacaaactgt aaaaacaaac aaatacaaat ttcatcccag aaagatggac ttaaaactgc 133260
atttcagaca tctctagaga tgtgcagtaa gaaagctagc acagcggcct gacaacagat 133320
gaaggcagtg atgccaggta gggatggcaa caggggccgt cgagaggaaa gagcagtagg 133380
actgggtgac tgactagtca cagcctgggt cagtaacctg agagagcaga tgagtgaaga 133440
tgccacctgc aggcgggtat gctttgcatg tgtgactgcg cctgaggcac ctcaagtgca 133500

-continued

```
caagggcaga ggatcggact atgacatatc tggacccaca cacagacagt ggctgaaggc 133560
ctggctcaga aaagaggcaa ccggaaggag caggagtgag agcagggagg ggttccagaa 133620
ggagaactga agaccactga aggttaacag agaaaggaca ctcacagggg ccaagacagg 133680
accgagaaca ggaacaggtc attatggaag ccaattctgg atgaggttca agtacatggt 133740
gagtggacca caaacttcaa attccttccc cttaccccaa cccttttctc tctccaaaaa 133800
gccacccctt cctttttttac tatttattat tttatattta ttttcctttg agacaaaaca 133860
ctgcgcgcgc gcgcgcatgt gtgtgtgtgt gtgtgtgtgt gtgtgtgtgc gcgtatttag 133920
ggctccaaag acagccaaag aaatgaagag cgcagcaggc acagtgcaac aggcacggtg 133980
cagcaggcac ggctatgaca agatccacct gcggctatgg agcaagtgcg agttcaggga 134040
aattctcctg ccaaagattc tgcagggtga ccagcaagca cagcagccag ccagcctgca 134100
actgcagtcc ctccttgacc tcaggaagaa ctagagtcag attccagaag cagcctgaag 134160
gacagaagac aacgccttag gctggcgcaa gtgcaaagtg gattctgaca ctcaaatagc 134220
aattataaaa cctgagcaaa ataagtagtg gtttaaggca tgtgtgagcg ctaaagcaga 134280
aagaaacatc ccaataggag ggggttagcc agagggtacg ttctcggtcc acacagctca 134340
agtaggccac aggcagaacc acaggctgac tggcttgagg tattagtggc agtgggaaga 134400
gtggctacaa aattaaggag aagtcctggg agagagacac tggttatgta cagcaaaggt 134460
cacaccaagc tttggtgact cactatgtat atgcagagga cctgtagcag ccctgtcaga 134520
gtgcagcagc cagaggcaag acctgagccg agatgttagc tgctgcccac tgcaagggag 134580
acgggttcag tgtagagtaa aactccagac aaaaatcagc agagaaacgc agcaggagcc 134640
aaagctccac tatgtattcc tcataaataa aagacctaac aaataagcca actggaaacg 134700
gaaaataaca tgtactcaaa aaaagttagc cagttacagt gtcagtcaca cataatctca 134760
acagtcagga agctatggta ggaaggtctg agtttgagat cagtttgggc tacatagcca 134820
gctctaaatc agactggcct acagagtgag accctgtccg tcccccaaag agaggggagg 134880
caggggacag gttattaaca aaaagcaagt ctgtggtgag cagaatgttg taatcagcag 134940
acaaaacttc aaaacaccat ttataaatat tttccaaaat gagaaaacag tctctaaatg 135000
ggtgagcaga tgggaaatct cagtgcagac atgcaagcca tcagatggga attctggacc 135060
caacgcagct gagacataac agcaactgag agaaaacaac taaggtatca ggacagttct 135120
gtaaactctc aagccacctt agcctaacag agttttataa agcaccatca tcccaagtaa 135180
ttgctgaatg tatattaagg gcatcagtca ctagggagaa tcaaaagaat gggaaaatat 135240
tctacatgta tttagagaac tttctcaatc taccactcaa gtaattttct gatggtgtat 135300
aataaaaacg tcagcatttg gaaggtgtgt aaaactcagc caacctgtaa gttacaaatg 135360
accaacatat gattcaagtg tgcactggta aaagatgtaa agaataataa agaccatgac 135420
tggaaagatg gctcaggagc tgctcttcca gaggacctgg gttcaattcc tagcacctat 135480
ctgtaattcc cgtcttgagg aatctgacaa ccccttctgg ctgccaagat tacttcctga 135540
acagacttcc atgtaggcaa aacacccaga cataaaaaat aaagaggaag aaaatgatca 135600
tgaattgtgc aggcatggcg gcacatgtct ttaatcccag aacttggtag gtagatctga 135660
gtccaaggcc agcctgtcta tatagggagt tccaggtgag ccaggactac tagagagacc 135720
tgtctcaaag gaaaaaaacc cacaaagatt ataaattgta atgcaaaagg atcaatagtt 135780
ctctccatgg ctacagacca cacaacagcc ttgaaggaga cagctcttct gtgtgccaca 135840
```

-continued

```
ccttcctctt ctgctggtga catggcaggc tgggttctcc tcctgcattt cagctcaaca 135900
cttcacaata gacaaattca gaacccagct gtctactatt agtctagtca ttaatgttat 135960
ttgcaattaa aattattttt gttttttttaa taattagttt tcgttaaaaa tagtggtaat 136020
tatattagta tataatggtt tattctatat agtgaataaa tgctctttta atttttaata 136080
tagtaactat aaatgtataa taaacataaa caaaagcttc ttggggtctc caaaagcttc 136140
tttaaaaatt ctatttgttt acagaggcac acacacacac gcacacgcac acgcacacgc 136200
acacgcacgc acgcacacac gcacgcacac acacgcacgc acacacacgc acacacacac 136260
gcacgcacgc acgcacgcac acacgcacac acacacacac acacgcacac acacgcacac 136320
acacacacac acacacacac acgcacgcac gcacacattc aaatgagtgt gtggaggtca 136380
gagaacaatt tgcaagaggc agttctctcc tgctatatgg gtatcaagac ttgaactcac 136440
atcattagtc ttagcagcaa gcgcctttgc ccacagagca atctcagtaa cacagagtat 136500
caaggggtct tgagattgaa aactcggaga accctcacac tacacgctca tgttccatgt 136560
ggacaaaggg agatgggatc tgcgacaact ggcagaagcc atcccatcag tcaggaagcc 136620
cgagtacact ctgagacgct ggccagtaac cagatgaggg ggcaagactg gaacattacc 136680
cggggctccc tcccagaatt acagagaatt aaatgttcaa acacaacatg ttaaagacat 136740
aacacagaga tggctcagca ggtaagagca ctgactgctc taccaaaagt cctgagttca 136800
aatcccagaa accacatggt ggctcacaac cacccttaat gagatctgat gccctcttct 136860
ggcgcttact tatttataat aataaataca tcttttttaa aaaaaaccac aaaatcgggg 136920
cagttgtggc gcatgccttt aatcccaagt actggcagag gcagaggcag gcagatttct 136980
gagtttgagg ccagcctggt ctacagaatg agttccagga cagccagggc tatacagaga 137040
aaccctgtct caaaaaaaca aacaaacaac ccccctcccc caaaacatac aaaaacacct 137100
acaacacaga aaaggctcaa gaccacagcc cttgtccacc ctctaaccct tagaatactg 137160
agcatgagca atgtggcaaa caaagtgggg cttgtccgtc actcatcctg agcttttcca 137220
agtttatggg aaggagttgg gagaaaccca agccttgaaa taccgagctc aggagctgaa 137280
gcacgagttg cttgctactc cctgtgactg cagagtgaga gcaagggtgg agggacctta 137340
gactctggac aaagcctact gtggccccca ggctctatcc ccatgaccta ggaggtagtg 137400
cacgagttgg agtcagccta gctaggaagt gagactctgt ctcaaaaagt aggaaaaaat 137460
aaatataaaa aagaaaaaga aaaaaaaaaa ggaaacgaaa accagaaagg gtcaaggtca 137520
ggcagaagag aaaacaaaaa tataggaaat agactcacct gtccactcca tcccagcgat 137580
acccaggcca aatgttgaat ctattgggag gaggagcagg accactgtag cggggcttca 137640
ctaaagacag gaatgagaaa aaagaaatta gctactgaca caatttaatt cagagctaga 137700
tggctatggg agaaaattct tcatggaagt tcctattatt ttgattcaaa cttccaaaca 137760
caagggcatt acagtagtgt ggggcagccc tctgacaact ctcagtcacc tccagctcca 137820
gcaaccccaa gtctcacctt tcttattctt gttctcctta gctttattct tcttaataaa 137880
gttggccatc gggtcccctt ctctttcttg ttctctcagc atccgatcca gatcttcatc 137940
atctatgtag cgggccagag gcttctgcat ctccttcatt gcatcttcta cattctgttg 138000
ctgctgccgg ctctgggcaa gcctgggcaa aaaagaagca tcctgcttga gaattctctc 138060
ctatactgag agcccacagc gctgccctgg aggactccct ctttgtagca gccccagaat 138120
ccggacgggt agcttgaacc aaccatctca ggagactgtg cacctgaggc tcgccccgta 138180
tcagctccca gaaatgcaag gcagaggctg gctcaggtct tgcagtctag ctttgtgctc 138240
```

-continued

```
aggggcgccc ttaccctttc ccccactggg catatagctc atctcgctct gagtctttct 138300
ctgcttttct cctctgttcc aagcgctcta gcttcaaatt cctcttccga ccagacttgt 138360
ctcgaaatac agtttcagtg aattcaaact gtgctatgaa ggaaaaaaca cattttaaag 138420
atacacacca ggcatcacag tcagaaatca cattctagca ctagaaacca actgcttggg 138480
atcttttgct gaaagaactc tgcagacaga ccatcctacc agcactcttt cacatactgg 138540
gaaggaaagg agtgcttgta ctactgaggt aaggtacata aaagcaagga agtttccgat 138600
agcaaataca agccacatta acaacagaaa agagagctat aggaccttca gtggcccctg 138660
caagctcaca attgtacctc cgaggtctgt ggtgtcctgg tcttgtttct tgagttcctg 138720
gtgctcccgc tgaacatcag tgaccaaccc agtttttgct ccggaataca tgtgtgcagt 138780
ctgtgcaaga gaaaaggaat acatgtgtac agcctatgca aggggaatac acgtgtgcag 138840
tctgtgcaag agaagaggca acagcaacac catttttcca ggaggcagat agctgctcca 138900
gtgcctgact gttagctata accaaaccaa aacctctagt tttatattct cagtattgac 138960
cacaaacagg gctcacaaca tagaatggga aatatctaat ctcatagaac actttatggt 139020
atcaaatttt aaagtaaaca gaaacacaaa catggggcac atagaaggga gtaagaattt 139080
gcatgacttc tctttttttt tttttttttt aaaaaaaaaa gatagagtcc cctacagcac 139140
aggctggctt tgaactcact tatgcacatt ttaaaaagca aaaagctgac atttagagga 139200
atataatttc tcgtccaatc ccacagatac taagtagcag aagtagaatt tacagctatt 139260
attggtttca cagggttctg cacttctaac tgcactttat aatctgtaag cctcaattta 139320
ctgttaggaa aacaggtggt gccagcctgt atatctatca acaggtggga agaggcagat 139380
gggtcagaag ttcaaggcca gccttggagt acactcaaaa caacaaagac aagacactga 139440
gatgagactg gtggcattac aaggctctga gaggcagctg ggcactcctg atccaaaacc 139500
agaaatgcac aatagtccaa aatctacaac attctgagca ccatttgggt gcagaagcac 139560
agccttcaaa ctccaacact ctggttccca agcttcactg aggcccagct aagacgagtt 139620
ccacccatgt caccgtcaga gaaagttcca gaaatgcttc taactccaac ttcctgtacc 139680
actttctcat tctctgctgg aggagtcacc ctgataaaga aagacacaac tcctggaaac 139740
ctaccttctt gccaggacgg ggactccttc gaggtggaga gaggtcagaa tcagaggatt 139800
tggtcctctg tcttctccgg ggtggagaga ggtcggagtc agagctctgc cgccttggtc 139860
tgttccgtgg tggtgacaga tctgaatcag aatcctggtg ccccgaattt ttttttttcc 139920
gtggaggaga aagatctgaa tcagaggctt tttggtagac acctaagtag aaaagaacaa 139980
aagcgtctat gaaatctcct gtgtctaaga gaatctaggg attaaagaat gaattaagga 140040
tggggatggt tcagcagtaa aatgcctgcc tagtacgtca gacctgggtt tggtcctcag 140100
cacaggagag aaggggagga ccattaatct ccttaggaga ttgcttaaaa gaacttacca 140160
tgctgggcac ggtgtctttt tagccatcct atgaaataac atgactaacc aaaacacagg 140220
cacaagtgac acagagaaga acaaaggcgg gggcttggtt tcctggctac cagtgtctgg 140280
tgactttgaa aagcgtatga gatctcagac acagtctctc actgccaccc tcttcagaac 140340
tggcatcaga aatgagttgg cccgtgcggt gtggcagagt caggaagacc tggactatat 140400
gctgatctcc ccagactcaa gaaaacaaag taatttcatt ttaagattaa aactatagct 140460
aaaacaaatg atgaagtaaa acaaaaccct ttctgcaggg gcctgttcta gatgacagtg 140520
tcaccagtca cctcctgaaa agccactata tagcaggtac taggtagtag caacagccac 140580
```

-continued acattctgac ctagtaaata actccatagt tttctaggaa cctatcagtt aaatccccag 140640
gagatctaag ataagaaata atacaggggg ctggtgagat ggctcagtgg gtaagagcac 140700
ccgactgctc ttccgaaggt ccggagttca aatcccagca accacatggt ggctcacaac 140760
catctgtaac aagtgactcc ctcttctgga atgtctgaag acagctacag tgtacttaca 140820
tataataaat aaatctttta aaaaaaaaaa aaaagaaata atacagggct agagagacag 140880
ctcagcagtt aagagcactg actgctcttc cagagctcct gagttcaatt cccagcaacc 140940
acatggtggc tcacaatcat ctgtaatggg atctgatgcc ctcttctggt gtgtctgaag 141000
agggcaatag tgcactaata tatttaaata aataaataac tcttaaaaaa aaaagaaaaa 141060
gaaaaaagca gcaatcccag ttgtgctatc agtgtatgta catgatgatt gtcaaatatc 141120
ctcagggcaa actcagggaa gactggtaag tggagcgagc aggcaagaat ccacaggcaa 141180
caagtatgct ctgtacactc aggcccaact acgcccaaca tgcgtgccca aaccacctaa 141240
ggacaccggc tacaacacta gcaatgacgt tgtctaaatg atacaatttt gtgacactgc 141300
tgtgtctata cattcctgta cgtcagtgta tttattatta ctgtatgtgt gcatgtgtgt 141360
acatgatcgc agacatacac atgcggaggt cagaggacaa ctttcagggg tcggttttct 141420
ccttttactg cagtggtgaa gacaatgctt taccctctga gcctctgagc ccacccccatc 141480 tttgcctttt tatggggagg gtgagtgagc aaaaggacat gaaactttcc ccccaccctt 141540
ttatttttca actcccctaa gtctagtctc tcttttttca aaactttcca aaagaaactc 141600
attcttacac tccccaggag gaaggtcctc ttatgcatag ccttatgctc acctttagaa 141660
tcaagctgtt tcttagcttc aaaatgagcc tttgcttgcc gtttccgtgg aggagagagg 141720
tcagagtcgt gctcgtactt gctgttggtg gagagtgatg ggtgagaggg tcctagccca 141780
ctctgggatg cagccttgct aggggctctt tctgcagctt tactactttt ggctttgtgc 141840
agttccaaat caggggactc atgatgggcc cttctgagat gctgtgtacc tgaagagtca 141900
agagtccttc tatgctgggc tgcagtaggg gagtggttat gggtctgtct cggagaagag 141960
gtacctaagg aaccatgatg gcctctccta ggagatacgg ctgaagaatt acgatgagac 142020
ttcctggggg gagaagcatc taagtcatgg cggactctcc tgggaggaga tggatccggg 142080
gtgtcatggc ggactctcct gggaggagat agatccgggg tgtcatgacg aactctcctt 142140
gggggagata gatccggggt gtcatgacga actctcctgg gaggagatgg gtctggggtg 142200
tcatgacggg ccttcctggg aggagatggg tctggggtgt catgacgggc ctttctggga 142260
ggagatgtgt ctggggtgtc atgacgggcc ttcctgggag gagatgggtc tggggtgtca 142320
tgacgggcct ttctgggagg agatgtgtct ggggtgtcat gacggaccct cctaggagga 142380
gatgaatctt ggtcatcgtg atgaaaatgt ccatcttcac cgtggcctaa acacaagagc 142440
aaacagtaag agtcccacaa tgtgctctgg cctaatggca cagagggtaa caaaccccac 142500
ttaggagaca attcttttgt cacctatgta taagaaaaga gcaagcacca ggaatattct 142560
atagttaaat agatctcaag aagtaagatt gaatcacagt gacctagact atagactgag 142620
accgtctcaa aggtttaaaa aaaagaaagg aaggaaagga agacacaggg gatggaggag 142680
aagatgggag agccttgttt atggaaagtc aggagaacag agaaatagtc acaaagtgaa 142740
agacaaaact ctggctctga ccacaggagc tgtttcattc tagaaccgtg gaaaggctgg 142800
tctccaggct ctgacaagtc agcctctaat gttccatgcc cttcttctaa agtcctgaca 142860
tctttgtccc atcatgtttt tcatcatcac tgacataaaa caaaccaggc attcccctaa 142920
ggcagggaag cagaaggaac ccatcctgga aatgagatgt gcagttgtgt tgctgctgac 142980

-continued

```
actcacctcc cagaagcttc cacttggcac tggagcggaa ggcctccatc tgctttacct 143040
cttctggacg ctcatccaca aactcagcca cctgcaggag taggggcact acagtgagga 143100
aacccacagg acccagccaa ggatcacttg tctcaagaac ccagagccat agcttacagg 143160
cagagaactg cctgcttctc cttgtgatcg catgactgac ttctactgcc catcatgaga 143220
ctatcatacc aaacagtgct agccgaagat caaaaattca aaaccatttt ctgctgaaaa 143280
tgtatcatgt ccacaccact gcacagtcaa aacattaagt tggagcaggg tgtggtggcg 143340
cacgccttta atcccagcac ttgggaggca gaggcaggtg gatttctgaa ttcaaggcca 143400
gcctggtcta cagagtgagt ttcaggatag ccagggctac acagagaaac cctatctcga 143460
aaaaccaaac caaaccaaac caaaccaaaa aaaaaaaaaa aacattaagt tgggactgtc 143520
tgtctgtata agcaccatga aggaaacagt gccacacagc tctcttgagg gtcacctctc 143580
cccttgctca gtgtcaagtc tgagaagcct ggatcatttc aaagtcctga caaaagtctc 143640
cacgagatac ataccacagg caaatctcca tcctcttcct cctccttttc cggcttagca 143700
gtagagatag ccgcccagcc cacatcatca tcaacaatcc gcattctaga tgagaacaat 143760
aaaaactcaa aacggaagtc atgctgtaac acgggcctac ctacctgttg ttctttacag 143820
atggttgtga gccaccatgt agttgctggg gattgaactc aggacctctg gaagagtagt 143880
ctatactctg agccatctct ccagcccctt acctgttgtt ctttgacatt tagagtgtgt 143940
gtgtgtgtgt gtgacagtga tggtgtatat atgtgatatg gcatgcatat ggaggccaga 144000
ggacaacctg caggagtcag ttctctccct ccgctatgtg ggttcagggg atggaattca 144060
ggttgtcagg cttgtcaagt gcagagccat gtcactgccc cctactggct tttaaactta 144120
aaggtatggc tcaatgtttg tgtgctgtca attcactcca tcactgtcca cctttggtaa 144180
tatcagtttt tacaaaggca ccccccttcct tctgccagac ctactcttct cactgttaat 144240
cacgaatctt attttctttg ggccctgtgt attagtcagg gttctctaga gtcacagaac 144300
ttatggatag tctctagata gtaaaggaat ttattgatga tttacagtcg gcagcccaat 144360
tcccaacaat ggttcagtcg cagctatgaa tggaagtcca aggatctagc agctactcag 144420
tctcacgcag caagcaggcg aaggagcaag agctagagct agactccctt cttccaatgt 144480
ccttatattg tctccagcag aaggtgtagc ccagattaaa ggtgtgttcc accacacctt 144540
taatcccaga tgaaaggtgt agcccagatt aaaggtgttt tccttaaact gggagattca 144600
atcttctgga atccatagcc actatggctc aagatctcca aaccaagatc cagataagga 144660
tctccaagcc tcaagataag ggtcactggt gagccttcca attccggatt gtagttcatt 144720
ccaaatattg tcaagttgac aaccaggaat agccactaca ccctggtttt taataacttc 144780
cttggaccta tctttcttgc tcactgtctc ctactcccag agtagaaata cctctacaca 144840
ctcttagaat gctttcattt gtatttatca gcccatattc tcattaaatt ctaagttcca 144900
acagccaagg gctaaggcat tctcttattt attcccttct tcttgttgtt gttccctata 144960
gctagcttcc agctctctat cctccagccc agcctcccct gtgctgggat tatagacttt 145020
taccaccata tcctgctgac taatacattt tttgttcatc aaggcttctt caacacaact 145080
gtcacaggag gtattcagcc ctccacaccc atggacttca caactgcaaa ctcaaccagg 145140
ggaaaaggaa tggccaatgt attaaacaga tagactttct ttagttacaa tggcctatat 145200
aacgtaacta ctggcatact acctaagctg tagtgggctt ttaagtaatt aatctaagga 145260
tgatttaaag aggatgtgaa tagttgacat gaaaatagtg tatcattttg agcttcagga 145320
```

-continued

```
accagtgccc caattactgt aaggtggtgg caagccaata aataaatgtg tgccacacag 145380
atgaactgtg ctgcaaggag gaggttattt gaaatgccag gaacacatga cacagcttta 145440
atcacaacaa ccatttcaga caagtagtaa ggggctggga cttcaggctc agagagatga 145500
acatctctct cttttttttt tttttttttt tggtttttg agacagggtt tctctgtgta 145560
gccctggctg tcctggaact cactttgtag accaggctgg cctcaaactc agaaatccgc 145620
ctgcctctgc ctcccgagtg ctgggattaa aggcgtgtgc caccacgccc ggctgagatg 145680
aacatctctt gccctggacc actcaggcta taagtagcac agctaggatt ctaattctaa 145740
tcagtattgc tccaaagctt aaactttccc cctgcatgcc attgcccctt cttccaggga 145800
catcagccac actgaattca acaccacctt aactgaatat aggctcatct taactggtaa 145860
caccacaaag attccatcta taaatgaggt catgctcaag ctctaatgaa gagaagtgtg 145920
gaaatgaggg actaattcga cccagttcaa tggaccatac ggtaataata ctgttagacc 145980
atgatactgc cccacagaga gggtgagcca cactttgtat cctatctagt actctcttta 146040
agctgataag catttagtag acctgggggt ggagtgtgag aatggaatta gcccccagag 146100
tttcaacttt ctatccaaaa tagcaccttc agtaagctgc taaacttagg gctgctgctc 146160
taaagcctac aaatacagac atttcctttt gttctgtagg ttgatgttgg atatcctaac 146220
ccaacctttc cagattccag tggccaagtt actaatggac atttcatctg aactctgtct 146280
cagcacatct ctttgcaatc tggaagtata gtgtttaata taaatgtctg ctccattaca 146340
atgttctgaa agctatatgg tcaactattt tagaaagagg ccaggcacag gatgtgaact 146400
gttcccattt tagttgttac tgttagtagt agatgtgagt aataggatat gggtctttga 146460
ttccagatca gttcctggca ctttggaacc ctcagaaaga gatttttgga tctagaaaga 146520
aagaaagaaa gaaagaaaga aagaaagaag agggaagaga aaaagaagaa ggaaagaaag 146580
agaagggaag ggagaaagag agaaataaag tgagaaagaa aaaggtttga atcagctttg 146640
ctattcttgg acacgacttt caatctgtac atggaacgac gtaagctaca aacgcgggga 146700
gaaagtgagt taagttctag ctgcctttaa cacaaggaag gcgctgctca gaggatgagg 146760
tctgagctgc cagtggcagc tacaatcccg ccccggggca gtggagcggg gcctgagctc 146820
gggccggggt cggcagcacc gcgcgggcca ggacgaggaa gagctgcggc cgagggcgcc 146880
accgggcagc gcgacacctc accagtccac tcaccccttg ccgccagcgc ctccaggctt 146940
cggccgtttt ttgcgccgct tgcgaccggc ctcgggacct ccttccaagc cagcatctgt 147000
cccagacaag taacgcttca gatactcagc tttggtgagt ggcggagctg ccgccatggc 147060
agcggcgagg gcggggcaac agctcggcgt gggggacaaa attcttcaac gcgaaacggt 147120
aggggtggag ccagaagcgg aagctttagg acggggactt tttgaactgc tggacttaaa 147180
gacttgagcc ttaagaggct ccaggggaga gtgcgtgcat ctcgggctgg ctgtgctttt 147240
cctgagacga cgaatcggtg caacagcctg cagcccacgc tgtctcagct gagaagccac 147300
aggccgatgt aacatgatcc taccctggca gcatcagcgc cagagtaagg aagaacacct 147360
gtatgaatgg tgggacttac catagctgta ccactagggg cacattcttg agcagcgttt 147420
taataatgga cgctgtacca aacgtttcaa tttcaatcac ttttattgct ataaatacct 147480
tttggtggga agtctgctgg aagaggcttc cgggtaccat ttaggggaag tcaaacttgt 147540
gactataaaa gtttgatagg tttttatcaa acctgtactg accttctcac ctttgatatg 147600
tctttctaaa aaatgatata aactcttccc agtgaaatgg attcgtggtc agtgtggcaa 147660
agaaaccagg aagattctgg agtttcttct ataaagggtt aagtgtttta tgacttctca 147720
```

cttaaccctc acaatttttt tttctttcat ccagcaccga ggattaaacc caaggccttt 147780
tgcacatggt atgcaggagt tctatagaac tacatcccca ctcttttgaa tgttgaagat 147840
ctaaattgcc taagctgccc ctgaatttgt tagccttcct cctcagcctc tcaagtggct 147900
ggacaccatg acctaccctt cagttttatt agcctccttt atagataata agaactttcg 147960
ggtaagtaca ggaacccaca catcttcata ctgcctggct ctaatttttg ctagcagagg 148020
ccaaacaagg atggtgctgg ttatccagtt tgaattcgtt ttgtcttgaa tcagggtttt 148080
tctgtgtagc ccaggctgtc ctggaacttc ctctgtagac caaatcggct tcaaactcat 148140
agaaccacct gcctctgctg ggattaaagg tgtgtgccac cctgcttttc cagactgctt 148200
taagctgcat gagaacagct agactccaca caggtgtacc tggctcagag cagacaggat 148260
ggcctattgg agtgaatcaa atgctgcctc tacagcagcc acctcaagaa agatttgctt 148320
aggaaactaa actggttttt ccttcctcat ttcttttcat gaagacggac tctcactgca 148380
tggcccaagc tgtcctcagt ctcctcggag ctgagtgtga ctcagtgtga cccagcttag 148440
tctagcacat ggtaatcagt aaggacatga acgcagaggc gggtgtcgtt taaaggccat 148500
cactttaatg tggcgtcttc acctgtgcct gctcggcccc tccgacatcc ttccctgctg 148560
agtcagtact tcacatgccc agagccagca gaaacttgta tttcacttcc ccagacttca 148620
aaggtccagc actggaggtc agagagctga caggcaaacg gtgatggcag accgcctggt 148680
gtttctggga ttcttctcac gccgacttta aaacctccaa aagaaggtca aggagcacag 148740
tagggctgca gctgcctcgt ccgtcagctg ctaatcttgg gtgcttacat ttctaactca 148800
agtggtaacc tcttcaccat ggacgagggc ttgagcactc ctcgtcagtt ccccacagta 148860
acagataacc ctgcagtgtg agtggcactg tagctggcca gtgagctggc cactgctacc 148920
gctgtggggc caggcccgcc tcatagccct ctgtcttcat gtcattgagc ccgagctcct 148980
cattttggtc aaaggtgcgt ttgtaccgct cgaccttcat ctctggatcg tcttcaggtg 149040
catacacatt ctgcagggcc aagagcagac agacgacggt cagcgcctgt gcagcccgcc 149100
atcccctccc acggctgact ctcaacctcc gaagaaatgc acaggatttg cagggtctct 149160
agagcccacg gctacattct gcaaaagtgt gtgtgtgtgt gtgtgtgtgt gtgtgtgtat 149220
gctagtatca aacccaagcc cctgtacatg catacaagtg tttaaccccc agttctaagt 149280
acttttatat atgggccttc ctataaaaaa tgtagccaaa gttggtgatt gcttataatc 149340
tcagcactct ggagactgag gcagaaagat tacaaattta aagccagcca ggctacataa 149400
caaagacttg tctcaaaaaa aaaaaaaaag gttttgaggg aggggggacca caatgatctt 149460
aattatgtga aaaactaggc cagttttgcc aggcccatca gtgctcatta atactaaagt 149520
aaggaggagg ccccaggttc aacacaattt tgctgcagtt tgatatggat caattgccag 149580
atgtttgctt gcccgttcag ccaacacctc tcggctttcc tgtcctgacc tctggccagg 149640
ttcctattgc tccttacttc acagtcagat gcagaatgga agctccaatg ctgagggtga 149700
gaataagaac aagacaagca gacccaggaa gaggaggtcc tactttctta tatattcact 149760
ctgtacctag ggccctgagc acgctagcca ggtaaacagt tactcttggc tttttcttca 149820
cattattgta tcttaagaca gtcttgaaaa tcgcacaggc tggtcttaaa ctttccattt 149880
tcatggcctt ctgaggacct aagattgcag ccctgcacta ggtctttgtt acacacactt 149940
gggagtccca ctatcaccac cttccccttt cttccttacc ttccaagtcc tgcccaaggc 150000
cccaattgaa gacttaacaa ggctttcctt gttaagggct atcatgcaaa ttctataaag 150060

-continued

```
ttccgaaaat atgtctccat agaaccacca ggaaggccta acttacctgc agataactgt 150120
ttcctgctgg atcattcatg ataaagtggg ccttcatctt gccctcgatg atctacagga 150180
gagaggagga cttagcaggt aactcttaca aagatcctgg aaggaagagg ctatggctgc 150240
gagacaagag ccaatccagt ttacaaagtg cagttcccaa aagtttaaag aaagggaaat 150300
taggattgca gaaatggcct gggtcctctt acctggccca acttctggct aaactcctgc 150360
agtttctctg actggtcagg attagagctg tcgcccagtg tgaatgggtt cttggttacc 150420
tgtagcacaa cagctggatt actacaacac agactgtatg ggtcattacg ctgaaccaca 150480
aaccaggggt ggggagcagt ggactcccag tgggagaagc ctgctctcca tatcccacaa 150540
cgccttgctc acttagggga ggggaggaag gtggcccgag aacaggacag gagaagatgt 150600
ctatgagact gctttgccaa gaaggaaact ggcagtaggg actggaatcc agtagcgttc 150660
ttacagtatc taatcccaat atggaaaaga aatgcaatgt acaattcaca aagaaaagcc 150720
aggcagttac ttggcctgca gtgccagcac atggaaggct gaggccgaga ggtggcaggt 150780
gtgtgtgtgt gtgtgtgtgt gtgtgtgtgt gtggagtgac ctcaaggcta gcctcaatta 150840
tatcgcaaag ccatctctca aataaataaa ataaacacat ttataagatc taatataatt 150900
ttgcactact gtttaggaaa taccgacaag aaaagtctcc acatattcac tacagatgtc 150960
aaaaagaccc ccttctattt tgtaatgagg taaatgactt aagatcacaa aataactaca 151020
ctggcccact gctagccttg agaatttcca ttaaaaattc ctataactgc tggacagtgg 151080
tggcgcacac ctttaatctc agcacttggg aggcagaggc aggtggattt ctgagttcaa 151140
ggccagcttg gtctacagag tgagttccag gacagtcagg gctacacaga gaaaccctgt 151200
ctcgaaaaac caaaccaaac caaacaaaca aacaaaatcc tataactaat ttctcttcct 151260
tctcttcata attaatactc aaatctcttg aatgagcttt tttttttttt tttttttttg 151320
tttttcaaga cagggtttct ctgtgtagcc ctggctgtcc tggaacttac tttgtagacc 151380
aggctggcct tgaactcaga aatccacctg cctctgcctc cctagtgctg ggattatact 151440
cgtgcgccac cacgcccggc ttaaaccagc tttaaggcaa agaaatcccc agttataagt 151500
gacaaaacag aatttggttt tggtaggagg catttgggat agggtctcag gctgtcctca 151560
aatcctgtct tcttgcccca gcttctcaag tgccatcata cccggacaaa caatgttacc 151620
ccttcccact gccaaactgc taacagaagc gatgcagcac actctgcact caccagttct 151680
cggatgtctt tcagcagtcc ttctagagtg gtgaacttgc ccccaagtac agccattccc 151740
agttcaaact caagctctgg gatttccaca ctacaggtct cagactataa gacaacaggt 151800
caaatttaca attaaatcac aggatggcag catagcttca tccaagagcc cttgtctagt 151860
attaacagag gtcccaggtt caatccatag cactagacag atggacagac atacagagag 151920
acaaactgat ttaaaactag gaacaaagaa agccaaccaa attaataaac cagtgacagt 151980
ttgaagacaa agttagaatg ttagtttact cttaatacct ggctaaaagc cagggcctca 152040
ctcccccatc tgaaccaaca cgaagttaac ataacaacct gaaactgagt cacacctaca 152100
agctattgta ccttgtcatt agggtcagag aagagcccat atagccaata gaaactaaaa 152160
agcagccacg tcattgctca ggaagactgg ggccaccttc tgagtctgta gtcccagtca 152220
tggaaaaagc ttcctcaggg tcactcaagc ccaggggagt tacagggttc cttgtgttct 152280
taagcactaa gatgatcact tcctctagac tgaagcggct atacgacaac agctattttc 152340
caagtaggct accttgagga ggtctctggt catgtctgag ggatctgtga tgtggagggt 152400
gatcctggta cccaaaggtt ctacagctcc tccggacttc acctgtggaa acaacggtca 152460
```

-continued

```
ggagcaggtc cagagaagag cccaggcctc acctgctgcc acaaagactt gggctttatg 152520
taggctccca tcaccagctt cccatgacgg aagctcctaa tccagcaagg gcatcagtga 152580
cagaaataga aaccatcaag agtccacaga acactgctcc gccctggtgg catgccaact 152640
ttaggcaact gccaagaaac cctgaatata ccttaaaaag aaaaaaagaa aagaaaagaa 152700
aaaaccctga gactgtcaga ggatgaaaga ggcttgtaag catttcagtc catccctgca 152760
tttgctgtca taatctagga atttagtcag ggctgggaca tggctcacta acagcgctct 152820
tgccttgtct gcatgaggcc ccaggtttgc tgttcactgt gtccccataa cttaagttta 152880
atcagcttat gctcgataca cttaggaatg aaggcttaca acctccacag cagccaccaa 152940
atccattccc gacagctccc ctgagttctt cactgagtca cactctgtcc aacctccagc 153000
cttctgagaa ccacaacccc ttccacaagg tcagttttcc gtccatcttg caatcttgta 153060
tttccaactt ctctctaggc taattctcag ctccttcagt ggctcctccc cagcactaag 153120
cccccaaaag acccaaatac agctgatgcc catcctcaag tagattcagg aagctggcag 153180
actgctacaa aggcgttgcc cctacgccaa tcttctccca cccacctcat tagtccgatg 153240
cccacaattc tcacagttgg tggccatgat gataacctct ttaaagtggg ggatttctgg 153300
aagatggagt taaagaagtc tatctgcttc aaggaaaaca cccccacccc cacccccaag 153360
gaaaagcaaa gccaagtccc acacaaacag atgcaggacc caagagtaca ataaacgggc 153420
ctgtgctcac aaacacggag acctggccac actcagaagc caggtatgca gtatgtagct 153480
tcattaaagg ttcatcctca ccactgagga taaagcactg gctttccctg aagggaaggc 153540
tcccgtctgt aatataacgt tcatgcccga gtcagctgaa gagcaaccca attgcctgct 153600
gaaagatacg gacaagcttc atgttggtct gagccggagc gttgcactct gggcagttag 153660
tgttgaactg gagcacctag gacataatat aggggcacag actgagcatc cccacccctt 153720
cgagctgaag acatcccgca ggtggtcacc catgtgagct gtgatggtga cacactggac 153780
attcgtcagt ctctacccac aactccacta tggtcttcaa agggagccag caccactcac 153840
ttcgtttcta aggtcttcct cttccgcctt ctcctctggt gcttctgcct gaaagaacag 153900
aggcccaaac cacaagttgg cagatagacc tcagcctaca gtagagccct gccctactta 153960
aagagggaga gaatgccttt gttccctgta aggtaccaaa ggacacctca aaggacagat 154020
ggatagagaa gccaaagcaa atccccagac aagagaaaga cggggctcaa ggctgggttc 154080
ctgtgactga cacctgcttt gtgagcgtga taaaaggccg agacaggatg cattggatga 154140
tggtggcagc aatagcaaag tgacttcagt gacttcagga cccagaacac agggcagccc 154200
cagagcatcc ctctgactta atcagtccac ttacttggag ccccagcatc tcagcttgct 154260
gtggggttcg gtcatagtat gtgatcacca aggcattatc tttctgggga gcatgtgggt 154320
tttctacaaa gctgtttccc gagggatcat caatgacctg acaaataaga gaggagagag 154380
taagataaac catatataac ttccatccag cgccagaaca cactagaaaa atcctgctcc 154440
actttttat ctttaggttg ggcttcagca tagcctagcc tggcctatac cgtgctatga 154500
agtcaaggat gagtccaaac tcttgatctt cttacctctt ccacttgcca agctccatgg 154560
ttaccagcat cagtcagtgc caagggatgc tcgcctcctc cttacactga aagtggctgc 154620
agtagcccag tacttaccag tgtgaaaggg gaagccattt gctttaggtc cttcagtttg 154680
ccaatgaact catcaattct ctctgcgatg gcaccttcca ctgcctgtca ggaacaggat 154740
gaaaactgca gacttggcag tacaccccac accccaaccc tccaacagcc atatccctcc 154800
```

-continued agtcagatcc ttaacatcca cttagactgg gagcacaggg acctgaattt tatagtgaga 154860
cacaagaagc tcatctgaag tttataaacg atgctggggg ttaggaggcg ggcttatttt 154920
cttatttatt attccactgc actgtaactt cgtctcagtg gggaactgtt gtaacagtgg 154980
ggaactgttg cttctggctc acaaaggtat ctgccatcac atttacatct tacatcacac 155040
gggcacataa cacataatta aaaagaaatt cctttaaaaa tccaaaattc tgttatgcct 155100
ctctagccag ttagagacag acagcagcaa tgtgcaatga cattatttct ataataacaa 155160
gtacagatat aaaagaatcc tcaggaagct gtagagaagc cgaagactct tcaagataat 155220
gtgacattat ctgaagtgca ggagggcaca ccgagacgtg ggctggggac agcacaacat 155280
ggagaactag ctcctttatg tgctcaatca aaaagttccc caacatttgg tctgatacag 155340
tttgactcat ccctactcac ccgtcgtgtg ggctgatcct gttccaggcc agagatcgca 155400
cggctgatga gtccttcaac agtggtcaga gcttgtggta aatgaaacat gagacaagtg 155460
agtgctgacg tgctatcact tgtctgtgtg accctcaaca ctttccctga actctgcagg 155520
cctccttctc ctcatctata aagctctaaa ctaagcacac cgtggtctgt ctcactactg 155580
gactcttaag agatttaatt agacgggcag tggtggtgca ggcctttgat cccagcactt 155640
gggaggcaga ggcaggcaga tttccgagtt tgaggccagc ctagtctaca gagtgagttc 155700
caggacagcc agggctacat agggaaaccc taaaaaccaa caaaacaaaa caaaacaaaa 155760
caaaagagag agagagatta actataactt tttactcaca ttaaaacatg aaaatccact 155820
ataattaaat gaccaaacac aagccactag gcgtgacctg gaccaggctt tgaaagaaaa 155880
taggaaacat ctcagcttgt gaacagctca cacacctcac acacctgatc ttaaaactca 155940
cctcccttct ggctgaaggc tggaatctca aaatccagct cggggatcct tgtggtggca 156000
gagtctgtct ttaccacttc tctgttcatg tcctggacag aaagcaaacc gttctagcta 156060
aagaggtcag caataaagct tgggaaataa ccagaccatc tctccatcag atgccaaccc 156120
agatctttct tcttcccgcc ttccattcag aagagtccaa actacttcag gatagtacac 156180
atggtgtcag cctgactacc cagaaggtaa gaacaccacc cacaaagccc agctcttcca 156240
cataaatccc atcactccca caaaattcgc aaagcacgtt caccactcaa agcagcagaa 156300
ccgaggccag caccaccgac accactgtca aaggacgaca ctaagggctt gggacaggtc 156360
tggtgaaggg ctgatggtcc gattgggggc tctgaccccc agtgcgctct ctgaaaccgt 156420
gggggtacct tctctggtct gcgctcacct cttggcttct cacggtcaag gtgtagcgca 156480
ctccctggtc ctggatcctg cctgcagact ggatctccgt gttgttccag ccacagtgtt 156540
cgcaggaaaa ggagctcacg atgatttctc taaagaaggg gatcttggtg agcagaagtc 156600
gcgtcgtgcc ctagggaagc agaagcggcg ttggggagaa tgacttcagc ttgtttacac 156660
cctgtacgcc agagctgcct ctgggtgcac ggctgggtgg ttccccgggc tcagactcac 156720
gttccggtaa cagttcatgc acagtgactc gatctcggtg ggctgttgct cctcatcctc 156780
ggcgctgagg ggccggaaca aaggcccggt ggctggtgac gcagccgcag cgggcgaggg 156840
cccgacggcg gcccccgggt gtcccggctg cacagccccg ctggcagaca tctccccacg 156900
cgttgctccc gcggcggctt ccggcttccg cggcccctgc gacctcactt cctccagccc 156960
ctgttcccgc cccttcttaa agaggccgca gaccctgcgt ttcctaggtc agtctctgac 157020
aaagacttcc ggttcctaga ctgcacttcc gtaactagag aagacccaca ctgggctgga 157080
gagatggctc atcgggtaag agcactgact gctcttccaa agatcctgag ttcaaatccc 157140
aacaatcaca tgttggctca caaccattca taatggggtc tgacgccctc ttctggtgtg 157200
tctgaagaca gctactcgtg agtagctcgc tagttgtggc ttctctatac gggtagcctg 157260
tttgtcccca ggactccagg tctatgtaaa atgccccggt tgctttggaa tcgcctaggc 157320
tgtgcccccca cgggctggtg agatggctca gtgggtaaga gcacccgact ggtcttccaa 157380
aggtccaaag ttccgagttc aaatcccaac aaccacatgg tggctcacaa ccatcggtaa 157440
ggagatctga ctccctcttc tggagtgtct gaagacagct acagtatagt tacatataat 157500
aaataaaata aataattaaa aaaaaaaac tgtggccaga ccttgcctgg gtcccctctc 157560
ctgttatcta gcttctcccc tccctgactc tctttccccc agctcctcac ttctgtcctt 157620
ttaaacaccg cccctaactc taaatacact gctcttcttt ttactcattt ttctcattcc 157680
ccccaccgca ttcgctgtct taatctctcc ttgtttccta acaaaacacc ctactttatc 157740
gggttttttc aaatttcctt tctagcgctt cctctctaag tcttggacca caacccagtc 157800
acatggctga cactgactct atctacagga ttgagggtaa caagggtgtg gttgcgtgga 157860
gtgcagcttc acagaggatc tgtagtgggg aggtatcgag catcctgtgc agagaaggct 157920
gagctgggaa gaaagggtgc tgagctgggc tttccttccc cgcccctgtc ttgtttcact 157980
ggtccctggc gatctttgat atctgagtga gtgtgtatac gaaagagagt taagagttct 158040
taggtctccg agcatgttgt taaccctagt acttaggaga cagaggcaag ttgatctcta 158100
ttaatgtgag gctaacctga tctacataat gtattccagg ccagcaaata ctctgtagtg 158160
agatctgtct caaagagaga gtttttatca atcccaagaa gagagtcaag caggcatgag 158220
gaatctggaa catgggacca agggtaaggg gatccttcag ggatttcagg gagagcatgt 158280
ttccccatta cacactccat cacatgttct ctgcatcatg ctctcctcct gctcccttcc 158340
aacaaaagct ctcatgacag ccctggggag acaggagttc ctctccgtgg accaactgta 158400
acagccagca ccaggctgcg agaattaatc cacgctgtcc tgtgatccgt agactgtgga 158460
acaagacagc ctcctcccca cccaacccca tcaaatgtga cagccattgt ctagccagga 158520
gtcctacggc agaactcgcc cagagtggac caagaatgga aaagagacag aaagagcaag 158580
tgaggggtac aagtggatgg tgggtgtgtt ctgagacaga ggggaaacaa ttgctctcag 158640
acatggtcca atgagagtca cgccagacca acaacgttcc atcacgagca tctatttcat 158700
tccaaccaaa agtcagttcc accctgagag tcaggaggta gggactgtat gatgaggaag 158760
gcacacagtt tgttctgtac aggatttttt tagaagccct ccttcatcgt gtggatggct 158820
cagttcctta tctggattca gagttctcta aggaaatagg ggctctgccc ggtcccatca 158880
ctggacccac cagcaggacc actggcaggg acgtacacac tccatcacat gttctctgca 158940
tcatgctctc ctcctgctcc cttccaacaa aagctctcat gacaaccctg gggagacagg 159000
agttcctctc catggaccaa ctgtaacagc cagcaccagg ctgcgagaat taacaggagc 159060
ccaactccag gttgtagtgg catgggtttc cagcacggtc aagcactggc ttgcggtcag 159120
tcaccccaca caccatctcc cactcctgtc acctcactct tgctacttag gattgccaaa 159180
tgagtaccag aagctgggtt tgcaaagcct actgagtgta atgcccctga gtaggggagt 159240
tgaggaggct gggtaggttg ggacagcagc acctttggtg gtgtgcagga ccctccaccc 159300
tctgcctaat agaccatgct agcggctcag ggtccagaca atgagctgga gggttaaccg 159360
gagtgaccct cagggtcact caaatgacta tgaccctggt cttgaaggcc ataggcaata 159420
tcttcccaca ggtcgtccag tcggctctgc agtctgctca gggccttatt actgtctgag 159480
tgtcccagct caggagcgaa ggcgctgtgg ctaggcgggg gtggggctag ctggtgctga 159540

-continued atttcctctg tctcctggtc aatggcctga gtaaatgcag caatctgcag gtaggtgtca 159600
tgccgaaaag cctgcagtct ctggcggacc tcctcggaga gagcctgagg gtccagggaa 159660
tctccatctt ccgccccatc tgtgctgacg cggatgaagg cactgagctc atcgcgcagc 159720
tggtccaggt tgcgttggat gctggtgtgc aggtccttcg ccttacgtgt gagtttgtgg 159780
gacagagtct gcacgcagcg actgagtcgc gcggggctgg cagctgcgtg aggagcgaca 159840
ctgcggtgca gctcctgcac gtggtgccca attccagtca ccaagcgttc tgcgtaaggg 159900
tggaagagct ctttgactcg gtcggtatgg tgcagcactc gactctgcat gtcctgcagc 159960
aggttcagcg cctcgtccac gccccccagg agctgagcct tggtgtcttc tcccaccacg 160020
cgcagctgct cctgcagctc ctgcacactc aggcccacct gctccatcag ctccgccgtg 160080
tagggtttca actgctgcct caggccctcc aagttccagc ctacctgctg gtgcttcgca 160140
gccatgtagg gctccaggcg cgagctcact tcccccagct cctgctgcag ctgtttccga 160200
atgccttctg ggtcctgggc cagcagagga ggctccttcc caggccctct caagggtccc 160260
agcttttcta ggtaattgtt catattgtag aggtcttgct cgaagctgcc tttcaggttc 160320
ctggagaagg agaaagacag agaatcaggc cattagactg ctagcattga aatctccctt 160380
tccccaaagc tgtgggacac taatattttg cagaagccag gacaggagga gtggccccag 160440
agcctggtct ttagtcctga ccccagccaa cttcattgtt acattcagaa cacaaaatgg 160500
cattcggtct tacaatacca tccaagaagg tgtcacacac acacgccaag attcacacca 160560
tcttgtcatt ctgtggcatg ctaatctcag gtgccatggg caggagaaac ttggacaaga 160620
gggtgcccaa gatgactgag gtgtgtttgg ttctataggc agggctggtt ccttcagctt 160680
ccatgttaac cacagagcca agggatcatc ccacagtagg gctgtctcgt gccctcagca 160740
cagccttgcc caggctactt actcctgtgc cagcttctgt ggctggccca tcacgccttt 160800
gctccaactg ttttggctga agtagtccca gaggctcttc cgtgcctgag tgcttgcgaa 160860
cactgcagag gaagatgaga cagttaaggg ccaggcccct cagcccatcc tccatcccaa 160920
acccacactg cagtgggcca gaagacccac ctgcgaggag ggcgagggcc caagtgatga 160980
ctgcagccat gctttccacg atggcccctg agaaggaagg tagatgaagg cttgatcagg 161040
aggagaggca aagccaggga ctagatctag gaagcctggt ctaggggggtg cctgccccaa 161100
atcccgataa cccttcccca gtgtgtaggt aacatcatgt caaaagctcc agagaactga 161160
actaggcact tgcggggact gggggtgggg gagtgaggca ggagggaaga gatgacttcc 161220
tcagacaaca gggttggatt gctccttacc tcggtcacaa agtagggaac ctggaactca 161280
ggctgcccta gagagatgac ccacccacct caatgcaatc tagctccctc gtttgcctgt 161340
cttcctgcct ccgagcccct tttagggatg aggactggta cacacaattt ctgctagcct 161400
gtatctgcag ctctctccta cctttgctgc caccccaccc ccaccatccc tgtgccatgt 161460
aagctcacct gctcggttct gggcacagag agcagacact cttactttat actctaggcg 161520
ccagggagtc tgacaacaat tcctctgagc aaacaccacg tggagggtca aagaaggatg 161580
accccagctg gttactagca cactcacctt ttccccttct cctggcactg ttggggttag 161640
taagctcccc agcctcaggg gggctgcccc agtagacaag tggctccctc gagcctttac 161700
taagtgtggg cagaacccac cccccaaatc ctgtgaccag caaccgcccc acttactgaa 161760
tgactggcca gccaatgaac actgcttgtc tgtccactgc gggccctgcc tttacttaac 161820
tccccagcgc cttctgcact agccagctgg ccagagggac agtgtccagg actggctaga 161880
gcctgggctg gccttacttg tcccaccatg gccactgtga cagcctgaga agagccagta 161940
cttacagggt tacagaccta tggcgcctag agtataagtg tctccaggat tgagctggag 162000
aagtcaggtc ctgttgaaga tggatggggc aagctgcatc tgggtcagag actttgggta 162060
tcagaagtta gtcccctcaa gagtcttccc tcacagggaa ggctgggctc cacccccttg 162120
agcttccgag gagggaagcc gggaagccca gatgtttctc ttatgacaag cttcttccat 162180
aggcttgcat ggacatacct gagtgcttca tcctttctct tcaacctcca gtcggtcccc 162240
ctgcctccac ccacacgctg ttcccgtcac tttcctcaga acttccctct gcccttcacc 162300
gtgaccagtt cagcctcctc ccttgtctcc acacaaaact tctgccatcc tcgatccact 162360
tacctctcag gcacaggggg atgtctgcct ataatcacgg cactggggag gctgaggcag 162420
gagaattgta agtttgaggc cagtctgggc tgctgtggga ggtcctatct caaacaacaa 162480
aactaagaag agaaaaagaa gctgccaagc ttcccactct gtcccagcac atgggtcgtt 162540
aaagaagggt tgtaagctgt acttacctaa aatatacata gtccagagat tgatctcaaa 162600
cacggcataa aacaggatta caggcgtgtg cttggaatcc tgagacaggg aaactgcagg 162660
gacctgaagg ggacaggaac tctagaatca gaatggagcc tctcacctag gcaagaatac 162720
ctacaccatt accatgtgct atacattagg tttcaaaact ggggcagaag gctgaggtgc 162780
ctatttaaca tatcaaagtg ggtctggccc ccacattcgc cctgttacag gaccctcctg 162840
gctggcatac tccaccccta ccctaggctt ctccaaccca gggagctgtt ctaccctata 162900
taatccaacc attttggtta cccacttttt ttgtgtcttt gtgcctcccg gttgcacccc 162960
tctctccccc cccccttat ccctccccct ttcctctctt cccatgtggc ccagctcagt 163020
ctggcctgtc tagtctcttc cagatgtccc cacctctggc tctgctctcc catatatcta 163080
ctataaactg tctcctccac cacagagcta ggatcagtca tgttcctttc ctttcgcctt 163140
ttttattttt atttttcat tcactataaa ggctgctgac atagctacga tttctttctt 163200
tatagatgct ttatgttaaa atagagacgg agatagaatc tcaagcaggg actccttgct 163260
tttacccaga cactgcttga aaatctcaaa cactgtttac aacaaaggta ccctcctttc 163320
ctatatcccc atggactaga cttttgaatc aattattata ctgataagat agtaacgtca 163380
aacctcatcc aagtcctatg tatgactgct gtaaaaacag tgagccacgc ctctcttgag 163440
gagcccacac ctgaacacat cttacatttt tctgaatatt tatttctcct aatattcatg 163500
tgttaaccta tattataatg ttttagtaaa cttctggtcc agttctaact tactgtatca 163560
gctagtctta tttttatttt ctttttagaa gattgttctt aaatatctgt atatatgtgt 163620
ctgtgggttg gggggtgcct caggaggcca gaagagggtt tcagatcccc tggaactgga 163680
gttgcaggca gttatgagcc aaccactatg agagctgaga cccgaaccca gatcctctgc 163740
aaaagcagcc cgggctctat cctgctgagc catctctctg gccagccccc gactgttaca 163800
acacttcatc cctgcacaga agacttggtg cttgaagcat gtggaatggc ttctcttttt 163860
tctggctgaa cctagacacc tggtgaatgt aaggcatagg catgctttct tgtttgccag 163920
caccgtgggg cttcagtgtc gatgtgttca gggtggttgg aaatatgtgt gtatttgttt 163980
tatgatctgt gaaaataaaa tcagttttga tagcttaaaa ataaatgatc aagggctagt 164040
gagatggctc agcagttaag agcactgacc aaagccaggt gtggtggcgc atgcctttaa 164100
tcccagcacg tgggaggcag aggcaggcga atttctgagt tcaaggccag cctggtgtac 164160
agagtgagtt ccaggacagc cagggctaca cagagagagt tccaggacag ccagggctac 164220
acagagaaac catgtctcaa aaaaacaaca acaacaaaaa aacaaaaaca aaaacaaaaa 164280

-continued

```
caaaacaaaa aaagagcact ggcttctctt ccgaaggtcc tgagttcaaa tcccaccaac 164340
cacacggtgg ctcacaacca ctcataataa gatctgacgc catctcgcca tctcctggtg 164400
tgtctgaaga cagctacagt gtacttacat ataacaataa gtaatctttg gaccggagcg 164460
agcggggcca gagcgagcaa aggtcctgag ttcaatttcc cagcaaccac atgatggctc 164520
acaaccatct atatagctac agtgtactaa tatacataaa acaaataaat cttttttttta 164580
aatcaaatgt tggcaatttc atgtctaaca agatctattt atatgtaatt tagtatatct 164640
aatgcataca gcgttcttag cacatggacc tgaacatacc acaaaggcag ggttgctaag 164700
aatgcaccat attgatgatg ggactccttt gaacagtggg gaactaaaat attaaaccaa 164760
agtaatgtag aaaaagggaa ggagacatca aagtgaaagt gttctccagt cttgctttat 164820
ccatggagaa gataggaata ttgatcgtct cttgcttttt acatcaggca ccaccattaa 164880
agttttaaag agaatccatt aaatgagtag aaagaaaggg taacttgcaa actggtaaat 164940
ggggaaaaga gactaaagag cgtcgggttg gccgctagtg aaggtgctga ttgatcgcac 165000
atgctcactt caagctgttt cctgaaagcc caataaaatg tcattcaaat gctcccctta 165060
gagaagcacg aatccacgag gacagaaaag gagacaaaga cagccacatt ctggaaacgg 165120
taaaacttct cggcagtcaa acagtagtta ctgaaaacac atgaaatgat ggctttttga 165180
aatggcaatc cagaacgtta agaacttgct gggtttagct gttcagagac agcagcacta 165240
gattcttctg gacatatggg gagggggagg cagtggcacc aaaagagcag cacctgggtc 165300
aaaagacatg ggagaaacat gtctccttta gctctactta gtaaagtcag acacttgttt 165360
tctagatgtc tcacctcgtg cctggggtgg tggtgcatgc ctttaatcct agcacttggg 165420
aggcagaggc aggcagatct ctgactttga ggccagcctg gtctacagag tgagttccag 165480
gacagccagg gctacacaga gaaaccctgg ctcaaaaaaa gggggggggg ggaattctag 165540
actacagtca aatgctagtc ctaacctttt cctacttgtc tctgtctggt tgtttttgag 165600
acaaggtctc aatgtgtagc ccaactagc ctgaaactca taccccctcta gcctcaggct 165660
ccacatatca agttctgttt taagtgtttc aggtaagaat attatcaggg agaggtgggg 165720
ccttcccaac acaccacact gggggaagca tatcatggtg ggtccttcca attgcctagt 165780
tctgggggag cagagaaaaa gaactgagac tgcaaacacc cggaggcttc tgcgcaaacc 165840
tttgtttaaa actttttttta ttgagatgga aaggtaggga ggaagacagg gagggaagga 165900
gggagtgtgt gtatgttaga gtttctgtgt gtgtgcacgc tatcatgcac atagtgaaaa 165960
cgtacagaag tctctccttc catcatgagg gatccaagtc aagtccgcag gctggacaac 166020
aaatgcctct acctgctgag ccacctcacc agcttgcaaa tatcacttca tatcccaaat 166080
tcatcagtta ccaagaatct gaggatgcta aaggtggtga ctctgtcacc tactaaagac 166140
agaaaatgga gctagagaga tgactaagca gctaagagta ctgtctactc ctccagagga 166200
ctcaggtgca attctcagca cccacatggc agctcacacc tgtctgtgac tccattccct 166260
ggtcatctgc gggcaccaga cacatgaggt gtacatacat gtgtgcagga aatacactca 166320
taggcataga aaaaaaatgt aatctttttt taaatggctg aggggagagt tgagacaggg 166380
tctctctaca tagccctgac tgtcttggag ctcactaagc aggccaggct ggccttgaac 166440
tcacaaagat ccaactgttt ctgccttcag agtgctggga ttaaaggcat gtgccaccac 166500
acctggttta taattgaaaa aaaaataaag acaaaataaa atatcttttg aaccaaaaca 166560
atttacttat gatcacctta ccccatggta aaatctccac ttgttcatag tgggagaagc 166620
aaagtctgag ctgggaccaa gccatgaaca catgggcttc tgcggagcat aggtcattca 166680
```

-continued

```
ggcccacgtt atagccacat aatatattat gccacggtga gggattttct gtgtctgttg 166740
tttcattcat gtttcgagat gttagtttta ggtagatgct tagatgtggg attggtggat 166800
taagcatgag tgttgggttt gtttgatatt tctcactaaa ggaattgttc tcttttgtga 166860
gtctataaag cctgaataaa agtgtcttta gtttgtttgt ttgtttgttt gtttggcttg 166920
gtttggtttt gctttacctg cctggagtgg tagcccgtgc ctgcaatctc agcactagag 166980
agacacacac cacatttata cacataacac acacacacac acacacacac atacacatat 167040
cacacacaca cacacacaca cacacacaca cacacaccac taaatgaata taataacaaa 167100
agcatacctg acaatctgac acatgagaaa gtacatgaaa attcacgtac ttcctgacaa 167160
tctgacacat gagaaaatct attttcatgt acttctgctg ttcccgttcc tcccactatt 167220
agtaaagcgg gcatatattc tagtctgaat ggttatttga cctttctgtg actgttttgc 167280
tcatctcttt cccttcattt tctactgaaa atcttatctt ttatattcac agcatatata 167340
tatatgatga tctgtttctt attagtgatt gtatcagtca gggttttcta gaggaccgaa 167400
actgatacaa tgaaatatat atatgcacat atgcaccata tatgatatat atggtttact 167460
acaggctatc attcagctgg tctgacaatg gctgtctacc aattgaaagg ccaagaatcc 167520
ggtagttgtt cagtccacaa ggctgcatgt ctcagctggt cttcagtata tgctggaatc 167580
acaaagaaac aagctgtaat gccagtgaag gaatggattt gccagcaagg gcaagcaggc 167640
aaagggcaaa aacttccttc ttccatgtcc ttaatatatg ttgtcaccag aagatgtggc 167700
tcaggttaaa gatgggtctt cccatttcaa atgatttaat taagaaatgt ctttcacaaa 167760
tgtacccagt tgggttgacg agatggctca gcgggtaaga gcactgactg ctcttccgaa 167820
ggtcctgagt tcaaatccca gcaaccgcat ggtggctcac aaccacctgt aatgagatct 167880
gacgccctct tctggtatgt ctgaagacag ctacagtgta tttatgtata ataataagta 167940
actctttggg ccaaccagag caagcagggt tgacctacag gactacagga ttgaacagag 168000
gtcctaaaaa ttcaattccc aacaaccaca tgaaggctca caaccatctg tacagcgata 168060
gtgtagtcat atacataaca taaaaataaa taaatctttt ttaaaaatat acccagctgc 168120
ttcagtttta gttaattcca gatgtagtca agttgacaac ccaaaacaac caccacagtg 168180
atataagttt attggagctt gccagcaagt gcttccccga ccgagacaac tcgccagtca 168240
ggttttctct tactttgctt actatgtttt atttgtttgt ttgttatgta gagcattgct 168300
tagtatttat gccattaaat ttaccttgca tcattttgaa cttgggagtc agaattataa 168360
caagactcac tgcttcctgg cattaaagga aactgcctgc ttttttcttc atgtcccagt 168420
gtgaaaggtt tctttaatgg gtcaatcaat agtccagatg cttggcatag ccaggtgtgg 168480
tgagacatgc ctttaatccc agaacgcagg aggccgaggc atgtaaatgt ctgtgagttt 168540
gaggccagcc tggtctctat gtagtgagat tcccatctca aaaaaaaaaa aaaagcaaac 168600
ttgagcaaga atgttgacat atactttaat cccagcacat gggaggcaga agtaggtgga 168660
cctctgatca gatagagctg ccaagggact tctcccgcag ccatccaggc acctggagtc 168720
cgtcgcagtg tggtccaagt agacctggct ctggctcctg ctaggtctac ttctggccga 168780
ccttggagtc agccacgtga caagagttgt gcaatacaca ggatgggaga gttgtgggct 168840
cacccagggt tccacacaga tttcaagatc tgggggtgaa ggtgggagaa agcatatggc 168900
agaatctgaa tctcgtagcc ccctgggagg gcaatggcgg aaacagtgac agtggaagcc 168960
atactgctgt gaccccagga agtcagagat gccagcagtg gaatgtctgc caaggaaagc 169020
```

-continued cacatcctgg gccacagtgg tggggctgcc caaaccctac atcatagcat cacatgccca 169080
cagggtacag gatctgccat ttcccttgct ggggttggat ctggccccaa tttccatttt 169140
tatgtctcta ttccatttgg atcagggata tttatctcac atcatatgga agtctgtaac 169200
ttgtggggtt tttttgtttg tttgtttgtt tgttttttgt tttttgagac agggtttctc 169260
tgcatagccc tggctgtcct gaaactcact ttgtagacca ggcttggcct cgaactcaga 169320
aatctgcctg cctctgcctc ctgagtgctg ggataaaagg tgtgtgctac cacgcccagc 169380
ttatttttat ttctattctt atagatgctt gttactaggt gtttgctgag agtgatgggg 169440
aacactctgg acttggactt ttgtataatg atagaactgg tgagaatttg aggactatag 169500
gaaacatcct atattgggca gtggtggtac acacctttaa ttccagcact caggaggcag 169560
ggacaagtga atctctgagt ttgaggccag cctggtctac agagcgagtt ccaggacagc 169620
aaaggctaca cagagaaacc atgtcttcaa caaacaaaca aacaacaaca ataacaacaa 169680
caaaagagag agaagaagaa agagagggag ggaagaagaa aaggagagag aaagagggag 169740
gggttctaaa tgcattttgt gtgatgagat ggatgtgggc ctttgaggga ggtcaggggt 169800
aggatatgaa atgcttttcc ccaaattatg ctttgtctcc agtcaatgta cagaggtttc 169860
ggaggtggag cttctgggaa gtgaccatgt cccagggttc taactgaatc aatggatcaa 169920
ttcttagctg gttgtaattt ttgggatgtg ggacttagtt gtgtgttgtg cctgtgaagt 169980
gtccaccttg tctctaattc ctctttctgt ctttctactt cttggctcct ctgaggtgaa 170040
ccgttttgtt cttctttcca tattggtcca cttacccaca atcccagaga cacagagccc 170100
gttgaccagg cactgaaatc ctggaaacag gaacccaaat caatcctccc tcctctagac 170160
catttcttgg acatttcgtc aaagcgatga aaaatcaaat tgggttgggg agatgactca 170220
gctgggtaaa catgaagctt cccaaaactc atgtaaacct gaacccatgt ctgtagtccc 170280
aggatgggag acagagactg gagaatgcct gcaagttagt tcatgggcca gctagtcctc 170340
aagagacagc tagagaccct atctcaaaca agatgtaagg caaggaccaa cagttgagac 170400
tgctctgtcc cttctgcctg tttgtgtcac ctgagcatcc ttactcacaa actagagcat 170460
gcacatatgt gcacacatgc acatgagaat taaacaacaa gaaaagaaac gttcattcat 170520
gggctggagg tgtagctcag gtgtagagag cttgactagc agacacaagc tctggcattt 170580
catcctggca ccatggaaac tggagatgct ggtgtacatc tgaagtcctc aaatttggga 170640
ggtggaaaca ggcggatcag gagtttaagg tcttcctcag ctatgcagtg agttccagtc 170700
cagcctgggc tctatggccc tattgattaa catgggaacg caaatatggt ccatggacag 170760
catgctggtg gatagcaaag gaacgccata atcaatagaa aattcagagt gatttggcaa 170820
aagtcgggcg tgaatcacag ccagatcaca tagtttgagg ccacagagct gcactgaaaa 170880
gttagaatgt tgcaactcct caggtctttg ccctcatttg taaaatgaag gtgataccag 170940
tacccaactc tagggctaca cactgaaata acgcttttta aacatgattt atttaaagtc 171000
atgtggtgat gaaccacatc tttagtccca gcactcggga gacagaggca ggtggatttc 171060
tgtacattta aggccaacct gccctacaga gctacttcca ggacagccaa gtgtgggaac 171120
agggaccggg aaatagggtg ggggagtgga agcggagccc acaaagattc cctgggattt 171180
ggactctgga gaccagcatc gaggtccagc tctaacttta ctgtttagta catatgctga 171240
tatgcagttt ttcagccaat tagggtacgt ttatgtatcc agggacaaat ctgggtgcaa 171300
catgtgttgt ttagctgaat ctgtcccatc tgatcatgag cctgtagggc aggtgcctgt 171360
catccaggaa gatttctgtg aaggccaggg gaaggagcca ccactctgcc ctctggtcct 171420
gtgagttgtc tcatggtgtg ccaggatgaa gcctatgtct cttcactctc cttcccactt 171480
gttcctccac caggtttatt tccactttcc ccacagccaa ggctgcaagc ccgtcacaaa 171540
aataagtaag taagtaagta aataaataaa taaataaata aataaataaa taaattttat 171600
ttatttttaa ttaatttatt attttggttt ttttgagaca gaatttcatg tatccctggc 171660
tgaccaggaa ctcacttgta gaccaggcag gcctcaagct ctagagatcc acttgcgtct 171720
gcctcccgag tgcaggatta aagatgtgta tccctaagcc gggcaagatg tgtttacttt 171780
tatttcccac gtctgggtgt ttctccaata tgtatgtaag tgtgctgtgt gtgtatctgg 171840
aactagaaga gaatattgga cccctggaac tggagttggt tgtaaaccat ctaggtgcaa 171900
gacacagtgg tcacatgaaa atacacaaga gaataaaacc tgggtggaaa agaggctctg 171960
ccccctgcag gtcagtaaga gagaaaagca gggataaata gggagttcgg gaaggaatag 172020
aatcagttta agtgggacta aaaggtcact gaaggagtgg taaggcccag gaagaagagc 172080
ctgaggaaca gggtgtggag ttcccagtag acatgaaagt cccagtggga cagcatgggc 172140
agaaggaact ggaactaaga cacatggtgg ggacagaggg ctcgcctctc tgggatatga 172200
agaagcagca ggagcagagg ccctggcaga agtcaggaag ggaagacaga gtcccattga 172260
ggcccagccc acaaaggaat gtgttgtcag ggtcagtgga aacaggaagg ggaggcctta 172320
ggaaatggga ggggcccctt gctcccagga gtgaggtaat atcctgtgga tttgggtgag 172380
aagtgtcaga catgcccaaa gtctatgaaa gcaacatggt cacagaagcc cacatggctg 172440
gaaatggagg gacgcatgct accgtgtctt ggagagtcat aagatacaac ccccaggtag 172500
tgtaccagaa aagaagttta acaagaagct caggggaagg tggcccaggt cttccaggtt 172560
tcctgagtct ggcccaggag gactggagaa aactgatgga tagtctcctt ttacattgca 172620
ccctctgtgt atctcttagt actcaagtca acactccaaa gcagaggttt ctctctacag 172680
agaaaccagg attcaaagag atgtcagctc ttgttcaagg tcttatcctg ggtcaatttc 172740
aggcctatgg cctctgatgt ccagttcagt tcactgcctt gtactcagag gctactcaag 172800
agctcatctc ctacccaaag cagcagctga aacatctgct cttctcagcg ggagaagcca 172860
gtgctcaggc acgaagccag ttactttccc gttgtcccac gatgttgatg attcagggac 172920
aaggctgtta gagacacatg ttgactaatg tgaatacagg aaaagaaacc cagggccagg 172980
cagaggctag ccagtctcaa gtcaaggtgc agctaccaag tcaccctgag actgggactg 173040
ccctcttgtc ccctcctcag tctccctctt ccctcaaact cctcacagtc agaagtaaat 173100
ctagctacag ctaggacacc aagttcccag acctccaaca tgcctctatg acctgtctgc 173160
cctctgagac catggtccac agagactgtg aagttacctc agcctggtgt ttatgccact 173220
gacgcccgtt gatggagcaa tgctaggtgg ggccagtgac gtcgactgat accacaagat 173280
gtacccagca tgatgaataa acaccgtgct ggtgtgccag acaagataaa tgttattatt 173340
tgtgccactt gtcttgagag agacccctgt gcaccatcac aggaaatgaa tactgagaga 173400
gatgtcggtg gagaccaggg caagaggcag agagaggaga accttagggc cagagatgat 173460
gacaagacaa cagaagatca tgcgctggta aaaaaaaaaa aaaaaaaaaa accaatcaca 173520
gagtgagtaa gaggtggcaa aggtgtagaa cccgaccttc accctggccc cgggtttctc 173580
agaatcctgg gaaggggatg gttcatccag ttacataact agcatagcca gaaaggagcc 173640
atgccagatt cgcagaagag ggtttcacca catcgcatga aagaaatggc ccagagggtg 173700
tttgtttgtt ttttatttat ttggatgaga tgtcgccatg tagccctggc tgacctggga 173760

-continued

```
ctcgctgtgt tgaccaggct ggcttcaaac tcacagggat ctccttgcct ctgcttcctg 173820
ggtgcgggga ataaagccag gagccaccac tatgcatggc ccattactat ttgtaagaca 173880
aggtttcaca atgttgccca agttggcctc aaactcttgg attgaagaga tccccactcc 173940
cacccctgta tagagggagg gtcttgagtc atgcagctgg ggatggagct cagtggatag 174000
tgtttgcctg ccacgcaggc cgtcctggct tcaatacaat gcactgccat gaatggccac 174060
tggctcgggg catagagcca gtccaggatg ttcaagcttg ggttcagtcc tcaagatacc 174120
gagcagcaga aacaaaccac gaacccaaac aaacaataag aacaaactga agcagcctca 174180
tggtggcctg actgatccat aggtagaaat aaacaggcct tttgagtata agatcttttt 174240
tttaaaagat ttatttattt attatatgta agtacactgt agctatcttc agacactcca 174300
gaagaggcat cagatttcgt tacagatggt tgtgagccac catgtggttg ctgggatttg 174360
aactcgggac cttcagaaga gcagtcagcg ctcttaacca ctgagctatc tcgccagccc 174420
tgagtataag atcttatgtg ttaaaatatt aaaaatgcat aaattaacca aaagctttat 174480
atttgggtgc ctctgtgtct gtctgtctga ctggctctct ctctctctct ctcgtctccc 174540
tctctctctt tctttgagac aggggtttctg tgtagctctc ataagctatg tagaactcca 174600
ctcctagtga ttcctctgcc tctgcccctt tccgagttca tcttataaaa gaacacaata 174660
cagaaaatgt gaagatacac ataagcaaat agaagaccgt cactcataat tatactatca 174720
gcaattatat attcttctat attatttatc taggaatatg ttcacataaa catttttatc 174780
atagtgtgtg tgtgtgtgtg tgtgtgtgtg tgtgtgtgaa gagccagaga gagagagaga 174840
gagagagaga gagagagaga gaatgtgtgt gtagatgcag gtagaggctg acatcaggac 174900
agatgtgtct taactagcct ccaccttatt ttttgaagta gtagctctca ctgaacctgc 174960
ttgattcaac ttggcttcca gacaacgagc ctcagaaccc agagctgggg ttccagtgtg 175020
tggctactcc tggcttttcc atgacttctg ggactccagg ttcaggtatt tgtgcttgtg 175080
aggccgacac ttttcctact aagccatctc cccatcccgg tataactact ttttatttta 175140
gtgtacacac acgtacacac acgtacacac acacacacac actagaggac aacttgtgtg 175200
aatcatctct ctccttccat catttccatc ttgtgggttc tgtggatcca actcagatca 175260
gcaggcttgg cagcaagagc ctttatctgc agagccactt gctggtccgc attgtggctc 175320
ttgatggatg agaatgtggg catactgtga tttatccggc atgctcctct tactgcattg 175380
tttctaagtt ttagcgttac taatagggtt agagagagaa caattgtaac aagggattct 175440
gagccctctt ttggcttctg ttgggtcctt gcagtcatgg ggtacactca caacacagtc 175500
acatacatac ttataaaaac tttaaaaata ataaaattaa cgtataaata agattataat 175560
gaacattctt agtgagatat atgtgcttca tgattatttt cctcagattg aaaggggaag 175620
tggaagaaca ctgtgctgga caagctagat cctctccatg aatcctttgc cgcaagtacc 175680
ccagccctcc caggcgcctg gcaccagcgg cctccatact aaaggagaga tgcagagcag 175740
agcctctggc agtctgtcta ggccacttct gtagacaagt gtgcagaaat ggctaactga 175800
ggacaatacc tgctctcact tggggctgag ctctcctaaa aacagaggag aagccaggcg 175860
atggtgcaca catctttaat cccagcactc gggaggcaga ggcaggtgga tttctgagtt 175920
tgaggccagc ctggtctaca gagtgagttc caggacagcc agggctacac agagaaaccc 175980
tgtcttggaa aaccaaaaca aacaaacaaa caaacaaaaa aaagactcag ccatatcaaa 176040
ctcaccagcc ttcctggtaa gcgctttgcc agccgtctcc tcagcctgat cttgccaatt 176100
ctgtagatct gtcaggaggc tgcaagcaga agcgctcgtc atgtaaaggt tgggctgagc 176160
```

```
ctggggatat ggtgacatgg tctgcttcta aggcagctca tgcatgtggc tggcaagttt 176220
ggggcagagt ttccattcat ctctttaggg aactctccat aggactgctg gaatatcctc 176280
agacatcatg gctatcttcc tgactgcagt ggttccagag aaagagtcag ggagccgcaa 176340
tgccctctac acccctcctt tgggcacata cagtctgtct tccacaacag ctccttgatt 176400
acacagacca cccaaactgt gaataccggt atggaggagt gcagggacca tcagtgaatg 176460
aaggtgatta agcagtgtaa ccccacccac ccccacacac accaagaaat gactaactcc 176520
ttactacttc atccaaatga acatgcacat aagacttgac gagaaaagat gtgctaattc 176580
cagtcattat tgcttgaaca aatgtttatt gagcacctac tagtggaggc tccaattaag 176640
ggaccagtct acagttaaga tcagggacac aaggcagtac cctccagccc tacatgggtg 176700
tgacagttct aagtcccaga tctttaatcc ctagagcact agcccaccat atcagaacct 176760
ccttcccatg ctcggaaatt ccagactctc taatgtgctt ctctgctctc agctgctcgc 176820
catccttgcc aagaccacca ggaccccact ctatttgttc tcagacatag acatccccag 176880
agaacctcag gctagtttct ttctctgaag agcaggcttg gacttccagt gccaacagca 176940
gaaggccagg atgcccccag gcaggagctg cttttgaccc tgccagggaa atctctcaaa 177000
agcccactga cctgaagaga aggtgggcga catgctagtc catcagtcct accttggcta 177060
gggcagccct gtggggaagc accaggatac tgcttctttc agattctaga agtcacaggc 177120
ctgtgaggag gggaaggaca accagggact caaggtcgtc cttagctaca cggtgagtgt 177180
gaagccatcc tagatcctgt gagactgtag agagcccggg gacactgctg ggaagaaggc 177240
gagttgaagt ggctactgtg aaacctatgg ttcttccttc cttaaaacta agcagagagg 177300
gaggagagac agcccagtgg gtaagagcac tggttactct tttagaggac ccacgttcga 177360
ttcccagcac ctacgggata ggtcacaatg gtctggaact ctgtttcatg catgtggtgc 177420
acagacatac atgcagacaa atgtttatac atttaaaata attataatta attaattaat 177480
taattaatta aaaaccagcc acggagagcc tggagatgtg gtcagtggtt acgaatgctg 177540
gctgcacagt catgaggtct gcagttcggt ttttacttgg gagccagaga caggcggatt 177600
tctgagtttg aggctagcct ggtctacaaa gtgagtttca gaacagccag agctatacaa 177660
agaaacactg tctcgaaaca aacaatacac acacacacac acacacacac acacacacac 177720
acacacacac acacacacac acacacatac tgtagctgtc ttcagacata ccagaagagg 177780
tcatcggatc ccattacaga tggttgtgag ccaccatgtg gttcctggga attgaactca 177840
ggacctctgg aagaacagtc agtgctctta accactgagc catctctcca gcccagagtt 177900
caaatcttag cactcaagta acaatctggg tgtccaccta ggctaatgtc tccagctcca 177960
gtggggtgaa gacaggagga tccctggggc ttgctgtctt tcagaacagt tgagaaaatg 178020
ggaggccagc ttcaggaagt aaccctccct caacagaaaa ggtggccagt aacagaggag 178080
gaacaacagg ccctcttctg gtctccatga aggcacacag gtgacatagc tgcaccctat 178140
gtgcgtgcac acacagagag aagttgacga atagaccttt ttaaaaagtt aagcatagaa 178200
ttaccacatg acccaccagt gtctcctcca agatacacag tcggaagcac aaggagcagg 178260
gactgggatg gctctgagtg cagctgagtt catcacagta ttcacaatgg ctgaatgagg 178320
atgtgttttc tgtctggggt gtgttgctac aattccttcc ttgggaaaaa cataaatact 178380
actcctcctc ttgaggtcca gtgactccaa gttcactgtg gaaacaatca gtttcctggg 178440
tttatttaca aagcaatgtg agaggagtgc cagcagaatc ataggtgact ataaaatagc 178500
```

-continued

```
catgctgaaa tgtcttcacc cagcagggat agtgatttcc ccatggctgt gtagaaggaa 178560
ctcctaccct taaccgtacc atctctactg gctagctact cttcaataca acatgcagct 178620
atgcagtgat ggtacactcc tgtaaccctt acacttgcga agcagaagca ggcagatctt 178680
tgagnnnnnn nnnnnnnnnn nnnnnnnnnn nnnnnnnnnn nnnnnnnnnn nnnnnnnnnn 178740
nnnnnnnnnn nnnnnnnnnn nnnnnnnnnn nnnnnnnnnn nnnncttgct tcttncatcc 178800
acctcntttc ttccttcttt cttccttctt cctttttttct ctttatgaaa tagggtctta 178860
ttctgtactg tagtccagac tggcttgaac ttgctgtgta gatggtgcag gggccttgaa 178920
cttgtagcag tcctcctggc tgtgcctcta catgctaaga ttgtaagtgt acaccactgt 178980
ctctagctaa gatttcttgg aaatcttgat agaattgtta tataagccag cactcgggag 179040
gcagagaggc agacaaatct ctgggtttgt ggccagccta gcctggtcta cagagtgagt 179100
tctaggccaa caggaacagg atggcctata cagagaagcc tgtcgaagga agaaaggaag 179160
gaaggaagag gaaggaaggg aagaaggaag gaaggggggg ggagagggga aagggggaga 179220
aactgggcaa agggaagcaa gtcaccttca tttcttacat accagttgca ccttcatgct 179280
taaacagtga tcatcattct cttctcagtg tttttctcat ccacagacta atctccaggt 179340
cattgaggac atgtctgtct tgtccctatt gttctgagag cactttggtg gagcatcaga 179400
cattagaagt acttttctat taccacatac atctctcagg gttacagctg taatgtctct 179460
ggtcaggtga attatgttaa tctcttagct ttgacctaag aaggcatttt tttcacttgc 179520
ttataactcc gaggctatac ctttgagctc tctaaatgcc actcccacct tccgtattgg 179580
gtcatgtctg aattatattt atcattgtgt gtgtccacga tgaatgtgtg tcactgtgca 179640
tgccaacggg cacctgtaga ggtcagagga caactctgtt gagtcggttt tttccttcca 179700
ccttcacatg gtttctaggg accaaactca agttaccaaa cttgctccat cacccactga 179760
gagccttctc cctggcttca tagtgtttgt ttgtttgttt ggttggttgg ttggttggtt 179820
ggttggttgg ttggttggtt gattggttgg ctggctgtgg ttgctgttgt ggtggtggtg 179880
ttggtggtgg tgattttgag acaggatctc actgagtagc agtggctgtg ctccaatata 179940
cagagagcca cctgcttctg tatcctgaat gctaagatta aaggcatgtg ccatcatacc 180000
tggcccttga tttttaattt gaaaaatact gtatttaaat actgggtttt gggctggtga 180060
gatggctcag tgggtaagag tacccgattg ctcttccaaa ggtccagtgt tcaagtccca 180120
gcaaccacat ggtggctcac aaccatccgt aacaagatct gacgccctct tctggtgtgt 180180
ctgaagacag ctacagtgta cttaaatata ataaataaat aaatctttaa aaaaaaatac 180240
tgggtttcca tttggtatca ttaggttctg tttaaaaatg aaagaggtct ttattcattg 180300
tgctctataa aaggtgtact aaaacttctg agtaatatgc tcacctgcaa gtattgggaa 180360
cacactgagt ggacctttgt ggctctaatt tgttgtgact tagaattctg atgatggcat 180420
gcatgttact attcctaaca gtttcggtgg gtattgtcta catgtcttat agaaactgtc 180480
tgatgacagc accttttaaa atggactcat ttaaacaagg agacttctgg tagggctttt 180540
caattttgct ttcttatggt aagagtgggg ttgccaggca gtggtggcac atgcctttaa 180600
tcccagcact tgagaggcag aggcaggccg atttctgagt tcaaggccag cctggtctac 180660
agagtgagtt ccaggacagc cagggctaca cagagaaatc ctgtctcgaa aacaaaacaa 180720
acaaaaaaaa agaagaagag ttgggtagta gtatctgcag tagtgttgag attggccaat 180780
ttggtgatcc cacctgctag tgcatgttgg gaaaacccca taagttcttc atcataaatg 180840
ccatttcccc atgaagggat tttccctgaa tgtgtgtttc aggccgtgag tctctcatta 180900
```

cttctttgtt agcttctagt cagtaagttc agccaggggt tgatgcaaat gctaaacact 180960
aaggattccc ctaacttttc ttcaccgtga actcattgat tcctggaaga tttcaaaatc 181020
acctcatcag tgctgtgtgt gatcctacga tccacactgc cttctgttgt tttattcatt 181080
aaagaagtaa taatagcaac caatgcttag tgaatagtct tgtaggcgac ttaaagaact 181140
agttctcttt ctttgctgta tgtcatatta gcagcctggg taacaacccg attcttattt 181200
atataacttt ttccactcat tttggtcttt attatttttg agtcatctct aacaagcccc 181260
ctttctctgt aagtccatgg agatctcaga caaggaccag agttaactgt gcgttggggt 181320
gtttgtctct ggttgtaagt tgtcctcaga agattacagc tttgacagaa tgagggatct 181380
tgtctcagtg cttcctggtg cagatggaca cttggaaata cggatatatt tccaatttat 181440
tgtcctccca agctatactc tccatatata tatatcttgt tgagtctggt agacctctta 181500
aatctttccc tctgagtgtg tatatataca tgtgtgtgcg tgcacacaca cacacacaca 181560
cacacacaca cacacacaca cgcacgcagg aagggaagtc tagctctcca gaaggcttgg 181620
ctgtcagctg cattgctttg ggagcaccga gaacactgac actagctgaa ggctctgccc 181680
cgtctgctca catctgcttt ggattgttcc ttggtcaacc aggaaagatg tccttgttat 181740
tgctctgaag tggtggactg aacaagaaaa tttgctcttg gaattgtccc gatttttaaa 181800
ttagtgccac cagccctcct ctcttttccc accatgtttc acatacccag ctaatgatac 181860
gcttatttta ggatacagta tcactacctt atatagcctc aggcgcctca tctcgcctag 181920
aacaaagagt ttcaaggctc aaaatcaatc ttggcctctg gtatttaaac catcctaggc 181980
gatgaacata gggttcaaat taggcctctg ctttgtatta agagaaaagg atgtaaattg 182040
ccttttgagc ctgcagacaa atgctaacta accggggtgt tgggggttgg aaaagacact 182100
taacaaatta agttgagttg cttaggagtg gagaaataaa tgaccatagg ctccacccat 182160
atggcttctg ctgtgttggg tgtaactgct gtatccagtg taaccaattt cctttgtgtg 182220
tgccaccaca cgtgtgtatg ttcatgtgtg tacaagtggg catgtatctg tgtgtatatg 182280
taagccaacg gatttcactg ggaattgttt aagtgttatc cttctagcta cctatgaaca 182340
cagggtctct tactggagcc tgttaccccc tgattaatcg gggatgcctg gccagcacac 182400
ttccacaccc gcctccttct ccccagcacc ggatttagaa acatttgtca ttacatttag 182460
ctttggggaa tcttaaactc aggtcccctt gcttgcatcg caagcatttc ctgaatgagc 182520
catctctcta gcccttagtg gtctctttct gttatgactt tgatttcttt tgtttgtttg 182580
tttttaaaga tttattatct atctatttat ttttatatga gtatactgca gccgtcttca 182640
gacacacact agaagagggc atcagatccc attacagatg gttgtgagcc accaagtggt 182700
tgctaggaat tgaactcagt acctctggaa gagcagtcag tgttcttaac cactgagcca 182760
tctctgcagc ccacgacttt gatttcttag gtaaaaatct ttatgacatt tatcacctct 182820
ggttgagtct gtaggccata aatcttttcc tatcctctga aaagggactg ctggctgtct 182880
ccatctatta ttcaaggcga tgctttaagc tggacatcca gtgctcacct gtaatctcaa 182940
catttgggag cccgaggcag aagaattgaa aattctccaa cctggtctca atctcccacc 183000
ccaaaagtaa tattttaaca tctgtatatt tgaaagagca tagtgaattg taggttcatg 183060
tatgcttacc cttggaagtg taaatgaaag atttctaaac attgcagata taaccttccc 183120
tctaagatac tggtcattct gaaatcattt cttcccgggg cttgttttct gtatacagtc 183180
agcatatcta caattatgct tttcccttta tgtcacctca agtatccgat ccaggatgct 183240

-continued

```
ctgtaaaatc accgtgtgcc atgttgcatg caaagcaatg tacaagtaca ggtaggaaga 183300
atctttgatc caccctgaat tactgcatga atatccaaat tgctcttcca tatccaaagc 183360
ccccttcatg acgttggctt cagcgctgca cacctcccgc tttctcgggc ttttaggatg 183420
ccctgtaact ccaagtattt acttgccctt gtgagctcat cagatcccat ttgatccgag 183480
tctttcctct gcttccgttt gtatgtgact tgtatggttt cactgtggtg acattgcacc 183540
agagtttagt ctatggcatt ctccatcctg ggccacatat gcctttcagc cataatagca 183600
gagataagct aaggtcactg tctagtgagc ccagccgcag agcgacacgt cctggcactc 183660
caggttttcc aggtggtact ggttctgggg acgcagggac cttttctagc acagaacatg 183720
tacttttgca gaagtggctg ggctatgctt ctgctaactc cagggatatc atgcatgact 183780
taaaaagtat agtcggaaaa atgtttttaa aagttctgcc aaaatctcat ccacttttag 183840
ttatctaatt ttttaaaaac tctatcctga gttttctttt ttcttctcgc tgtccatttg 183900
acttgaccct taagctagac atgctgaaag aaggatgcca agtccatagt gacagacagt 183960
ggggagtgga tggacgcctg gtgctgggat ggtgcttagt acagggaggg cttctttctg 184020
tggtaaagta ctctaaatcc accctggtta cccaattctg aacgtaccaa aagccactgt 184080
cgatgcccct taattagatg aaattataaa gtgtattata aagagtggat ctctgctgag 184140
catgtatcaa gaagcacagg atggtctcat cttgtcttat agaacttctc aaagccgggc 184200
agggagggga gggaagcaga ggcccatagc acccagcatt tagagctgag ctcatttcac 184260
ctgatgcagc tgtgcattct gggtagtgcc acaagcccca cgcaacaccc agggcagtcc 184320
cttcatagtc tcttgtattc acttagcaag caagttctga gtgctctgtg cttgatcatg 184380
ttcccctcca cccccattca gtttccagtc cacttttctc tctttacctt cccagatcac 184440
ctaagtgtga tcttgggttt gttttaggtt ttgtgtgtat gggtgtgtgg tgtatgtatg 184500
atatctacat gtgcacattt gcacctgcac taggaggcca tcagatgtcc tgctctatcc 184560
ctctccattc ttttgtttga ttggtttttc aagaaagggt ttctctgtat agccctggct 184620
gtcctggaac taactcgatg tgccactact gcctggctcc ctctccatac tctttctctt 184680
tctctctctc tctctcaaga tttatttatt tatatgtata ttattaagat ttatttattt 184740
tatgtagctg tcgtagacac accagaagag ggctcttaac ctctgagcca tctctccaga 184800
cacacacaca cacacacaca cacacacaca cacccattct cttcagacag ggtttctcac 184860
tgaccctgca gccgacctgg caaccagcaa accttagatt tccccctcct cagcaaatgc 184920
cggttggcta cactcagcct tttagtgagt gcttcagatt tgaactcagg cttgcacagg 184980
aagcaggctt catgctgagt catctctcta gccccctgct tcctttttga gtcatccctg 185040
agatggtgtc ccttctgtag ggattgtcat actgcagtat cccctgcaag tcctccagac 185100
actgatgttg aatgagtgtg tgaagagatg gaggcattca tttagagtcc tgtatgaggt 185160
gctgggagta tgcagcagta ggcagtgtga gtagcagaaa cagcagctcc tgagcccatg 185220
tgcctttgga agagaaatca taacttttta ggtacaaagt aactgatcaa accctggctc 185280
tgtgccttgt tgttgttgct gttgttgtaa atcttgttga tatttctgac ccaagccagt 185340
gagaatccat ccttgtttta gtctttgctt tatttttgtt agagtttttc ctcctgtgtt 185400
ggttgatatt tagtttattt cagttgtctg tcctataaac agtaaaggct gctcacccac 185460
gtcttcccgc ccctgcttca accacacatc ccagggtccc cctgctactt cactaaactg 185520
ccaacagttc tgaaaaatag ccctctgctt gaagtgtgca gaagctgccc acaacggtaa 185580
gcagctaaga gaaaccagag cacatatttc ctccaactca ttttttttcc agcccctcaa 185640
```

-continued

```
gtatttgtta gagggagctg agttttcaaa atgagttcca atgttcccgt gtgttaataa 185700
tttgaggttt ctcctgcatg gataatttaa atgttcaaaa ccaactcatg ctaaagttaa 185760
atgcacattg aactagccgt actcctagct taccatatac atggcagtga tggagaggga 185820
tgtgaggtaa agagccactg gcagggaaga tggccacaca gtgctaagga aacctcgctt 185880
tacagtgatg cattgtcagg aaggatgctg ggcctgcccc tgctaggctt ggaaacttaa 185940
actgcgttta aatcatcttt cacagcacca ccacaagtgt cccactgcag attcttgtta 186000
gtgatgccag cgagccctcc gcactgagct gcctgggctg acctcaaact tcgagtcctc 186060
ctgacttagc ctcacctagc cggggttaca ggcttgtgcc atcaagtcta gggtctgtta 186120
ggatttttaa caacctatcc tacttgctta tgaagagttt ggacaatttt gctcactgtg 186180
tgcagactgt gaggtgtaat tggacattga aaagattggt ggtatattct tctagtccta 186240
gcactcagaa agtcaaggca agaggattct gagttagaga ccagcctgaa ctacaagatt 186300
tccttcagct taggctgcct gtgtggccat agggagactc tccagcaagc catcaattgg 186360
tatggcttcc agctgatcca tgggcatggc ttccaatgtg ttctccttca gaagcagcat 186420
ctgctgtttg tttttgagac atgatctgac tgtgaagtcc tggatggcct ggaacccata 186480
atggagacca agctgacctc aaatccacag ataaccaatc ttcctctgcc tccagaatgc 186540
tgggattaaa ggcatgagtt accatgccgg tccataagca ctatttctta cacactcact 186600
gtgctcgaag aaatgctaag tatcatgaaa gccaggaaag aatagtagcc tttttaaac 186660
atgaatgcta ctctcccacc ctcccatctc ttcggcccct ttcatgtccc cccactcctt 186720
ctcaacttat ctcctctttg taccggtgtg tgtgtgtgtg tgtgtgtgtg tgtgtgagag 186780
agagagagag agagagagag agagagagag agagttactt ctgaccactt gggattggat 186840
aacccttggg gcctcacctc tgtcgaagag aagactgact ctccctctct tggtagcttt 186900
aattacatgc agctcttcat ctagaggtgg ggccttgtga gattccctcc atccatgcat 186960
gatggcgtgt cagctgtgtg tgttgtcatt ggacaggtct ccttcagcaa ctctaataag 187020
tagttctaca gaaactacgg agaaagaata gacttctcta agagaggtag agtgttttta 187080
aagctgaaag aattacacac acaagataaa gagtcacagg ggagtacaga gaaaggggga 187140
gggggattgt cttagtcagt actctatttc tgtgaagaca ccatgaccac agcacctctt 187200
atgaaggaaa acatcttgtt ggctggcttc agaggtttag tccattagcc ttagggcagg 187260
aagcatggca gagcagaggc agacatgctg ctggagaaag agctgagagt tttacatctt 187320
gatccacagg cagcaggaag ttacagtgac tttgacttct gagacctcaa agtctcaccc 187380
cctagtaatg cactttctcc agcaaaacca cacccatgcc aacgaggcca cacctcctaa 187440
ttgcatcact ccctatgggc ctatgcaggc agtttttact caaaccacca cagtgatcta 187500
agagacttca caacagggtg tttatttctg ttgacaaatg gcactgtttt ggctgtatca 187560
gaccctgaac taaacccctg gtgatcagta agctactagc ttcagcagct tgggtgagag 187620
aggttggaga tagaggttct ggtaggtggc cattgacgca gcagtgtgag aaggcaccag 187680
tcagtgttca ggagcgactg acacagtaat ttaactggct catttttgtg aacctttcta 187740
tcgtatatca aagattctgt gaaaagatga gaacaaataa acctctttcc tctccactca 187800
gtagtcagta gaaagcttga acacatcata tagctaagaa caatgtaagg cagagtggag 187860
actgggatgt cagagaataa acaaaaggct ctgacaacca aaggaagcaa ctgatatggt 187920
attttctgct ggaaatcagt taaagcttca tacaggaagt aatatttgac tgcaccttga 187980
```

-continued aaacggatga cattttaaag gtgggagaga caggaacagg cctggcacag acaggaagta 188040
tataaagaaa ggcatataaa cacaggatgt gggccctcta gtactgaaga ttagccaggg 188100
gtactcagga gagctgggta gggtggggct ggctgtgatg gaacttaatg acaatgctaa 188160
aatagagagc tgcctctttt tttttttttg agcaaagaga taacaggatc tgattttgta 188220
tggcagccat tgagctctga gtgaatagct taggaggtgt aaaaggtaag attctaagca 188280
agaggggctg gagagatggc ttagcagtcc agaacacttg ctgcttcatt gtgaggacca 188340
gagttcaaat ccctgcacct atgtgagaca gctctcaaag aggctgtaat gccaagaaat 188400
ccagtttcct ccgctggcct ttatgggcac tcatacaaac ttgggcatac acccacatgt 188460
aaaagtattt ttttatcccc tgatgtaaat gttgcttcgg aggctattgc ctctgtctgc 188520
taacctagtc ctggaagctt ctagcctcag tacgacctaa tctaggccta gagtgttttc 188580
agcccctgag acttgctgct gaataagctc accctttcta gttctttctg agctgtagcg 188640
caaacactct ccaagctgac tgattcaatc tggctccccc gccccctccc tccctctcct 188700
gagagttagg catatcctgt tctgtcaaat cattctctga ttcatcactg tgtcactttg 188760
ccactcaatt tgacatcact ttccacatgg gcacttcctt ccacaaacta aacttaacct 188820
tcattgtttg agattaaagg tgtatactaa gggtgtgtct gtgtccatcc aggtagatta 188880
aaggtatgtg atgagactga gccacaccac aactagaaat aggattttcc agtaaataac 188940
acaatcgcag agttcacagt gtgatcagat atcctgcaac acccataccc ccacacacat 189000
gatttttgtt ttaagttgac agatggaaac aacatgggaa caaagccagt gtattttctt 189060
ttaagatttt atttctttat tttatatata tgataagtac actgcagctg tcttcccaca 189120
cacctaaaga gggcatcaga tcccattacg gatggttgcg agccaccatg tagttgctgg 189180
gaattgaact caggacctct ggaagagcag tcagtgctct taacctctga gccatttctc 189240
cagcccccaa agccagtgtc ttttgtaaca gagcatgcaa agatagtctt aaccagcagg 189300
tcctccgtgg gagaattctc tggctagtta gagaaatgca cagggcagaa ggagaagggc 189360
aaaagagttg gagaagggaa aggggctcca gggaggtagg tatgtcgcct taagattgct 189420
gcagggaatg gaaaaggcag ggagagtgcc aggagttcag ggccagccag ggaggctggg 189480
gtgtccttgg ggtagagtcc atcaattaag aagttttcca gcatgggtct cccctccttc 189540
acctttcctc tgtccctcct ctccctttc caggtgcaca tgaacaaggc aggtgaccca 189600
gtcccagcga gctcagatgg ttcactgcct acttcctaga tttgctcttt cagcctggtg 189660
acacagctct gtgttccgct aaccagagac cagtgcctgc tgggatgctg acatgagtgt 189720
tgttcccttg cttctctaga ctttggcttc agcaacctct tcactccagg gcagctgctg 189780
aagacgtggt gtggcagccc tccctatgcc gccccagagc tcttcgaagg gaaggaatat 189840
gatgggccca aagtggacat atgggtgagt atgtcccgtc ttatcacctg tcccctctgc 189900
agatgacagc tgtcctgtca tgtgggagtg cagagcacgt tcacctgcac ttgcaacccc 189960
agtctccccc agcacccaag tcacatgagc cttggctttc aactactccc tttgcacctg 190020
cagaggaccc ctgtgagggc ctgagcagaa gatggctgtg gcaacaacag agattacctt 190080
ttcttgagag gctgggtctg agaaatgttt ggaatctcac cctaaattca tgtctggaag 190140
cagaaatgtt acctgctctg aagacaattg actttgacac tgacccatat tatatcctaa 190200
aaagaggaca agttggtccc atcatctgca catacactaa tggtctcttt tgtttcctcc 190260
aatgctatta accgtccgta ctctctgttt gggctacaga gccttggagt tgtcctctat 190320
gtgctggtgt gtggcgccct gccgtttgat gggagcacac tgcagaatct gcgggcccgc 190380

-continued gtgctgagtg gcaagttccg catcccgttc tttatgtcca caggtaaggg acccgccagc 190440
ataaagccat gactgcattc acggagaggc aggcatgtgg agtaatttca caagtgcagt 190500
gatgctgggt cagtggccat ttggctgctc tctaagctgc agctgcctca gctcgtccag 190560
gaggcaaggt tccttaggag cgaaataagc cacctgcttt ggcttgggga tcgggctctg 190620
ctcagtatca attcatctga gctgttgtac ctcagtctaa gacggctaag gctttgcacg 190680
gcccctggca tacagattag attaactgct gtgtgagtca ctggtgccat catggtgcta 190740
cagtggcatc agtgcgtgtc acctgtcctc cccacagcct ccactggagt gccagagctc 190800
cgcggttggc actgatgccc aggacaaagc aggctttcgt ctttgtcttc ctatggtctc 190860
atttcctagt tctctagttc tccttcagat tctaactatt taggaaaatt ttttaagtaa 190920
gcagacaata ggataatagc tttttggaaa ttttaacact gaaaacggat accagaaacc 190980
cagatgttat agttagcaga caactcagaa cctctgggtt tggcttcagt ttgggatgtg 191040
tttagttggt tggtttggga tttctttgtc accatttctg tgcatgtctg atccactata 191100
gacagtgtta ccttttgtct agctactttc ctcttaagga gagcatgcac acctttagaa 191160
tatgtaggtg gagtgtgggt tccgtttaac tgagtcagct cagaactgat gacttagaag 191220
gtcatgtgtc aggtgatgat aatgctaagg aaaggggaag aagaaacctt tagaatggtg 191280
ggtgggagat cgttcaaaga ggaacagttg gaaaacgtga catttcaggg acaactggaa 191340
acgaaggata ctggaggatt actgcccgaa ggccccaggg agggagcaat tggggtgtgc 191400
ctgaaaggag ttgagcatgt agactctctg cttttactct gctggaatcg gaagaattag 191460
aagctctctt aaaaatagag aataatatgg ttagacctgt ggggtttttc taaattttta 191520
ttacgaaaac tttttaaaaa ttgaaaagat ttttttcatc agcttttaaa gacaatccct 191580
gtagttgcta cactgcttgt tgaaaggaga gtgcagtgca gtgctgtgtg gtgcagtgca 191640
gagctatgtg gagtagtgca gtggcatgta ctatcacgca acacagtgca gtgctgtgtg 191700
gtgctgtgtt ctaaggcaca gcacagtgta gtgcagtgtt gtgttgtgga atgctgggca 191760
gtgcagctca gtgtaatgga gtgttgtgca gtgcagctca gtgaagaagc ctggttggta 191820
ggagacttag agagcatgtt cccagactga ggaatagagt gatttgggac ggatcgctgc 191880
tgcacactac ctggttgatg tgtcagagga attttacaga cattagctcc cttcagtatt 191940
atgagctata tgaggttgtt accccacttt gcaggtggtg ccacatccag gagagtgtaa 192000
gcagtgtccc catgtagaac agcttattag tggctaaact agaatttgag ccaaggcagt 192060
atgtctcaaa taatgtttga tattgcattt aaggtaagaa agaatagtta caggtaaccc 192120
cgagatttgt acctgagcaa cagaaaggat gaatttgcta ctaaatcaag gataactgaa 192180
tcgtcaacat tttggagaga tgtttttaga aatgtcaagt ttgtggtgcc tattagccgt 192240
ctaaaagact gttctggtca gcagttggaa aggagagagt tgtaactgtc aaaactggcc 192300
tctttgagtg tcatagaata tactctaatg ctaccaggaa ggctcgctct ctgtgcctct 192360
caggatggtt agagatgagg aaggtgacaa gggccagaag aatggttagg gaggaaagcc 192420
agagtcactt gaagacaagt gaagctgccc caggaagctg aggtagagga cagagaactg 192480
agtgctggat ttagaggaat ggagctccct ggtggggttt ggtgccactg ccacgggaag 192540
ctgatccatg cacacagtag gaccgagtgc aaggcacagg aaagggggaa gccttgactc 192600
ttcccagttt gactgtacag tgatggagac agagaagtgt gctctggggg gctccaaccc 192660
tggtcatcag atgtcctgcc agtagctgca tttcctgttg tcatggtgac tgcattttac 192720

-continued

```
cattccctac taaggaaaaa aatgaggaca gttttaggtt cactgcagaa ttaaagggac 192780
agaagatgtt catatgcccc ctgcctcact tcccctccca cacacataca cacacacata 192840
tgcacacgca cgcacgcaca cacacacaca cacacacaca cacacacccc ttcattcaga 192900
gcctgtcatt tacaagaggg ttcactgtca gggttgtaaa ttcgctgggc tctgacaagt 192960
gtataaaggc atttatccac catgatcctg tcagacagag agccccacct ctgggatgat 193020
cctgtgtgct ccccccattc ctcccatctt tctctcccca ctggtgatca tcgtctccat 193080
acatttttac ttccgggatg tgatatggtt ggaagtgccg ttttacgttg gccttccact 193140
taggaacatg cacaggcatg caatgtctct tgtgtcttgc tagctcattt ccctttacta 193200
ctgagtactc ccttgcctga atgtactaca gtttatcctt ttgcccactg atgagtgtca 193260
tggctgctct ccagttttga cagtttgtaa ctgagattgc tttgatagcc ttgtgcggat 193320
ttgtgtatgg acacacgttt tcggctcact tgagtaagtg ccacggagca tgcctgtgag 193380
gccatatggt aagagcttgt ttagatttgt agtagactgc caaacggcct tccctagagc 193440
tgggctgtgt tgttgtaaat aagagttctt actgctgccc gacttgcggc ttttgcctga 193500
ttagcctgtg gggcgtggtc ccctttcaca tgtgtgtggt gttcctttca tgtgtagttc 193560
tgaagtctgt gatcctgaac atccttgtat aggtgtctca tcaggtcttc atttttttatt 193620
cctctccaac aaaatctcat agtgtttttc caagctgcct ttgaactcct gggcttacac 193680
agtcctgcct cagtctcctg aggatctgga attgctcgtt tatttattag ggtttttcac 193740
tgtcttctaa accccattgt ttcttactgc ttctgagatc cattccttct gtcccctaag 193800
tatactctta gtcatctctg ccagattttt cgttctctct taagccttac atctcctctt 193860
acccaaatga gctgtctgag ccatctcgtt tactgccatg gcttcaccga tcccttttgg 193920
ggactgctcc caattaactg tctccaaatt ctctcctgag gtctagggcc acaaatatcc 193980
atccatttgc tatttagcat ctttaaaaaa attattttcc ttgttttgta gtactgagac 194040
tcgaacccag aaccttgagt atgttaggtg ggcaccctgc ccctgaacta caacctgtta 194100
ctcagtgtct tcctttaaca tcttgaaatc acattcactg aagcattttc caaaatgaac 194160
tttattccct atccacagtt ttgctctatt tggtgtccct ggtgtccccg tctgaggctt 194220
ggcagaaaca agtcttgatt gtttcttctc ttatcaccac cagagccaac tggttagtaa 194280
aggctgtgca gtcagtctgc tattccagta accatgctgt catcttctct tgcctaagtt 194340
agactttgtc aaatctgtgg atgctgagtt ccatccttgt cttctccatg tttctgcgtg 194400
accttggcag acacgaataa taaaaactac acctcacatg caaacctcac aggtacacgc 194460
atacaaacgc acaaatctga tgatatcatt ttatagttta aaaatgtttc agcagtttaa 194520
cattgcccta aagtttactg ctaatgtgtc taaagcactg aaattcaaga atttttacta 194580
cagccatgat aaaaaaacat actttatact ataacttaga acacacacat atatgttttc 194640
aaaaatcaaa atatattgtt ttgagacaga gtctctttct ataacccagg ctgattttaa 194700
actaaagaac catctcgccc agtctcctga gtgctggagt tgctggcagt ctagcctgat 194760
cgagtgctaa gccgatgatc ctgagggtga tggtcaagat tgttctctgg cctacacacg 194820
tgcatattca agaaaaggca aattcagata ttttccgggg tttttatctt tctgaacctt 194880
gtcttactac tatgacattt atcaaaatat actgtaattg gaggctagag tggctcagca 194940
gctcagagca ttgtctgctc ttccagaggt cctgagttca actcccagca accacatgat 195000
gggagctgat gccctcttct gacatgcagg tatatatgca aagtcatgta catgagaata 195060
aattggtttt tcgagacagg gtttctctgt gtagccctgg ctgttctgga actcactttg 195120
```

-continued tagaccaggc tggcctcaaa ctcagaaatc cacctgcctc tgcctcccga atgctgagac 195180
acatatattt tttaatctta atttatttct tattgtaatt gattctttca ttataagcct 195240
tccacaccag actctgaact taaagaatat gcagagaaag cctccagcct tcccacagtt 195300
gtttataatc tagcagtgtc tggtacagca gcacttccta cacactcttc tgtgtcagag 195360
tcaactgcac cgaccttgtg ttccaggggc tttcattgac tcttaaaatc aggctgctgg 195420
tggtgcaggc ctttaacccc agcctgggag gcaggtagat ctgttcaagg ccagcctggt 195480
ctgcatagtg aattaagacc ttgtctcagc ccggcggtgg tgatgcatgc ctttaatccc 195540
agcacttggg cagaggcagg cagatttctg agttcgaggc cagcctggtc tacagagtga 195600
gttccaggac agccagggct acacagagaa accctgtctc aacccccccc cctcccaaaa 195660
aaagaaaaga ccatgtctcg aaaaagaaaa atgagaaatg tacacaattg tgacttcttc 195720
tgtagcacct cacccccgcc ccctccccca gtcctgtttt ctcttgttct gacctcaggc 195780
cctgggcttt agtcaggata gtgtttgtcc tttctcagac atagcaagca cactctgctg 195840
tcccctcagg tgggcactct gaggcctcta ttgacaccgc cctccccact gccaccaaca 195900
gcttccataa ttgtgtttgt cttaaccctt gtctcagctc cacatgctct aaattgtttt 195960
cccacctccc atgtcatcat tgtcgttgtt gtcgtcatca ttgtcatcat tagctggcag 196020
ggatgagcgg ttttggataa gttttgttca ctgctatatt cccaggccat ggggtagtgt 196080
ctggtgtcta aactcataaa gatgtattaa aggagggaac tcatacacag gtttgttaaa 196140
aatacagtct acgggggtgg gggtgggtac ggcccaccaa agcccttcca caggaaatac 196200
tctcactcaa acaatatcaa gaaattacat tgtgcgtgtc taatctcagc acttgggagg 196260
tgaaagcagg aggctcagga actgaaggtc attagctgct cagtgagttt gagtctagcc 196320
tgggccacat gagatcctgt ttcagtcctt gctccaccct taaatacaca caaaaataac 196380
tacatttctc taaggctaga gtttgtgaag tattttcctg tatttcgtct gctttaaacc 196440
ctgcagctgt gctctggaat tgttactata tactattttc ctgcttgccg tgacgtgtag 196500
agaagtgagt tgccttgtaa aagccacaca gttcacccca gtcagccact cctcggatgc 196560
tgtattgttc tgctcaacct cactgttata aaaaaggggg gggcaggtca ataaaccact 196620
tcctctgctt ttccagtgtc cacagtattt cctgtgagga gtttggatat cctccatctt 196680
ccaccccagc ctctcagacc atgcaaggct cttcaggcct ccccaaagca ggctgctgag 196740
catagctcct ggcaaataac ctagctgctg aaaccacgct cctagtgagt tatcatgagt 196800
gctgaaaggc tctgagaatg gcagcgtgat tgtcccaaat agtgatactg tataatcccg 196860
gagaggagat tccccaagtg aatgaaacaa tgctctgtaa gatgaagcac agaaagcaag 196920
aaccagtgga ggaaaagagc tggcggtcac catcttactg catgctcgtt ctcatcctca 196980
gcgatgtgca tgtgcttagc tttatcctgt accatagacc tgaatcccaa gactcatcag 197040
aggctggtac tatccatatg gtgaggcaca gaggaaaagg aaatcatagg atattccttc 197100
aagcatcatg gagttcagtt tcaagggaag tacacttgag agtctcaccc ggggtcctct 197160
ttctgtctct gggcatagct gtgactcact agacctggaa ttagctcttc ctgtggaggt 197220
cgaagctgtc aggtctgctc tccctctttg tgcttctgtc tctttcctat agagggcagt 197280
gtgggtgaaa aacaagacct gttctctgct gtcaccacct tggcctgagc ttactgattt 197340
ctgtgaaaag atgtagaaac tcagtcaggg ctgagagagc tttccacatt agcctgtgaa 197400
acactagaag atcctttcct ctatctttta tggccaagtc agactccaga gtgtctccag 197460

-continued ctgggagatc agtctctgaa gatggacact gtttctatag taactgtggg atgaagttgt 197520
cttctcatag taggtcaaag cttgttagac acgagtgttc ttccatagct gtcctgagat 197580
caactaaggt cacatattgt tacatggcat ttgtcatggg ctaatgagtg tcatgagtgg 197640
gttttaacta cctagtttat tatggcctaa aacaaccaga tgtgttttac acagctgcat 197700
cttctggaac ctagaggcac ctggcaggaa ttacatgtct tttcagtgac aattttgaat 197760
gaaatatgga aggaatcaca acgttggtct tatggtggtg gataccactc aggagacaaa 197820
ggcaagcaga tcctgtgagg tcaaagctag cctgctctac atagcaagtt ccaggacagc 197880
cagggctaca taatagaaac tctgtctcaa tgtcccaacc tcccacccca ccaaaaaaag 197940
gaaagttgag aaaggactta ctacttaact gtagactctc ctgtcgcttc ggcattgtac 198000
tattaaagtg agaggtagct ccccaccgat ggttggacac actcaggaaa ccaattggct 198060
ttataatctc ttgttattat tttgtagatg actagatcaa gtgacttctg gttagtttgc 198120
aaaggtattt tgagccagtc atcccggcac tcaggaggct gaagcaggag gaacataagt 198180
gagttggaca ccagcattgg ttacatagga ggttggaggc cagacggggt tacataatga 198240
gaccatctca cagcgaaaaa caaaacaaaa caaaacaaac tatttgattt actgtaattt 198300
ggctctccta gtctctgata aatcatgttt gttacaaacc atgtttgttt tgttttgttt 198360
ttaaggttta tttattttta ttatgtataa agtgctctgc ctgtatgtat tcctgcaggc 198420
cagaagaggg caccagatct cattatagat ggctatgttg gaaattgaac tcaggacctc 198480
catagccatc tctccaggcc cagaccagtg tttttgagtg aagcttcttg gattgaccca 198540
gagctcagag ctgtcatcca gggagcattt cagcctttgc cacaagatga taaggggact 198600
catttccttg agctcatata aaatgagacc tggtctagcc agtgtcagca gtggccacat 198660
ctgactccac ccactgatgg aagccagcaa tatacacatt tggttactag attcactccc 198720
tgataataca tttttaaacc cttggatatg tgttttgcct tatcctcttg ttaaatacca 198780
cctatgagca aatatagtcc aaccatttac ttaacggaag gaaaattaat ttaccatgaa 198840
gaaactgcac tgatgctgag tgcattgaga tctcttgtgg gcaatatttt tgagtcctta 198900
ttgattagac ttcattggga cttaattagc tgtaatattg cataagcatt ttatcactgg 198960
gaatgcagat cccacttaca taatgcttct gatggagaat atggcctaca gctactgcca 199020
gaaagctttc acttagagga aggtaactct gccctatccg agtacccatc aagaaccaca 199080
cagtgtctcc ctgggcgaaa gcactttgtg gagaggagca agagtgggaa tgggcgtcac 199140
ttgcccgagc tataagtgca gaggcacgtc tttggaggtc tgctctccat ccagggagaa 199200
aaacctgtgg tgctttggtg tctatccacc tgggaacaca tctcaaacca gagagctggg 199260
tgtggtgcca cacctgtaat cccagcactt ggcaaggcag aggcaagaga atcacaagtc 199320
accctcaact atatgtaagt ttcaagggca acctggggtc tatgagaccc attttaagac 199380
aaaacaaagc tagacctcat ccgagtgaat caggcctcgc cctagtccca tgagtttatc 199440
taagtttcta gaaagccagg gatgaaggtc cttgatagtg ttccagttat aactatacct 199500
ttcaagcaaa ctgttttctg atttatggaa agcctttata gaagaataaa gaaaactcca 199560
agtagaagaa gcttgattcc agaggttggg tgataactaa ctttgggttc ctgtgcacta 199620
ggcacagttg atttaactac ttagttctca gcaggctcta actatcccgt gagatatgct 199680
gaatgctggg ttgtttgatt ggtataaaaa tgaaggcata gcaaggataa gagatgctca 199740
cttagaaaat gctagaacta acctttgaac cttagccctc tgaccccaga gagttcctaa 199800
ccattctcag ttacagttag ttctcgtaaa tagatacctg gtaaggtttt cagagtattt 199860
ggagagtcct ggagaggata tcaaagaaag cattaatagg aggccacgag atggcagtgc 199920
aggtaaaggc acttgccaca aggcctgggg gcttaagttc acttaccaag actgcccctg 199980
ccccatgccc acctacacta gagcttaaat acacattttt aaaacttctt aattaatagc 200040
acatacttta gactctggga gatttctagc tccagccaac ctcttaccaa agctgtcttg 200100
gttaaaaacc aaaacacaat gctattttaa gaatagattt aacttttcat tatctgtata 200160
gagatgatga caaactttat tttctgttta tagagaaaag tggcagagcc aggtttgatg 200220
gtgcatgtct acagccccat cagctggagg gatgagagca aactagtgcc agcctgggct 200280
atatagtgag aagtagtttc aaagactggg aggggaagag actgagagac caagccagga 200340
gggaatctga gaggatatga gaatgtttta tttgcggttt tctttctgga aaaagtagtc 200400
agcattactg agacactgag tcacaaacat ctgaaggcct ggagcgcaaa gcaccagact 200460
cctaaagcca tgtagctctc tgtgcagagg ctcctcacag cccctctcca tctgcgcagc 200520
cagctctcct gttttgatcc ctgacctggt cagagcttgc gagtaacaga agctgacagc 200580
agtgtgccag cttgcatcca attctgacat gcagtttaac tgtttgaagt tctgaaagtt 200640
gttcattatc cacagaaagg gatgttttag agattggact gccggttaat ttttgttccc 200700
attttggatt ttgagattta gaaaaataga gctgtctaaa atttggattg ctataaaagc 200760
aatctataac taaggagtaa acattgatgg gaagcatgct aaaattgtcc aaaatataga 200820
ctttggtgct gaacacttga gaatcccata tgtatttaaa catatgtatt gagcatatgc 200880
cttgttgact ggaaagacta agagaaacta gaccaaacac cttcttgtac acacttagag 200940
gaagcatggg tttctgggta attgtttctt acactcttac aatgccctct ggcaaacaga 201000
tggcttctct ttccaccagc tcaaagaagc tgtgcgcgtg cagggacctg gcacgtcgtt 201060
tctttgagac tgttcttctg cacagacccc ggagcagagc tttatgatgg cactacttga 201120
aaggttcagg gatggcaggc tttccttcat ggggtcagcc cagagatgct ggcatcccag 201180
tcccacagag ctcagttctc cttgtatgat tccttgattt gcaacgcctg tctcatccat 201240
cccccacaat caccagagct caggcttcag taggactgtt cattttagcc cctgacctca 201300
ttagcaggtg aacacgggta cacacacaca cactcctcac acatgcgcgc gcacacacac 201360
acacacacac acacacacac acacacacac acacaccttt ccatgttctc ttgctcccag 201420
tctcgcacac actcgctgtc agcccacctc acagtccttg tcatctcatt agtagttgtg 201480
agcatgccct ctactgcttc gtttggaacc tgcttgtagg tgaatagtgc cgcaacagcc 201540
tttggagctc acacagcacg tcatcagctg gatgcgagaa ttgtttggat ttgtttttct 201600
aaagctatgc tgggtgctac ctcaaacact aaaaatggtc attgtttgtt tgtttgtttg 201660
tttgtttgtt gaggcaaggc ttctgtgtag cncaaactgt cctggaactc actctgtaga 201720
ccagactggc cttgacctca gagatctacc tgcctttgcc ttccgagtgc tgagattaaa 201780
agggtgtgcc accacgtcca gcttctaata atgtattttt aaaggtagtg tttagattaa 201840
gaattctcta ggggggctgg tgaggtagtt cagtggataa aggccctaac tacacaagcc 201900
tgctaaccca agtttgtttc ctggaccact aaccagtcca tcctccctta aaggtggaag 201960
agaatgaatt gaattcacaa agttagcctc tgacctctac acataggcca tgtatgcatg 202020
catgtgtgtg tgcacacaca ataataataa aataaaccac ccccagaaat ccaaatgctt 202080
agaagactga ggcaggagga ccatgagttt aggattaacc tgagtctggc ttatctcaaa 202140
aaaacaaaga aaggacaaca ataaaaataa acagactcta ctgtttagta tctgcctaag 202200

-continued

```
tttcttaatg tctcagtttt aatttcttaa aaaatgtaga ttataatagg tgtcctgtat 202260
aggttgaggc tttacaggac gtagtactct gcctaccaca ccatagccaa ccatgataat 202320
atgggcagga atgtctctgc aggaatcact ctactgacat ttcatttccg tctctctggt 202380
tttgacccca tacagcagca cacctaaatc tttagtaaaa taatggtttt ctggcaactc 202440
cagcttgaag ggtgggaatg actgttctgt tgtgacttct taggtatttc catggtagtc 202500
agcctccaag tgaacaggca gaagccattg ttctccaggt ctgttgcttt tggtttggga 202560
acaatattga gcacgcactt ggccttgatg acctcctgtc tgggccccta ggtactgagg 202620
ctctaggaat acacctccac agctagcctc tgaggacggt gctacagctg tcagcaaggt 202680
ttatcagtca ctgatgcgcc tgccatttgg gaggacctgg ctcatgtttg gacattgatg 202740
ctgttctgaa aggtgcaatt gctgtcttgg aagcttccca ttcttcaaac atgagtctgt 202800
gagtctgtga gtgacagcag gagactacca tgtgacgcat ttctagtgaa aatgagatta 202860
ctacatcata cacagaccat tcctttatca ctgtcacaga gttttgagaa ttgggggtag 202920
gtgaccaagg agttccttat gtccccttgt tatgcagaag agtgatctgt aaaataagta 202980
gctgtgaccc tctgggaagg gtcagtgagg agccactttg ctggggcgtc ctgaagagcc 203040
gacaggttcc ctctgctctg cttccttctc cgtctgctca cttgagtatc ctgtggttgt 203100
aggtttgaag acggtcattg ccttcatttt cacatccttt ccatattttg tgtagaataa 203160
cgtgtccaga gctcgcctga attcaatttt atgagctata tgatactgag aaaacgtggc 203220
ttgatgctga gttcggccat gtttcaccct ctgcagcaga tgaaatgtgt tagcttctga 203280
ccgtcggcca gtttctgctc catgtgacag ctaggatcag tgcttgccct tgtgccaccg 203340
acacaaaaca gagtccctaa tctggggaag ctatgaaaac tctttggctc cttgaacaat 203400
caaagattaa tacaagtttg tgtacataat ttcataattc cttgtgggtt ttttggtttt 203460
tgggctttgg tttttttttt tgtagtgaga ctttcagggt ctcttaggat aaaatctgtt 203520
aaggatgact gagaagaagt ttcagaagcc tggagttgag atttgcactg ggacttatga 203580
caggttattt tgtttgtttg ttgttgttta aagaaattgc ctaggagaag aactctttgt 203640
tttaaagcaa gcctgttaca gacatttttt ggccttggcc ccctaatgtc ttacatgaaa 203700
ttttgtgcag aaagaccaaa ggaaaagagt ggactgccat ctagaggctt gaacaacaat 203760
gttacaactt caaaagctta accggcctct gtgtactcaa ctttgtgaat taagaacaac 203820
ttttttcttt cttcttctct tttcttttct tttcttttct tttcttttct tttcttttct 203880
tttcttttct tttcttttct tttcttttct tttcttttcc tttcctttc cttttccttt 203940
tctttccttc cttccttcct tccttccttc cttccttcct tccttccttc tttctgtctt 204000
tctgtctttt tgtctttctt tctgtgatga cagacatgta tgtcatagat gcttcactgc 204060
tgtgtctacc cttgctactg tagacataat tttagaatgg agatgccatg gtctttgaga 204120
taggaactgt acttgaatat acctttactc acaaagtaaa aacaaatcaa tgtttttatt 204180
tagcatctgt tttggatttt acattaaaaa ttaagagtaa ttcttttaaa tgactctgag 204240
tgtatatttc atgataatga tgctactata agtggtgtag aaattgcaga gttgaatttg 204300
ttctggaaaa aaatagatga ctagaatgta tatccgcctg atgatgcatt ataggacagt 204360
caatagcata tccttatggt agctgaatgt tttaacattt caaagtcttg tttgttcatt 204420
tataaatgtg catctttata gtacctgatc taggattgtt atgaagacta agtgaaataa 204480
aaagcatctt cacgatacag tcttacttgg ttaagatgaa tattcaataa atattcatac 204540
attcagttcc cattagatat aatgatcatt tttggtattg gatattccat attgcagtaa 204600
```

-continued aaaggacaca tgccttgcat tgtcgcagag attgtgtcag caagcacaaa tacgaacaag 204660
agaagtcctt aaataattca tgtaaagaaa agtcacgtga cacagtgaag cgtaaccgag 204720
cctgttttca tgtcagaggt cagagatgag tttctgagga agtgacagtt aaactctttt 204780
tttttttttt tttttttttt tttttttttt ccattttta ttaggtattt acctcattta 204840
catttccaat gctataccaa aagtccccct tacccaccca cccccagaca gttaaactct 204900
tacccgcatg acaggcagcc ctccatgaga aggcctgtgg agtttccatt tcaactagag 204960
gactaagcat ggaggccaga cagctaagag aacttcactg tgggaaatca gacaggaact 205020
ttttaggccc aggacttaac attttcattt tgagggtcat gagaagaaac tgtagagtta 205080
ttaaagtggt gatgttagcc ttagccttag aaaaatgcca gtggagacta agacagacag 205140
aggcaggaag cccgcttggg aacctttct ggctgtctca gccagcagcg acggcttggg 205200
atggaccctt tggctctgta ggattgtggt taacggcacc aggtcagggg ttaggggtaa 205260
attcttgggg taaactgctt acattgctgt gtttggatcc ctagcaccca tgcaaaagta 205320
gacatggtgg tacacacccg aaatcccaac actgagggtc aggatgcgaa gatctcgggt 205380
tcaccagcca gctcatatag tggagcttca ggcttatgtg agtcactgtc tcaaaaagta 205440
tatagtggaa acaattaagg aagccatcgt agcgttacct ctgacctcca tccttgttca 205500
catagacaaa tgaccctgac acacatgcac acacccatcc ttgttcacat agacaaatgg 205560
tcctgacaca cacgcacaca cccaggtaga catccagact attggtttgg atctgactgt 205620
ggcctctggg ctgaacctgg gccatttcta aagtgggaag gatgttcaca aactgctctt 205680
aggtttgtgg tggggctgag gtagcagttg taaagcgctg tgaatacgtg cgcaacgcgg 205740
cctcatcact gtctgccgcc ttccctatga ctgttgctcc agcatggtca tcagagctcc 205800
cagtttacac atgagagctt ttgtaaagtg ggtggctttg aaatcagaat ataggcttct 205860
gttttggaac tctctctcca ggataacctg gagtgtgagt tgaaggcaga agagaaacag 205920
aactaaaaca gggagccgag actctaccta ctgctcttac atctagccct atcagctcta 205980
ccagcccccc agaccccccca ctagactgag gacagctgtt tgtctgttgc agagtgtgag 206040
cacttgatcc gccacatgct ggtgttagat ccaaataagc gcctctcaat ggaacagatc 206100
tgcaggcaca agtggatgaa gctcggagat gcagacccca actttgacag ggtaagccgg 206160
acccttgcct cagggaactc ctgattaact ccttctcttc ttcagtggtt gtgatctgcc 206220
taggacctaa agagatgagc agtaggaacc agctgctggc taagaccagt ggcaggtgaa 206280
ttcacaggga gccgcgggat ccagcaaggc tgtggagaca gtgatactgg gcattaccac 206340
agaaatcata gtttgctttt gacttctgag acagcatact cccagttctg caggtcactg 206400
ccaccagagt gcctttcttg tcttgagtgc gctcccttca acagcttctg tcacatactg 206460
ctgcacccca ttatgatcac tctcgtaccc caggagctca ggaagcagcc ctgagggttt 206520
tgtcagccca tagctgattg ccagaactgt cttgcttaga cttcgtatga cacccacaga 206580
atctgcagca gtggggcata gaacagcttt gtcaatgtgt atcccatgcc gtgttgatgt 206640
agttaactgg ggtctgacgg cttgcctcta taactgtatt atattacagt taatagcgga 206700
gtgccagcaa ctgaaggagg aaaggcagtc ggaccccctc aacgatgatg tcctcttggc 206760
tatggaagac atggggctgg acaaggagcg cacacttcag gtacctaaga aggagtgcag 206820
agcagtgaga taagcggccc ttcctcttgc ctgcctttcc tgcagtgtcc ccttcctgag 206880
ctcgtgggtg ttcctgcttt cctccctttc cctcttcctt tgcccttcct ggacctgaga 206940

-continued gggaaggaag gagctgcttt gtgctgtgcc ggttgtgtct ggtgtgtcag tgaggcgcca 207000
cctccgagtc tcactctccc tttctctatt ggtagtcatt aaggtcagat gcctatgacc 207060
actatagtgc aatctacagc ctgctgtgcg atcgacacaa gaaacataaa actctgcgtc 207120
ccggagcact tcccagcatg ccccaagcca tgactttcca ggcaccagtc aatctccagg 207180
tgggcaatgt ctctgagacc taggtgagaa gaggttatac cagggcaagg gctagctact 207240
gctcatcagc ttttggtcag gagagattca tattcatcca tctatctgta tctcctccct 207300
tgtcagaaga ccatcaaagt ctgggtcttt ctttgagaga aagtcgcatg gcagaaacag 207360
ttgtcttctt cgttttgttt aaagaagtag caaatcattg tgagatacca ttctccctaa 207420
agaatgcttc cttgctgtgt tgcctgagag cagaagaacc aggctttggc aatcaagact 207480
gctttgaata taatcctagc cattgggaat ctgaggcaga ggaatgagtt caaggctagc 207540
ctgggttaca tagcaagagc atgtcttaga ggaagaggtg agggaagaaa ctactttgaa 207600
aagctgtcat tatttcttct agtgtctcag gtctctgtgt gtctgtatgt gctgctttct 207660
aggcggagca gacaggcact gctatgaacc ttagcgtccc tcaagttcag ctgatcaacc 207720
cagagaacca aattatagag gcaagtagcc acatctgatc actgtcaact gaaaccacgt 207780
ctcttcccat agctacaatt cctttccttc cttctgagtt acttctgatc aactgtgttt 207840
ccctccacct tagcctgacg gggctgtgaa cttggacagt gatgagggtg aagagccttc 207900
tccagaagcc ttggttcgct atttgtcaat gaggaggcac acggtgggag tggctgaccc 207960
acggtaagta cctggtcagc atcctgctca gccctaagtc aaaaggttcc gccagggtga 208020
gtgcctcttg tggcacgttt tctgagaggc cacactaggc catggccaat ctgactagtt 208080
attctcccta tatgcagtgc ctcttagcag ccatgtgagg agagtgtaat aacatctttg 208140
ttgatagatg gagttcttct agtctaagtc atcagaaata ttctgtagta ttcagtcacc 208200
tttagaaaag tgtagtagtg caagcctttc atcccagcac ttaggaggca gaggcaggag 208260
gagctcttga gttcaaggcc agcatgatct gtatattgag ttcaaggaca tatagagaaa 208320
ctctgtctca aaaaataagt aaataaatct gccaacttta gcagctttta gagatgctat 208380
ctacctcgtg ttctatattg gaactcttct agaaagagga gacaaggtgg tgtggcatca 208440
tttatatatg tggacagtta gaggcacttg cctgacacaa gcaagaatca ggattcagta 208500
tcctgctttg tctcaaaatg aacaggaatc ccaaaacata tttcccaaag tgttccttga 208560
ggtcctcgtg ttggggaagt ggattcagga ccagctcact ccatttctac tctgcagtcg 208620
agacctgtca gcatgagcga cagcccatct tgttggtgaa tgttttcctc actgagcagg 208680
aaagagaggg ttatatatag ctagccttgt cctgagagtt cagctcaggg cggagctggc 208740
tttcttatgt ctgtcttctg agtggatccc cagaagaaac gcccatgcct gctcgtttgc 208800
ttgttttccg tgcttgttct cgatgtgatg aaacaagcaa gtgagagaac atttgggttc 208860
cacacagaat gtgtcactgc caacgagggg tggagtcctg agtcgtgatt agtggaaaaa 208920
tctcttattt aaagtctgct gggcatgaca gtcccgaaca tccagttctt atctgtcctg 208980
tcagcatgga cggtagtaac cgaattcttt ccctggtgaa tcagttgcta cttcaggcag 209040
tcattgtctt agcggatgcc ctgtgctctc tagaaacttg ctgttcccct ccaagctttg 209100
agagcctggg ctagagttgt gccagcctgt gtgtctccta ttggctttcg aaagggatca 209160
atgaagtaga ctccccaata actcagagtg aaattccaca taggagacag actccacttt 209220
gctttagtgt cttagacaga aatagaaatt taggaggagt aacgtccgga aggtggtgct 209280
tctgccggca tagagacctc agttcagatc ctcagtgttc atagagagcc agctgtggca 209340

-continued gcctctgttg taactacagc tctgtagagt ggagacaggc agatgcacca agctcacaga 209400
cagcctgaca acaagcgaga ccgtgagaga cccgggagag catgggagag gaaggcttcc 209460
tacctctggc ctccatactc atgcatagac atatgttggg gcactcacat gcatttacta 209520
tcgtacacac atagactaca tctgcacaca catgtataca catatgaaaa aaatagaaaa 209580
agtcagacag tggcacacac ctttaattcc agtactcaat agacagaggc aggtgggtct 209640
ctgagttgga agccagtctg gtctatagag caagtaacat gacagccaag gaaggataca 209700
aagggaaacc ctaacccaaa agaccctcct acccacctcc aaaaaagatt tgtgtgtctg 209760
tatgtgtgtg tgtgtgtgta aaattttttt actgtactag ttgtagcggt agtattgact 209820
actgtactag ttgtggtggt agtattgact actgttctag ttgtggtggt agtattgact 209880
actgttctag ttgtggtggt agtattgact actgtactag ttgtggtagt attgactact 209940
gtactagttg tggtagcatt gactcagact taagcattct gagtaaccac acttctctct 210000
tcctgtttcc cgttagcacg gaagttatgg aagatctgca gaagctgctg cctggctttc 210060
ctggagtaaa cccacagggt ccattcctac aagtggcccc taacatgaac ttcacgcaca 210120
acctgttgcc catgcagagt ctgcagccaa ctgggcagct tgagtacaag gtaggaggcc 210180
atggaaagga cctgcccaca agaaacaaac ttgatcttcc cttggtaggc tctgacagtt 210240
ctgttccagt actggagagt ttcctgaggg aggggagttc ccttctgtaa actgctgtgg 210300
tgatgggcga tatctccagc ccccctcacc ccagcagatc ctctcactgt agtagatgag 210360
ggtgggctgt ttactccgtg ttttcccatc tcaccactgt atctgcctac tctcctggca 210420
ggaacagtct ctgttacagc cgcctacact acagctactg aacggaatgg ggccccttgg 210480
ccggagagcc tcagatggag gcgccaacat ccaactgcat gcccagcagc tgctcaagcg 210540
cccacgggga ccgtccccac ttgtcaccat gacaccagtg agtagcagcc cagcctggct 210600
ttctcaaagg tttttgataa gaagtctgta ataaaggggc tggacttggc tgaaataccc 210660
acagtcctct ctaatacagc atcctgtgtt ttctctgacc tgcctcctct tccacagaga 210720
cacctcggag gactttcccc agcagatgca gttcacacgg gcagtgctct ctagaatgaa 210780
ctgcttttta attttcatct tataaagaca agctggcagg gggtgcacac gtgcttcagt 210840
gcattcgtgg ggcttaaagg acagctttag ggggtcagtt ctccccttcc cccttcatgt 210900
gggtagttcc tcaggcttgc aaagcaagct cttaccgctg agcacctcac cagctctcct 210960
gtcgtcagca ccacctgaca tttctggctc agcctcgggt gatcgtgtga ttacattgtg 211020
gctctaactt cagtcggtgt ctcagtcaca ccattttgta taatggtgat atgcaaaggt 211080
ttaatctcac agattggttt ctgtttattt ctggtgtgtt tctgtcatgg tcctgtcaga 211140
ctgaatagta tctccacagc ccttctgagc tatttggggg agtattgctt gaaatcacat 211200
tacttggtga cttctgttca ccgatccatc gtggatcaat acgttttaaa acactcggtt 211260
aacagaagct cactctggct ctctctgctt tacttctcct gggtttggtc acagagcggt 211320
gtgtgagccc atgagtcacg ttgtcagttg cactgcagtt cagaaaacag ttgcaccaga 211380
tctggtggtg tgctggttat gatatcaaag ccgagttccc ctgtatggag aaaagcttat 211440
ggagccgtgt agtcccagcc cctacaagtc aggccaggag ggtcagtgca gccttgcagc 211500
taacctggtc tacattgtaa gtcccagtct aaccacagct acaaggcaag acacagcctt 211560
aaaaaaccag catgccagat tgaatgccaa agtgaatgac atggctgatg ggtggcagag 211620
gctcttcatg ggcaaggttg gcattggttg gcaaggatca gcatcagcat tgtggatagt 211680

-continued

```
ggggtgactt cctctgtcca ctggactcgt tgctgccaag gtcactaaca agctcttgtt 211740
gataaatcca gtaggcattt ttaatcttta tctttttgga tggctcaact ctattagtca 211800
ttgttgacct tcccctcctg ccccccttct ccgtagtact ttgtttttgt tttttgtttg 211860
tttgtttttg tttttgtttt ttggcttctg tagttatcct aggttttcct tcggccagtc 211920
agtcccctct gaggtttctg ctcaggattg acttagccac caaggcccgt ccccttcctt 211980
ctctggatga gcctgtccac ttcccgtcag ctgccatctg gccttgcacc caggatgctc 212040
ttctgagctc tacacatctg catgtgtgat cacctctacc ataggtttaa tagctacctc 212100
acaagtgctc acagtgtgaa tgcagcatgt ggcacttgtc tttctttctt ttctctccca 212160
gggataggga cagcactgtt tgttttggtt ttttatcttt atacaatttt tgttattccc 212220
tctgtcagtc agttgtctga tgtttgtgaa taaacagatt tcatctctcc atctctgccc 212280
ccttccgtca gccgtggtca ccagtcacct tgattaacac agtgactccc agcaggcacc 212340
tggcttgact cctggttacc actggcttcc ccttgcaccc tgcaagtaaa gagaccccac 212400
tttcccaaac acagatcctg taacaccatg cttctgctta aaatcctaca gggattcacc 212460
actgcccatc ccaaaatcag tctgtgtgct cttcaaggcc gttgataaca gcgtcttccc 212520
atgcctcagc catagctact tcttgtccaa ctgtttacta cagccttaga gctaaagtag 212580
aggatgtgaa aaatttcaga agttggaatt atttcaataa ggttttgttt gtttttgttt 212640
tgtattagcc agttttaaag ataatattta tttttatttt tggttaatct tttttttttct 212700
tcagtttttc gagacagagt ttctctgtat agctgtcctg gaactcactc tgtagaccag 212760
gctggtcttg aactcagaaa tctgcctgcc tctgcctccc gggtgctggg attaaaggcg 212820
tgcgccacca cacccggctg tttattttta tttttaatta atgagagaag tgtaccagag 212880
ggcaggtgct ggcagaggtc aaaggtgcgg ggtcctttgg agtttggttt acaagttgtt 212940
gtgaaccacc cagcatgagc aaggggtcaa actctggacc tctgcaaggt cagtgtgtgc 213000
tcttagccct gagccatctc tccagccctg gaatccagtg ctttagacct gttggccatc 213060
aagtatggtt tctaaatagc acctgaggca tgggtgatgc ttatctgggc cactgggcca 213120
agaatatttt ctgagggtgc acaacatttc tatcttcacc cagggaagag ccaggaacct 213180
cagtgtggta cttctcattg cgtttatgtc tcagagtata gtgagtattt aaaaacatgg 213240
aattacaact atttgattat atgttatgca ccaatcacca tgatgctttc ccggagttca 213300
gacatccaga ctctggagct gacattaatg tgaggccacg gtcagttcct aggcactcta 213360
ggtaggcagt tcgatgcatt ccaggtcctt ggacactgta ggccttccct cttctctcag 213420
cacatgaccc tttgctctct gctggatgtt cactcctgtg cacacctcgg gtcacaggcc 213480
agctgctgct tcctccaaag tgccttcttt ccttcccaag ctcccatgga ggacctgaga 213540
gctcagtcgt gcacttacga ttgtctgctc gtttttctct aaacaaaggc aaagaccaca 213600
gctatgaatg cgcagctggt cctaaaggag gcctcgagta ttagatgaac aagcacatgc 213660
ctgtgaacaa gggaagaaat ccagatatag cacctgagcc cgatggagct ggaaagcaag 213720
atggaagaaa gtcctctcta gccaccgttc tagggaagcc tttgaaataa gaacattaac 213780
aagacccttg gcctcagtcc agttaccaga gttgagggca tcacagaata agctgtcacc 213840
ctgagccttt ccttcctgtc tctctgcagg cagtgccagc agttacccct gtggatgagg 213900
agagctcgga tggggagcca gatcaggaag ctgtgcagag gtaatgtggc acctggcagt 213960
gcttgcagaa cgtccttggg caggctcccc tgcaaccagc gaaaggtcac ctctgcccag 214020
ggaggtggtg cagtgcagct tcaacacttg tgtggtctct ttgctcaagc cagatggcat 214080
```

-continued gttcctcccc acacggaagt aacagaagac tgcccagaaa atttcatttc tataagcgcc 214140
attggaagcc ccttaagtga cagcaatacc cttaagaacg ctttctctcc tccctccctc 214200
ttccttgtcc ccgcgttcat attgcaactt tggtagtgtt caggcctaac gcctgctcct 214260
ccctgccacg aactgtttac tgaaaaggag ttggagattg gagatgacag tgatcctagc 214320
tagtctggcc atggacctct ggcatggact catccgtccc aggagaatga atgaatgaat 214380
atctcctgca ctgtttgctg tgtgtttcct ccactccctt gtaccaacac tgagatattg 214440
ggaagaaaaa acaaacatgg gggttggggg gaggggcagg gacagttgta aatatccatt 214500
gtttgcagaa ccttgttgag agatgcctga ttcacagagc gacagtgacc atcaggtgtg 214560
ctgtgcagtc cgatggcctc agttccagta gccatggtct gcagctccat gcatgccccc 214620
ttgtggagtt gtctttctta ttttctgtga aggggttttc accagaatcc agcatgtatt 214680
ttcccagaaa tacaggtgtt cttcaagatt atatgttttc ccttgaggga agttgaaata 214740
aaatggtttt catgggctct cggggaaact gtgggtgttt ttatcaatgg acattaacca 214800
cagatggctt ctttaagcaa gtttgcatac tacaaattac agtctgatga cagcttttaa 214860
ctgacgtagg caatgtagtc aggaatgaac taagagcctt atggttgttg ttcaggaatt 214920
gttcttcacc cagaaggtct ataggaaaga ccaaagaagg tgcccttgtg cagaaagaaa 214980
gccctagtga tcaggggtaa tgctggccta gtcaacataa ggaaaacaaa aaacacaaaa 215040
acaaaaacct ggtgactttg cctcagtctg atactcttgc ttctatggtt tgctgataaa 215100
aatgaatttg caaatgcgtc ctactggtgt cttgaagaaa cgagaaagta gggaatgttc 215160
tggatccccc tccacccctt ggaaaggtgc agctgggttt taccttcttg ccttagagtt 215220
cacgtcctct gcccccacct tcttcagacc aacattggaa ggccagtgag cctgtcagtt 215280
ggaagggaca gaaaggagtc ctgcttctct tatctgtatt caagacaagt gaagtgctgc 215340
agggggcctg gagcaaacgc aggcccccgg gtcttgttat ggtgctgacc tgtgtaggtt 215400
cgcaagctcc gtagagtgaa tggcttcatg gagaccttgg cctcctcttc tgtttccttt 215460
cctttcttct ttacctcctg aaaatagatc tgaacatcct gtgtggtttt atttcttcat 215520
cctctaagtc tgggagccac atcagttttt cttctccagt gattgagttt tggtcacagg 215580
acataaggga agaactcagt tgtcctcaaa caagagtctg ttttctttgg catgtagtaa 215640
ggacaccaca ggcctctgac ttcaggggac gtaaattgat tctttctgaa tacctcactt 215700
gtccctttaa taggccttag gttctatttc ttctaactta tagtttagaa atttggaaaa 215760
aaattaatat gtaggagaga taacttcttc tattgaatgg aataaaggaa attggttcca 215820
ccgcctttgc aagctagatc tccctttctt ctcttaatgg cgactcgcaa gctcgaaagc 215880
agccacctca gtggtgagcc aactgttggc cggttaggca agcttcacct ccatcctgtt 215940
gggggttgct tactgtggag ccctttggc accccatact gtcctaccca gtgcttcaga 216000
ctaacttctg ttgcttcttg cgcgggaaca ttcttgtctt tttttactat gaaatgtcct 216060
ccctgcttgt tgcaggtact tggcaaatag gtccaaaagg cacacactgg ccatgaccag 216120
cccgacagct gagatcccac cggacctgca acggcagcta ggacaacagt ctttccgttc 216180
ccgggtctgg cctcctcacc tggtacctga ccagcatcgg tgagtagccg cttggcagtg 216240
tgagcatccc ggaggctcat tggatcagca cccttctgac tagcctccag cttagagtga 216300
ctagctctgc ctagcagcca cctgccatcc cgagctcaca cctccgctcc tagccctaac 216360
caatgcacag ggcaaaagct ttctcttgga ttctggagca gccaaggctc ttccatctca 216420

-continued

```
tttcttagac cacctactca tcacctgcat ctgctgcatg taggcctttg agagagtggt 216480
actctcagaa ggcagctcta gaagtaagga ctttgtagca acatccccaa acatgaccgc 216540
caatagttca tcgccttcag aaaatgggca cttgatgtgg cattagagca gcaggctggc 216600
tgtagacaga ggcataccct tgttgtgtgg tagaacagga gtgttgcatc cttttgagtg 216660
ctgtgtttgg gaagtaattc tttgagtatt ctgacagcaa gatcttttgc taggcctctg 216720
ttatttagaa ttcattacct tgaagagaga aaccaagttt ccctctaact ctaactagat 216780
aaatttgctg attccaaggt agcctgccag caagagagct gattgtcctc catgactcct 216840
tgatgactgg cagtcttagc catgtccatt ctgatgctgt cccctagctc ccaggtcatg 216900
tttcccaagt cgtcagccat tgcttgatct tgtttcttcc agtcttcttg gggtagggtg 216960
ggatagtgga atgcagcctc ctccagaagg cgaaagcaga tgggttctga ggaaattcag 217020
tacacatgtg tgccaatcgg agggaacact tgcaactagc cactcagatc agctccatac 217080
agggttctca ttgtgcttct tgtgagcagc aggtaatcag ctgaggcagg tgaactctga 217140
gcagacaggg acataattag tgccacgctg gaactctgga agaaggaaga taagctttca 217200
taattgaccg tgaacaattt agaaagaaaa agtcctatta ggaactaaaa gaaacggtga 217260
aggttctcat gcaagattgc gatggtgcag cccccgtgac ggaaacccct gggttgctgc 217320
agtcagtcac ctcagagagc gcctctgtgc tggctggctg gcgagctgcc cccaccccaa 217380
ggcagctcgc atcgtgcact ggtcctgaag gtgctttcgt tgcttctcac ctcttcctcg 217440
tctgatattt gacttgtcag ccctccccca gggccttttg tttacctttt gtccattgaa 217500
tacctggctg tacttctccg tgctccttgg gaaaatggtg atgagcactg tccagccagc 217560
cttcctcaca gacgctctat tctaccaaca tttgttaaaa gaagaccaca gcagcctgcg 217620
gacagggtcc atccgtggga catgcattgc gcctgcagat attgccaggg ccttgctgcc 217680
tagagccctg ctgcctgttc ccatctgcac atgtgttacc tgggtttcta gggccaaggc 217740
agtttgagtt ggaaacaaat gaatgcttga gtgagaaatc atgtactgtg gggcggtggg 217800
gtcactatac aacgcacaag agattaatgc taattcagaa gaaaagagaa gtgttctaag 217860
gccgtaaaac acacgatgtg acgcaggcag cctgtctgcg tcaccggatt cctttcgttt 217920
tctggagcat gattaaaaga acagaatata tatctattct ttgtgttata ataggtgaag 217980
tccaccatgg agaccgaaga ggggctggtc aacatttaca cccctggaag tgtatgcttt 218040
aaaagttggc acaaaacagg ttctatccag ttgggggcta catcactgtt ggaagagtat 218100
aggggagata gcagcctatg caaggctgcc ctgggtgacc gtggttgctg ttgaaaacaa 218160
agttgtacac gcttgacact gcccatggct ctgcagtggt caggtccctc ggaaccaatc 218220
ccctgaagtg actgagccag gctgagctgg ggccgacttc acagcctgag agtccggaaa 218280
acggtgccac accttgaacc tgggatattc ttgctataat gagaaagaaa tggtttcatg 218340
cagaaagaca gctcgaagaa catccctggg tgacggaaac ctgtctattg cctgaaaata 218400
ctgaaagtgt aggcgtccga tgtgagggga gataataccg gtgctgggtt tccattcaga 218460
ggctgaagtg cagagagaac aggtgtctgc aagcatcctt ggtgaactca gtgtctggac 218520
cgtgacatcc tttccccagc cctgattaat ctgccttgta tgttactaaa acaagtagga 218580
ctccatgggc atttcactag ctcaccactg cttgaagctt tgatgacgtc tgagtaaggg 218640
ctttcacccc gacatcagca ctctcttggc ctcgctgcct ggtcctcatt tctcctcagc 218700
ccttccctgt ctgcactgta tttgaacttg cttgttcgcc tgcttccttg gttttggctc 218760
tgcttcagtc caaactggca aggttcccca ccccctcacc attggctcag cgtgatgtca 218820
```

-continued tctctgcctt agacctgcta ccctgaccct ttccatcagc tgtggggacg ctcgctgcct 218880
ctgcagtctt taacctgctt atctcagctc ataaacatct ctttctggct aggcagcaag 218940
tgtaggtgtt agccagcccg gtgctatctt agggctcctg atcaacggtt cttctttctc 219000
cccataagac atggctgtgt tctgactgaa cactggggac ccctctgtca gcaggaagtt 219060
gggcaggtgc tgctgtgtga ggagatagca ttcacagtag gaaggaggcc tcatgtgtgt 219120
tcataaggta cgtgcaggat cttgaggccc acccacattc ctgaggaata cgctgtctcc 219180
gtgctgggat cagaggtccc tgtcttcccc caccccagcc tccaccctcc cttctctaga 219240
acagaactgt gagttccagg ccagaccttt gaccacagaa ctgactttgg tttcatccta 219300
gccacacata gattactgct agaggtaact cagggtcaaa cggtgaattc taagtttcta 219360
aagataccag gcagggatct ggttttaaaa accatagctt gcacaacatt atccacacac 219420
cgccccccaa atgcaactac aatagaaaat aaatgagtga ctataagaac caagcctgtg 219480
tggttcagcc agtcctggcc gtactgcgga gttgcaccct gctctagtat gtttatataa 219540
gaaccggatg tagttgaccc caggacctca gcaggcctgg gaagtaggac caacctgagg 219600
taagtggagg tgggagatga gggcctgtag tccactcagg gggacagcca cctcaggaag 219660
tgacacggag taccatgtgc agggctcctc atgcatccac tgtctctgta ttcatgtaga 219720
cccatggtcc cgtgtgattg gtcataaccc cccgagtcct ggctgctaac cgtctcttcc 219780
catatattca gctccaccta caaggactcc aacaccctgc atctccctac ggagcgtttc 219840
tcccccgtgc gccggttctc agacggggct gcaagcatcc aggccttcaa agctcacctg 219900
gaaaaaatgg gcaacagcag cagcatcaag cagttgcagc aggtaatctc tggaggggca 219960
gggggagcag tacagtgcca ggacccgggc agtaactctc catacccttc atgtcaacca 220020
cactgaggtg ttctagctta aagcagaata gctttcttca atatctactg ccctccctag 220080
ggtcaaacct gcttccctca taatgagact aaaaattttt tcccaccatc tggaattcat 220140
tgggaaggca tttctggttt gattttttc ttgggaacgg tacttgtaag caatcttggc 220200
aggccccttg tatgcagggc acggggtcgt agtggacccc attgctgtac tttctcaccc 220260
ccggcataat ccccagctgg tattgctccc agaggtagca aacctgctcc caggatactg 220320
tgacgagcca agggcttcaa gtagcacgtg ctctctctgg gtttatagtt gattccacac 220380
tgggcattcc acagtgtgtc cttggcgttt cccactgctc cccagagagc agggcgtgag 220440
gatcactgtg tgcatgccca acaaggatac cgttcttcca tggctcattc cgcccatgag 220500
accttggggg cagatctgcc tctcctgagg tcatggcatg gggtagactt ggccgtgtcc 220560
cgtttgtccc cactgctttc ccttcaggag tgtgagcagc tgcagaagat gtacgggggg 220620
caggtggatg agaggaccct ggagaagacc cagcagcagc atatgttgta ccagcaggag 220680
cagcaccatc agatcctcca gcagcaaatc caagtaggcc ctcactccct cttcgctctc 220740
tcagaatgcg tttttgagtt tgctggcagg cacattggcc tgtgcattgt ctgaaagact 220800
cagggcagcg tggagtgtga gccacgtttg tgggtgacat gtctgagtca cagcgctttc 220860
tgccccttcc caggaatagc cctaatgcct ttcgtagctc acgatgctgc cgttcccccc 220920
ttttgtgttt taggattcta tttgtcctcc tcagccctcc ccacctcttc aggttgcctg 220980
tgaaaaccaa ccagccctcc tcacccacca gctccagagg taatgaacta cttagcctct 221040
tcctgcattg ttggctggct ggacggtgtg gctcccttgt ctgacgcatg gggacgcttg 221100
actgacttga gcatttggga tagtcttcta gaagaacagg gaagccgagt tagagtttga 221160

-continued agggcttact agaatgctga ctatttcctg agctccatga acacagtggc ctgacatcca 221220
tcgaaggcca ggccagtgag tgctgagttg gtggcaggga aggactggta gactgaggtg 221280
tgggcaagct gtggtggcct gctaccgcag ttgtccgccc caaactacaa actgtctgtc 221340
tgcatggatt gtctggctga atgttaactg cagatggttc tgtcagctca ggaggcttat 221400
gtacctgttc tgtccttttc taaggttaag gattcaacct tcaagcccac cccccaacca 221460
tcccagcaac catctcttca gacagccaag taacagtcct cccccggtca gcagtgccat 221520
gatcacgtct cacggtgagt agaggccgag ggagtggata catattgtgc cgtgcaggga 221580
aagcctggct tttaggcttg gatttgttgc tggtggtggt ggtggtggtg gtggtggtgg 221640
tggtggtggt ggtggtgtgg tggggtgtgt gttaaacttt gtttcttgac tgtgaaacct 221700
tgggtaataa gtacttggct ttctcaacaa taactgtaat aatagcaaca cttaagaaat 221760
atatataaat cacctgggac agtacccaat ataatagtcc ttaatacagg ttagccacta 221820
ttgatgtagc tattaaaacc tctccagtcc tcgtactagg tgtgaagact atgggtgcag 221880
atcctcagac ccagcacaca gtcaggtcct tgccagtctc cttggcattg tggagaaaca 221940
tagaattgct cttcctcctc caggtgacct tgagtcagag ttggctcttg ggttctgtcc 222000
cagaaccacc gcacgagaat gtgcagctta accaactctc aggatcattc ctgcatatcc 222060
ttggttaaga aacactgcat acaaactccg ctaccctaaa tccagccata gagcagctct 222120
tgggggactt aattggaaat aaaattgcag gggagcccac ctgaccgact gagtcctagt 222180
tctgtgggta ggacccagtg agttagatct gtttctgcca gtttctggtc ttgtcttgta 222240
tagtgaggtt gaagaaggct gttctagatg ctacctgctg tggggtctcc tctagctggc 222300
aggtaacctg ggcacttggt caccctgtgg tccctttctc tgcaggtgct acgtctccct 222360
cccagtttca aggcttaccc tcccatggtg caatcttcca gcagcaaccc gagaactgtt 222420
ccccgcctcc cagtgtagca ctaacctgcc tgggcctaca gcaggctagc cagtcacagc 222480
cagtgactat ccagctacag gagccagttg acatgctcag caacatggcc ggaaccgcgg 222540
caggctctgc agggcggagc atccccatca gccccagcgc cagtcagatt cagatacagc 222600
accgagccag cctaatggct cccttcagct atgggcaccg gcccttgtcc aagcagctga 222660
gcgctgacag tgcagaggcc cacaggtgag tgagaaggga caagtctgct tgtgctctca 222720
tgtcacccat ggtcaaagcg gcatggtggg cttgttgatg agacaggttg ttagtgagag 222780
aagaggaaat ggcagagggc cttcctgatg gcctgaagga aggaagatct gttagaggaa 222840
catgtctgtt cccctgactt attattctag ggttcttcct tctctgttgt ctctaagaga 222900
ctattattct aaacagctca gattattatt atttttgttg ttgttgtttt gttttgtttc 222960
gttttgtttt gagacagggt ttctctgtgt agccctagct gtcctggaac tcactctata 223020
gtagaccagg ctggcctcaa actcagaaat ccacctacca ctgcctggct cagattattt 223080
tttaagaaca gctagattag actgtgtgta tagctctggg ggtaggaggg caagcctgaa 223140
tccctggttt cagtccctgc caccagagaa gctaggtgtg gtagcacatg cctagaaccc 223200
cagcgttcta gaggcagagg caggagtggc aggagttaga ggtcctcttc agcaacatag 223260
cgagtacggc tagcctgggc tgcatggaga ccctattcaa gaaactatcc aaggtcagaa 223320
tgttgctttc aggataatta catgcccagt gccttatggc tcttcaaaaa cttggatgag 223380
cagataaggg gatgaatagt ggtggtgtgc acagtcctcc ctgccacagc acaggtctgt 223440
accatgagag cttcgtgcta aggaaggcga gtgactgtcc ccagggaagc tggtgtagtt 223500
actggaatgc ctggtactca taccattttg tgtctgcagc ttgaacatga atcggttctc 223560

-continued

```
ccctgccaac tacgaccagg cgcatttaca cccccatctg ttttcggacc agtcccgagg 223620
ttcccccagc agctacagcc cttcaacagg agtggggttt cctccaactc aagccctgaa 223680
agttcctccg cttgaccagt tccccacttt ccctcccagt gcccagcagc agccacccca 223740
ctataccacg tcagcactac agcaggccct gctatctcct acaccgccag actatccccg 223800
acaccagcag gttccccata tccttcaagg actgctctct ccccggcatt cactcaccgg 223860
ccactcggac attcggctgc ctccggcaga gtttgcacag ctcatcaaaa ggcagcaaca 223920
gcatcgacag cagcagcagc agcagcagca gcaacaagaa taccatgaat tgttcaggca 223980
catgaaccaa ggggatgctg ttagcctagc tcccagcctc gggggacaga atatgacaga 224040
gcaacaggct ttatcttatc aaaatgctga ctcgtaccac cgccaccaca ccagccccca 224100
gcatatctta cagatcaggg cgcaagattg tatctcacag ggtccctcgc ccacccccac 224160
ccatggctat gcccatcagc caccactaat gcattcggag agtatggagg aagactgctt 224220
gtgtgagggg ctcaaggagg gcttcccaga caagagctca agcacactga ccaaaggttg 224280
ccacaacagc cctctgctct tgtgtaccag tgggcctggg gaccctgagc ctttgctggg 224340
aactgtgagt caggcccggg agctggggat ccatccctac ggacaccagc caactgccac 224400
cacgttcagt agaaataagg tgcccagccg aggtaagagt cccctcagag aaagactctt 224460
gggagagttt gctggaattt aagtgtgcag gggtgttagc ttggttctgc tagtattctg 224520
tgcgcctaag caaaacaaaa caaaacaacc ctaaacagac cctaggacca tttgggggga 224580
gaggtgaagc atgtggaaag gcgattggtg ggtgagaagt cacctacaaa atagacagca 224640
gtcgacaggt ggcacccagg acactcctgg tcacaccacg ggtcctagaa gtccagattt 224700
gcccggctgt catcagaaag tcgcagtgga aaccgtcagc agtactaagg aaatgtgtaa 224760
actgtggggc tgagagtcag agcctccagc ccgtcctcct ctgtcctgac tgcgagatct 224820
agactctatt ctcatcgtcc tcttgtgtga tagaagggca atggacactg gccctctgca 224880
gcatcttgtg acgatccgag catttgtgtt cgtacagact gcctctgtgt gtgtgtgtgt 224940
gtgtgtgtgt gtgtgtgtgt gtgtgtgtgt gtgtgtgtgt gagagagaga gagagacaga 225000
gacagagaca gagacagaga cagagacaac ttgataacta agtatgctgt atactgtact 225060
ggggctgcct ccattttcat ctaaagatta gagtttacct gagtgagttt tgtttgcata 225120
gcaaaaccag agcatcagac cccctgtagc cttttgcttc accctcctca ccacaaccac 225180
agagggagta aagcgactta cccacagagt ctgggactct gggcgtttct tcctcattcc 225240
ccctggagtt acccatatct cttgccttta aaggcgatgc acacaactcg gacccatggc 225300
tggccaagcc ctgcccagca gcaggtgtgt gaagacttgg tgctgtcaga tggacttggc 225360
atgtgctcag agaggaggga aatgtgctgt ataaaatgac agtttaagtc ctgaccactg 225420
cagccaatgg tgtcaccagc ccggagatct gccctccaca tgcatgttga actctgctgg 225480
ttgtatttag agtggaactt tataaacagg ttgtgtgtag aatgagagac acctagcagc 225540
attgggggtg gggatggaac aactttgaag gagcagatct gtcagatgga aggactcaac 225600
ttttatgtgt atgataagga agagactcta aagtgggtag aaatcacggt agattatagc 225660
tctccagaga agactgttac gagagactgc catcacaggc tacctgagca gctttttgtt 225720
gggtgtgttc tggaagaggc ggatgccttt gatggacaca ctgtagaaga gcatccatgt 225780
gtggaaagtt tctgatgact cagctcgctg aaactgcatc gtgcatgcgt gcctccagtg 225840
tgcacacacc gagtgctgct ccatcctttc ttcttattgt gatgctaggg caaaacccag 225900
```

-continued

```
ggcctcacac acatgctagg tgagcaagct ctacacggag ctgcacccag cctgttgtcc 225960
gttttaccag tgacgcagct aagacttagg agatttataa tttgcctctg ggtcagagct 226020
gacaatgact gccaaaccct gctgccagtc gatcaccacc ccaacaatcc atgaatgtgt 226080
ctgatgttca ggctactgaa gaaatagtgg agcgggtccc agaacagtga agccatgcac 226140
tggaggcaga gatgcattag tgaagcccag tgcatgctgc tgtctttaat tcagatctcc 226200
ttggggccag aggtctgtgt gttaaaagtg attctttgtg gaggtgcccc actgtcctta 226260
ggctagcaca ggttgccttg gagcctacta ggtaagcaca cttccgttta ttctggcagt 226320
gaggggtgcc aagctaaata aactcctact ctatgcttgg cgctctgact caagacatcg 226380
gttccttttc acacccaccc tcggaagtgt gtgtcaaggt accattttgg taggagctgc 226440
cctggcctga cctgacatgc ctgtgaagcc ttcagttgtc cttttcctct ctccccctcc 226500
ctctcccctc tttttaagga cagggtctca ctgcataacc caggctggcc ttaaactcat 226560
gatctccaag tcagctgtgc acgtgccggt cggggttcca ggctatgcac cacaccaatg 226620
ttttcagttc tgggaagaaa ttccagaatg ggctggggag agggctccgt gggtgaggct 226680
ctggccacac aagcctgaca gcttgtaatg gtggaggaag aaaagcagct cccaattcac 226740
ctgacctcca ccctcacatg catcacacac acactcgata atgagataga aacttcacag 226800
gtcatttgcc atgggttttg tgaagaaatg gttctaacag tgtgctgcac tgcaggcgac 226860
cgcagaaccc gcacccatgt ctccctgttt cgacagagga ccttgatggt tcttggtgcc 226920
cttccatcaa acaggctagt ctcttggcgt ttaacctatc actccatggg agggcagctg 226980
agtacaagtt agtgagccag ggtcatgggt gctgcgggaa tgtggaaagc caaagggcct 227040
gtcttcagga agaagagctg tatcagaagt ggcgtggaat atgtgctaca gttcacaaga 227100
gcagaactct gcatttattg gcatttctga agggtgaatg ggtaaggctt accaatgtta 227160
gtctaggaaa cttagatgcc ccgttacccg accgagtctg tgctttcctg ttccctataa 227220
agctgtttgc caccagccag taggaagcca gactgggcag agcactgagc acctactgtg 227280
ccagaaatgt cctccagacg ctgcaagtgt cagagctaac ctgccttcta ttgcctacgg 227340
tctcattgtc ttccacttaa ggagtgaaga taaggtgggt tgccctcctg cagtattgca 227400
ggagcttaag gcttttgact ctgcacgtaa atgaatacaa ctgcacagtc agttgagatt 227460
accaccttaa actcagatag aaaaccgcat cctcttcttt gagcccagtc agcttccagc 227520
cttgtaaggg ataaagtgct gacagccttg ctggggttaa gacagtagcc cttagagcct 227580
ctaagagggg tgtgcaaaca tgccgtttct catttactct taaaacccag taaatgaata 227640
aggatgagtc aacattgaca gattgcacag ttacgcaagc tggcccagag tcccccaggg 227700
tgtgggggtg tgccttggat tctcattgtg cattttgtcc cttacttgtt tgggtactct 227760
cccctctgta ccctctgggt tcttggaaga catagtccct gtattattta tagatccttc 227820
tgtaagcctg gctgttctct tactcctaaa atggcctaaa gggtgccaaa ggttctagtt 227880
ccctggtcag tgggttagtc tttacagcca gccactggtc agcagggctc agctaaggac 227940
tttgagtccc agactcagca cccttccttg tctgactcgt ttacctacgg agccctcagt 228000
gcttatcgca gaccttccac tggtgttagg cttttggagc cctggaacag ccctttcctg 228060
tcagataagg gacattaagg gtaaggggag actgcctggc cgtcaggctt tgtgtactct 228120
ggtgataacc tggaacctgc ctcctgcgac cctcattctt ggcccctgta tgtattcttt 228180
ccccatgtta gcttcctgtc actgggacaa aatacccaag aaaatcaact tatgaggagg 228240
gaaggtttgt cctggctcat ggtgtcagca gtctcagctc ataatttgtc cttgttgctt 228300
```

-continued tggagcctgt ggagagagac atgccatggc aaggggcatg ttggacaaag ctgcacttta 228360
ttctgactgg gaaacagaaa ggaagccatt gaggacccag ctcccaaatc ccagtccagg 228420
gcatatccca gtgtcctaac ttattttctt ctaaaatttt tctcatttat atttattttg 228480
tgtagtgggg ataagtgggt tgtgttctgt tctctccttc tactctgttg gtcccaggga 228540
tgaaactcag gcttagggta agcaccttta ctcgctgagc catcctgtca ctcccaaaag 228600
ggagaaggag ggagggagtg tgtgtgtgtg tgtgtgtgtg tgtgcgcgcg cgcgctcagg 228660
acagttgagg ggagtcagtt ctcttctccc acctatgggc cctagggatt gaactcaggt 228720
catcagactt gatggcagat gcgtttatgg ctgaatcatc tcagcggccc caccctaact 228780
tccctttatc aagctttgcc tcctaaaagt tccattatat cttcttagcg ccacatactg 228840
atgaccaagt ctcaacatgg gagcctttag gcaacagcca agatcctcac agggccctct 228900
ctaacccttc ccaggttcct ctctagccct tcccagcaca gcttctgagt gggagacact 228960
tcattttcct ctactgcggg gggtcttgtg atgcttaagg ctcaaacatg gtcctacact 229020
ctctaggcaa acattccact gcagagctgt gacctcagcc ctggatctgg tttataatct 229080
catttgcttc tttcagacca aaggctgcta ccctggtaac taaaaattgg gtaacttact 229140
tgtttattgt cctgctctgt ctatcagcag cctgtggggt aggctccaga ggcacaggtc 229200
cagaaagatc cgccacctcg ctcaagttcc cttccacctc ctcaggaagc aatgaagcta 229260
gaatcaagct gagtcttccc accccggcgg tgcctgtggc acctttgcca cctccacctg 229320
acagagaagt gagccctcag ctgggcactc aggagagctg gtcaagtgat agcctcttgt 229380
gacctgaggc ctgggaacat cactcaggaa agcagacagg agggcacaga agggaagtgg 229440
agcccacaag acctttgaaa agcctgggtg ggagcttaga tttggagaaa cctcattttc 229500
aggtctaaaa aaaaaaatcc aaaaggggag aaagagaatt taacagacag gaaaacacat 229560
ggggggagag tgctggtctg gaagagggag tggggtggaa atatcaagat tctgttagtg 229620
aagagaggcg cttgccatct gctcctgatt gatcacaggc cttaaagtct cggcccaagg 229680
tcagaggtgg cagagagtaa acccccatga cctgagtttg agccttagaa agggaagaga 229740
aagccaactc ctgaaagttg tccctcacct ccacatacat gccataactc cacatacatg 229800
ccatagcgcg tgtgtaccca tgtacacagc taacaattgt ttaaatgttt tcaatctcta 229860
aacaagggat ggaaacagag cactacatat atacaacaca tgcaccacat ataccacatg 229920
tgtacacatg tactcatttg catgtactgt gacatgcaca catatgcata tattttaaaa 229980
gtaggagctg ggcgtggtag tgcacacctt taatcccagc actcgggagg cagaggcagg 230040
tggatttctg agttcgaggc cagcctggtc tacaaagtga gctccaggac agccagggct 230100
atacagagaa accctgtctc gaaaaaacca aaaaaaaaaa aaaagtagga acgggatttt 230160
ttttaaagtg tggcctttat agggaagtaa ctaggggtgg ttagaaaatg atctaggcaa 230220
gagatactgt cccttgactg gaagcaggca gtctgggggc tgaggtgtcc accactgaac 230280
gagcggactc tttagactta gccgctgtgg ggccgggaag aaggaattaa gcatgactcc 230340
aggaacttac acctcaaaga ttgggggaag ggaggcggtg ccaaacaagg gctcttaaag 230400
gagtagcagg cttctgggga agttaatgag tttgaaattt aacgtaagtg ttacatacta 230460
gtaagataac caagaaaaaa agttggatct atggatctgg aaccaaaaaa aaaaaaaaag 230520
gatttcagta actccgttta catttagtgt gtgtgtgcgt gtgcatgtgc gtgtgtgtgt 230580
gtgtgtgtgt gtgtacatgt gtgtgcacat atgtatgagt atgtgtgtgt gtgtgatcat 230640
ttctcttact aggcgggttc tgaggataca actcaggtca tcaagcctga tgacaagtgc 230700
ctctcttcac tgaacatctg gctcattcca tccactgcag tacatgagca gtgtggctga 230760
agccatggac ctagatgatg tcaaaatggg catggggagt gaggtcaggc acagctgtgt 230820
gcaagcactt atgaaaggtg aaggagccat aggcagcacc agcagtggcc gtgggacagt 230880
gggagagacc tgggatggca ctaaggcaga ggccaaggcc atggatacag gccagaagcc 230940
cctcatctct agagctctcc atgagctcaa tcaggagctg agcacaagct aagccagcag 231000
agtgatgggg aaagaagaag atgggtatgg cccagctcac accccatagg tggatttttc 231060
cttctagggt aaggagtgtc ttaaacccct atttgctgta ggatttgatg ttgttaggct 231120
ggccccagct cctctaacac ccatgccagc tgactgagca ttggcatttg ggcaaatgtg 231180
gtccctcccc tctcactcat tgtgtcttac aaggggctac atgggagttg gcgtcacctg 231240
tcacctggag aagctctggg cctgctcacc ctgctactct tgctctgtct cctagagtct 231300
gtcctaggga actgcctgga aagaagttct cctggacaag caatggagct gccggatcac 231360
aacggccttg ggtacccagt acggccctta gtcagtgagc acctcaggtc ccggacgctc 231420
cagagacacc acacgatcca gaacagcgac gatgcctatg tatgttggcc cctcctgctg 231480
cttagaggtg ggatggtgcc atctcaacct gaaagcagag tgtccccttc tgccgccatc 231540
tcctcagtcc agccctctgc aagctgtgga gaccttttt ttttctttga ctccccataa 231600
cagaccagca ttaacaggag agtcttgcgg ccatatgtta gacttaggaa tcaaatgatc 231660
tgacatccag ggtcttgacc tctcccagaa atctaaatcc aggcttcaat atatgaaccc 231720
tcaatttttg gtccattcct ggcaactgtt ttgctttctt tggctttctt aagagttgac 231780
ctgtcagagc aagtcttgtc aactgggaca cacccagcca tggtagcacc tgtatgcctt 231840
caggcaacca tttgtggctg ttcaaatgta aatgtgttta agttacacaa aattagaaat 231900
ttagttctgc ggtagtaaat aacagttaca cttcacacac acagcagtca ccatgttaca 231960
tgggcacttg agaacagaac tgttagacct cactgtctat agatgggttg gggagggaca 232020
ggggtcccct gagagtgaca cactgtctgt cactcattgc tgctggttcc actctacagg 232080
tacagctgga taccttgcca ggaatgagcc tggtggcagg caaggcgctg agctctgccc 232140
ggatgtcaga tgcagttctt agtcagtctt cactcatggg cagccaacag tttcaggatg 232200
aggaagatga aggtaaggcc ttgcccatgg gcaccccggg gcagtcttct gtggaaattg 232260
ttcactggct gaggtgctac gcacatgtgc acacgttagg ggctctggct tctgtcagca 232320
cagggacatc acagtccaag ttcagtgctg gagcaggatg taccttcaac aatagccctc 232380
tttcagcttc tccttagagg gcttcatatc cttgtagaac atttatttct atgtctttgt 232440
agagccaggg tgggagacca tgatagagcc tggagacgga caggttcacc ctttctaagg 232500
tccacaggca aagcctagga agtcttcatc ccaagtcttc acctgtgagg acatcaagag 232560
agcagtgccc atgtcctggc ttgggtccta aggatgctgg cctcctgagg tttattagtg 232620
tttattagtg tgatgctcaa gagaaagtgg cctggcctgg ctcctatagc actcactaca 232680
gttatcctgc cccctaacca caagaaaagg ctcttgaagg gtttttcatc ttcaccccca 232740
tatgtcagtt gctcatgagg gtggcgaaag gaaggggcag gtggtcagga agggtcccta 232800
acatctgaag ggcctgctgt ggcctgagtc agagctggac tcaggctggg ttgctagaca 232860
agacctcccc agcctcctct ctcctgtccc acttgctccc ccacctccac ctcacatgtt 232920
ctttttggtc ttgcagaatg tggggtgagc ctgggccacg agcatccagg cctgggtgat 232980
ggcagccagc atctcaactc ctctcgctat ccagctacgt gtgttacaga catcatgctc 233040

-continued agccacaagc acccagaggt ctccttcagc atggagcaag ccggcgtgta gcaagatatg 233100
gaaagtgagt gccaccctgc tcaggcccag gcagccctgg ggcccagtgc cagcccctca 233160
tagcctcaat gtgttcattc cttgtgtggt accccactaa acttgagcga cactcttttt 233220
gtgcaacctt ccccgtctgc ctgtttcttc attaagtact gtgttagttt tgaggtgggc 233280
tgaggacttt aatttaggga agaggtacat ggcccacctc atgttataga tgctatggct 233340
ttaatgagat ccaagctaca gttgcagagg ccagaggcca atgacctttg gccagctctc 233400
taaagctagt ctttacactc catcctgaag agtgaaaccc aaccagaaaa gggaaaaaga 233460
gcagatccag tcaggctcct tcactggtgg tttttattgt ttggttttgg cattttggtg 233520
ctaagcatag aacccagggc cgtgtaagcc ccagccccag cctcaacccc agccccagcc 233580
ccagctggac tttttagggg gtaaacccat gctgaaaaga cagaaggctc accggccctg 233640
ttggcctagc agaggtcaca tggatggtga gtactagtgg ctctatctct acagagacag 233700
aacaacttga ggaaggtaaa gccacaggca gaggcatggc agagcctcag tgtggcaaga 233760
ctcatacagt gacaccaaga aaagacttca ctgagagcct gcatgcctgt ggctcactga 233820
cagagcaggg catggacaca tagggccctg agtcccagcc ctagtaccat tagaaagggt 233880
ggggagaaag ggtgaagtca tgtccctctc cttcaaggtg ttcttgtctg cttcgtaggt 233940
tcgagtacag ctccaggagg aggctgagtc tagaccaata gaccaacagt gtccaacagc 234000
gccgcaccgc tcctccgtct gtgtctccac cacaacagtg cagctccttc ccctacacta 234060
ggcaccagta ggccggcgct tgggttgcga gggacatttg ccatgtttgc ttgtatgacc 234120
aaggcaccaa ggaaataaac aggaaatcag tgtcctccat ctttcatgag ccagcatctg 234180
gtgtgcttga gttgagttct gctgttagga ggtttgcttg tgttttgttt tggaaatttt 234240
cctttggaga taacttattc tctttgcctt gcccacccct accccccttga gcatattccc 234300
cccccccctct cgttttcacc taccatttct gaggtagatg aaccagaggt tagtattcag 234360
gggctgaacc tcaggaccct cccttccaca gcctgtctca gaccagactc tctccctctg 234420
ccccggtcta ccaggaacaa atgctagacc ggagcttggt ggccaagaaa aggagaggag 234480
ggggcagtgg cccctgcctt tggagattgg aacagaagaa aaaactgagc ctgggatctg 234540
gcagaatctc ctgctggcct ctactagaat cctatctggc ccagcagaat tccatcagat 234600
cccagcacag gccggatggc ctggtgctga aggtttgcca tccagaatag ctcagtgtag 234660
gcccctctgg tgtgtggtcc agttccccctc cagtcaccaa ctggttcccc ctcatgagtg 234720
aacacccagg agtggtgcac tgtgctgttt gtgtgatctc cattcttatt ctctactgcg 234780
ttgtaaaaag ggccgttggt ccatttgtgt gcacacgtat gagtgtgtac atgcccttcc 234840
ctgcggcctc tttgtcacag acaagaattg gaggctgtac tgggtctctt aaccttctcc 234900
tctccccagc atcctcggcc cctatatttt aattcttgat catgtaggaa ttgtttttga 234960
taaatgttga tattattgtt attattgtta ttattaataa agacaaaaag gattttgttt 235020
atttgtttaa aagagaaatg tttaaccaga ttctgtgctg ttgaactgtg gcttgcaact 235080
tctgtttgaa gtgttttcct tggctttggc atcgtgagcc actctcctgt gccagcagcg 235140
gatgcagtgg cctcccttcc ccagccgaag cagcacatag gcagtggcta ctgtccttgt 235200
cacttccttt ctctctgcag tcagaaacca aagtctgggg ccaaacgagg ccggcccggc 235260
ttctcttctg gtcttcaaaa ccagagaggg atggtccctg ctctgactcc cagccctcat 235320
ttctgagagc caggggccac caacctctga gtatgcacag aagaaagccg ctgcctgcca 235380

-continued

```
tggcatctgg acattaccag cagggtccct agccatttta tccttccgca ccaaccctga 235440
aagcttgcct ctttgaacaa atccattgtc tcttgaatgg atttgttttc aatgtgagag 235500
cttggctggg gacctgtttc gtggtcccat gtcctccaat ttcccctcca cttcaggtgt 235560
cactaattac tagccagaag atgtctgact cccaagaaag cttgacaagc cattgtcagc 235620
ttccaagctc agtccagctc tgatactcca gccccgccct gctgctcccc acgctcagcc 235680
tgacctgttt acgtggtact ggattgatgg aagagcaggc accaccctcc agagccaccc 235740
agacgaaagc cagtgagcct attaaccgtg ccatcttgcg aactattttc aagatcacca 235800
ttgctttata ttgtagtaac caatatgcgc agtatatgtt gaatgtatat gaatctactt 235860
tgctatttct gttctttgaa aatgtaagaa gtatttttcc tttctcattt ctgttgatct 235920
aaaaatgata ataataataa taatctccag attcaagttg ctaagagctt ttgtccttgt 235980
ttgtgtggga catctacaac ttagtgactt ggttggactg taggaggttg tggaaataaa 236040
aacctgatta tgtactaacg ctgatatgtt gtttgcctta cggttcagag tctaattgag 236100
agaatcacat ggggtagggg cagaggtgac ccaggtgtct ggagaagtcc ccagacttag 236160
ggtggggctt ggagcagcac attctcacct tgccttttgg cctctgaacc tggcaaatca 236220
gactcacact gtgtccaggc atccgtgtgg actctaaccc ctcagaaggg acacatttgt 236280
gtttgcagag ttgggtggga aaaggattcc ttggggtcct cagaaggaga gccttgcatt 236340
gaccctggct ggaaccttta tgaggtggcc tccctcagct gtaggacaga agggcttttg 236400
gtactgtttc ccaatgtctg ttcctggatt ccaggtggag ggcagaattt ccaacagggc 236460
cccaggctct gctgaaagag ctgaagtcac acgagaaaaa agatcaatga tctggggaat 236520
acggagattt gtagaaagag tgacagaggc tggaaggatg gctcagtggt taagagcacc 236580
aacttcctgc aactcacacc acacagaact ccaattccaa ggacccgaca tgcttcccag 236640
gctcctgtgt acagataaca tacactcata cagatagaaa actctttagg cagggagagg 236700
cgcatataag aaagcctttg aggctagaat tgcaatgaaa ctgctcagag tggaaggtgc 236760
cttctcagcc cctggaggtc ttgaaggtgt acgcaccgca cagaggtgag ctggctttgg 236820
aaccagtgat gggccctaag gactcccaaa aggtcaggac acctttcact gatgctgtgt 236880
ctgcaaagtt tttggctaga ggtcgggtag gtacccagag gcagccagat tgactctggg 236940
atctgaacct ggacatctct gccctccaag aaggaaagaa agacttcctg actttgtact 237000
ggagccaggc cccacccact taaccacgga gactttagtc tcctgagcag gaggcaggaa 237060
catcattcag agctgatgac agtgtccttc caaacaggaa tcactgggga tccagtctgc 237120
ttagggagac cctccccagc cctggctccc cattcctgct agcactaccc cttgttgggt 237180
acatattccc agaaggggct ggcaccattg aaggcctgcg cctttctgtg accctttgcc 237240
agtctgagaa gctttggtgt atcaatgtta ttcatttagt aaatgtttgg tgtctctggt 237300
gccagtccca ctaaaggaca gagtccttgc actgccctgt gcaggtgatc tgtgctgaga 237360
cagaagttgt gaaatgggct acattcgctg ctgctgaagc taccagcact cccgggatcc 237420
caggccagca cttgctggtc caatccagga gtcactttgg aggttcccaa gatgaggggg 237480
tgaagggtag tgagagaaat gccaatgata ggcactatct tcactccctg gtcacccaac 237540
acctctaaca gcagccaacc tgtctcaatc tgtgatgagc ccatttgact cttgatctgt 237600
ccagaaagac ttcctgttca gaacagtaag tagctattta gactagttta aaccaaatgt 237660
ctcctgataa agtaagtcac tagcaagtaa gtatggggtg tgggggaggg agcatggagc 237720
atacacctat aaccttagca tagaaagcca aggcaggagg attaccacaa gtttgagacc 237780
```

-continued

```
agcctggact atataccaag acaggagcac acttattgct cagtcaggtt gtcccagagt 237840
cgtctaccgt gatgtcatgg attccagtcc ccaagccatg tccctggaga gagtacaaag 237900
gctttggaag tgaagaaatc accatcagag aactagaggc cggacccgat ccctagcccc 237960
ttgggcactg tctcaaagct ggggggcaag aatgttctta gcatctctga gctgccgttt 238020
tttctgacag gcaaactacc aaggggggtga acatggcgtc cagccttaca ggggtgtctc 238080
aagtttactt taaatgagtt gcggagcaaa tgttaggttc aattaggatt agccagcacg 238140
gtttcagtaa cgagccagaa agaaagatag gactgtggga agcatcctgg aaaccaacag 238200
acaccccccac ccccacccca cccccaaaag acctaaaaaa ctactcctgt ggaggccacc 238260
tccctctgag tgctcccaca gccctcgggg gctggtttca acctggaaaa gatgtcctgc 238320
atcacagcac ctgcaagcca gacacctgcc ttaccccatt tttgctgcca gcaactgggg 238380
tcacaggcta tggcctagta acagaatgtg ttcgtggcag tgacctcagg agtctgggat 238440
gcagaacact tgccatttgc tgttggtcac ctttcagcag ttttgcttga aatgtgttca 238500
gacttcacag acaacacaac acaaataaaa ctctggagtt cagaagctca aatcatggct 238560
aaaagcatgg gattgtcaga gtgatattct gtctgaaaac tctttcattc agagaaaacc 238620
tgcattttct cttctctctt ccagcaccca tggatgggta gccgaaaccc gcttggctca 238680
tctgcacact cagattgctt ggtctctatt tctgttctca agtttctcca tggttttggc 238740
ccttctgcct cctctagcat attgagagac ccttgtgatt actgtgccct ctggatatcc 238800
caggctaccc ttgagttcaa gtcccctaat cacatttgcc atgttagaca ccacgcacag 238860
gttcctggac ttagtaagtg cacacacatc ttttccattt tgcttcccat acagtgactg 238920
ggatcataag gaagctgtgg catgctctgt cattatcttt ccttagcaga taagagaccc 238980
agggacggag aggttatgta acctgtccgg gtcacctgga gaataagttg cagatcccag 239040
aaccaaggtt ctctctggtt gcaaagcctc ctgggatggg agcagcctgg aatcccagcc 239100
actccctgaa ctggtagaca gattccaagc tggtttctag ggagttgggg agtttcctag 239160
ggagatgggc agagtacatt cctgccctgg gtcccaaatg cagagacctg ggcgcaaggt 239220
ccatccttgc ctctaaggct gagagataaa ggacacagca aattccttcc actctcaaca 239280
ggcccttatc tagaaggaag ttcatggtag aacctcaaat agatggtctc aaaagttcct 239340
cttagcttga aaactcactt tccataatgg gattttagag atgatctgtg gtttttgttt 239400
gtttgtttgt tttgttttgt tttgttttgt ttttagatat tctcatatag cccaggctga 239460
cttcaaactt gctatatggg caaggctgtg gttttgaact ctcaaccctc tgaccttcca 239520
agtgcaaaaa ctggccaccg tactcagccc actctacaca gctacccagc tctcccatcc 239580
tggcaagtga gcctaggccc tcaccactct gggaagacat atcgtcactg aactacatga 239640
cccctttttag tggtcatggt atatggtgag gttttctctg gaagggaggc tgaataacag 239700
catctacaca taacaaaaac attggcaact ggggctggag agatggctca gcggtttaag 239760
accactagct gctcttccag aggtcctgag ttcaattccc agaaaccata tggtggctca 239820
caaccatctg taaaggaatc tgattccatc ttctggtgtg tctgaagaca gagcgctcat 239880
gtacctaaga taaggaagaa aggaagggag ggaaggaggg agggagacaa ggaaggagct 239940
aacaactcca tgttggcctc tgtcatttct tctgaagcat cagaggggtc ttcatcctca 240000
gcttggggat atgagcctgt ctgcatctca ctcaggctga cacctcagtt gtttttggat 240060
ttagggttgg gaggctggct aaacatgtgg catctggaaa gacaaatccc caaacctggg 240120
```

-continued ggaccagggt gaggtgaaag ggggaacccc ttggaaagca aaaaaaaaac tttggggtgg 240180
ggctgtgagt gaaggagccc acaattcctc cctccctccc ttgttccagg ctcagagggc 240240
actagcaaca cagaggagtc caggagtggg ctccatgaga ctatcttgaa gaagacatac 240300
acctcgggat ggtgcaactg ccttacccct ggggacccct ggagtctgca gccacccccct 240360
gctgccccca cctgaaccct tgatcccagc tcggcagccc ccgcagtttc ctgtttgccc 240420
actctgtttg cccagcctca ggaacagagc tgatccttga actctaagtt ccacatcgcc 240480
agcaaaagta agcagtggca gggccaggct gagcttatca gtctcccagc ccagcccctg 240540
cccacacaca tatatagacc agggaagaag agctggacac ccagactgtc ggagagctcc 240600
ggggaggtaa gtgctgctac ctgccttcgg tggctctggc tccatagcgc ctcccagttg 240660
atgctccact gtccaaatca ataccgtgga tatctcgcac ctttagccat tctagccaat 240720
gcttccatgg gcttgaattg tgtgtggagc ctttccatga caatgcctcc cttcagccca 240780
gccctcctcc tccttcttct tcttcaggtc acccacaccc ttcaggatga aagctgtggt 240840
gctggccgtg gctctggtct tcctgacagg taggtgcctc ttgacctgcg tgggactacc 240900
ttcctgggca cagagaacag aattcccact gttctcttcc ctgactccga gtctaaccta 240960
acatgggtct cccctccatc cccagggagc caggcttggc acgtatggca gcaagatgaa 241020
ccccagtccc aatgggacaa agtgaaggat ttcgctaatg tgtatgtgga tgcggtcaaa 241080
gacagcggca gagactatgt gtcccagttt gaatcctcct ccttgggcca acagctgaag 241140
taaggaaaga cctagcgtgg ggcctggagc aggtcaaggg ctgcccatcc agggtgggca 241200
gagagaccag tgagaagatg ctggaactga gctggctagc ccttcacggg ctttcctacc 241260
agctgggcac catggcaggt tccagtggag gactagggat gggattcatc tggctgttgg 241320
gtaaccacag cccctcattc agcctatgag tgccaaatcc cttttccttg gtaaccccca 241380
gtactggtca gacagcaccc aaaacaaaac aaaacaaaac aaaaaacaaa aaacgggact 241440
ggccttgtaa ccagcaccga ccacatctgt gttcttggtg ccttccgcca tgtgtacaga 241500
ggaatgtaaa gggaaggcag tgagttagag ggttgcatgt tcggggaaac taggaccata 241560
gcaactgcac attaggggac aggtggcacc cagctatcat gtgcatggat ctgcagacca 241620
ggggcagcgc atgatgcctg ggctcgtctc tcagccgctc tcttcccccct ctagcctgaa 241680
tctcctggaa aactgggaca ctctgggttc aaccgttagt cagctgcagg aacggctggg 241740
cccattgact cgggacttct gggataacct ggagaaagaa acagattggg tgagacagga 241800
gatgaacaag gacctagagg aagtgaaaca gaaggtgcag ccctacctgg acgaattcca 241860
gaagaaatgg aaagaggatg tggagctcta ccgccagaag gtggcgcctc tgggcgccga 241920
gctgcaggag agcgcgcgcc agaagctgca ggagctgcaa gggagactgt cccctgtggc 241980
tgaggaattt cgcgaccgca tgcgcacaca cgtagactct ctgcgcacac agctagcgcc 242040
ccacagcgaa cagatgcgcg agagcctggc ccagcgcctg gctgagctca agagcaaccc 242100
taccttgaac gagtaccaca ccagggccaa aacccacctg aagacacttg gcgagaaagc 242160
cagacctgcg ctggaggacc tgcgccatag tctgatgccc atgctggaga cgcttaagac 242220
ccaagtccag agtgtgatcg acaaggccag cgagactctg actgcccagt gaggtgcccg 242280
cttccactcc ccacccccgc attggctttc ttacaataaa cctttccaaa atggaatagc 242340
ttctttcttt gggggacata gggcgggcgc taaggggaca tcaagggacg tgagaacatg 242400
gtgccgcact ggggattcct ttgtacgcga ctactcagct cttaacgctc actcaagctg 242460
ggcacctggc tggttcaggg tatgagacag aatcccttcc taagaaggct ccaagggaaa 242520

-continued

```
tggatggcca ggcaaagcaa caaggaaccc caaaagggcc ccacagaggc tcagaacact 242580
agtgctgtaa accaggatga gagtgtctgg caataggact ggctttgaga ccgctggttt 242640
cttgtgctag ccgagtttcc aggtggggtc cagagggtgc aggacgggag cctcttccac 242700
tccctagagc caggattcct tcaggagcca ggaagattgg agttattggg tgggtgctaa 242760
taaaaagcct ggagctgaac ccgatctcgg taaacaattc cctttgatct ttccctccgg 242820
tgcacccaca cagtgtgctg aaagggtcaa ggctgcagct actctacctg acagttggat 242880
acaaaaacaa acaaacaaac aaacaccoct ctccatgatg ctggtgacca cacatttact 242940
agagaggcct tcatatccat ctctaaatcc tgaaggatgg cctttaagtc cacaccagtt 243000
ggggaagctg agctgggagg tctgaagtta gtcactgcag aaaaggtggg tcaggatgtg 243060
ccgttccatt ttaaaacaaa acaaaaacaa aacaaacaaa caaaaaaacc ccttttatta 243120
catggggctg gtaaggtggc ttatcaggta gaggcacttt cggaagtctg agaacctgag 243180
ttcagtgctt agaagacaca cacacacaca cacaccccac aaatataaat aaaggtatat 243240
aaaatattta aatttttatt agacttattt agtgtgtgtg tgtgtgtgag tgtgtgtgtg 243300
tgtgagtgtg tgtgtgtgtg ttttcacgtg ccacagaaca tgtgtggaga ttagaggaca 243360
atttgcaggt atctgttctc ttttccacca tataggtccc aaagatcaaa aactcaggtc 243420
accaggatta gtgtagcgag cgtctctact agctaagcca tcttgccagt tcttgtttgt 243480
atttatctac tagctaagcc atcttgccag tccttgtttg tatttatttt atttggagac 243540
agtgtctcca ctagcccagg ctagactcag atgagctctg atctttctgc cccatctccc 243600
aagtgctggg ggtttcaagg atggtccacc actgttactc tgtgctgaga caaacccaga 243660
gctctgtgca tgcaaggcaa gccctctacc acctgagctg cctgccaagc ccagactgtt 243720
cattgtatag acttgcccgc tatggagtgt aaccaagcac tcatgttcac agggttgagg 243780
atgtctgcag aagcactctc acaccaacag ccttcctctc atctgcccct cttcatgcct 243840
gtgttggtat gcaggtggtc tccatccatc cccggtgtat cttcatgagc ccctggctga 243900
aggggtgagt ttttaaatcc acaatcatgc agagccacag cagacattaa accaggtttg 243960
ggtaggaaag tttcccggtg tggacaatga gacttctggc tcttggtgga caggaagaga 244020
aaccccctatt ggatttccag agagaacata gtccagtctg ctggctgtgc caatgcagtc 244080
tggaaaggag cttccaacac ctggcagagg cttttccggt gccagcaacg tggaaaatgg 244140
aaagctggcc ctgcagtgtg ttttctcctg atccggggca gccactggca ctctctgaac 244200
attagtcttt tactctataa tgtgcaagac ctgttttgtg acactgggtc tctttgaagt 244260
gagtgtttgg gggtggcagg aacttagcaa gcagcccttt tgggattctg aggacactgg 244320
gtctccattc cagtctagaa ggtcacctag tttagctatc acagtgagga ctgtttacaa 244380
ggggtgtgcg catgcggcac ctcatgcttt tagacactac catttcattt ctacaacaaa 244440
ccttcagggg aggggcaggt cctacccact ttattcataa gaaatggaag ccgctacact 244500
gcagtggggt tgagacttat ccgaccaccc tcccaatctg cctccttcct ttccgcctgt 244560
ttaaagggc caggcagcct gggctgtgca aaccagctgc acggggttgg tgatcatatc 244620
tgaccttaag cctggagatg acataagact gctagctaga cagatactac actccagcca 244680
cgtcgtccac gttgtcctgc ccttgacagg tttatcacag attgtaactg caaatctgtc 244740
gttacctgat ttgatctttc ccattaagtc aagcagggaa gcggagttag tcccacgtac 244800
aaaggaagaa gcaccccaga gaccactaaa gaggtggatg acctacagcc ccaggtccac 244860
```

-continued

```
ccccttcaaca ggcctagctc atccccatgc ccagacgtcc aggcacatgg gacacccact 244920
aacagcagct tcttatccag ctttattagg gacagcatgt ttaggtgaga tctagggagg 244980
ggtgaagaca tgagaacata ctttcccctt aaagcaacct tcaggggcca cctggcaggc 245040
ctggaggggg gcagcaggat ggaggaacag gcacatctgc aacacagaag tctcacgact 245100
caatagctgg agttggttgg tcctcagggt tagaatccca gaagccggtg aacttgtcag 245160
taaacttgct ccagtagcct ttcagggatc tgaagtgatt gtccatccag cccctggagg 245220
ttaaagcagt aagaggcatc cataggagag agggagagag agagagaggg agagagagag 245280
agagagagag agagagagag agagagagag agagaggtgt gtgtgtgtgt gtgtgtgtgt 245340
gtgtgtgtgt gtgtgtgtgt gtgtgagaaa agctcccccg tgggcagcta gacccaggac 245400
tgcacgcagg gctccactgg ctctctcagc caccagcacc accttgccta tcacacccca 245460
aaatcacctg cagctaccta agaaacccca ccttcatcaa ggttggatca gaacctcagt 245520
gccttccatc caatctcctt tcaggccgga ggcaccaagc accggggagc tggatactaa 245580
ggtcagctac aatgcagctg cctgtatagg ccatacaaat cactcccttg aggtacccca 245640
tccctggctc taagtgggtg aggcagaggc agggccagtc tctcatttga aacattactg 245700
aatgacttct aagctgtgtg atctaggcca ggttatctaa ctctttatca tcagcaaaac 245760
cgagtatcta atatcctccc cacagcctgt tctggggata gagactgtca acatcttttg 245820
ctacataggc aactaaacta tcaaatgtca gccaaagcca ttggccaggg ggtgatattt 245880
catagtgggc aagatgccta cctcagactg agcccaggga tagaaacagg gcagactccc 245940
accctctaac ccccaacttc ccacctcact tcccaccact accccctgca tacaggcaga 246000
aaccagagca ggtaggcctc ccatcgtgtg cgcaggaccc agaggagaaa acctgcagcg 246060
aggctaaatg cccctcaggc tgctctgagg aaaagcagag aagataggag aaggctgctt 246120
gccctgcctg tcatcttggt cacagtaccg aaaggcctca tgagggacca gaggctcggg 246180
caggtcccag gccctggtaa acttggtgga ccacagtctc tgtgctaggg tctcagcacc 246240
agggcatgag aggagaagac acaggaaagg aggccagtgt gcctacctgg ccaccacagc 246300
tatatcggac tcctgcacgc tacttagcgc atcctggacc gtcttggagg cttgttccat 246360
gtagccctgt acagagccca gcagcaagga tccctctacc tcttcagctc ctgcgagaga 246420
gcagagttgg gccacgccag ccctcagctc ctgcccagcc accacttctc agggcagggc 246480
cccctgacca gctcccactg aaacccagcc ccactcccac catcttacgg gcagatgcca 246540
ggagagccaa gagggccaca gtgaggagcg tccggggctg catggcacct acgtacctgt 246600
gggaaagcat ctcgtgagaa ggtactgtgg atctgccaca tctaggtcct cccccttgaga 246660
atgccatgac tcctgggtca tgaatcccaa gcctttctcc cactgatatt agatagagaa 246720
ctacagtaga cccagccccc caagtggggt ggaaggtgga gtatagaaat actctgcaga 246780
acgggacatc tactctaata tgctgagaaa caataggttt cttttcctcg ctaggactca 246840
gtttttttcag tcctgggtag gcatggatac caaaggcttc taatagctca gagcaagcta 246900
aacaagggac agcatgaccc aattgcaggc agctctgcca ctacccagtg caaggctttt 246960
ggcccatagc ctccctttcc ccagcttcta gcccccccca caccaggaac ccaagggtgg 247020
agaccatgag tcccaagcct tctgtgggct agatggctgg gtggtgagag cttctccctc 247080
cagctctttg tttcttccct tccttcctct cctccccagg ggcattacct ggagtagcta 247140
gctgcttcta gggataaaac tgagcaggca agcggggagg gctgtgacct gttttatatt 247200
ggctccagga tgggacagcg ggcacagaag gcccagtgag ctgggcaaag gtcacctgct 247260
```

gagcagtcca gaccagagcc tgaggcagga aggccatgca gccatctgcc agaggagttg 247320
agaaatccct ctgagattgc ccatgctttt cacggccacc tccgccacca agggatcagc 247380
taccggctca cctagatgag gtcggtgaga caggaaaaga caggggacaa gccttggacc 247440
tcaggcctgc tttacagcct agagccagtg acaggctcct tcacagaagc cacctgaaag 247500
ccttccagta gaatggaatg gggaatctgt ggtgccactg tggagcaacg gaggaagtgg 247560
ggtgggaggg ggcagagtga aggttacatg cccccacact gacctccacc tgtgatccca 247620
acagtctcct ctgccgtagc tgggcaggga ttagtgagag aaggacaaag gtcacatgga 247680
acccaaggcc ttgcccctcc ccaactcctc cacaggcctc ctcttgccct ctggacctat 247740
cgttagtaat cctgagatag gagcagggcc catggctggg tgatatctga cccctacatg 247800
agccctatct atgagaacct gcaagcagca aggtatagac agggcattca caaagaaggt 247860
gaggatgaag gaggcgctct ggggcaacta agatagtccc ctgagctagt actgagaccc 247920
acagcctaga cagcaacaga ggacatcatc ttctggatgc agactttgga gccaagaaat 247980
cctaggttta gggttttttt tggttggttg gttggttggt tgattttttt tttctgagac 248040
aaggtttctc tgtgtggccc tggctgtcct ggaactcact cttgtagaca aggttggctt 248100
tgaactcaga aatctgcttg cctctgcctc ctgagtgcta ggattatagg catgagccac 248160
tacctgccaa aatcctaggt ttaaatgcta cattcgggac tagagaaata ggccaattgg 248220
acaaaatgct cgtcttgtaa gtaggaagac catagttcaa tccccaaacc ccatggacag 248280
cataagtgca gtagtgtcca cttgtaatcc caagcactgg ggacagggag ataggtagca 248340
ggccaggagt tgatgtccca ccagcctagc ttcttcagtg agccccagat accactgaga 248400
gactctgtct cataaggcaa ggtaaacagc tcttgaaaaa tgatacctga gccaggcagt 248460
ggtggcgcat gcctttaatc ccagcacttg ggaggcagag gcaggtggat ttctgagttc 248520
gaggccagct tgggctacag agtgagttcc aggatagcca gggctacaca gagaaaccct 248580
gtctcaaaaa accgaaaaag aaaaaaaaag tagaaagtag aaaaatgata cctgaaactg 248640
acctgtggcc cccacagttg tgcacatcac acatgcctat tgacctgcac aaacgcctaa 248700
gcaactgacg cctttgaggc tgacatgtag ggtctgtggt cagaagttaa cgggatggga 248760
cactgacttc ccagcgtgtg gagaaacaca cagcagctgg cccagggaag gactcagttt 248820
ccctacctcc caaacactga cagcccagcc agagacagca ggcagtttcc atgcagaaac 248880
agggcttgct gcaggcagca acctctctga atgaaatctc agcctgagag gagcctggct 248940
ttcccctcag aactcttaat ctctgtcttt ggctgagaca cgaagctcat ctatcagaaa 249000
tacattcttt tgatataaga ctgttgtctg gggtagctgt gatagtgttt gcttaaaaga 249060
ccagcactca ggaaaatagt gttagaggtc agcctggact aaataatgtg actgtctcag 249120
aacaactcaa aacagtttgt ttcctgttaa aatgtaagtt gtccgaatta tgtagcttag 249180
acattactaa ctccgtttat ggctaaaaac caaaggccca gtggggtaga gactgctcaa 249240
cacatgccac ccagcagtgg agaagctggg tctcagcacc tgagctggtc ctcagcaccc 249300
atttataccc aagcttcctc tgagaaaagt ccctggcgaa gctgagaggg aacaaaggtg 249360
gtaccagggc ggggcactgt gtgtcgtggt ggagggagat gccatgttct tttttcttct 249420
cagcctgttt cttgttccta ggcaaagggc acagcaggga tcagatccca atctggggtg 249480
tgatatcaag tctttggccc tgagaatgat ttaacaggct gactgggtca ttgtccattg 249540
gtagggaggg tctgggaagc ctgtcacctc ccctgtatgt agaacatggt cactgaatca 249600

-continued agaaaagtca aaagatgcca atagagagtc ccagccatgc gatacttagc tgcacagaaa 249660
acttaggtgt atgaatccca cagagtggtt ggcaggcagg tgataccttg gaacctgggc 249720
tctgggactt agtcccttcc aaaaaccctt gtaccctctc agccatagga gccttatggt 249780
ggcctcttgg tggctttctg gcctagggtc ctctggggaa aggacagtgt tcttgactta 249840
cagacccagt cccatggagg aaggtagcag tggggggggg ggggagtttc ttaatttctt 249900
ttcctgttgc tatgatacaa tatcccgacg aaaacaaagt gaggagttat cctggctcac 249960
acatggggag ccatggtggc aggaacacga agtagccagt cacatcacgt ttacaactaa 250020
aagcaaagag ccatgcaaag ccagtcctca gctcggctcg ctttcttcat tttgtgtggt 250080
ctgggatcct tcatccaaca accccccccc accccctcag gtgattccag attctgtcaa 250140
attgacagtt aaaactaatc accacactgt ggaagatgtc ttgaacattt gggctgagaa 250200
cagccctcag gagtggcttg ccagccctcc tctgtttggc taacagcagg ttgggtggat 250260
gagagcccca gggctctact tggatcctat aggcagatgg atggtgcaca gctaccaatc 250320
agccttacta gccatgagct ccgtgtgagc acaggcagag actgagggtc agacagagac 250380
gtgagttgcc aagaccactt gaccctctgt gcccgaggct ggcataaggt ggtctgctct 250440
ttttccccag aagctgacac atagggttct cattttgcct caccctctat gcaaatcacc 250500
agcagatgca tatgaagtat gccccagtct tggagaagtc aatatgatga tttatgacgc 250560
gccaggaggc aatacaacct ccctgtaggg gctggtgcat acgtgagtgc tagccacaca 250620
tgtgtgtacg atgacccagt ctcttagctc agagccaact tctgaacccc tggacaactc 250680
agatatctat gcatatctga cagcccgtca ctggaaacca cccttgaaca aacttaggta 250740
acacaggtct tctcagagag ggtatgagtg ggcaagcacc tctggacctg tcccacgctg 250800
ctggcacttg agagactcag tctgcaggtt caggaggtgg aactgtagct gagatgtcct 250860
acgtgactca tcccccatca gttctgacct ttgggcacag cacaggctgg accaggcatg 250920
attaggtaaa gcaagatgag gaccaatggg tcaatggtac acagagagaa accgtacata 250980
gctaatattc aacgaggaac ctaaggggag ccagactatc tcacagaatc ttcacaacga 251040
agactcatcc aagaccacac agcacagact gtgtgggatc cacgtgcaaa cacagggagt 251100
cgactccaga gcctgaactc agaaaacatt gaaagaccac caagatgact cagtgaacaa 251160
agtcacccag cctgatgaca tcagttaaaa ccctagaacc caaatggtag gatgagagaa 251220
caaacctctc cagttctcat ctgacctcta tacatgtatt gtgatgtata catactcacc 251280
cctaccaaat attagtaaat aaataacatt atcactatca tcattatttt tgtttgtttt 251340
gttttgtttt gttttgtttt gttttgtttt gttttgtttt gagacagggt ttctctatgt 251400
agccctagct tcctggaact cactttgtag actatgctgt ccttgaactc acaaagatcc 251460
accaatctcc acctcgtgtg tgctgggatt aaaggcatgt gccatcacac ctggcataaa 251520
ttaattttct taaactcact aagcatggct gtgctaggaa ggaatgagct cggggaagct 251580
cgagccctgt ggggagccat gcagtgcagt ggggcccagc agaggagcac aggtatccag 251640
ctgtcttcag tcccatgaga caagctaatc tggacacatt ttaaaaaatg gatggcaaca 251700
cagcaaatca gactgggcac aatcgtggtc tattctaatg gctgtcattt cacaaatgct 251760
gtcttgtgga tggcagtcaa tgggacagta tgatggatgc cctcatctag tccctggtgt 251820
ggtccactga ggctccacac tgaccacagc ctggcatctt gcctgtggat atctgctgca 251880
attgtatgtg tggacacatg tggagtctca gtaggagacc tcaaaaaact cactttccac 251940
agcagtgtct gtcaccttct gtgggggggg ggggggtggg aagagagaga gagggagaga 252000

```
gggagagaga gagggagaga gagagaggag tcactctgca tggctcttgc atatggctga 252060
gaacagtggg gcagcaatca agccttagcc agccctgctc tctcactgtt gcctctagcc 252120
cacttggtga ccctctgagg gaaagggtgg ctctccctct gccactgtca ggagaggatc 252180
aggttctctc cttccttcct gtgctgatgc acacagaaaa tcattgtcat taatttcagc 252240
ccttactctg ggctaagctc cctgcagcca tctcacaagt accacctaat ttaatgtaac 252300
aaactacaca ttgttcaaaa gagaaacttg aagcttcatg ataactggac ggaggtgagc 252360
cagcttgaca gtcatgagat acaaagccca ctatgattaa ctcctttgat cctgggttct 252420
gatcctctcc tgaccaaggg tatcacagac acctcaactg aggctcactg tctgctgcag 252480
ccctatgcca tctctgggcc tggtaccatc tctgtagctg atgttctgag acaaagttca 252540
ggttggtggc agctgtcaga ctggtggctg tctcactggg gtggaaagag gagacctgga 252600
ccttgttctc tcagactggc acagacccag ggctgccaac cgggcctctg gggcctcagt 252660
tctgttcagg gactccccta gactcccagg ctcattcctc ctgaagtttc tggctatcct 252720
tcccagcctc ttggacaggg tggagccaac tcaagaagac tgcttccctc tgctgcctgt 252780
gtgctgtcag cttccacgtt gtcttagggc cactaaagtc caagaggcct cctgggagtg 252840
tgtcaccttc caacgtggag tcacactggg gaggaggcgg ggagagaggg ctggaggggc 252900
tttaaatgag tggctggcct tgcctgcagt caatctgcac agggacacag gtacaccgtt 252960
tcttctgact ccgggaaaca tccagtgtag ccgaaactgt cccagcccag tgaggagccc 253020
aggatgttcc tgaaggctgc ggtgctgacc ctggccctgg tggccatcac cggtgagtag 253080
acactgcacc tgggaggcag caagaaaagc cagctctaga actggcggac agctcggggt 253140
ggccttgtat ttgcccagca gctcatagga gaacaggcct ttgttctccc tggcacttgt 253200
gctccctggg ttatcccagg gatggggcaa tggtttgggt tatccaaact ccaacattat 253260
ccagctcaga gctgaggcag aggggccagg agagagatga tcctcataaa gttgccttct 253320
gctctctctc tgcccaggca cccgggctga ggtcacttcg gaccaggtgg ccaatgtggt 253380
gtgggattac tttacccagc taagcaacaa tgccaaggag gctgtagaac agtttcagaa 253440
gacggatgtc actcagcagc tcaggtaagt gcgatcagtc tacaaggcga ggcttgaagc 253500
ccatagctga cctcagaggt gggacactgg ctcctggagt tcttctgttc tcactaaagg 253560
agtcttgcct ccctggacct agattgtccc tgtaaacagg aaagctggac ccagggatcc 253620
atccctatag ttccttccta tctgcatgtg ctagagtttg gtaaatagcc aaatcccatc 253680
acaaactctt agcaggaaga ggaaagagac gtgtcctgta aggacatgag gttctgggca 253740
aacaggggaa ggagggctgg tattttgggg gacccactga gcacatgcaa ggacatcaga 253800
ccctgtgcca ctggaagaca tgtgttgcac aatgtgaccc tgggagggga gtgatgccaa 253860
agtccagccc cattctttat ccacaggtaa ggaaagcaaa cttctcaagt cacatggtgg 253920
gcagataagg atgcagaggc tcagcagaag ccttgcagat aaaactccaa agtcaaacta 253980
atcctaggag atttcctgaa agcatgacct accccagggg agggtcaaag ggacaagacg 254040
gaggtctctg ttcccatgga cacactcctg acctaagcag gtgtatagag ctgagtgttc 254100
tacaagcgta tctaatggtg cttccttgtc tccatccttt ccctgaagta ccctcttcca 254160
ggacaaactt ggggatgcta gtacgtatgc tgatggggtg cacaacaagc tggtgccctt 254220
tgtcgtacag ctgagtgggc atctagccca ggaaactgag agggtgaagg aagagatcaa 254280
gaaggagctg gaggacctac gtgaccgcat gatgccccat gccaacaaag taacccagac 254340
```

-continued

```
gttcggggag aacatgcaga agttgcagga gcacctgaag ccctatgccg tggacctgca 254400
agatcagatc aacacacaga cccaggaaat gaagctccag ctgaccccat acatccagcg 254460
catgcagacc acgatcaagg agaatgtgga caacctgcac acctcgatga tgccccttgc 254520
caccaactta aaggacaagt ttaacaggaa tatggaagag ctcaaggggc acctaacccc 254580
ccgtgccaac gagctgaagg ccacgatcga ccagaacctg gaggatctgc gccgcagcct 254640
ggcccctctg acggtgggcg tgcaggagaa actcaaccat cagatggagg gcctggcctt 254700
ccagatgaag aagaacgcgg aggagctcca gaccaaggtc tccgcaaaaa tcgaccagct 254760
gcagaagaat ctggccccgc tggtggaaga cgtgcagagc aaggtgaagg gcaacacgga 254820
agggctgcag aagtctctgg aagacctgaa caggcagctg gagcagcagg tggaggagtt 254880
ccgacgcact gtggagccca tgggagagat gttcaacaag gctctggtgc agcagctgga 254940
acagttcaga cagcagctgg gtcccaattc gggggaggtg gaaagccact tgagcttcct 255000
ggagaagagc ctgagggaga aggtcaactc ctttatgagc accctggaaa aaaaggggag 255060
cccagaccag cctcaagccc tccccctccc ggagcaggcc caggagcagg ctcaggagca 255120
ggctcaggag caggtgcagc ccaaacctct ggagagctga gctgtccctg gtgccctcag 255180
cccatcacag cagcagacac ctgtcctgcc ccaccacctg tctgtcactc tgtccccagg 255240
cacttcttgt accagcttga ggacacatgt cctgtgggag gtgaagccac atctcgctac 255300
tcaataaagc aactgagaaa ttagccccat cgggttgccc tgtgattcct tgggggctgg 255360
cctgacgtag ggaggaaatc aaggcatctg gctggggaca tggggggtgag gggtggggcc 255420
ggtaatgagc cttcgggtgg gtcaggggtt ggtgtgctag agaggagaat gcagaaaaga 255480
cgccagtcta tcagaaaaca aaacacgcat cccgttcaca gcctgcagaa aacaaaacac 255540
acatcccgtt cacagcctgc aaacagttat caaacgccct tgaggttcca gtcaagattc 255600
tgagcactag tcaaaacagc ctttgtggca ttgtgtgcct gaagaccggg cttggtgttg 255660
acagggacac ctggagggca gcaagaccca gtccctgacc ttgaagagtt tactgcacgg 255720
caagtccctt cttgaacatg cctgtgcctt tgaacttatt tatacaaaag taagccactc 255780
tgtcccactg taaagtactc atgtttgccc cggagttttc tccacctatg gataaatctg 255840
ttgactccag agctgtataa tagatgccac gggatatgaa cgagccttgg cagccaaggt 255900
ggaacaggct ttgcccagga gcctcctgat gggtggcttg cctgtctatg acaaagctgg 255960
tggtcgctgg ggcaaagaaa tgaacccatc agaggacccc agtggtttta tggggacagc 256020
cagccacagg aggctgcagt ctctggaatg aattttccct gcccttggag acttagagcc 256080
tccctaagga gggaatctca gagtagagta gttcagggat tccttccaaa agatttcaca 256140
tactggctgt agcctctgcc tcaggtctgc aagtcaaacc cctctgcctc agaatgggta 256200
aagttcccct gggatggact ggaacatgct gtgggtggtc ccagctgctc tggccttctc 256260
cctcccttcc aaggcgtcct ctgtgtgtca taagcccaga cctgggtttg catcctagtt 256320
tcctgatact tctactgggt gatttggagc aggtaacaaa acctgttttg gaaaggaaaa 256380
atgaggaacc ttgggccaga gttattcaga aggtctgatg gtgccaagca cttaatataa 256440
ccatcaaggc aatgtaaata ctaaatgtgt gtgtgtgtgt gtgtgtgtgt gtgtgcgcgc 256500
gagcacacgc gctcacagga tcacgcgcgc gctgtgctgc tctaatgtag cagacaccta 256560
ggaaatgtcc tcctctgctc acatctccag accccagatc caggccacca aatgctttga 256620
gtctccccag cccctgctaa cctcagctac atgggcccaa ctgtcacagc tacttacact 256680
tactaccccg agcagggaag acccaggtga ccacatccta ctagggaaga cccaggtgac 256740
```

-continued

```
caggggacca cagtcgtcaa ggatgcatgg cagcaggagt ctggctgaat ggctttaaga 256800
aatgcttgct tagagaacca gaggcactac aaggaggcag gacaagggct ggttggtgtc 256860
ctgagctgtt ctggaagctt ctggtagatc agttaggtga gctctgtctc tcaaagcctc 256920
tgagtctccc agtctcttgt tcatagtgca aatcccgagt gggacccctg agttctttcc 256980
tgctgtcttc aggactgtta aacacatctc ccaggggcct gccttactcc tggtttctct 257040
gaatgagggt atacttgctt actttctctt gagccaggat gtcactccta accttcagtc 257100
ttttaggtca cagcttccag gtcacagcat ttgcttttgg ctgctgtaat agactgggtg 257160
ttcctgtgaa cacactgtgg tgcatgcatg tgtgcgtgcg tgcgtgcgtg cgtgcgtgcg 257220
tgcgtgtgtg tgtgtgtgtg tgtgtgtgtg tgtgtgtgtg tgtgtgtatg tatctgggtg 257280
gatgagtgca tgtataggtc agaggataac cctcaagaaa accatttgct tcctttggga 257340
cagggtctct tattagcctg gagctcacca attagggtag acaggctgaa cagtgagaga 257400
caaggaccca cttgtccacg cctccctgaa atgaatgtat tccaaccatc aatgtaaagt 257460
taggtatggt tgcacatgcc tttaattcca gcactcagaa gacagaagca agtagatcac 257520
tatgagttca aagccagcct ggcctacatg ggaattccca ggctagccag ggctatataa 257580
tgagacctta tcacaaatga aaacaaataa acaaacaaaa gagactgcgt tagattggtt 257640
tattttacct cctattgctg cggttctgag gttttgtctc ttccatggtt aaacaatttt 257700
atttgcagtt acttttgagt tctgagctca ttgccattaa gtaataacac ataaataaac 257760
catctgtgac ccctaggtct tttcaaatgt cctatgaaga aaacttccct caagattcag 257820
ctggctcaca gccagaaatg ataatgaagg acttttgcaa cttaatcctc aacccagtac 257880
caagtatccc taccctctac cagtagatgg gccccagccc caggacaggt agaaaatgac 257940
ccagaaacca cagtcagtgc aaagagacac actagtcaaa ttgagaagag agcaccagct 258000
tagaggagaa ctgagagaca ctggacttaa gggaggtcag agagaagcac agagcactct 258060
gctgccacag ccctgcagtt cctgtcatgg acaggtcctt ctgagagtgc cagaggagaa 258120
aacaactgca tccaggaggt gacagctcac actcactcag aggcaggtag gtctctgtga 258180
gttcaaagtc agcctggtct atagagtgag atccaggaca gccagaacta tactgagaaa 258240
ccctgcttcc cccacccccc acccaccaaa aaaaaaaaaa aaaggaaaaa gaaaaagaaa 258300
acaatcattg caaagattca atttaggcct aaatcttata atatcttcct ttaactttaa 258360
aactacattt acttatgtgt gcgaggacat gtgtgtatgt gtgtgcatat aatccatgaa 258420
cctctcccag acttgccact agtggtctat aaggattgtg tatggtttga atgtatacaa 258480
ataacctttt aatacctcta tgcattgatt tgacccaaag aaactctaat gagtttcaat 258540
tactcccgca tgctttagaa gcttcaagta ttagatgaaa tagaacaacc gtggggagtt 258600
aaggttcgat tacattgcta ggtctttttt tttttttgt ttccaacaaa acattatctg 258660
tgttcattta gagagagaga gagagagaga gagagagaga gagagagaga gagagagaga 258720
gattaggagg ggggtctttg ggagaggatg aggtctgtaa aacaggattg gaattctcac 258780
agaaggatca cggaaggatc cccatggaac gttcgccttg cttcaaatgt cagacatagc 258840
tagacagcgc catctatgga tcagagggtg gccttcacca gatacttgat ggctggaacc 258900
tgggtgtggt ataggagtat agaagagaga gcaagagaga gcgagagaag agagagagag 258960
agagagagag agagagagag agagagagag agagagagag agagagtgag agagagagag 259020
cgagagagcg agagagtgag agagagaaag cgagagagcg agagagtgag agagagaaag 259080
```

-continued cgagagagcg agagagagat gtttttatga gtctccatgc ctatagtact atggtatttt 259140
gctagaacag tctgagtagg tttctgacaa cagctgccca gcttctgaaa gttccttgct 259200
ttggctgaag aatgtccttt gaggaagttt tgtttctggg gttttgtttt gttttgtttt 259260
gttttgtttt gttttgtttt gttttgaaaa aagagtctca tgtatcttgg gctggtctca 259320
catttgaaat gtaccaaaga tcaccttgaa cttctgatcc tcctgactcc atgtcccaaa 259380
cgatagaact gcagatgtgc actaccaccc ctggccctct gggcagtttt atttttaatt 259440
ttcttattta tacatttatt tgtttgtgca ttgattgatt gattgattgt gtgtgtgtgt 259500
gtgtgtgtgt gtgtgtgtat ggacacacac atgtgtgagt atgtgcatat gggtatgtat 259560
gcatgtgtgc actccggcta tatgtatgta aaggtcagag gacaactttc gatggtgggt 259620
tgggttccct ccctttacca tgcgggacct gaagattggg ctcaggtaat ccaacctgac 259680
cgcaagcgcc tttacttact gagggaattg acctgtgact cctggtacag atgccaaaca 259740
gcagcctctt acagcatggt gtggtggaag aggcctgcaa tcctaggatt aggaggatga 259800
agcagtttgg gggccatact ggacttcaca gagagaatcc gtaaggaagg taggaaggaa 259860
ggaataaagg gaggaaggga ggaagagaga ggagggatga agggaaggaa gaaggaaagg 259920
gaagacaaga agaaaagaag gacaggggga agagggacaa aggcagcata gctctccacc 259980
agtctggttt atggtgacgg cagctagagt cctctcctgc tttccctgat gtcttttttt 260040
ctaagctgtg tcctccaact ttgcaggatt tttaaaaacc tagtccaatc agttaaattc 260100
tggctcacat cttccagcac agaggtccat tccagcagat ggctcagcaa gtaaaggcgc 260160
ttgcggtcag gttagattac ctgagcccaa tcttcaggtc ccgcatggta aagggaggga 260220
acccaaccta cactcgaaag ttgtcctctg acctttccat ccatacaggg gtccaccaag 260280
taagagcctt acccgacaca ccttctcatc ccttcttagg aagccctatg tgccttggcc 260340
tttggaagcc atagtctttg ccctgcctgc acaagtcatg ctggcctgtc tgcaggaggc 260400
ttagtcctta gaagattggt tgctcctcaa ggaaagagcc accccctttg tgctaagaca 260460
ctgagtggac ctagtctccc atagcccagt ttatcccagg tcatctctag cagctaagat 260520
actggacaaa ttgaaagtga catctgtctg ggcttaagtg accagtctca tctgtcctgt 260580
tcagggaccc tctgacagct gagttcaagg ggaagagggg agtcctgata tgggtctaca 260640
aacctctgta tttttttaag agagagagag agagagacag acagacagac agacagacag 260700
acagacagac agagactaga acaggttagc cctgaccttg cctgtagcta agggtgactc 260760
tggcatgctg ataccccctcc tatcccctac ctcccacatt ctgagatttt ttgagccatc 260820
atgcctggct tatccagtgc tggagactga actcagagtc ttgtgtatgc ttgtcaatca 260880
ctcgactggc tgagccacat tcccagctct ggtattctat tttggatgtg tgatggtctg 260940
gctccatagt ccagaacagc cttgaactcc tgaccctagg gtcagcccta aattctggga 261000
ttacaaatgt atgtcaccat tcccagatat tttatgaaaat atctcccaaa gattttaagt 261060
taatgatatg ttgacaaata cacgatacat acgtctattg ctacagcttg gatttgagct 261120
gtccctcaaa ggcccatgtg gtaagatgtg accactagcc cctggcactg ttgggaggtg 261180
gtggaatctt taggtgctgg gacccagtgg gagaaaagtc actggaggta tcatggtcct 261240
tgaaagggat acaggtgcct ggtctctctg ctctccctcc ttgcttccct gtcagcacaa 261300
ggtaaacaac ttccttcaaa cacatgttct cgccatgatg cccttcttga cataggtcca 261360
aaagtaacag gctaactggc cttggaatct ctgagaccct tagagaaaaa taaactgttt 261420
ttttttccac attaggttga tttctcgtgg gtatttgtaa tggtgacaga aaactgatga 261480
acacagagac tgtatttgaa tatgataacc caaggcagtg tgtagttaag atagctggac 261540
ctcagcaccc atcagtcaga ggcactgtta accatgctgg gcaatgaaca ggagaccctg 261600
aaaaatggca ggaaggagat ttgaaatcca gatggcttca acaggccttt ggagagtaca 261660
gagggaggag gggttgaaga agggaaaatg aagtccacga gaaggctaac cacccatctg 261720
agaccgccat ggagaaaggc ccagtagcaa ggcctgtgag gcgcttctga caaacaatta 261780
tccgcgttgg gtcattgtgt catcctttta acagactgtg acctcagtgg tgaagagggg 261840
aagaaaaggc agttgggtcc ctaggggtgg acctgggatt tgaacacgtg atctacagac 261900
tggaaacttt tctgttagct gccaagctgt gatggaagct gtgatggtga aatgttcata 261960
gatgagcagg gatactcttg tacaaggagc aggcttgggt cctgtctcat catgctccaa 262020
gcccagcatc aggctcttac cggagaaagg aggccggatg ctaaaggaac cgctcccagg 262080
actcctgtga ggaagaaggg gcttccgttt ttattttata aatttctaaa acgttggaat 262140
ttttctcctg gttttctttc tttctttatt tacatccaaa cgctgtccct tctcccagtc 262200
ctccattgaa gtgttcctcc cccacatccc tcccctttgc ctctgagaag gttgcccccct 262260 cgcaggtatc ccccaaccct ggtgcatcaa gtctttgtag gattaagtgc atcctgtccc 262320
actgaggcga gacaaggcag tccactgata catgtgtctc tgtgtgtgta tgtgggggtg 262380
gtggtggtgg tggtgtttgg accagcccgt gcttgctctt tggttggtgg ctcagtcact 262440
aggatcctca actctgcctc ctgagtactg ggaataaaaa tgtgagccgc caccaccctg 262500
caaacattag aattttaaaa aagatttatt tttattttta ttttctgggc atgattgttt 262560
tacctgcagg tatgtgtgtg tatcatgtgc atgcttggtg cccacagaga tgtgaagaag 262620
gcatccaata ccctgaactg gagttacaga cagttgtgag gcactgcgtg agtgctggga 262680
actgagcacg ggtcctctga aagagcagca agggttttaa cctttgagcc atccttccag 262740
tcccagacat tggaattatt tttaaagatt tatttttgtt ttatatgtat gagtgttttg 262800
cctgcaccac atgcatgccc agtgccttca gaggtcagaa gaggatgcca gatttccttg 262860
aaatgaagtt acagacactt gtaagtcacc atgtgggtat tgagaacaaa gcccaggtct 262920
tcagcaagtg ctggtaacca ctgagccatc cttccagccc aagatctggg atataaaaat 262980
gaacttttat actacttttt tcttcccctt ccttccttcc ttcctttctt ccttccttca 263040
taccatacag agatatataa gttccggact ctggaatacc tcttaaatat gtccctctgg 263100
gtgagtgtat atacatgtgg gtgcgcgctt acatgcctcg catgctctct tgggctcttt 263160
tcacagaatg ccctgtaacc agggtaaggt ggcactctct ttgagtaatg ataagaattg 263220
gcccgctttc taatttccat atgcggctgt ccaaaacgaa aaaaggagtc gaccccttaa 263280
gagctggaga ggccctcttg taaatacacg atcaaggtgg tccctcactg aataggttac 263340
ttgggcgagt gggtcttcac atttcgtggt ctaaaaccac agcgctaacc tataaaatgc 263400
gtgtccggca cgaaatacaa ttgcactccc gagaaaacac ccgcgggggg ttacgattga 263460
atatctattg agagcacaac actctccccc tatttcggag aaactattgg gccctaccca 263520
tgttttttat aaactctcaa atgggcccta cccaaacaac atatcgcggt tttttttgtt 263580
aaatcacaac gcaaagaggg gtcgaaaata aatccctcgg cgggacctcg acacacaatc 263640
tttcaccata tgagcgcgcc cacaacactg atcacatata tcgctgctcg cggagaaggt 263700
accgacctct catctctttg gggtccgtcc acacaaaaga aaag 263744

<210> SEQ ID NO 7

-continued

<211> LENGTH: 366
<212> TYPE: PRT
<213> ORGANISM: Homo sapiens

<400> SEQUENCE: 7

```
Met Ala Ser Met Ala Ala Val Leu Thr Trp Ala Leu Ala Leu Leu Ser
1               5                   10                  15

Ala Phe Ser Ala Thr Gln Ala Arg Lys Gly Phe Trp Asp Tyr Phe Ser
            20                  25                  30

Gln Thr Ser Gly Asp Lys Gly Arg Val Glu Gln Ile His Gln Gln Lys
        35                  40                  45

Met Ala Arg Glu Pro Ala Thr Leu Lys Asp Ser Leu Glu Gln Asp Leu
    50                  55                  60

Asn Asn Met Asn Lys Phe Leu Glu Lys Leu Arg Pro Leu Ser Gly Ser
65                  70                  75                  80

Glu Ala Pro Arg Leu Pro Gln Asp Pro Val Gly Met Arg Arg Gln Leu
                85                  90                  95

Gln Glu Glu Leu Glu Glu Val Lys Ala Arg Leu Gln Pro Tyr Met Ala
            100                 105                 110

Glu Ala His Glu Leu Val Gly Trp Asn Leu Glu Gly Leu Arg Gln Gln
        115                 120                 125

Leu Lys Pro Tyr Thr Met Asp Leu Met Glu Gln Val Ala Leu Arg Val
    130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
        195                 200                 205

Leu His Arg Ser Val Ala Pro His Ala Pro Ala Ser Pro Ala Arg Leu
    210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ser Arg Ala Phe Ala Gly Thr Gly Thr Glu Glu Gly Ala Gly Pro
            260                 265                 270

Asp Pro Gln Met Leu Ser Glu Glu Val Arg Gln Arg Leu Gln Ala Phe
        275                 280                 285

Arg Gln Asp Thr Tyr Leu Gln Ile Ala Ala Phe Thr Arg Ala Ile Asp
    290                 295                 300

Gln Glu Thr Glu Glu Val Gln Gln Gln Leu Ala Pro Pro Pro Pro Gly
305                 310                 315                 320

His Ser Ala Phe Ala Pro Glu Phe Gln Gln Thr Asp Ser Gly Lys Val
                325                 330                 335

Leu Ser Lys Leu Gln Ala Arg Leu Asp Asp Leu Trp Glu Asp Ile Thr
            340                 345                 350

His Ser Leu His Asp Gln Gly His Ser His Leu Gly Asp Pro
        355                 360                 365
```

<210> SEQ ID NO 8
<211> LENGTH: 21
<212> TYPE: DNA

<213> ORGANISM: Mus musculus

<400> SEQUENCE: 8
gaggatgtgg agctctaccg c 21

<210> SEQ ID NO 9
<211> LENGTH: 22
<212> TYPE: DNA
<213> ORGANISM: Mus musculus

<400> SEQUENCE: 9
ctgtgtgcgc agagagtcta cg 22

<210> SEQ ID NO 10
<211> LENGTH: 20
<212> TYPE: DNA
<213> ORGANISM: Homo sapiens

<400> SEQUENCE: 10
cccgctgcag tccccagaat 20

<210> SEQ ID NO 11
<211> LENGTH: 22
<212> TYPE: DNA
<213> ORGANISM: Homo sapiens

<400> SEQUENCE: 11
cagggtcgag ggctcttgtc ct 22

<210> SEQ ID NO 12
<211> LENGTH: 34
<212> TYPE: DNA
<213> ORGANISM: Mus musculus

<400> SEQUENCE: 12
tgactctaga taccettggt cccatgttcc agat 34

<210> SEQ ID NO 13
<211> LENGTH: 34
<212> TYPE: DNA
<213> ORGANISM: Mus musculus

<400> SEQUENCE: 13
cattgaattc gacaagagaa agacggggct caag 34

<210> SEQ ID NO 14
<211> LENGTH: 39
<212> TYPE: DNA
<213> ORGANISM: Mus musculus

<400> SEQUENCE: 14
tatgactgcg gccgccacca atcccacatc taagcatct 39

<210> SEQ ID NO 15
<211> LENGTH: 21
<212> TYPE: DNA
<213> ORGANISM: Mus musculus

<400> SEQUENCE: 15
gctcggttct gggcacagag a 21

<210> SEQ ID NO 16
<211> LENGTH: 23

<212> TYPE: DNA
<213> ORGANISM: Mus musculus

<400> SEQUENCE: 16
cttgaggatg ggcatcagct gta 23

<210> SEQ ID NO 17
<211> LENGTH: 23
<212> TYPE: DNA
<213> ORGANISM: Mus musculus

<400> SEQUENCE: 17
gctcactaac agcgctcttg cct 23

<210> SEQ ID NO 18
<211> LENGTH: 22
<212> TYPE: DNA
<213> ORGANISM: Mus musculus

<400> SEQUENCE: 18
acagttggag caaaggcgtg at 22

<210> SEQ ID NO 19
<211> LENGTH: 22
<212> TYPE: DNA
<213> ORGANISM: Mus musculus

<400> SEQUENCE: 19
cttgctcgaa gctgcctttc ag 22

<210> SEQ ID NO 20
<211> LENGTH: 25
<212> TYPE: DNA
<213> ORGANISM: Homo sapiens

<400> SEQUENCE: 20
gattgattca agatgcattt aggac 25

<210> SEQ ID NO 21
<211> LENGTH: 22
<212> TYPE: DNA
<213> ORGANISM: Homo sapiens

<400> SEQUENCE: 21
ccccaggaac tggagcgaaa tt 22

<210> SEQ ID NO 22
<211> LENGTH: 20
<212> TYPE: DNA
<213> ORGANISM: Homo sapiens and Mus musculus

<400> SEQUENCE: 22
gcgcgtggtg ggrgaagaca 20

<210> SEQ ID NO 23
<211> LENGTH: 20
<212> TYPE: DNA
<213> ORGANISM: Homo sapiens and Mus musculus

<400> SEQUENCE: 23
tcgcgcagct ggtccaggtt 20

<210> SEQ ID NO 24

<211> LENGTH: 24
<212> TYPE: DNA
<213> ORGANISM: Homo sapiens

<400> SEQUENCE: 24
tgctcacctg ggctctggct cttc 24

<210> SEQ ID NO 25
<211> LENGTH: 27
<212> TYPE: DNA
<213> ORGANISM: Homo sapiens

<400> SEQUENCE: 25
ccagaagcct ttccgtgcct gggcggc 27

<210> SEQ ID NO 26
<211> LENGTH: 30
<212> TYPE: DNA
<213> ORGANISM: Homo sapiens

<400> SEQUENCE: 26
tggtgcacca cgaggctctg cagcagtccc 30

<210> SEQ ID NO 27
<211> LENGTH: 27
<212> TYPE: DNA
<213> ORGANISM: Homo sapiens

<400> SEQUENCE: 27
aggtggccct gcgagtgcag gagctgc 27

<210> SEQ ID NO 28
<211> LENGTH: 31
<212> TYPE: DNA
<213> ORGANISM: Homo sapiens

<400> SEQUENCE: 28
atgacgtggc agacgtaatg gcaagcatgg c 31

<210> SEQ ID NO 29
<211> LENGTH: 27
<212> TYPE: DNA
<213> ORGANISM: Homo sapiens

<400> SEQUENCE: 29
cgcgccgagg ataatggcaa gcatggc 27

<210> SEQ ID NO 30
<211> LENGTH: 30
<212> TYPE: DNA
<213> ORGANISM: Homo sapiens

<400> SEQUENCE: 30
gcctccctcc acctgtcttc tcagagcagt 30

<210> SEQ ID NO 31
<211> LENGTH: 31
<212> TYPE: DNA
<213> ORGANISM: Homo sapiens

<400> SEQUENCE: 31
atgacgtggc agacgaaaac gctgtggaga g 31

<210> SEQ ID NO 32
<211> LENGTH: 27
<212> TYPE: DNA
<213> ORGANISM: Homo sapiens

<400> SEQUENCE: 32
cgcgccgagg caaaacgctg tggagag 27

<210> SEQ ID NO 33
<211> LENGTH: 23
<212> TYPE: DNA
<213> ORGANISM: Homo sapiens

<400> SEQUENCE: 33
gcctttccgt gcctgggtgg cct 23

<210> SEQ ID NO 34
<211> LENGTH: 29
<212> TYPE: DNA
<213> ORGANISM: Homo sapiens

<400> SEQUENCE: 34
atgacgtggc agacgtggtg ggggaagac 29

<210> SEQ ID NO 35
<211> LENGTH: 25
<212> TYPE: DNA
<213> ORGANISM: Homo sapiens

<400> SEQUENCE: 35
cgcgccgagg atggtggggg aagac 25

<210> SEQ ID NO 36
<211> LENGTH: 24
<212> TYPE: DNA
<213> ORGANISM: Homo sapiens

<400> SEQUENCE: 36
aggagctgca ggagcagttg cgct 24

<210> SEQ ID NO 37
<211> LENGTH: 21
<212> TYPE: DNA
<213> ORGANISM: pPNT2T vector

<400> SEQUENCE: 37
ctttttgtca agaccgacct g 21

<210> SEQ ID NO 38
<211> LENGTH: 21
<212> TYPE: DNA
<213> ORGANISM: pPNT2T vector

<400> SEQUENCE: 38
aatatcacgg gtagccaacg c 21

<210> SEQ ID NO 39
<211> LENGTH: 23
<212> TYPE: DNA
<213> ORGANISM: Homo sapiens

<400> SEQUENCE: 39
atgacctgtg ggaagacatc act 23

<210> SEQ ID NO 40
<211> LENGTH: 23
<212> TYPE: DNA
<213> ORGANISM: Homo sapiens

<400> SEQUENCE: 40
agccagaagt gactagagcc aaa 23

<210> SEQ ID NO 41
<211> LENGTH: 23
<212> TYPE: DNA
<213> ORGANISM: Homo sapiens

<400> SEQUENCE: 41
agtccccaga atcaaaggat gat 23

<210> SEQ ID NO 42
<211> LENGTH: 22
<212> TYPE: DNA
<213> ORGANISM: Homo sapiens

<400> SEQUENCE: 42
atcgtgtagg gcttcagttg ct 22

<210> SEQ ID NO 43
<211> LENGTH: 24
<212> TYPE: DNA
<213> ORGANISM: Homo sapiens

<400> SEQUENCE: 43
cctgtcttct cagagcaggt aatg 24

<210> SEQ ID NO 44
<211> LENGTH: 23
<212> TYPE: DNA
<213> ORGANISM: Homo sapiens

<400> SEQUENCE: 44
agccatcttc tgctgatgga tct 23

<210> SEQ ID NO 45
<211> LENGTH: 23
<212> TYPE: DNA
<213> ORGANISM: Homo sapiens

<400> SEQUENCE: 45
aagacaccct agcctccttg act 23

<210> SEQ ID NO 46
<211> LENGTH: 21
<212> TYPE: DNA
<213> ORGANISM: Homo sapiens

<400> SEQUENCE: 46
acagaggttg aggcagcaga g 21

<210> SEQ ID NO 47
<211> LENGTH: 23
<212> TYPE: DNA
<213> ORGANISM: Homo sapiens

<400> SEQUENCE: 47
gtagtgaaaa tcaggggcct tct 23

-continued

<210> SEQ ID NO 48
<211> LENGTH: 23
<212> TYPE: DNA
<213> ORGANISM: Homo sapiens

<400> SEQUENCE: 48
atgcataaac ccaaagggaa aat 23